(12) United States Patent
Shokat et al.

(10) Patent No.: US 10,646,577 B2
(45) Date of Patent: *May 12, 2020

(54) MTORC1 INHIBITORS

(71) Applicant: THE REGENTS OF THE UNIVERSITY OF CALIFORNIA, Oakland, CA (US)

(72) Inventors: Kevan Shokat, San Francisco, CA (US); Masanori Okaniwa, Kanagawa (JP)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,210

(22) Filed: Sep. 10, 2018

(65) Prior Publication Data

US 2019/0091340 A1 Mar. 28, 2019

Related U.S. Application Data

(63) Continuation of application No. 15/455,727, filed on Mar. 10, 2017, now Pat. No. 10,117,945, which is a continuation of application No. PCT/US2015/049693, filed on Sep. 11, 2015.

(60) Provisional application No. 62/049,186, filed on Sep. 11, 2014.

(51) Int. Cl.

| *C07D 498/18* | (2006.01) |
| *C07D 519/00* | (2006.01) |
| *A61K 47/55* | (2017.01) |
| *A61K 31/436* | (2006.01) |
| *A61K 31/519* | (2006.01) |

(52) U.S. Cl.
CPC ............ *A61K 47/55* (2017.08); *A61K 31/436* (2013.01); *A61K 31/519* (2013.01)

(58) Field of Classification Search
CPC ............................ C07D 498/18; C07D 519/00
See application file for complete search history.

(56) References Cited

U.S. PATENT DOCUMENTS

| 3,929,992 A | 12/1975 | Sehgal et al. |
| 4,316,885 A | 2/1982 | Rakhit |
| 4,650,803 A | 3/1987 | Stella et al. |
| 4,861,760 A | 8/1989 | Mazuel et al. |
| 4,911,920 A | 3/1990 | Jani et al. |
| 5,023,263 A | 6/1991 | Von Burg |
| 5,023,264 A | 6/1991 | Caufield et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,212,162 A | 5/1993 | Missel et al. |
| 5,221,670 A | 6/1993 | Caufield |
| 5,233,036 A | 8/1993 | Hughes |
| 5,252,579 A | 10/1993 | Skotnicki et al. |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,403,841 A | 4/1995 | Lang et al. |
| 5,411,967 A | 5/1995 | Kao et al. |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,563,145 A | 10/1996 | Failli et al. |
| 5,665,772 A | 9/1997 | Cottens et al. |
| 5,780,462 A | 7/1998 | Lee et al. |
| 6,277,983 B1 | 8/2001 | Shaw et al. |

(Continued)

FOREIGN PATENT DOCUMENTS

| JP | 2004-161716 A | 6/2004 |
| JP | 2008-273976 A | 11/2008 |

(Continued)

OTHER PUBLICATIONS

Dao, K.L. et al. (Apr. 18, 2012, e-published Apr. 4, 2012). "Design, synthesis, and initial biological evaluation of a steroidal anti-estrogen-doxorubicin bioconjugate for targeting estrogen receptor-positive breast cancer cells," *Bioconjug Chem* 23(4):785-795.
U.S. Appl. No. 13/862,348, filed Apr. 12, 2013, Tanaka et al.
U.S. Appl. No. 14/458,641, filed Aug. 13, 2014, Knight et al.
U.S. Appl. No. 14/668,797, filed Mar. 25, 2015, Knight et al.
U.S. Appl. No. 14/523,581, filed Oct. 24, 2014, Tanaka et al.
U.S. Appl. No. 14/738,169, filed Jun. 12, 2015, Tanaka et al.
U.S. Appl. No. 14/934,187, filed Nov. 6, 2015, Knight et al.
U.S. Appl. No. 15/159,689, filed May 19, 2016, Knight et al.
Apsel, B. et al. (Nov. 2008, e-published Oct. 12, 2008). "Targeted polypharmacology: discovery of dual inhibitors of tyrosine and phosphoinositide kinases," *Nature Chemical Biology* 4(11):691-699.

(Continued)

*Primary Examiner* — Bruck Kifle
(74) *Attorney, Agent, or Firm* — Mintz, Levin, Cohn, Ferris, Glovsky and Popeo, P.C.; Doris Lee

(57) ABSTRACT

Disclosed herein, inter alia, are compounds and methods of using the same for modulating the activity of mTORC1.

8 Claims, 14 Drawing Sheets

Specification includes a Sequence Listing.

(56) References Cited

U.S. PATENT DOCUMENTS

| | | |
|---|---|---|
| 6,323,201 B1 | 11/2001 | Carson et al. |
| 6,358,969 B1 | 3/2002 | Shelley et al. |
| 6,562,819 B2 | 5/2003 | Carson et al. |
| 6,720,344 B2 | 4/2004 | Kerwin et al. |
| 7,429,596 B2 | 9/2008 | Tanaka et al. |
| 7,585,868 B2 | 9/2009 | Knight et al. |
| 8,604,032 B2 | 12/2013 | Ren et al. |
| 8,642,604 B2 | 2/2014 | Knight et al. |
| 8,697,709 B2 | 4/2014 | Dar et al. |
| 8,785,454 B2 | 7/2014 | Ren et al. |
| 8,980,899 B2 | 3/2015 | Korennykh et al. |
| 9,321,772 B2 | 4/2016 | Dar et al. |
| 9,493,467 B2 | 11/2016 | Knight et al. |
| 9,512,125 B2 | 12/2016 | Shokat et al. |
| 9,629,843 B2 | 4/2017 | Shokat et al. |
| 10,117,945 B2 | 11/2018 | Shokat et al. |
| 2005/0085472 A1 | 4/2005 | Tanaka et al. |
| 2005/0101624 A1 | 5/2005 | Betts et al. |
| 2005/0192311 A1 | 9/2005 | Isozaki et al. |
| 2008/0032960 A1 | 2/2008 | Knight et al. |
| 2008/0249123 A1 | 10/2008 | Gu et al. |
| 2009/0074831 A1 | 3/2009 | Falotico et al. |
| 2009/0124638 A1 | 5/2009 | Shokat et al. |
| 2009/0181988 A1 | 7/2009 | Tanaka et al. |
| 2009/0270426 A1 | 10/2009 | Knight et al. |
| 2009/0274739 A1 | 11/2009 | Marks et al. |
| 2009/0292118 A1 | 11/2009 | Lee et al. |
| 2009/0312319 A1 | 12/2009 | Ren et al. |
| 2010/0009963 A1 | 1/2010 | Knight et al. |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0065154 A1 | 3/2012 | Tanaka et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |
| 2013/0289271 A1 | 10/2013 | Perrin-Ninkovic et al. |
| 2014/0066462 A1 | 3/2014 | Pearce et al. |
| 2014/0288096 A1 | 9/2014 | Knight et al. |
| 2015/0031881 A1 | 1/2015 | Tanaka et al. |
| 2016/0000789 A1 | 1/2016 | Shokat et al. |
| 2016/0168151 A1 | 6/2016 | Tanaka et al. |
| 2016/0354377 A1 | 12/2016 | Dar et al. |

FOREIGN PATENT DOCUMENTS

| | | |
|---|---|---|
| JP | 2009/507234 A | 2/2009 |
| JP | 2014/513102 A | 5/2014 |
| WO | WO-92/05179 A1 | 4/1992 |
| WO | WO-93/11130 A1 | 6/1993 |
| WO | WO-94/02136 A1 | 2/1994 |
| WO | WO-94/02485 A1 | 2/1994 |
| WO | WO-94/09010 A1 | 4/1994 |
| WO | WO-95/14023 A1 | 5/1995 |
| WO | WO-95/16691 A1 | 6/1995 |
| WO | WO-96/041807 A1 | 12/1996 |
| WO | WO-01/014387 A1 | 3/2001 |
| WO | WO-2005/007085 A2 | 1/2005 |
| WO | WO-2005/007085 A3 | 1/2005 |
| WO | WO-2005/105760 A1 | 11/2005 |
| WO | WO-2006/009518 A1 | 1/2006 |
| WO | WO-2006/068760 A2 | 6/2006 |
| WO | WO-2006/068760 A3 | 6/2006 |
| WO | WO-2007/028580 A2 | 3/2007 |
| WO | WO-2007/028580 A3 | 3/2007 |
| WO | WO-2007/114926 A2 | 10/2007 |
| WO | WO-2007/114926 A3 | 10/2007 |
| WO | WO-2007/121453 A2 | 10/2007 |
| WO | WO-2007/121453 A3 | 10/2007 |
| WO | WO-2008/047821 A1 | 4/2008 |
| WO | WO-2008/065887 A1 | 6/2008 |
| WO | WO-2008/127226 A2 | 10/2008 |
| WO | WO-2008/127226 A3 | 10/2008 |
| WO | WO-2009/046436 A1 | 4/2009 |
| WO | WO-2009/088986 A1 | 7/2009 |
| WO | WO-2009/088990 A1 | 7/2009 |
| WO | WO-2009/131631 A1 | 10/2009 |
| WO | WO-2010/006072 A2 | 1/2010 |
| WO | WO-2010/006072 A3 | 1/2010 |
| WO | WO-2010/006086 A2 | 1/2010 |
| WO | WO-2010/006086 A3 | 1/2010 |
| WO | WO-2010/025406 A1 | 3/2010 |
| WO | WO-2010/036380 A1 | 4/2010 |
| WO | WO-2010/051042 A1 | 5/2010 |
| WO | WO-2010/051043 A1 | 5/2010 |
| WO | WO-2011/022439 A1 | 2/2011 |
| WO | WO-2011/047384 A2 | 4/2011 |
| WO | WO-2011/047384 A9 | 4/2011 |
| WO | WO-2012/024558 A2 | 2/2012 |
| WO | WO-2012/024558 A3 | 2/2012 |
| WO | WO-2012/066502 A1 | 5/2012 |
| WO | WO-2012/103959 A1 | 8/2012 |
| WO | WO-2012/103960 A1 | 8/2012 |
| WO | WO-2012/149255 A2 | 11/2012 |
| WO | WO-2012/149255 A3 | 11/2012 |
| WO | WO-2012/151562 A1 | 11/2012 |
| WO | WO-2012/154695 A2 | 11/2012 |
| WO | WO-2012/154695 A3 | 11/2012 |
| WO | WO-2013/077921 A2 | 5/2013 |
| WO | WO-2013/077921 A3 | 5/2013 |
| WO | WO-2013/077921 A9 | 5/2013 |
| WO | WO 2018204416 | * 11/2018 |

OTHER PUBLICATIONS

Ayral-Kaloustian, S. et al. (Jan. 2010). "Hybrid inhibitors of phosphatidylinositol 3-kinase (PI3K) and the mammalian target of rapamycin (mTOR): design, synthesis, and superior antitumor activity of novel wortmannin-rapamycin conjugates," *J Med Chem* 53(1):452-459.

Banerjee, S.S. et al. (2012, e-published May 7, 2012). "Poly(ethylene glycol)-Prodrug Conjugates: Concept, Design, and Applications," *J Drug Deliv* 2012:103973, 17 pages.

CAS Registry No. 53123-88-9, accessed Feb. 27, 2018, 2 pages.

Choi, J. et al. (Jul. 1996). "Structure of the FKBP12-rapamycin complex interacting with the binding domain of human FRAP," *Science* 273(5272):239-242.

Drachman, J.G. et al. (2013). "Antibody-drug conjugates: the chemistry behind empowering antibodies to fight cancer," *Hematology Am Soc Hematol Educ Program* 2013:306-310.

Dowling, R.J. et al. (May 28, 2010). "mTORC1-mediated cell proliferation, but not cell growth, controlled by the 4E-BPs," Science 328(5982):1172-1176.

Feldman, M.E. et al. (Feb. 10, 2009). "Active-site inhibitors of mTOR target rapamycin-resistant outputs of mTORC1 and mTORC2," *PLoS Biol* 7(2):e38.

Flygare. J.A. et al. (Jan. 2013). "Antibody-drug conjugates for the treatment of cancer," *Chem Biol Drug Des* 81(1):113-121.

Hara, K. et al. (Jul. 26, 2002). "Raptor, a binding partner of target of rapamycin (TOR), mediates TOR action," Cell 110(2):177-189.

Hsieh, A.C. et al. (Mar. 16, 2010). "Genetic dissection of the oncogenic mTOR pathway reveals druggable addiction to translational control via 4EBP-eIF4E," *Cancer Cell* 17(3):249-261.

Hsieh, A.C. et al. (Feb. 22, 2012). "The translational landscape of mTOR signalling steers cancer initiation and metastasis," *Nature* 485(7396):55-61.

Infante, J. R. et al. (2013). Abstract C252: A phase 1, dose-escalation study of MLN0128, an investigational oral mammalian target of rapamycin complex ½ (mTORC1/2) catalytic inhibitor, in patients (pts) with advanced non-hematologic malignancies. *Mol. Cancer Ther*. 12; C252.

Jacinto, E. et al. (Nov. 2004, e-published Oct. 3, 2004). "Mammalian TOR complex 2 controls the actin cytoskeleton and is rapamycin insensitive," *Nat Cell Biol* 6(11):1122-1128.

(56) References Cited

OTHER PUBLICATIONS

Kim, D.H. et al. (Jul. 26, 2002). "mTOR interacts with raptor to form a nutrient-sensitive complex that signals to the cell growth machinery," *Cell* 110(2):163-175.

Kolb, H.C. et al (Jun. 1, 2001). "Click Chemistry: Diverse Chemical Function from a few Good Reactions," *Angewandte Chemie International Edition* 40(11):2004-2021.

Lamming, D.W. et al. (Mar. 30, 2012). "Rapamycin-induced insulin resistance is mediated by mTORC2 loss and uncoupled from longevity," *Science* 335(6076):1638-1643.

McCormick, M.A. et al. (Jan. 12, 2011). "TOR and ageing: a complex pathway for a complex process," *Philos Trans R Soc Lond B Biol Sci* 366(1561):17-27.

Naing, A. et al. (Sep. 25, 2012, e-published Aug. 30, 2012). "Safety, tolerability, pharmacokinetics and pharmacodynamics of AZD8055 in advanced solid tumours and lymphoma," *Br J Cancer* 107(7):1093-1099.

Neasta, J. et al. (Jul. 2014, e-published Apr. 19, 2014). "mTOR complex 1: a key player in neuroadaptations induced by drugs of abuse," *J Neurochem* 130(2):172-184.

O'Donnell, A. et al. (Apr. 1, 2008, e-published Mar. 10, 2008). "Phase I pharmacokinetic and pharmacodynamic study of the oral mammalian target of rapamycin inhibitor everolimus in patients with advanced solid tumors," *J Clin Oncol* 26(10):1588-1595.

O'Reilly, K.E. et al. (Feb. 1, 2006). "mTOR inhibition induces upstream receptor tyrosine kinase signaling and activates Akt," *Cancer Res* 66(3):1500-1508.

Rhodes, N. et al. (Apr. 1, 2008). "Characterization of an Akt kinase inhibitor with potent pharmacodynamic and antitumor activity," *Cancer Res* 68(7):2366-2374.

Rodrik-Outmezquine, V.S. et al. (Aug. 2011, e-published Jun. 17, 2011). "mTOR kinase inhibition causes feedback-dependent biphasic regulation of AKT signaling," *Cancer Discov* 1(3):248-259.

Ruggero, D. et al. (May 2004, e-published Apr. 18, 2004). "The translation factor eIF-4E promotes tumor formation and cooperates with c-Myc in lymphomagenesis," *Nat Med* 10(5):484-486.

Sarbassov, D.D. et al. (Jul. 27, 2004). "Rictor, a novel binding partner of mTOR, defines a rapamycin-insensitive and raptor-independent pathway that regulates the cytoskeleton," *Curr Biol* 14(14):1296-1302.

Sarbassov, D.D. et al. (Apr. 21, 2006). "Prolonged rapamycin treatment inhibits mTORC2 assembly and Akt/PKB," *Mol Cell* 22(2):159-168.

Su, K. Y. et al. (Feb. 1, 2012). "Pretreatment epidermal growth factor receptor (EGFR) T790M mutation predicts shorter EGFR tyrosine kinase inhibitor response duration in patients with non-small-cell lung cancer," *J Clin Oncol* 30(4):433-440.

Thoreen, C.C. et al. (Mar. 20, 2009, e-published Jan. 15, 2009). "An ATP-competitive mammalian target of rapamycin inhibitor reveals rapamycin-resistant functions of mTORC1," *J Biol Chem* 281(12):8023-8032.

Umeda, N. et al. (Jan. 12, 2011, e-published Dec. 13, 2010). "A photocleavable rapamycin conjugate for spatiotemporal control of small GTPase activity," *J Am Chem Soc* 133(1):12-14.

Wood, E.R. et al. (Sep. 15, 2004). "A unique structure for epidermal growth factor receptor bound to GW572016 (Lapatinib): relationships among protein conformation, inhibitor off-rate, and receptor activity in tumor cells," *Cancer Res* 64(18):6652-6659.

Xu, C.X. et al. (2011, e-published Jun. 14, 2011). "The combination of RAD001 and NVP-BEZ235 exerts synergistic anticancer activity against non-small cell lung cancer in vitro and in vivo," *PLoS One* 6(6):e20899.

Yang, H. et al. (May 9, 2013, e-published May 1, 2013). "mTOR kinase structure, mechanism and regulation," *Nature* 497(7448):217-223.

Zeng, H. et al. (Jul. 25, 2013, e-published Jun. 30, 2013). "mTORC1 couples immune signals and metabolic programming to establish T(reg)-cell function," *Nature* (7459):485-490.

International Search Report dated Dec. 14, 2015, for PCT Application No. PCT/US2015/049693, filed on Sep. 11, 2015, 3 pages.

Written Opinion dated Dec. 14, 2015, or PCT Application No. PCT/US2015/049693, filed on Sep. 11, 2015, 7 pages.

\* cited by examiner

SEQUENCE LISTING

```
<160> NUMBER OF SEQ ID NOS: 5

<210> SEQ ID NO 1
<211> LENGTH: 2549
<212> TYPE: PRT
<213> ORGANISM: Homo sapiens

<400> SEQUENCE: 1

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160
```

```
Asn Glu Gly Arg Arg His Ala Ala Val Leu Val Leu Arg Glu Leu Ala
            165                 170                 175

Ile Ser Val Pro Thr Phe Phe Gln Gln Val Gln Pro Phe Phe Asp
        180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575
```

```
Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
```

-continued

```
             995                 1000                1005
Arg  Glu  Phe  Leu  Phe  Gln  Gln  Leu  Gly  Met  Leu  Val  Ser  Phe  Val
    1010                 1015                1020

Lys  Ser  His  Ile  Arg  Pro  Tyr  Met  Asp  Glu  Ile  Val  Thr  Leu  Met
    1025                 1030                1035

Arg  Glu  Phe  Trp  Val  Met  Asn  Thr  Ser  Ile  Gln  Ser  Thr  Ile  Ile
    1040                 1045                1050

Leu  Leu  Ile  Glu  Gln  Ile  Val  Val  Ala  Leu  Gly  Gly  Glu  Phe  Lys
    1055                 1060                1065

Leu  Tyr  Leu  Pro  Gln  Leu  Ile  Pro  His  Met  Leu  Arg  Val  Phe  Met
    1070                 1075                1080

His  Asp  Asn  Ser  Pro  Gly  Arg  Ile  Val  Ser  Ile  Lys  Leu  Leu  Ala
    1085                 1090                1095

Ala  Ile  Gln  Leu  Phe  Gly  Ala  Asn  Leu  Asp  Asp  Tyr  Leu  His  Leu
    1100                 1105                1110

Leu  Leu  Pro  Pro  Ile  Val  Lys  Leu  Phe  Asp  Ala  Pro  Glu  Ala  Pro
    1115                 1120                1125

Leu  Pro  Ser  Arg  Lys  Ala  Ala  Leu  Glu  Thr  Val  Asp  Arg  Leu  Thr
    1130                 1135                1140

Glu  Ser  Leu  Asp  Phe  Thr  Asp  Tyr  Ala  Ser  Arg  Ile  Ile  His  Pro
    1145                 1150                1155

Ile  Val  Arg  Thr  Leu  Asp  Gln  Ser  Pro  Glu  Leu  Arg  Ser  Thr  Ala
    1160                 1165                1170

Met  Asp  Thr  Leu  Ser  Ser  Leu  Val  Phe  Gln  Leu  Gly  Lys  Lys  Tyr
    1175                 1180                1185

Gln  Ile  Phe  Ile  Pro  Met  Val  Asn  Lys  Val  Leu  Val  Arg  His  Arg
    1190                 1195                1200

Ile  Asn  His  Gln  Arg  Tyr  Asp  Val  Leu  Ile  Cys  Arg  Ile  Val  Lys
    1205                 1210                1215

Gly  Tyr  Thr  Leu  Ala  Asp  Glu  Glu  Asp  Pro  Leu  Ile  Tyr  Gln
    1220                 1225                1230

His  Arg  Met  Leu  Arg  Ser  Gly  Gln  Gly  Asp  Ala  Leu  Ala  Ser  Gly
    1235                 1240                1245

Pro  Val  Glu  Thr  Gly  Pro  Met  Lys  Lys  Leu  His  Val  Ser  Thr  Ile
    1250                 1255                1260

Asn  Leu  Gln  Lys  Ala  Trp  Gly  Ala  Ala  Arg  Arg  Val  Ser  Lys  Asp
    1265                 1270                1275

Asp  Trp  Leu  Glu  Trp  Leu  Arg  Arg  Leu  Ser  Leu  Glu  Leu  Leu  Lys
    1280                 1285                1290

Asp  Ser  Ser  Ser  Pro  Ser  Leu  Arg  Ser  Cys  Trp  Ala  Leu  Ala  Gln
    1295                 1300                1305

Ala  Tyr  Asn  Pro  Met  Ala  Arg  Asp  Leu  Phe  Asn  Ala  Ala  Phe  Val
    1310                 1315                1320

Ser  Cys  Trp  Ser  Glu  Leu  Asn  Glu  Asp  Gln  Gln  Asp  Glu  Leu  Ile
    1325                 1330                1335

Arg  Ser  Ile  Glu  Leu  Ala  Leu  Thr  Ser  Gln  Asp  Ile  Ala  Glu  Val
    1340                 1345                1350

Thr  Gln  Thr  Leu  Leu  Asn  Leu  Ala  Glu  Phe  Met  Glu  His  Ser  Asp
    1355                 1360                1365

Lys  Gly  Pro  Leu  Pro  Leu  Arg  Asp  Asp  Asn  Gly  Ile  Val  Leu  Leu
    1370                 1375                1380

Gly  Glu  Arg  Ala  Ala  Lys  Cys  Arg  Ala  Tyr  Ala  Lys  Ala  Leu  His
    1385                 1390                1395
```

-continued

Tyr Lys Glu Leu Glu Phe Gln Lys Gly Pro Thr Pro Ala Ile Leu
    1400            1405            1410

Glu Ser Leu Ile Ser Ile Asn Asn Lys Leu Gln Gln Pro Glu Ala
    1415            1420            1425

Ala Ala Gly Val Leu Glu Tyr Ala Met Lys His Phe Gly Glu Leu
    1430            1435            1440

Glu Ile Gln Ala Thr Trp Tyr Glu Lys Leu His Glu Trp Glu Asp
    1445            1450            1455

Ala Leu Val Ala Tyr Asp Lys Lys Met Asp Thr Asn Lys Asp Asp
    1460            1465            1470

Pro Glu Leu Met Leu Gly Arg Met Arg Cys Leu Glu Ala Leu Gly
    1475            1480            1485

Glu Trp Gly Gln Leu His Gln Gln Cys Cys Glu Lys Trp Thr Leu
    1490            1495            1500

Val Asn Asp Glu Thr Gln Ala Lys Met Ala Arg Met Ala Ala Ala
    1505            1510            1515

Ala Ala Trp Gly Leu Gly Gln Trp Asp Ser Met Glu Glu Tyr Thr
    1520            1525            1530

Cys Met Ile Pro Arg Asp Thr His Asp Gly Ala Phe Tyr Arg Ala
    1535            1540            1545

Val Leu Ala Leu His Gln Asp Leu Phe Ser Leu Ala Gln Gln Cys
    1550            1555            1560

Ile Asp Lys Ala Arg Asp Leu Leu Asp Ala Glu Leu Thr Ala Met
    1565            1570            1575

Ala Gly Glu Ser Tyr Ser Arg Ala Tyr Gly Ala Met Val Ser Cys
    1580            1585            1590

His Met Leu Ser Glu Leu Glu Glu Val Ile Gln Tyr Lys Leu Val
    1595            1600            1605

Pro Glu Arg Arg Glu Ile Ile Arg Gln Ile Trp Trp Glu Arg Leu
    1610            1615            1620

Gln Gly Cys Gln Arg Ile Val Glu Asp Trp Gln Lys Ile Leu Met
    1625            1630            1635

Val Arg Ser Leu Val Val Ser Pro His Glu Asp Met Arg Thr Trp
    1640            1645            1650

Leu Lys Tyr Ala Ser Leu Cys Gly Lys Ser Gly Arg Leu Ala Leu
    1655            1660            1665

Ala His Lys Thr Leu Val Leu Leu Leu Gly Val Asp Pro Ser Arg
    1670            1675            1680

Gln Leu Asp His Pro Leu Pro Thr Val His Pro Gln Val Thr Tyr
    1685            1690            1695

Ala Tyr Met Lys Asn Met Trp Lys Ser Ala Arg Lys Ile Asp Ala
    1700            1705            1710

Phe Gln His Met Gln His Phe Val Gln Thr Met Gln Gln Gln Ala
    1715            1720            1725

Gln His Ala Ile Ala Thr Glu Asp Gln Gln His Lys Gln Glu Leu
    1730            1735            1740

His Lys Leu Met Ala Arg Cys Phe Leu Lys Leu Gly Glu Trp Gln
    1745            1750            1755

Leu Asn Leu Gln Gly Ile Asn Glu Ser Thr Ile Pro Lys Val Leu
    1760            1765            1770

Gln Tyr Tyr Ser Ala Ala Thr Glu His Asp Arg Ser Trp Tyr Lys
    1775            1780            1785

| | | | | | | | | | | | |
|---|---|---|---|---|---|---|---|---|---|---|---|
|Ala|Trp|His|Ala|Trp|Ala|Val|Met|Asn|Phe|Glu|Ala|Val|Leu|His|
|1790| | | | |1795| | | | |1800| | | | |

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Ala Ser Thr Glu Gly Ser Asn
1835                1840                1845

Ser Glu Ser Glu Ala Glu Ser Thr Glu Asn Ser Pro Thr Pro Ser
1850                1855                1860

Pro Leu Gln Lys Lys Val Thr Glu Asp Leu Ser Lys Thr Leu Leu
1865                1870                1875

Met Tyr Thr Val Pro Ala Val Gln Gly Phe Phe Arg Ser Ile Ser
1880                1885                1890

Leu Ser Arg Gly Asn Asn Leu Gln Asp Thr Leu Arg Val Leu Thr
1895                1900                1905

Leu Trp Phe Asp Tyr Gly His Trp Pro Asp Val Asn Glu Ala Leu
1910                1915                1920

Val Glu Gly Val Lys Ala Ile Gln Ile Asp Thr Trp Leu Gln Val
1925                1930                1935

Ile Pro Gln Leu Ile Ala Arg Ile Asp Thr Pro Arg Pro Leu Val
1940                1945                1950

Gly Arg Leu Ile His Gln Leu Leu Thr Asp Ile Gly Arg Tyr His
1955                1960                1965

Pro Gln Ala Leu Ile Tyr Pro Leu Thr Val Ala Ser Lys Ser Thr
1970                1975                1980

Thr Thr Ala Arg His Asn Ala Ala Asn Lys Ile Leu Lys Asn Met
1985                1990                1995

Cys Glu His Ser Asn Thr Leu Val Gln Gln Ala Met Met Val Ser
2000                2005                2010

Glu Glu Leu Ile Arg Val Ala Ile Leu Trp His Glu Met Trp His
2015                2020                2025

Glu Gly Leu Glu Glu Ala Ser Arg Leu Tyr Phe Gly Glu Arg Asn
2030                2035                2040

Val Lys Gly Met Phe Glu Val Leu Glu Pro Leu His Ala Met Met
2045                2050                2055

Glu Arg Gly Pro Gln Thr Leu Lys Glu Thr Ser Phe Asn Gln Ala
2060                2065                2070

Tyr Gly Arg Asp Leu Met Glu Ala Gln Glu Trp Cys Arg Lys Tyr
2075                2080                2085

Met Lys Ser Gly Asn Val Lys Asp Leu Thr Gln Ala Trp Asp Leu
2090                2095                2100

Tyr Tyr His Val Phe Arg Arg Ile Ser Lys Gln Leu Pro Gln Leu
2105                2110                2115

Thr Ser Leu Glu Leu Gln Tyr Val Ser Pro Lys Leu Leu Met Cys
2120                2125                2130

Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg 2180                2185                2190

Gln Asp Glu Arg Val Met Gln Leu Phe Gly Leu Val Asn Thr Leu
    2195                2200                2205

Leu Ala Asn Asp Pro Thr Ser Leu Arg Lys Asn Leu Ser Ile Gln
    2210                2215                2220

Arg Tyr Ala Val Ile Pro Leu Ser Thr Asn Ser Gly Leu Ile Gly
    2225                2230                2235

Trp Val Pro His Cys Asp Thr Leu His Ala Leu Ile Arg Asp Tyr
    2240                2245                2250

Arg Glu Lys Lys Lys Ile Leu Leu Asn Ile Glu His Arg Ile Met
    2255                2260                2265

Leu Arg Met Ala Pro Asp Tyr Asp His Leu Thr Leu Met Gln Lys
    2270                2275                2280

Val Glu Val Phe Glu His Ala Val Asn Asn Thr Ala Gly Asp Asp
    2285                2290                2295

Leu Ala Lys Leu Leu Trp Leu Lys Ser Pro Ser Ser Glu Val Trp
    2300                2305                2310

Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 2
<211> LENGTH: 8733
<212> TYPE: DNA
<213> ORGANISM: Homo sapiens

<400> SEQUENCE: 2

```
gctcccggct tagaggacag cggggaaggc gggcggtggg gcaggggcc tgaagcggcg       60
gtaccggtgc tggcggcggc agctgaggcc ttggccgaag ccgcgcgaac ctcagggcaa      120
gatgcttgga accggacctg ccgccgccac caccgctgcc accacatcta gcaatgtgag     180
cgtcctgcag cagtttgcca gtggcctaaa gagccggaat gaggaaacca gggccaaagc     240
cgccaaggag ctccagcact atgtcaccat ggaactccga gagatgagtc aagaggagtc     300
tactcgcttc tatgaccaac tgaaccatca cattttgaa ttggtttcca gctcagatgc      360
caatgagagg aaaggtggca tcttggccat agctagcctc ataggagtgg aaggtgggaa     420
tgccacccga attggcagat ttgccaacta tcttcggaac ctcctcccct ccaatgaccc     480
agttgtcatg gaaatggcat ccaaggccat tggccgtctt gccatggcag ggacacttt     540
taccgctgag tacgtggaat tgaggtgaa gcgagccctg gaatggctgg gtgctgaccg      600
caatgagggc cggagacatg cagctgtcct ggttctccgt gagctggcca tcagcgtccc     660
taccttcttc ttccagcaag tgcaacccct tctttgacaac attttgtgg ccgtgtggga    720
ccccaaacag gccatccgtg agggagctgt agccgcccctt cgtgcctgtc tgattctcac    780
aacccagcgt gagccgaagg agatgcagaa gcctcagtgg tacaggcaca catttgaaga    840
agcagagaag ggatttgatg agaccttggc caaagagaag ggcatgaatc gggatgatcg     900
gatccatgga gccttgttga tccttaacga gctggtccga atcagcagca tggagggaga    960
gcgtctgaga gaagaaatgg aagaaatcac acagcagcag ctggtacacg acaagtactg    1020
caaagatctc atgggcttcg aacaaaaacc tcgtcacatt ccccccttca ccagtttcca    1080
ggctgtacag ccccagcagt caaatgcctt ggtgggggctg ctggggtaca gctctcacca   1140
aggcctcatg ggatttggga cctcccccag tccagctaag tccaccctgg tggagagccg    1200
gtgttgcaga gacttgatgg aggagaaatt tgatcaggtg tgccagtggg tgctgaaatg    1260
caggaatagc aagaactcgc tgatccaaat gacaatcctt aatttgttgc cccgcttggc    1320
tgcattccga ccttctgcct tcacagatac ccagtatctc caagatacca tgaaccatgt   1380
cctaagctgt gtcaagaagg agaaggaacg tacagcggcc ttccaagccc tggggctact   1440
ttctgtggct gtgaggtctg agtttaaggt ctatttgcct cgcgtgctgg acatcatccg    1500
agcggcccctg ccccccaaagg acttcgccca taagaggcag aaggcaatgc aggtggatgc    1560
cacagtcttc acttgcatca gcatgctggc tcgagcaatg gggccaggca tccagcagga    1620
tatcaaggag ctgctggagc ccatgctggc agtgggacta agccctgccc tcactgcagt    1680
gctctacgac ctgagccgtc agattccaca gctaaagaag gacattcaag atgggctact    1740
gaaaatgctg tccctggtcc ttatgcacaa accccttcgc cacccaggca tgcccaaggg    1800
cctggcccat cagctggcct ctcctggcct cacgaccctc cctgaggcca gcgatgtggg    1860
cagcatcact cttgccctcc gaacgcttgg cagctttgaa tttgaaggcc actctctgac    1920
ccaatttgtt cgccactgtg cggatcattt cctgaacagt gagcacaagg agatccgcat    1980
ggaggctgcc cgcacctgct cccgcctgct cacaccctcc atccacctca tcagtggcca    2040
tgctcatgtg gttagccaga ccgcagtgca agtggtggca gatgtgctta gcaaactgct    2100
cgtagttggg ataacagatc ctgaccctga cattcgctac tgtgtcttgg cgtccctgga    2160
cgagcgcttt gatgcacacc tggcccaggc ggagaacttg caggccttgt ttgtggctct    2220
gaatgaccag gtgtttgaga tccgggagct ggccatctgc actgtgggcc gactcagtag    2280
```

```
catgaaccct gcctttgtca tgcctttcct gcgcaagatg ctcatccaga ttttgacaga    2340
gttggagcac agtgggattg gaagaatcaa agagcagagt gcccgcatgc tggggcacct    2400
ggtctccaat gcccccgac tcatccgccc ctacatggag cctattctga aggcattaat     2460
tttgaaactg aaagatccag accctgatcc aaacccaggt gtgatcaata atgtcctggc    2520
aacaatagga gaattggcac aggttagtgg cctggaaatg aggaaatggg ttgatgaact    2580
ttttattatc atcatggaca tgctccagga ttcctctttg ttggccaaaa ggcaggtggc    2640
tctgtggacc ctgggacagt tggtggccag cactggctat gtagtagagc cctacaggaa    2700
gtaccctact ttgcttgagg tgctactgaa ttttctgaag actgagcaga accagggtac    2760
acgcagagag gccatccgtg tgttagggct tttagggggct ttggatcctt acaagcacaa   2820
agtgaacatt ggcatgatag accagtcccg ggatgcctct gctgtcagcc tgtcagaatc    2880
caagtcaagt caggattcct ctgactatag cactagtgaa atgctggtca acatgggaaa    2940
cttgcctctg gatgagttct acccagctgt gtccatggtg gccctgatgc ggatcttccg    3000
agaccagtca ctctctcatc atcacaccat ggttgtccag gccatcacct tcatcttcaa    3060
gtccctggga ctcaaatgtg tgcagttcct gccccaggtc atgcccacgt tccttaacgt    3120
cattcgagtc tgtgatgggg ccatccggga attttgttc cagcagctgg gaatgttggt     3180
gtcctttgtg aagagccaca tcagaccttca tatggatgaa atagtcaccc tcatgagaga    3240
attctgggtc atgaacacct caattcagag cacgatcatt cttctcattg agcaaattgt    3300
ggtagctctt gggggtgaat ttaagctcta cctgccccag ctgatccac acatgctgcg     3360 tgtcttcatg catgacaaca gcccaggccg cattgtctct atcaagttac tggctgcaat    3420
ccagctgttt ggcgccaacc tggatgacta cctgcattta ctgctgcctc ctattgttaa    3480
gttgtttgat gcccctgaag ctccactgcc atctcgaaag gcagcgctag agactgtgga    3540
ccgcctgacg gagtccctgg atttcactga ctatgcctcc ggatcattc accctattgt     3600 tcgaacactg gaccagagcc cagaactgcg ctccacagcc atggacacgc tgtcttcact    3660 tgttttttcag ctggggaaga agtaccaaat tttcattcca atggtgaata agttctggt    3720 gcgacaccga atcaatcatc agcgctatga tgtgctcatc tgcagaattg tcaagggata    3780
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca agatgactg     3960 gctggaatgg ctgagacggc tgagcctgga gctgctgaag gactcatcat cgccctccct    4020
gcgctcctgc tgggccctgg cacaggccta caacccgatg gccagggatc tcttcaatgc    4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg ccccctgcca ctgagagatg acaatggcat    4260
tgttctgctg ggtgagagag ctgccaagtg ccgagcatat gccaaagcac tacactacaa    4320
agaactggag ttccagaaag gccccacccc tgccattcta gaatctctca tcagcattaa    4380
taataagcta cagcagccgg aggcagcggc cggagtgtta aatatgccca tgaaacactt    4440
tggagagctg gagatccagg ctacctggta tgagaaactg cacgagtggg aggatgccct    4500
tgtggcctat gacaagaaaa tggacaccaa caaggacgac ccagagctga tgctgggccg    4560
catgcgctgc ctcgaggcct tgggggaatg gggtcaactc caccagcagt gctgtgaaaa    4620
gtggaccctg gttaatgatg agacccaagc caagatggcc cggatggctg ctgcagctgc    4680
```

```
atggggttta ggtcagtggg acagcatgga agaatacacc tgtatgatcc ctcgggacac    4740
ccatgatggg gcattttata gagctgtgct ggcactgcat caggacctct tctccttggc    4800
acaacagtgc attgacaagg ccagggacct gctggatgct gaattaactg cgatggcagg    4860
agagagttac agtcgggcat atggggccat ggtttcttgc cacatgctgt ccgagctgga    4920
ggaggttatc cagtacaaac ttgtccccga gcgacgagag atcatccgcc agatctggtg    4980
ggagagactg cagggctgcc agcgtatcgt agaggactgg cagaaaatcc ttatggtgcg    5040
gtcccttgtg gtcagccctc atgaagacat gagaacctgg ctcaagtatg caagcctgtg    5100
cggcaagagt ggcaggctgg ctcttgctca taaaacttta gtgttgctcc tgggagttga    5160
tccgtctcgg caacttgacc atcctctgcc aacagttcac cctcaggtga cctatgccta    5220
catgaaaaac atgtggaaga gtgcccgcaa gatcgatgcc ttccagcaca tgcagcattt    5280
tgtccagacc atgcagcaac aggcccagca tgccatcgct actgaggacc agcagcataa    5340
gcaggaactg cacaagctca tggcccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg gcatgcgtgg gcagtgatga acttcgaagc    5520
tgtgctacac tacaaacatc agaaccaagc ccgcgatgag aagaagaaac tgcgtcatgc    5580
cagcggggcc aacatcacca acgccaccac tgccgccacc acggccgcca ctgccaccac    5640
cactgccagc accgagggca gcaacagtga gagcgaggcc gagagcaccg agaacagccc    5700
caccccatcg ccgctgcaga agaaggtcac tgaggatctg tccaaaaccc tcctgatgta    5760
cacggtgcct gccgtccagg gcttcttccg ttccatctcc ttgtcacgag caacaacct    5820 ccaggataca ctcagagttc tcaccttatg gtttgattat ggtcactggc cagatgtcaa    5880
tgaggcctta gtgggggggg tgaaagccat ccagattgat acctggctac aggttatacc    5940
tcagctcatt gcaagaattg atacgcccag acccttggtg ggacgtctca ttcaccagct    6000
tctcacagac attggtcggt accacccccca ggccctcatc tacccactga cagtggcttc    6060
taagtctacc acgacagccc ggcacaatgc agccaacaag attctgaaga acatgtgtga    6120
gcacagcaac accctggtcc agcaggccat gatggtgagc gaggagctga tccgagtggc    6180
catcctctgg catgagatgt ggcatgaagg cctggaagag gcatctcgtt tgtactttgg    6240
ggaaaggaac gtgaaaggca tgtttgaggt gctggagccc ttgcatgcta tgatggaacg    6300
gggcccccag actctgaagg aaacatcctt taatcaggcc tatggtcgag atttaatgga    6360
ggcccaagag tggtgcagga agtacatgaa atcagggaat gtcaaggacc tcacccaagc    6420 ctgggaccte tattatcatg tgttccgacg aatctcaaag cagctgcctc agctcacatc    6480
cttagagctg caatatgttt ccccaaaact tctgatgtgc cgggaccttg aattggctgt    6540
gccaggaaca tatgaccccca accagccaat cattcgcatt cagtccatag caccgtcttt    6600
gcaagtcatc acatccaagc agaggccccg gaaattgaca cttatgggca gcaacggaca    6660
tgagtttgtt ttccttctaa aaggccatga agatctgcgc caggatgagc gtgtgatgca    6720
gctcttcggc ctggttaaca cccttctggc caatgaccca acatctcttc ggaaaaacct    6780
cagcatccag agatacgctg tcatccctt atcgaccaac tcgggcctca ttggctgggt    6840
tccccactgt gacacactgc acgccctcat ccgggactac agggagaaga agaagatcct    6900
tctcaacatc gagcatcgca tcatgttgcg gatggctccg gactatgacc acttgactct    6960
gatgcagaag gtggaggtgt ttgagcatgc cgtcaataat acagctgggg acgacctggc    7020
```

-continued

```
caagctgctg tggctgaaaa gccccagctc cgaggtgtgg tttgaccgaa gaaccaatta      7080
tacccgttct ttagcggtca tgtcaatggt tgggtatatt ttaggcctgg gagatagaca      7140
cccatccaac ctgatgctgg accgtctgag tgggaagatc ctgcacattg actttgggga      7200
ctgctttgag gttgctatga cccgagagaa gtttccagag aagattccat ttagactaac      7260
aagaatgttg accaatgcta tggaggttac aggcctggat ggcaactaca gaatcacatg      7320
ccacacagtg atggaggtgc tgcgagagca caaggacagt gtcatggccg tgctggaagc      7380
cttttgtctat gaccccttgc tgaactggag gctgatggac acaaatacca aaggcaacaa      7440
gcgatcccga acgaggacgg attcctactc tgctggccag tcagtcgaaa ttttggacgg      7500
tgtggaactt ggagagccag cccataagaa acgggaccc acagtgccag aatctattca      7560
ttctttcatt ggagacggtt tggtgaaacc agaggcccta ataagaaag ctatccagat      7620
tattaacagg gttcgagata agctcactgg tcgggacttc tctcatgatg acactttgga      7680
tgttccaacg caagttgagc tgctcatcaa acaagcgaca tcccatgaaa acctctgcca      7740
gtgctatatt ggctggtgcc ctttctggta actggaggcc cagatgtgcc catcacgttt      7800
tttctgaggc ttttgtactt tagtaaatgc ttccactaaa ctgaaaccat ggtgagaaag      7860
tttgactttg ttaaatattt tgaaatgtaa atgaaaagaa ctactgtata ttaaaagttg      7920
gtttgaacca actttctagc tgctgttgaa gaatatattg tcagaaacac aaggcttgat      7980
ttggttccca ggacagtgaa acatagtaat accacgtaaa tcaagccatt cattttgggg      8040
aacagaagat ccataacttt agaaatacgg gttttgactt aactcacaag agaactcatc      8100
ataagtactt gctgatggaa gaatgaccta gttgctcctc tcaacatggg tacagcaaac      8160
tcagcacagc caagaagcct caggtcgtgg agaacatgga ttaggatcct agactgtaaa      8220
gacacagaag atgctgacct caccctgcc acctatccca agacctcact ggtctgtgga      8280
cagcagcaga aatgtttgca agataggcca aaatgagtac aaaaggtctg tcttccatca      8340
gacccagtga tgctgcgact cacacgcttc aattcaagac ctgaccgcta gtagggaggt      8400
ttattcagat cgctggcagc ctcggctgag cagatgcaca gaggggatca ctgtgcagtg      8460
ggaccaccct cactgccctt ctgcagcagg gttctgggat gttttcagtg gtcaaaatac      8520
tctgttttaga gcaagggctc agaaaacaga atactgtca tggaggtgct gaacacaggg      8580
aaggtctggt acatattgga aattatgagc agaacaaata ctcaactaaa tgcacaaagt      8640
ataaagtgta gccatgtcta gacaccatgt tgtatcagaa taattttttgt gccaataaat      8700
gacatcagaa ttttaaacat atgtaaaaaa aaa                                    8733
```

<210> SEQ ID NO 3
<211> LENGTH: 108
<212> TYPE: PRT
<213> ORGANISM: Homo sapiens

<400> SEQUENCE: 3

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
```

```
                65                  70                  75                  80
Tyr Ala Tyr Gly Ala Thr Gly His Pro Gly Ile Ile Pro Pro His Ala
                    85                  90                  95

Thr Leu Val Phe Asp Val Glu Leu Leu Lys Leu Glu
                100                 105

<210> SEQ ID NO 4
<211> LENGTH: 118
<212> TYPE: PRT
<213> ORGANISM: Homo sapiens

<400> SEQUENCE: 4

Met Ser Gly Gly Ser Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
                20                  25                  30

Asp Tyr Ser Thr Thr Pro Gly Gly Thr Leu Phe Ser Thr Thr Pro Gly
                35                  40                  45

Gly Thr Arg Ile Ile Tyr Asp Arg Lys Phe Leu Met Glu Cys Arg Asn
        50                  55                  60

Ser Pro Val Thr Lys Thr Pro Pro Arg Asp Leu Pro Thr Ile Pro Gly
65                  70                  75                  80

Val Thr Ser Pro Ser Ser Asp Glu Pro Pro Met Glu Ala Ser Gln Ser
                85                  90                  95

His Leu Arg Asn Ser Pro Glu Asp Lys Arg Ala Gly Gly Glu Glu Ser
                100                 105                 110

Gln Phe Glu Met Asp Ile
        115

<210> SEQ ID NO 5
<211> LENGTH: 480
<212> TYPE: PRT
<213> ORGANISM: Homo sapiens

<400> SEQUENCE: 5

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
                35                  40                  45

Glu Ala Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
                100                 105                 110

Gln Glu Glu Glu Glu Met Asp Phe Arg Ser Gly Ser Pro Ser Asp Asn
                115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
```

```
                        165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
            195                 200                 205

Phe Leu Thr Ala Leu Lys Tyr Ser Phe Gln Thr His Asp Arg Leu Cys
            210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
            245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
            290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
            325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
            370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
            405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
            450                 455                 460

Arg Arg Pro His Phe Pro Gln Phe Ser Tyr Ser Ala Ser Gly Thr Ala
465                 470                 475                 480
```

MTORC1 INHIBITORS

CROSS-REFERENCE TO RELATED APPLICATIONS

This application is a continuation of U.S. patent application Ser. No. 15/455,727, filed Mar. 10, 2017, which is a continuation of International Patent Application No. PCT/US2015/049693, filed Sep. 11, 2015, which claim the benefit of U.S. Provisional Application No. 62/049,186, filed Sep. 11, 2014, the contents of which are hereby incorporated herein in their entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 048536-551C02US_ST25.TXT, created on Sep. 7, 2018, 40,465 bytes, machine format IBM-PC, MS-Windows operating system, is hereby incorporated by reference.

BACKGROUND

The mammalian target of rapamycin (mTOR) is a serine-threonine kinase related to the lipid kinases of the phosphoinositide 3-kinase (PI3K) family. mTOR exists in two complexes, mTORC1[1,2] and mTORC2[3,4], which are differentially regulated, have distinct substrate specificities, and are differentially sensitive to rapamycin. mTORC1 integrates signals from growth factor receptors with cellular nutritional status and controls the level of cap-dependent mRNA translation by modulating the activity of key translational components such as the cap-binding protein and oncogene eIF4E[5].

Recently, mTOR signaling has been deciphered in increasing detail. The differing pharmacology of inhibitors of mTOR have been particularly informative. The first reported inhibitor of mTOR, Rapamycin is now understood to be an incomplete inhibitor of mTORC1[6] Rapamycin, is a selective mTORC1 inhibitor through the binding to the FK506 Rapamycin Binding (FRB) domain of mTOR kinase with the aid of FK506 binding protein 12 (FKBP12). The FRB domain of mTOR is accessible in the mTORC1 complex, but less so in the mTORC2 complex. Interestingly, the potency of inhibitory activities against downstream substrates of mTORC1 by the treatment of Rapamycin is known to be diverse among the mTORC1 substrates. For example, Rapamycin strongly inhibits phosphorylation of S6K and phosphorylation of the downstream ribosomal protein S6 which control ribosomal biogenesis. On the other hand, Rapamycin shows only partial inhibitory activity against phosphorylation of 4E-BP1, a major regulator of eIF4E which controls the initiation of CAP-dependent translation. As a result, more complete inhibitors of mTORC1 signaling are of interest[7].

Recently, a second class of "ATP-site" inhibitors of mTOR kinase, were reported[6,8]. Such inhibitors have been referred to by several names (Torkinib[6], Torin[8], asTORi[9], and others). This class of mTOR inhibitor will be referred to as asTORi (ATP site TOR inhibitor). The molecules compete with ATP, the substrate for the kinase reaction, in the active site of the mTOR kinase (and are therefore also active site mTOR inhibitors). As a result, these molecules inhibit downstream phosphorylation against a broader range of substrates[10]. The asTORi also inhibit mTORC2, which is not inhibited by Rapamycin, since the former do not require the FRB domain to bind and inhibit mTORC2. The compound INK128 (now termed MLN0128) is related to PP242[6,11] and is in numerous anti-cancer Phase I and Phase II clinical trials. MLN0128 has the effect of blocking 4E-BP 1 phosphorylation.

Although asTORi may have the effect of blocking 4E-BP1 phosphorylation, these agents may also inhibit mTORC2, which leads to a block of Akt activation due to phosphorylation of Akt S473. This dual action on 4EBP1-P and Akt-P produces a more broad acting agent. For example a dose limiting toxicity of MLN0128 in clinical trials is Grade ≥3 hyperglycemia[12].

Disclosed herein, inter alia, are mTORC1 inhibitors thereby providing solutions to these and other problems in the art.

BRIEF SUMMARY OF THE INVENTION

In an aspect is provided a compound including a monovalent active site mTOR inhibitor covalently bound to a monovalent rapamycin or a monovalent rapamycin analog.

In another aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim).

In an aspect is provided a method of treating a disease associated with an aberrant level of mTORC1 activity in a subject in need of such treatment.

In another aspect is provided a method of treating an mTORC1 activity-associated disease in a subject in need of such treatment, the method including administering a compound, or a pharmaceutically acceptable salt thereof, as described herein, including embodiments (e.g. a claim, embodiment, example, table, figure, or claim).

BRIEF DESCRIPTION OF THE DRAWINGS

(FIG. 2A) Overlap modeling of cocrystal structure of mTOR catalytic domain with PP242 (MLN0128 has not been crystalized in mTOR, but PP242 was the prototype for MLN0128 and thus served as a model) with mTOR FRB domain with Rapamycin. Dotted lines represent the distance between isopropyl group of PP242 and C40-hydroxy group of Rapamycin. (FIG. 2B) General structure of Rapamycin derivative conjugated with asTORi.

(FIG. 3A) Known inhibitors such as Rapalog and mTOR catalytic inhibitor (asTORi). (FIG. 3B) Novel Rapamycin derivatives conjugated with asTORi.

(FIG. 4A) Overlap modeling of co-crystal structure of mTOR catalytic domain bearing active site inhibitor PP242 (4JT5) with mTOR FRB domain/rapamycin/FKBP12 (1FAP). Dotted line with number represents the distance (A) between isopropyl group of PP242 and C40-hydroxy group of rapamycin. (FIG. 4B) Compound design and computational calculation of potential energies of various cross-linker (L=methylene) length compounds.

(FIG. 5B) MLN0128, M-1071, or a combination of Rapamycin+MLN0128. Legend: FIG. 5A: M-1115 (squares); Rapamycin (circles); M-1071 (triangles); M-1111 (squares); MLN0128 (circles); FIG. 5B: MLN0128 (circles); MLN0128+Rapamycin (1:1) (circles); M-1071 (triangles).

(FIG. 6B) HCT-15 Cells treated with M-1115, Rapamycin, M-1071, M-1111, and MLN0128. Legend: FIG. 6A: M-1115 (squares); Rapamycin (circles); M-1071 (triangles); M-1111 (squares); MLN0128 (circles). FIG. 6B: Rapamycin (circles); M-1115 (squares); M-1071 (triangles); M-1111 (squares); MLN0128 (circles).

(FIG. 8B) Time dependent signaling effects of MLN0128 (dose), M-1071 (dose), and Rapamycin (dose), in SNU-449 Cells.

FIG. 13A: MCF-7 cells were treated for 4 hours with E1035 and M1071 before harvesting. FIG. 13B: SNU-449 cells were treated with 3 hours with E1010 before harvesting. Cells were lysed and blotted for the indicated proteins. M1071 has the narrowest concentration range between mTORC1 and mTORC2 inhibition. The concentration range between mTORC1 and mTORC2 inhibition widens for E1035. E1010, which contains an extremely weak ASi, only partially inhibits mTORC1.

FIG. 14A: 786-O cells were treated for 72 hours with the indicated drugs before cell viability was measured. Legend: E1010 (squares); MLN0128 (circles); Rapamycin (triangles). FIG. 14B: MCF-7 cells were treated for 72 hours with the indicated drugs before cell viability was measured. Legend: E1035 (circles); M1071 (squares); Rapamycin (triangles tip up); PP242 (triangles tip down).

DETAILED DESCRIPTION

A. Definitions

Figure 1:
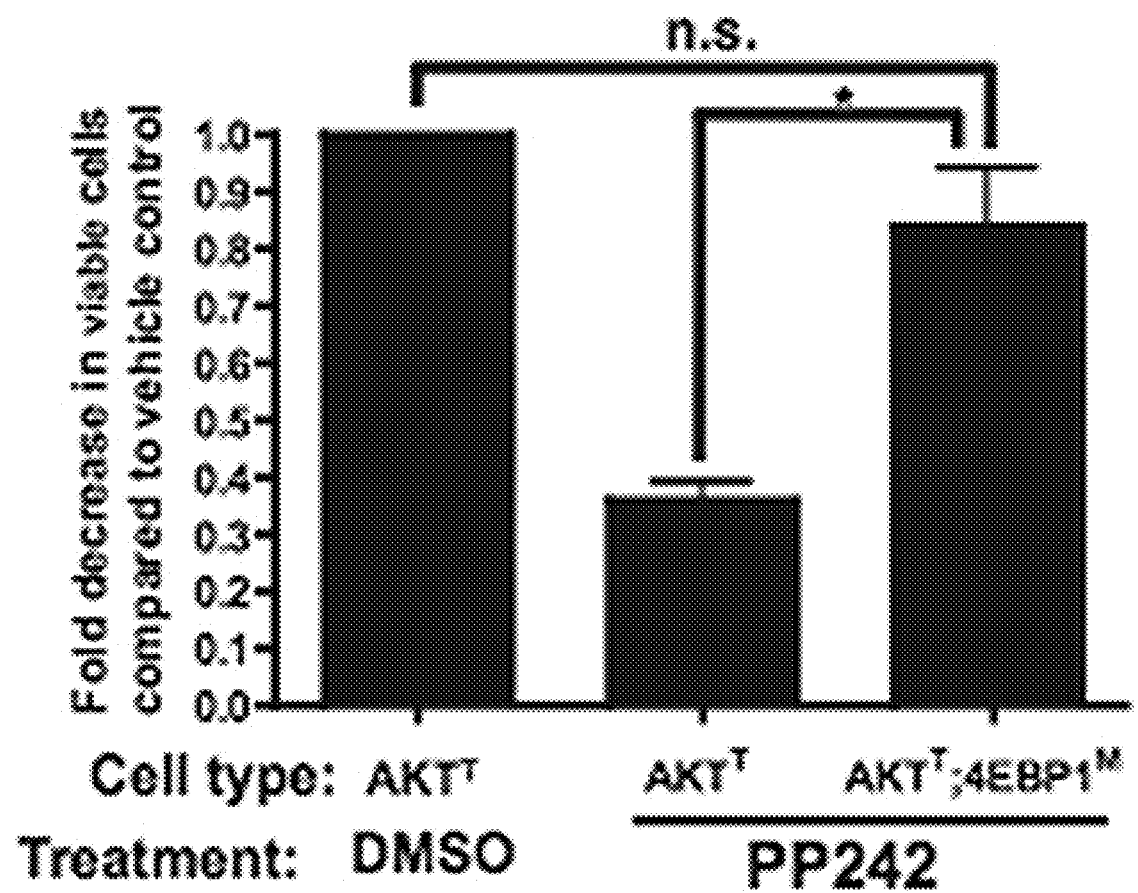
FIG. 1: Histogram depicting fold change (relative to vehicle control) in live $AKT^T$ and $AKT^T;4EBP1^M$ tumor cells after 24 hr treatment with PP242 (2.5 µM) ex vivo (n=3) (*p<0.001; n.s., no statistical significance). Data are presented as the average±SEM. Treatment: left bin: DMSO; center and right bins: PP242.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A substituent group, as used herein, may be a group selected from the following moieties:
(A) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cell, in the extracellular space near a cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "⁓" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with mTORC1 activity. Certain methods described herein may treat diseases associated with mTORC1 activity by inhibiting mTORC1 activity. Certain methods described herein may treat diseases associated with mTORC1 by inhibiting mTORC1 activity to a greater degree than inhibiting mTORC2 activity. For example, certain methods herein treat cancer. For example certain methods herein treat cancer by decreasing a symptom of cancer. Symptoms of cancer would be known or may be determined by a person of ordinary skill in the art. For example, certain methods herein treat an autoimmune disease. For example certain methods herein treat an autoimmune disease by decreasing a symptom of the autoimmune disease. Symptoms of an autoimmune disease would be known or may be determined by a person of ordinary skill in the art. For example, certain methods herein treat an inflammatory disease. For example certain methods herein treat an inflammatory disease by decreasing a symptom of the inflammatory disease. Symptoms of an inflammatory disease would be known or may be determined by a person of ordinary skill in the art. For example, certain methods herein treat a neurodegenerative disease. For example certain methods herein treat a neurodegenerative disease by decreasing a symptom of the neurodegenerative disease. Symptoms of a neurodegenerative disease would be known or may be determined by a person of ordinary skill in the art. For example, certain methods herein treat a metabolic disease. For example certain methods herein treat a metabolic disease by decreasing a symptom of the metabolic disease. Symptoms of a metabolic disease would be known or may be determined by a person of ordinary skill in the art. For example, certain methods herein treat transplant rejection. For example certain methods herein treat transplant rejection by decreasing a symptom of transplant rejection. Symptoms of transplant rejection would be known or may be determined by a person of ordinary skill in the art. For example, certain methods herein treat fungal infection. For example certain methods herein treat fungal infection by decreasing a symptom of fungal infection. Symptoms of fungal infection would be known or may be determined by a person of ordinary skill in the art. For example, certain methods herein treat a cardiovascular disease. For example certain methods herein treat a cardiovascular disease by decreasing a symptom of the cardiovascular disease. Symptoms of a cardiovascular disease would be known or may be determined by a person of ordinary skill in the art. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer, autoimmune disease, inflammatory disease, metabolic disease, neurodegenerative disease, fungal infection, cardiovascular disease, or transplant rejection) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with mTORC1 activity may be treated with an agent (e.g. compound as described herein) effective for decreasing the level of mTORC1 activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is an anti-autoimmune disease agent. In embodiments, a modulator is an anti-inflammatory disease agent. In embodiments, a modulator is an anti-neurodegenerative disease agent. In embodiments, a modulator is an anti-metabolic disease agent. In embodiments, a modulator is an anti-transplant rejection agent. In embodiments, a modulator is an anti-fungal infection agent. In embodiments, a modulator is an anti-cardiovascular disease agent. In embodiments, a modulator is a longevity agent. In embodiments, a modulator is a modulator of mTORC1 activity. In embodiments, a modulator is an mTORC1 activity inhibitor. In embodiments, a modulator is an mTORC1 activity activator. In embodiments, a modulator is a modulator of a signaling pathway including mTORC1.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, rapamycin, rapamycin analog, bevacizumab, PP242, INK128, MLN0128, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine daclix-imab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, *vinca* alkaloids (such as vinblastine and vincristine), epothilones (e.g. epothilone B), camptothecin and its clinical analogs topotecan and irinotecan, INK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, PKI-587, rapamycin, deforolimus (AP23573, MK-8669, ridaforolimus), temsirolimus (CCI-779), ABT478, everolimus (RAD001) or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of mTORC1 activity. In some embodiments, the disease is a disease having the symptom of an aberrant level of mTORC1 pathway activity. In some embodiments, the disease is a disease associated with mTORC1 activity. In some embodiments, the disease is a disease associated with mTORC1 pathway activity. In some embodiments, the disease is a cancer. In some embodiments, the disease is an autoimmune disease. In some embodiments, the disease is a neurodegenerative disease. In some embodiments, the disease is a metabolic disease. In some embodiments, the disease is an inflammatory disease. In some embodiments, the disease is transplant rejection. In some embodiments, the disease is fungal infection. In some embodiments, the disease is a cardiovascular disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is multiple myeloma. In embodiments, the disease is breast cancer. In embodiments, the disease is triple negative breast cancer. In embodiments, a disease that may be treated with a compound, pharmaceutical composition, or method described herein is Organ or tissue transplant rejection (e.g. heart, lung, combined heart-lung, liver, kidney, pancreatic, skin or corneal transplants; graft-versus-host disease), Restenosis, Hamartoma syndromes (e.g., tuberous sclerosis or Cowden Disease), Lymphangioleiomyomatosis, Retinitis pigmentosis, encephalomyelitis, insulin-dependent diabetes mellitus, lupus, dermatomyositis, arthritis, rheumatic diseases, Steroid-resistant acute Lymphoblastic Leukemia, fibrosis, scleroderma, pulmonary fibrosis, renal fibrosis, cystic fibrosis, Pulmonary hypertension, Multiple sclerosis, VHL syndrome, Carney complex, Familial adenonamtous polyposis, Juvenile polyposis syndrome, Birt-Hogg-Duke syndrome, Familial hypertrophic cardiomyopathy, Wolf-Parkinson-White syndrome, Parkinson's disease, Huntingtin's disease, Alzheimer's disease, dementias caused by tau mutations, spinocerebellar ataxia type 3, motor neuron disease caused by SOD1 mutations, neuronal ceroid lipofucinoses/Batten disease (pediatric neurodegeneration), wet macular degeneration, dry macular degeneration, muscle wasting (atrophy, cachexia), myopathies (e.g., Danon's disease), bacterial infection, viral infection, *M. tuberculosis*, group A *streptococcus*, HSV type I, HIV infection, Neurofibromatosis (e.g., Neurofibromatosis type 1), or Peutz-Jeghers syndrome.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of aberrant cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes *dorsalis*.

As used herein, the term "metabolic disease" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

As used herein, the term "fungal disease" refers to a disease or condition associated with a fungus infection of the subject. Examples of fungal diseases that may be treated with a compound, pharmaceutical composition, or method described herein include infection with *Mucor circinelloides*, zygomycetes, *Cryptococcus neoformans, Candida albicans*, yeast, and *Saccharomyces cerevisiae* among others.

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

As used herein, the term "cardiovascular disease" refers to a disease or condition in which the function of a subject's cardiovascular system becomes impaired. Examples of cardiovascular diseases that may be treated with a compound, pharmaceutical composition, or method described herein include congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. Examples of amino acid mimetics and polypeptide mimetics include peptoids, D-peptides, and β-peptides. Amino acids may be modified amino acids (natural or mimetics) including additional moieties, for example function, therapeutic, or detectable moieties. Modified amino acids may be modified in the side chain by the addition of additional moieties.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification

Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative. The terms apply to amino acid polymers in which one or more amino acid residue is an artificial chemical mimetic of a corresponding naturally occurring amino acid, as well as to naturally occurring amino acid polymers and non-naturally occurring amino acid polymer. When a polypeptide includes amino acid mimetics or modified amino acids, the monomer may be connected through bonds that are different from or derivatives of peptide links.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it (e.g., other proteins, lipids, and nucleic acid in a cell expressing the proteins). Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to a residue when the selected residue occupies the same essential spatial or other structural relationship as a specified residue relative to the rest of the protein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, anti-autoimmune disease agent, anti-inflammatory disease agent, anti-neurodegenerative disease agent, anti-metabolic disease agent, anti-transplant rejection agent, anti-fungal infection agent, or longevity agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer, autoimmune disease, inflammatory disease, metabolic disease, neurodegenerative disease, fungal infection, or transplant rejection). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer or neurodegenerative disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, autoimmune disease, inflammatory disease, metabolic disease, neurodegenerative disease, fungal infection, or transplant rejection, or with adjunctive agents that may not be effective alone, but may contribute to the efficacy of the active agent. The compounds described herein can be used in combination with other active agents known to be longevity agents or anti-aging agents.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

The term "specifically (or significantly or selectively) binds to" when referring to a compound described herein binding to a protein or complex (e.g., mTORC1), refers to a binding reaction which is determinative of the presence of the protein or complex in the presence of a heterogeneous population of proteins and other biologics. Thus, under designated assay conditions, the specified compound binds to a particular protein (mTOR) or complex (e.g., mTORC1) and does not bind in a significant amount to other proteins or complexes present in the sample (e.g., mTORC2). Specific or significant or selective binding of a compound to mTORC1 and not mTORC2 may be binding to mTORC1 with at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold greater affinity than binding of the identical compound to mTORC2 under identical assay conditions.

The term "mTOR" refers to the protein "mechanistic target of rapamycin (serine/threonine kinase)" or "mammalian target of rapamycin". The term "mTOR" may refer to the nucleotide sequence or protein sequence of human mTOR (e.g., Entrez 2475, Uniprot P42345, RefSeq NM_004958, or RefSeq NP_004949) (SEQ ID NO: 1). The term "mTOR" includes both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ refers to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the nucleotide sequence corresponding to reference number GI:206725550 (SEQ ID NO:2). In embodiments, the mTOR has the nucleotide sequence corresponding to RefSeq NM_004958.3 (SEQ ID NO:2). In embodiments, the mTOR has the protein sequence corresponding to reference number GI:4826730 (SEQ ID NO: 1). In embodiments, the mTOR has the protein sequence corresponding to RefSeq NP_004949.1 (SEQ ID NO: 1). In embodiments, the mTOR has the following amino acid sequence:

```
                                             (SEQ ID NO: 1)
MLGTGPAAATTAATTSSNVSVLQQFASGLKSRNEETRAKAAKELQHYVTM

ELREMSQEESTRFYDQLNHHIFELVSSSDANERKGGILAIASLIGVEGGN

ATRIGRFANYLRNLLPSNDPVVMEMASKAIGRLAMAGDTFTAEYVEFEVK

RALEWLGADRNEGRRHAAVLVLRELAISVPTFFFQQVQPFFDNIFVAVWD

PKQAIREGAVAALRACLILTTQREPKEMQKPQWYRHTFEEAEKGFDETLA

KEKGMNRDDRIHGALLILNELVRISSMEGERLREEMEEITQQQLVHDKYC

KDLMGFGTKPRHITPFTSFQAVQPQQSNALVGLLGYSSHQGLMGFGTSPS

PAKSTLVESRCCRDLMEEKFDQVCQNVLKCRNSKNSLIQMTILNLLPRLA

AFRPSAFTDTQYLQDTMNHVLSCVKKEKERTAAFQALGLLSVAVRSEFKV

YLPRVLDIIRAALPPKDFAHKRQKAMQVDATVFTCISMLARAMGPGIQQD

IKELLEPMLAVGLSPALTAVLYDLSRQIPQLKKDIQDGLLKMLSLVLMHK

PLRHPGMPKGLAHQLASPGLTTLPEASDVGSITLALRTLGSFEFEGHSLT

QFVRHCADHFLNSEHKEIRMEAARTCSRLLTPSIHLISGHAHVVSQTAVQ

VVADVLSKLLVVGITDPDPDIRYCVLASLDERFDAHLAQAENLQALFVAL

NDQVFEIRELAICTVGRLSSMNPAFVMPFLRKMLIQILTELEHSGIGRIK

EQSARMLGHLVSNAPRLIRPYMEPILKALILKLKDPDPDPDPGVINNVLA

TIGELAQVSGLEMRKWVDELFIIIMDMLQDSSLLAKRQVALWTLGQLVAS

TGYVVEPYRKYPTLLEVLLNFLKTEQNQGTRREAIRVLGLLGALDPYKHK

VNIGMIDQSRDASAVSLSESKSSQDSSDYSTSEMLVNMGNLPLDEFYPAV

SMVALMRIFRDQSLSHHHTMVVQAITFIFKSLGLKCVQFLPQVMPTFLNV

IRVCDGAIREFLFQQLGMLVSFVKSHIRPYMDEIVTLMREFWVMNTSIQS

TIILLIEQIVVALGGEFKLYLPQLIPHMLRVFMHDNSPGRIVSIKLLAAI

QLFGANLDDYLHLLLPPIVKLFDAPEAPLPSRKAALETVDRLTESLDFTD

YASRIIHPIVRTLDQSPELRSTAMDTLSSLVFQLGKKYQIFIPMVNKVLV

RHRINHQRYDVLICRIVKGYTLADEEEDPLIYQHRMLRSGQGDALASGPV

ETGPMKKLHVSTINLQKAWGAARRVSKDDWLEWLRRLSLELLKDSSSPSL

RSCWALAQAYNPMARDLFNAAFVSCWSELNEDQQDELIRSIELALTSQDI

AEVTQTLLNLAEFMEHSDKGPLPLRDDNGIVLLGERAAKCRAYAKALHYK

ELEFQKGPTPAILESLISINNKLQQPEAAAGVLEYAMKHFGELEIQATWY

EKLHEWEDALVAYDKKMDTNKDDPELMLGRMRCLEALGEWGQLHQQCCEK

WILVNDETQAKMARMAAAAAWGLGQWDSMEEYTCMIPRDTHDGAFYRAVL

ALHQDLFSLAQQCIDKARDLLDAELTAMAGESYSRAYGAMVSCHMLSELE

EVIQYKLVPERREIIRQIWWERLQGCQRIVEDWQKILMVRSLVVSPHEDM

RTWLKYASLCGKSGRLALAHKTLVLLLGVDPSRQLDHPLPTVHPQVTYAY

MKNMWKSARKIDAFQHMQHFVQTMQQQAQHAIATEDQQHKQELHKLMARC

FLKLGEWQLNLQGINESTIPKVLQYYSAATEHDRSWYKAWHAWAVMNFEA

VLHYKHQNQARDEKKKLRHASGANITNATTAATTAATATTTASTEGSNSE

SEAESTENSPTPSPLQKKVTEDLSKTLLMYTVPAVQGFFRSISLSRGNNL

QDTLRVLTLWFDYGHWPDVNEALVEGVKAIQIDTWLQVIPQLIARIDTPR

PLVGRLIHQLLTDIGRYHPQALIYPLTVASKSTTTARHNAANKILKNMCE

HSNTLVQQAMMVSEELIRVAILWHEMWHEGLEEASRLYFGERNVKGMFEV

LEPLHAMMERGPQTLKETSFNQAYGRDLMEAQEWCRKYMKSGNVKDLTQA

WDLYYHVFRRISKQLPQLTSLELQYVSPKLLMCRDLELAVPGTYDPNQPI

IRIQSIAPSLQVITSKQRPRKLTLMGSNGHEFVFLLKGHEDLRQDERVMQ

LFGLVNTLLANDPTSLRKNLSIQRYAVIPLSTNSGLIGWVPHCDTLHALI

RDYREKKKILLNIEHRIMLRMAPDYDHLTLMQKVEVFEHAVNNTAGDDLA

KLLWLKSPSSEVWFDRRTNYTRSLAVMSMVGYILGLGDRHPSNLMLDRLS

GKILHIDFGDCFEVAMTREKFPEKIPFRLTRMLTNAMEVTGLDGNYRITC

HTVMEVLREHKDSVMAVLEAFVYDPLLNWRLMDINTKGNKRSRTRIDSYS

AGQSVEILDGVELGEPAHKKTGTTVPESIHSFIGDGLVKPEALNKKAIQI

INRVRDKLTGRDFSHDDILDVPTQVELLIKQATSHENLCQCYIGWCPFW
```

In embodiments, the mTOR is a mutant mTOR. In embodiments, the mutant mTOR is associated with a disease that is not associated with wildtype mTOR. In embodiments, the mTOR includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

The term "mTORC1" refers to the protein complex including mTOR and Raptor (regulatory-associated protein of mTOR). mTORC1 may also include MLST8 (mammalian lethal with SEC13 protein 8), PRAS40, and/or DEPTOR. mTORC1 may function as a nutrient/energy/redox sensor and regulator of protein synthesis. The term "mTORC1 pathway" or "mTORC1 signal transduction pathway" refers to a cellular pathway including mTORC1. An mTORC1 pathway includes the pathway components upstream and downstream from mTORC1. An mTORC1 pathway is a signaling pathway that is modulated by modulation of mTORC1 activity. In embodiments, an mTORC1 pathway is a signaling pathway that is modulated by modulation of mTORC1 activity but not by modulation of mTORC2 activity. In embodiments, an mTORC1 pathway is a signaling pathway that is modulated to a greater extent by modulation of mTORC1 activity than by modulation of mTORC2 activity.

The term "mTORC2" refers to the protein complex including mTOR and RICTOR (rapamycin-insensitive companion of mTOR). mTORC2 may also include GβL, mSIN1 (mammalian stress-activated protein kinase interacting protein 1), Protor 1/2, DEPTOR, TTI1, and/or TEL2. mTORC2 may regulate cellular metabolism and the cytoskeleton. The term "mTORC2 pathway" or "mTORC2 signal transduction pathway" refers to a cellular pathway including mTORC2. An mTORC2 pathway includes the pathway components upstream and downstream from mTORC2. An mTORC2 pathway is a signaling pathway that is modulated by modulation of mTORC2 activity. In embodiments, an mTORC2 pathway is a signaling pathway that is modulated by modulation of mTORC2 activity but not by modulation of mTORC1 activity. In embodiments, an mTORC2 pathway is a signaling pathway that is modulated to a greater extent by modulation of mTORC2 activity than by modulation of mTORC1 activity.

The term "rapamycin" or "sirolimus" refers to a macrolide produced by the bacteria *Streptomyces hygroscopicus*. Rapamycin may prevent the activation of T cells and B cells. Rapamycin has the IUPAC name (3S,6R,7E,9R,10R,12R,14S,15E,17E,19E,21S,23S,26R,27R,34aS)-9,10,12,13,14,21,22,23,24,25,26,27,32,33,34,34a-hexadeca-hydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone. Rapamycin has the CAS number 53123-88-9. Rapamycin may be produced synthetically (e.g., by chemical synthesis) or through use of a production method that does not include use of *Streptomyces hygroscopicus*.

"Analog" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

The term "rapaymcin analog" or "rapalog" refer to analogs or derivatives (e.g., prodrugs) of rapamycin. Examples of rapamycin analogs include, but are not limited to, deforolimus (AP23573, MK-8669, ridaforolimus), temsirolimus (CCI-779), ABT478, and everolimus (RAD001). In embodiments, rapamycin analogs include esters, ethers, amides, carbonates, carbamates, sulfonates, oximes, hydrazones, or hydroxyamines of rapamycin. In embodiments, rapamycin analogs include rapamycins in which functional groups on rapamycin have been modified, (e.g., through reduction or oxidation, replacement with a nucleophile). In embodiments, rapamycin analogs include a metabolite of rapamycin (e.g., a desmethylrapamycin derivative or a linear rapamycin (e.g., secorapamycin, as described in U.S. Pat. No. 5,252,579). In embodiments, rapamycin analogs include O-desmethylrapamycin, desmethylrapamycin, or des-methoxyrapamycin (for example, as described in WO 2006/095185, U.S. Pat. No. 6,358,969). In embodiments, rapamycin analogs include ester derivatives or ether derivatives of rapamycin, including alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,411,967; 5,480,989; 5,480,988; 5,489,680); amino carbamate esters (U.S. Pat. No. 5,463,048); silyl ethers (U.S. Pat. No. 5,120,842); aminoesters (U.S. Pat. No. 5,130,307); acetals; aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); hindered N-oxide esters (U.S. Pat. No. 5,491,231); biotin esters (U.S. Pat. No. 5,504,091); O-alkyl ethers (U.S. Pat. No. 5,665,772); and PEG esters (U.S. Pat. No. 5,780,462); all of rapamycin. In embodiments, rapamycin analogs include ester, oxime, hydrazone, ether, or hydroxylamine derivatives of rapamycin, including those described in U.S. Pat. Nos. 5,256,790, 5,373,014, 5,378,836, 5,023,264, 5,563,145, and 5,023,263. In embodiments, rapamycin analogs include rapamycin 42-ester with 3-hydroxy-2-(hydroxymethyl)-2-methylpropionic acid (U.S. Pat. No. 5,362,718), 42-Q-(2-hydroxy)ethyl rapamycin (U.S. Pat. No. 5,665,772), and 42-epi-tetrazolyl rapamycin, or those described in U.S. Pat. Nos. 3,929,992, 5,362,718, and 6,277,983 (e.g., position 42 corresponding to position 40 shown in Example tables). In embodiments, rapamycin analogs include a substituted rapamycin e.g. a 40-O-substituted rapamycin e.g. as described in U.S. Pat. No. 5,258,389, WO 94/09010, WO 92/05179, U.S. Pat. Nos. 5,118,677, 5,118,678, 5,100,883, 5,151,413, 5,120,842, WO 93/11130, WO 94/02136, WO 94/02485 or WO 95/14023. In embodiments, rapamycin analogs include a 16-O-substituted rapamycin e.g. as disclosed in WO 94/02136, WO 95/16691 or WO 96/41807. In embodiments, rapamycin analogs include a 32-hydrogenated rapamycin e.g. as described in WO 96/41807 or U.S. Pat. No. 5,256,790. In embodiments, rapamycin analogs include 32-deoxorapamycin, 16-pent-2-ynyloxy-32-deoxo-rapamycin, 16-pent-2-ynyloxy-32(S)-dihydro-rapamycin, 16-pent-2-ynyloxy-32(S)-dihydro-40-O-(2-hydroxyethyl)-rapamycin or 40-O-(2-hydroxyethyl)-rapamycin. In embodiments, rapamycin analogs include 40-O-(2-hydroxyethyl)-rapamycin, 40-[3-hydroxy-2-(hydroxymethyl)-2-methylpropanoate]-rapamycin (also called CCI779), 40-epi-(tetrazolyl)-rapamycin (also called ABT578), 32-deoxorapamycin, 16-pent-2-ynyloxy-32(S)-dihydro rapamycin, or TAFA-93. The publications, patents, and applications described above are incorporated by reference in their entireties for all purposes.

The term "active site mTOR inhibitor" refers to a compound that inhibits the activity of mTOR (e.g., kinase activity) and binds to the active site of mTOR (e.g., the ATP binding site, overlapping with the ATP binding site, blocking access by ATP to the ATP binding site of mTOR). Examples of active site mTOR inhibitors include, but are not limited to, INK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, and PKI-587. In embodiments, an active site mTOR inhibitor is an asTORi.

The term "FKBP" refers to the protein Peptidyl-prolyl cis-trans isomerase. For non-limiting examples of FKBP, see Cell Mol Life Sci. 2013 September; 70(18):3243-75. In embodiments, "FKBP" refers to "FKBP-12" or "FKBP 12" or "FKBP1A". In embodiments, "FKBP" refers to the human protein. Included in the term "FKBP" is the wildtype and mutant forms of the protein. In embodiments, "FKBP" refers to the wildtype human protein. In embodiments, "FKBP" refers to the wildtype human nucleic acid. In embodiments, the FKBP is a mutant FKBP. In embodiments, the mutant FKBP is associated with a disease that is not associated with wildtype FKBP. In embodiments, the FKBP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype FKBP.

The term "FKBP-12" or "FKBP 12" or "FKBP1A" refers to the protein "Peptidyl-prolyl cis-trans isomerase FKBP1A". In embodiments, "FKBP-12" or "FKBP 12" or "FKBP1A" refers to the human protein. Included in the term "FKBP-12" or "FKBP 12" or "FKBP1A" are the wildtype and mutant forms of the protein. In embodiments, "FKBP-12" or "FKBP 12" or "FKBP1A" refers to the protein associated with Entrez Gene 2280, OMIM 186945, UniProt P62942, and/or RefSeq (protein) NP_000792 (SEQ ID NO:3). In embodiments, the reference numbers immediately above refer to the protein, and associated nucleic acids, known as of the date of filing of this application. In embodiments, "FKBP-12" or "FKBP 12" or "FKBP1A" refers to the wildtype human protein. In embodiments, "FKBP-12" or "FKBP 12" or "FKBP1A" refers to the wildtype human nucleic acid. In embodiments, the FKBP-12 is a mutant FKBP-12. In embodiments, the mutant FKBP-12 is associated with a disease that is not associated with wildtype FKBP-12. In embodiments, the FKBP-12 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype FKBP-12. In embodiments, the FKBP-12 has the protein sequence corresponding to reference number GI:206725550. In embodiments, the FKBP-12 has the protein sequence corresponding to RefSeq NP_000792.1 (SEQ ID NO:3).

The term "4E-BP1" or "4EBP1" or "EIF4EBP1" refers to the protein "Eukaryotic translation initiation factor 4E-binding protein 1". In embodiments, "4E-BP1" or "4EBP1" or "EIF4EBP1" refers to the human protein. Included in the term "4E-BP1" or "4EBP1" or "EIF4EBP1" are the wildtype and mutant forms of the protein. In embodiments, "4E-BP1" or "4EBP1" or "EIF4EBP1" refers to the protein associated with Entrez Gene 1978, OMIM 602223, UniProt Q13541, and/or RefSeq (protein) NP_004086 (SEQ ID NO:4). In embodiments, the reference numbers immediately above refer to the protein, and associated nucleic acids, known as of the date of filing of this application. In embodiments, "4E-BP1" or "4EBP1" or "EIF4EBP1" refers to the wildtype human protein. In embodiments, "4E-BP1" or "4EBP1" or "EIF4EBP1" refers to the wildtype human nucleic acid. In embodiments, the 4EBP1 is a mutant 4EBP1. In embodiments, the mutant 4EBP1 is associated with a disease that is not associated with wildtype 4EBP1. In embodiments, the 4EBP1 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype 4EBP1. In embodiments, the 4EBP1 has the protein sequence corresponding to reference number GI:4758258. In embodiments, the 4EBP1 has the protein sequence corresponding to RefSeq NP_004086.1 (SEQ ID NO:4).

The term "Akt" refers to the serine/threonine specific protein kinase involved in cellular processes such as glucose metabolism, apoptosis, proliferation, and other functions, also known as "protein kinase B" (PKB) or "Akt1". In embodiments, "Akt" or "Akt1" or "PKB" refers to the human protein. Included in the term "Akt" or "Akt1" or "PKB" are the wildtype and mutant forms of the protein. In embodiments, "Akt" or "Akt1" or "PKB" refers to the protein associated with Entrez Gene 207, OMIM 164730, UniProt P31749, and/or RefSeq (protein) NP_005154 (SEQ ID NO:5). In embodiments, the reference numbers immediately above refer to the protein, and associated nucleic acids, known as of the date of filing of this application. In embodiments, "Akt" or "Akt1" or "PKB" refers to the wildtype human protein. In embodiments, "Akt" or "Akt1" or "PKB" refers to the wildtype human nucleic acid. In embodiments, the Akt is a mutant Akt. In embodiments, the mutant Akt is associated with a disease that is not associated with wildtype Akt. In embodiments, the Akt includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype Akt. In embodiments, the Akt has the protein sequence corresponding to reference number GI:62241011. In embodiments, the Akt has the protein sequence corresponding to RefSeq NP_005154.2 (SEQ ID NO:5).

The term "longevity" is used in accordance with its plain ordinary meaning and refers to a long life or the extension of life expectancy beyond an average life expectancy. A "longevity agent" is an agent (e.g., composition as described herein) capable of extending the life expectancy of a subject in comparison to the life expectancy of the subject in the absence of the agent (Lamming, D. W., et al. (2012). Science (New York, N.Y.), 335(6076), 1638-1643., McCormick, M. A., et al. (2011). Philosophical Transactions of the Royal Society B: Biological Sciences, 366(1561)). A longevity agent may be capable of inducing one or more anti-aging effects in a subject wherein an aging effect is a condition or symptom of aging normally found in a similar subject.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

A. Compounds and Compositions

In an aspect is provided a compound including a monovalent active site mTOR inhibitor covalently bound to a monovalent rapamycin or a monovalent rapamycin analog.

In embodiments, a divalent linker binds the monovalent active site mTOR inhibitor (active site mTOR inhibitor moiety) to the monovalent rapamycin (rapamycin moiety) or the monovalent rapamycin analog (rapamycin analog moiety). The divalent linker may be bonded to rapamycin or a rapamycin analog at a position capable of being modified to include a linker. For example, a linker may be bonded to rapamycin or a rapamycin analog at position 10, 16, 27, 28, 39, or 40, among others (as indicated in figure immediately below). In embodiments, a linker is bonded to position 10 of rapamycin or a rapamycin analog. In embodiments, a linker is bonded to position 16 of rapamycin or a rapamycin analog. In embodiments, a linker is bonded to position 27 of rapamycin or a rapamycin analog. In embodiments, a linker is bonded to position 28 of rapamycin or a rapamycin analog. In embodiments, a linker is bonded to position 39 of rapamycin or a rapamycin analog. In embodiments, a linker is bonded to position 40 of rapamycin or a rapamycin analog.

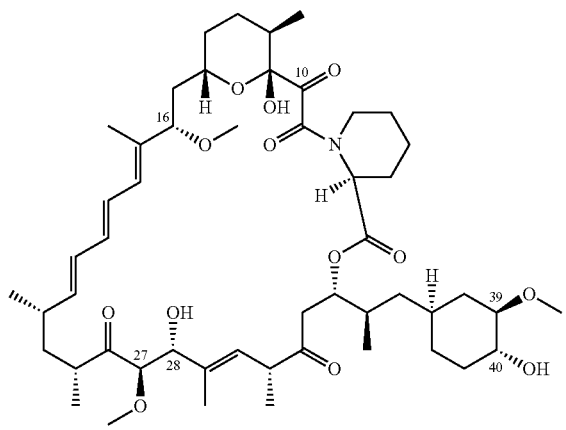

In embodiments, the divalent linker is at least about or about 5 Å in length (e.g., at least about or about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Å in length). In embodiments, the divalent linker is at least about or about the length of 5 methylene groups (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the divalent linker is at least about or about the length of 11 methylene groups (e.g., at least about or about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the divalent linker is at least about or about the length of 27 methylene groups (e.g., 27, 28, 29, 30, 31, 32, 33, 34, 35, 36, 37, 38, 39, 40, 41, 42, 43, 44, 45, 46, 47, 48, 49, or 50 methylene groups). In embodiments, the divalent linker is from about 5 to 54 Å in length. In embodiments, the divalent linker is from about 6 to 54 Å in length. In embodiments, the divalent linker is from about 7 to 54 Å in length. In embodiments, the divalent linker is from about 9 to 54 Å in length. In embodiments, the divalent linker is from about 11 to 54 Å in length. In embodiments, the divalent linker is from about 13 to 54 Å in length. In embodiments, the divalent linker is from about 15 to 54 Å in length. In embodiments, the divalent linker is from about 20 to 54 Å in length. In embodiments, the divalent linker is from about 24 to 54 Å in length. In embodiments, the divalent linker is from about 28 to 54 Å in length. In embodiments, the divalent linker is from about 5 to 50 Å in length. In embodiments, the divalent linker is from about 5 to 46 Å in length. In embodiments, the divalent linker is from about 5 to 42 Å in length. In embodiments, the divalent linker is from about 5 to 38 Å in length. In embodiments, the divalent linker is from about 5 to 34 Å in length. In embodiments, the divalent linker is from about 5 to 30 Å in length. In embodiments, the divalent linker is from about 5 to 26 Å in length. In embodiments, the divalent linker is from about 5 to 22 Å in length. In embodiments, the divalent linker is from about 5 to 39 Å in length. In embodiments, the divalent linker is from about 7 to 37 Å in length. In embodiments, the divalent linker is from about 9 to 35 Å in length. In embodiments, the divalent linker is from about 11 to 33 Å in length. In embodiments, the divalent linker is from about 13 to 31 Å in length. In embodiments, the divalent linker is from about 15 to 29 Å in length. In embodiments, the divalent linker is from about 15 to 25 Å in length. In embodiments, the divalent linker is from about 15 to 23 Å in length. In embodiments, the divalent linker is at least about or about 32 Å in length (e.g., at least about or about 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Å in length). In embodiments, the divalent linker is at least about or about the length of 27 methylene groups. In embodiments, the divalent linker is from about 32 to 54 Å in length. In embodiments, the divalent linker is from about 33 to 53 Å in length. In embodiments, the divalent linker is from about 34 to 52 Å in length. In embodiments, the divalent linker is from about 35 to 51 Å in length. In embodiments, the divalent linker is from about 36 to 50 Å in length. In embodiments, the divalent linker is from about 37 to 49 Å in length. In embodiments, the divalent linker is from about 38 to 48 Å in length. In embodiments, the divalent linker is from about 39 to 47 Å in length. In embodiments, the divalent linker is from about 40 to 46 Å in length. In embodiments, the divalent linker is from about 41 to 45 Å in length. In embodiments, the divalent linker is from about 42 to 44 Å in length. In embodiments, the divalent linker is from about 32 to 52 Å in length. In embodiments, the divalent linker is from about 32 to 50 Å in length. In embodiments, the divalent linker is from about 32 to 48 Å in length. In embodiments, the divalent linker is from about 32 to 46 Å in length. In embodiments, the divalent linker is from about 32 to 44 Å in length. In embodiments, the divalent linker is from about 32 to 42 Å in length. In embodiments, the divalent linker is from about 32 to 40 Å in length. In embodiments, the divalent linker is from about 32 to 38 Å in length. In embodiments, the divalent linker is from about 32 to 36 Å in length. In embodiments, the divalent linker is from about 34 to 54 Å in length. In embodiments, the divalent linker is from about 36 to 54 Å in length. In embodiments, the divalent linker is from about 38 to 54 Å in length. In embodiments, the divalent linker is from about 40 to 54 Å in length. In embodiments, the divalent linker is from about 42 to 54 Å in length. In embodiments, the divalent linker is from about 44 to 54 Å in length. In embodiments, the divalent linker is from about 46 to 54 Å in length. In embodiments, the divalent linker is from about 48 to 54 Å in length. In embodiments, the divalent linker is from about 50 to 54 Å in length.

The specified length of a linker is the through space distance between the ends of the linker (i.e., the ends or termini that are connected to the two parts of the molecule connected by the linker) wherein the length of the linker is measured when the linker is fully extended and wherein the linker termini are the furthest apart they may naturally exist in solution (i.e., the longest distance between the ends of the linker wherein the linker adopts allowable conformations, bond lengths, and bond angles following the principles of Chemistry), (e.g., without adopting non-natural bond lengths, non-allowed or non-preferred bond angles, or high energy non-preferred or non-natural interactions of different components of the linker). In embodiments, the linker length is measured when included in a compound as described herein (e.g., aspect, embodiment, example, figures, table, claim). It will be understood that a linker may adopt a through space distance (e.g., in solution, when bound to mTORC1, when bound to mTOR) that is less than the fully extended conformation used to define the linker length.

In embodiments, the linker is a hydrolysable linker (e.g., in solution). In embodiments, the linker is a non-hydrolysable linker (e.g., in solution). In embodiments, the linker may be cleaved by an enzyme (e.g., hydrolase, protease, cytochrome). In embodiments, the linker is not cleavable by an enzyme (e.g., under normal cellular conditions). In embodiments, the linker is a polyethylene glycol linker. In embodiments, the linker is hydrophilic. In embodiments, the linker is hydrophobic. In embodiments, the linker includes a disulfide bond. In embodiments, the linker includes a hydrazone bond. In embodiments, the linker includes an ester. In embodiments, the linker includes a sulfonyl. In embodiments, the linker includes a thioether. In embodiments, the linker includes a phosphinate. In embodiments, the linker includes an alkyloxime bond. In embodiments, the linker includes one or more amino acids. In embodiments, the linker consists of amino acids. In embodiments, the linker includes an amino acid analog. In embodiments, the linker includes an amino acid mimetic. In embodiments, the linker is a linker known in the art for use in linking antibodies to agents (e.g., antibody drug conjugates). In embodiments, the linker is a linker as described in Bioconjugate Techniques (Second Edition) by Greg T. Hermanson (2008), which is herein incorporated by referenced in its entirety for all purposes. In embodiments, the linker is a linker as described in Flygare J A, Pillow T H, Aristoff P., Antibody-drug conjugates for the treatment of cancer. Chemical Biology and Drug Design. 2013 January; 81(1):113-21, which is herein incorporated by referenced in its entirety for all purposes. In embodiments, the linker is a linker as described in Drachman J G, Senter P D., Antibody-drug conjugates: the chemistry behind empowering antibodies to fight cancer. Hematology Am Soc Hematol Educ Program. 2013; 2013: 306-10, which is herein incorporated by referenced in its entirety for all purposes.

In embodiments, the compound includes a divalent linker covalently bound to the monovalent active site mTOR inhibitor and the monovalent rapamycin or monovalent rapamycin analog. In embodiments, the compound includes a divalent linker covalently bound directly to the monovalent active site mTOR inhibitor and directly to the monovalent rapamycin or monovalent rapamycin analog.

In embodiments, the active site mTOR inhibitor is an asTORi. In embodiments, the active site mTOR inhibitor is INK128. In embodiments, the active site mTOR inhibitor is PP242. In embodiments, the active site mTOR inhibitor is PP121. In embodiments, the active site mTOR inhibitor is MLN0128. In embodiments, the active site mTOR inhibitor is AZD8055. In embodiments, the active site mTOR inhibitor is AZD2014. In embodiments, the active site mTOR inhibitor is NVP-BEZ235. In embodiments, the active site mTOR inhibitor is BGT226. In embodiments, the active site mTOR inhibitor is SF1126. In embodiments, the active site mTOR inhibitor is Torin 1. In embodiments, the active site mTOR inhibitor is Torin 2. In embodiments, the active site mTOR inhibitor is WYE 687. In embodiments, the active site mTOR inhibitor is WYE 687 salt (e.g., hydrochloride). In embodiments, the active site mTOR inhibitor is PF04691502. In embodiments, the active site mTOR inhibitor is PI-103, CC-223. In embodiments, the active site mTOR inhibitor is OSI-027, XL388. In embodiments, the active site mTOR inhibitor is KU-0063794. In embodiments, the active site mTOR inhibitor is GDC-0349. In embodiments, the active site mTOR inhibitor is PKI-587. When included in the compounds described herein, an active site mTOR inhibitor described above and elsewhere herein will be understood to be a monovalent form of the described active site mTOR inhibitor.

In embodiments, the compound has the formula:

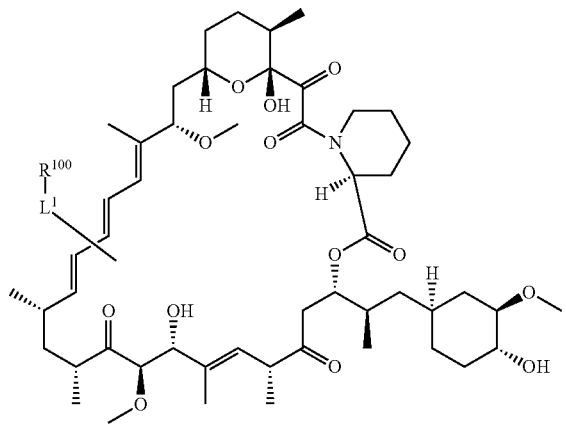

wherein $L^1$ is as described herein and may be bonded to any atom in the ring ($L^1$ is a floating substituent) and $R^{100}$ is a monovalent active site mTOR inhibitor.

In embodiments, the compound has the formula:

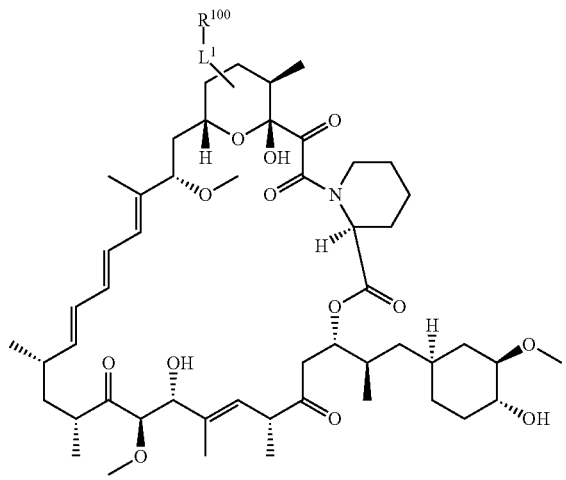

wherein $L^1$ is as described herein and may be bonded to any atom in the ring ($L^1$ is a floating substituent) and $R^{100}$ is a monovalent active site mTOR inhibitor.

In embodiments, the compound has the formula:

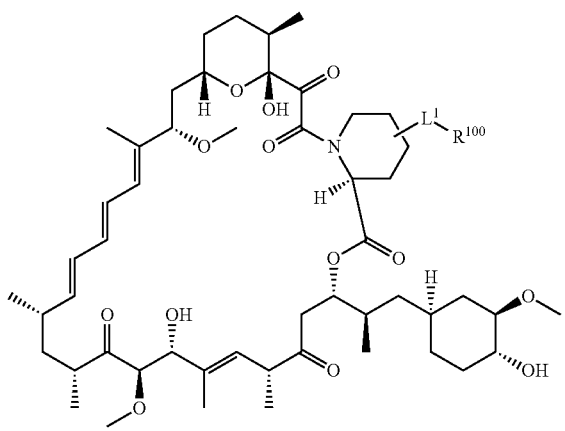

wherein L¹ is as described herein and may be bonded to any atom in the ring (L¹ is a floating substituent) and R¹⁰⁰ is a monovalent active site mTOR inhibitor.

In embodiments, the compound has the formula:

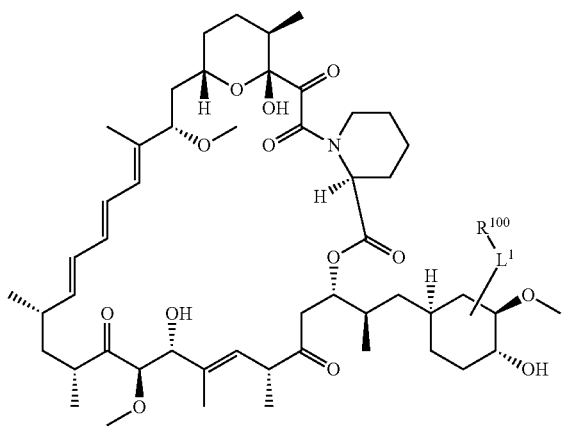

wherein L¹ is as described herein and may be bonded to any atom in the ring (L¹ is a floating substituent) and R¹⁰⁰ is a monovalent active site mTOR inhibitor.

R¹⁰⁰ is a monovalent active site mTOR inhibitor. In embodiments, R¹⁰⁰ is

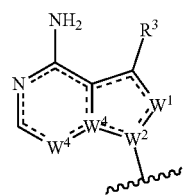

wherein W¹, W², W³, W⁴, and R³ are as described herein. In embodiments, R¹⁰⁰ is

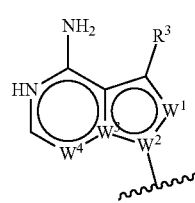

wherein W¹, W², W³, W⁴, and R³ are as described herein. In embodiments, R¹⁰⁰ is

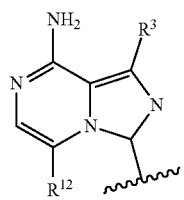

wherein R³ and R¹² are as described herein. In embodiments, R¹⁰⁰ is

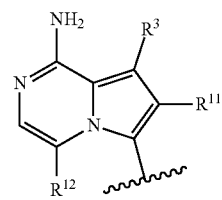

wherein R³, R¹¹, and R¹² are as described herein. In embodiments, R¹⁰⁰ is

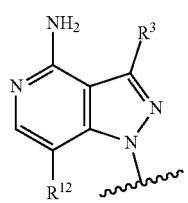

wherein R³ is as described herein. In embodiments, R¹⁰⁰ is

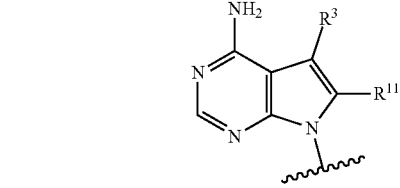

wherein $R^3$ and $R^{11}$ are as described herein. In embodiments, $R^{10}$ is

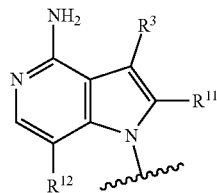

wherein $R^3$, $R^{11}$, and $R^{12}$ are as described herein. In embodiments, $R^{100}$ is

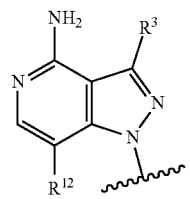

wherein $R^3$ and $R^{12}$ are as described herein.

In embodiments, the compound has the formula:

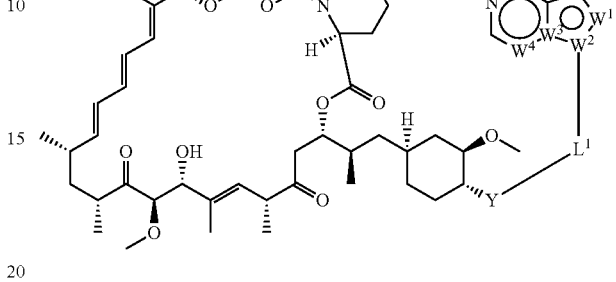

(I)

wherein $W^1$, $W^2$, $W^3$, $W^4$, $L^1$, Y, and $R^3$ are as described herein.

In embodiments, the compound has the formula:

(Ia)

wherein $L^1$, Y, and $R^{100}$ are as described herein.

In embodiments, the compound has the formula:

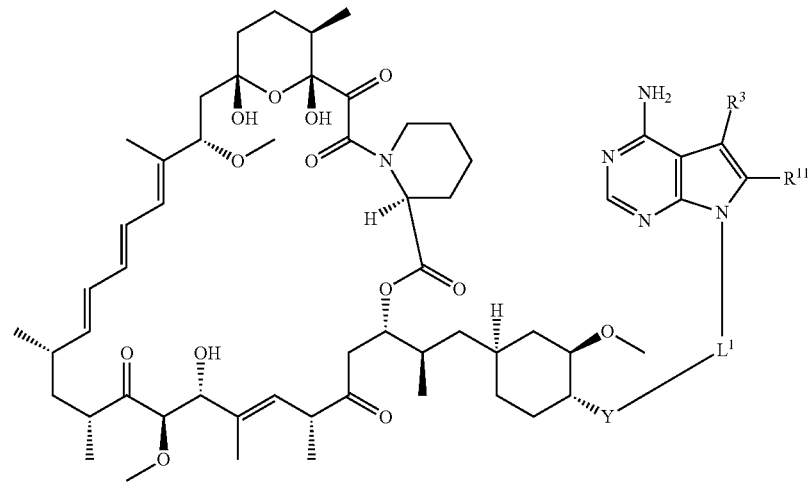

(Ib)

wherein $L^1$, Y, $R^3$, and $R^{11}$ are as described herein.

In embodiments, the compound has the formula:

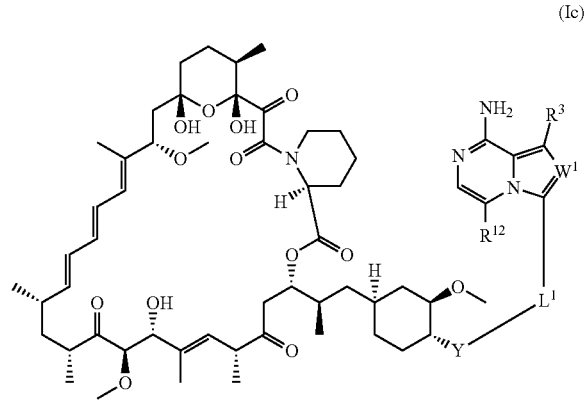

(Ic)

wherein $L^1$, Y, $R^3$, $W^1$, and $R^{12}$ are as described herein.

In embodiments, the compound has the formula:

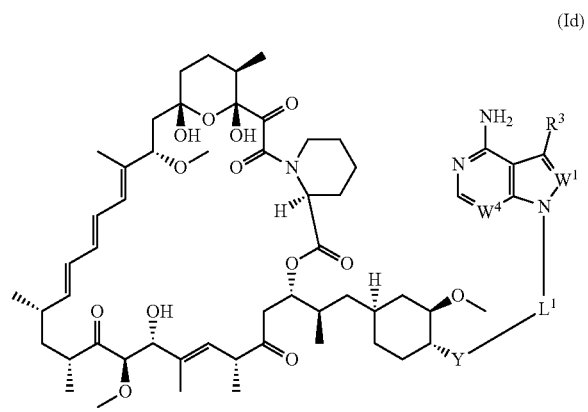

(Id)

wherein $L^1$, Y, $R^3$, $W^1$, and $W^4$ are as described herein.

$L^1$ is a divalent linker as described herein. $W^1$ is N or $CR^{11}$. $W^2$ is N and $W^3$ is C or, alternatively, $W^2$ is C and $W^3$ is N. $W^4$ is N or $CR^{12}$. Y is O or $NR^{13}$. $R^3$ is hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC═(O)$NHNH_2$, —NHC═(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$═(O)$R^9$, —$NR^7C(O)OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, and $R^{13}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ and $R^8$ substituents bonded to the same nitrogen atom may optionally be joined to form a substituted or unsubstituted heterocycloalkyl or substituted or unsubstituted heteroaryl.

The variables m and v are independently 1 or 2. The variable n is independently an integer from 0 to 4. The variable X is independently —Cl, —Br, —I, or —F. In embodiments, $L^1$ is a divalent linker including one or more amino acids. In embodiments, $L^1$ is a divalent linker consisting of amino acids (i.e. a peptidyl linker). In embodiments, $L^1$ is a divalent linker (e.g. a peptidyl linker) including an amino acid analog. In embodiments, $L^1$ is a divalent linker (e.g. a peptidyl linker) including an amino acid mimetic. In embodiments, $L^1$ is a divalent linker consisting of amino acid analogs (also referred to herein as a peptidyl analog linker). In embodiments, $L^1$ is a divalent linker consisting of amino acid mimetics (also referred to herein as a peptidyl mimetic linker).

In embodiments, $W^1$ is N. In embodiments, $W^1$ is $CR^{11}$. In embodiments, $W^2$ is N and $W^3$ is C. In embodiments, $W^2$ is C and $W^3$ is N. In embodiments, $W^4$ is N. In embodiments, $W^4$ is $CR^{12}$. In embodiments, Y is O. In embodiments, Y is $NR^{13}$. In embodiments, $W^1$ is CH. In embodiments, $W^4$ is CH. In embodiments, Y is NH.

In embodiments, the compound has the formula:

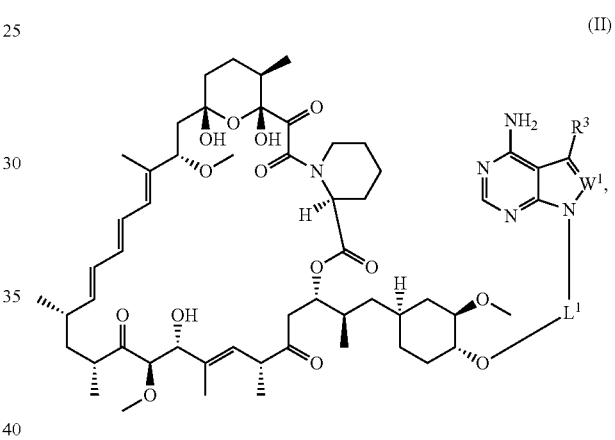

(II)

wherein $W^1$ is N or CH. In embodiments, $W^1$ is N. In embodiments, $W^1$ is CH.

In embodiments, the compound has the formula:

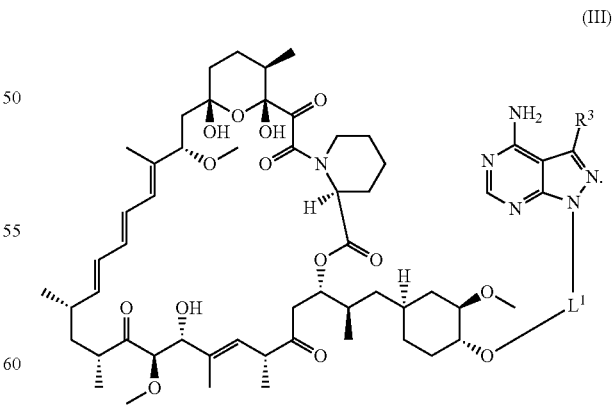

(III)

In embodiments, $R^3$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently substituted or unsubstituted cycloalkyl, substituted or unsubstituted heterocycloalkyl, substituted or unsubstituted aryl, or substituted or unsubstituted heteroaryl. In embodiments, $R^3$ is independently substituted or unsubstituted aryl, or substituted or unsubstituted heteroaryl. In embodiments, $R^3$ is independently substituted or unsubstituted fused ring aryl, or substituted or unsubstituted fused ring heteroaryl. In embodiments, $R^3$ is independently substituted or unsubstituted fused ring heteroaryl. In embodiments, $R^3$ is independently substituted fused ring heteroaryl.

In embodiments, $R^3$ is

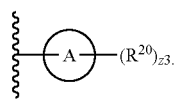

$R^{20}$ is as described herein. Ring A is an aryl (e.g., phenyl, diphenyl, or fused ring aryl) or a heteroaryl (e.g., monocyclic heteroaryl or fused ring heteroaryl). Ring A may be any of the aryl or heteroaryl rings in the embodiments of $R^3$ described herein (e.g., benzoxazolyl, indolyl, phenyl, or naphthyl). The symbol z3 is an integer from 0 to 7. In embodiments, z3 is 0. In embodiments, z3 is 1. In embodiments, z3 is 2. In embodiments, z3 is 3. In embodiments, z3 is 4. In embodiments, z3 is 5. In embodiments, z3 is 6. In embodiments, z3 is 7.

In embodiments, $R^3$ is independently substituted benzoxazolyl, substituted pyrimidinyl, substituted thiophenyl, substituted furanyl, substituted indolyl, substituted benzoxadiazolyl, substituted benzodioxolyl, substituted benzodioxanyl, substituted thianaphthanyl, substituted pyrrolopyridinyl, substituted indazolyl, substituted quinolinyl, substituted quinoxalinyl, substituted pyridopyrazinyl, substituted quinazolinonyl, substituted benzoisoxazolyl, substituted imidazopyridinyl, substituted benzofuranyl, substituted benzothiophenyl, substituted phenyl, substituted naphthyl, substituted biphenyl, substituted pyrrolyl, substituted pyrazolyl, substituted imidazolyl, substituted pyrazinyl, substituted oxazolyl, substituted isoxazolyl, substituted thiazolyl, substituted furylthienyl, substituted pyridyl, substituted pyrimidyl, substituted benzothiazolyl, substituted purinyl, substituted benzimidazolyl, substituted isoquinolyl, substituted thiadiazolyl, substituted oxadiazolyl, substituted pyrrolyl, substituted diazolyl, substituted triazolyl, substituted tetrazolyl, substituted benzothiadiazolyl, substituted isothiazolyl, substituted pyrazolopyrimidinyl, substituted pyrrolopyrimidinyl, substituted benzotriazolyl, or substituted quinolyl. In embodiments, $R^3$ is independently substituted benzoxazolyl.

In embodiments, $R^3$ is independently substituted benzoxazolyl. In embodiments, $R^3$ is substituted pyrimidinyl. In embodiments, $R^3$ is substituted thiophenyl. In embodiments, $R^3$ is substituted furanyl. In embodiments, $R^3$ is substituted indolyl. In embodiments, $R^3$ is substituted benzoxadiazolyl. In embodiments, $R^3$ is substituted benzodioxolyl. In embodiments, $R^3$ is substituted benzodioxanyl. In embodiments, $R^3$ is substituted thianaphthanyl. In embodiments, $R^3$ is substituted pyrrolopyridinyl. In embodiments, $R^3$ is substituted indazolyl. In embodiments, $R^3$ is substituted quinolinyl. In embodiments, $R^3$ is substituted quinoxalinyl. In embodiments, $R^3$ is substituted pyridopyrazinyl. In embodiments, $R^3$ is substituted quinazolinonyl. In embodiments, $R^3$ is substituted benzoisoxazolyl. In embodiments, $R^3$ is substituted imidazopyridinyl. In embodiments, $R^3$ is substituted benzofuranyl. In embodiments, $R^3$ is substituted benzothiophenyl. In embodiments, $R^3$ is substituted phenyl. In embodiments, $R^3$ is substituted naphthyl. In embodiments, $R^3$ is substituted biphenyl. In embodiments, $R^3$ is substituted pyrrolyl. In embodiments, $R^3$ is substituted pyrazolyl. In embodiments, $R^3$ is substituted imidazolyl. In embodiments, $R^3$ is substituted pyrazinyl. In embodiments, $R^3$ is substituted oxazolyl. In embodiments, $R^3$ is substituted isoxazolyl. In embodiments, $R^3$ is substituted thiazolyl. In embodiments, $R^3$ is substituted furylthienyl. In embodiments, $R^3$ is substituted pyridyl. In embodiments, $R^3$ is substituted pyrimidyl. In embodiments, $R^3$ is substituted benzothiazolyl. In embodiments, $R^3$ is substituted purinyl. In embodiments, $R^3$ is substituted benzimidazolyl. In embodiments, $R^3$ is substituted isoquinolyl. In embodiments, $R^3$ is substituted thiadiazolyl. In embodiments, $R^3$ is substituted oxadiazolyl. In embodiments, $R^3$ is substituted pyrrolyl. In embodiments, $R^3$ is substituted diazolyl. In embodiments, $R^3$ is substituted triazolyl. In embodiments, $R^3$ is substituted tetrazolyl. In embodiments, $R^3$ is substituted benzothiadiazolyl. In embodiments, $R^3$ is substituted isothiazolyl. In embodiments, $R^3$ is substituted pyrazolopyrimidinyl. In embodiments, $R^3$ is substituted pyrrolopyrimidinyl. In embodiments, $R^3$ is substituted benzotriazolyl. In embodiments, $R^3$ is substituted quinolyl. In embodiments, $R^3$ is independently substituted benzoxazolyl.

In embodiments, $R^3$ is independently unsubstituted benzoxazolyl. In embodiments, $R^3$ is unsubstituted pyrimidinyl. In embodiments, $R^3$ is unsubstituted thiophenyl. In embodiments, $R^3$ is unsubstituted furanyl. In embodiments, $R^3$ is unsubstituted indolyl. In embodiments, $R^3$ is unsubstituted benzoxadiazolyl. In embodiments, $R^3$ is unsubstituted benzodioxolyl. In embodiments, $R^3$ is unsubstituted benzodioxanyl. In embodiments, $R^3$ is unsubstituted thianaphthanyl. In embodiments, $R^3$ is unsubstituted pyrrolopyridinyl. In embodiments, $R^3$ is unsubstituted indazolyl. In embodiments, $R^3$ is unsubstituted quinolinyl. In embodiments, $R^3$ is unsubstituted quinoxalinyl. In embodiments, $R^3$ is unsubstituted pyridopyrazinyl. In embodiments, $R^3$ is unsubstituted quinazolinonyl. In embodiments, $R^3$ is unsubstituted benzoisoxazolyl. In embodiments, $R^3$ is unsubstituted imidazopyridinyl. In embodiments, $R^3$ is unsubstituted benzofuranyl. In embodiments, $R^3$ is unsubstituted benzothiophenyl. In embodiments, $R^3$ is unsubstituted phenyl. In embodiments, $R^3$ is unsubstituted naphthyl. In embodiments, $R^3$ is unsubstituted biphenyl. In embodiments, $R^3$ is unsubstituted pyrrolyl. In embodiments, $R^3$ is unsubstituted pyrazolyl. In embodiments, $R^3$ is unsubstituted imidazolyl. In embodiments, $R^3$ is unsubstituted pyrazinyl. In embodiments, $R^3$ is unsubstituted oxazolyl. In embodiments, $R^3$ is unsubstituted isoxazolyl. In embodiments, $R^3$ is unsubstituted thiazolyl. In embodiments, $R^3$ is unsubstituted furylthienyl. In embodiments, $R^3$ is unsubstituted pyridyl. In embodiments, $R^3$ is unsubstituted pyrimidyl. In embodiments, $R^3$ is unsubstituted benzothiazolyl. In embodiments, $R^3$ is unsubstituted purinyl. In embodiments, $R^3$ is unsubstituted benzimidazolyl. In embodiments, $R^3$ is unsubstituted isoquinolyl. In embodiments, $R^3$ is unsubstituted thiadiazolyl. In embodiments, $R^3$ is unsubstituted oxadiazolyl. In embodiments, $R^3$ is unsubstituted pyrrolyl. In embodiments, $R^3$ is unsubstituted diazolyl. In embodiments, $R^3$ is unsubstituted triazolyl. In embodiments, $R^3$ is unsubstituted tetrazolyl. In embodiments, $R^3$ is unsubstituted benzothiadiazolyl. In embodiments, $R^3$ is unsubstituted isothiazolyl. In embodiments, $R^3$ is unsubstituted pyrazolopyrimidinyl. In embodiments, $R^3$ is unsubstituted pyrrolopyrimidinyl. In embodiments, $R^3$ is unsubstituted benzotriazolyl. In embodiments, $R^3$ is unsubstituted quinolyl. In embodiments, $R^3$ is independently unsubstituted benzoxazolyl.

In some embodiments of the compounds provided herein, $R^3$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In some embodiments, $R^3$ is substituted with one or more substituents independently selected from halogen, —$CF_3$, —OH, and —$NH_2$. In some embodiments, $R^3$ is substituted heteroaryl, such as benzoxazolyl or benzothiazolyl. In some embodiments, $R^3$ is heteroaryl, such as benzoxazolyl or benzothiazolyl, substituted with one or more substituents independently selected from halogen, —$CF_3$, —OH, and —$NH_2$.

In embodiments, $R^3$ is independently $R^{20}$-substituted benzoxazolyl, $R^{20}$-substituted pyrimidinyl, $R^{20}$-substituted thiophenyl, $R^{20}$-substituted furanyl, $R^{20}$-substituted indolyl, $R^{20}$-substituted benzoxadiazolyl, $R^{20}$-substituted benzodioxolyl, $R^{20}$-substituted benzodioxanyl, $R^{20}$-substituted thianaphthanyl, $R^{20}$-substituted pyrrolopyridinyl, $R^{20}$-substituted indazolyl, $R^{20}$-substituted quinolinyl, $R^{20}$-substituted quinoxalinyl, $R^{20}$-substituted pyridopyrazinyl, $R^{20}$-substituted quinazolinonyl, $R^{20}$-substituted benzoisoxazolyl, $R^{20}$-substituted imidazopyridinyl, $R^{20}$-substituted benzofuranyl, $R^{20}$-substituted benzothiophenyl, $R^{20}$-substituted phenyl, $R^{20}$-substituted naphthyl, $R^{20}$-substituted biphenyl, $R^{20}$-substituted pyrrolyl, $R^{20}$-substituted pyrazolyl, $R^{20}$-substituted imidazolyl, $R^{20}$-substituted pyrazinyl, $R^{20}$-substituted oxazolyl, $R^{20}$-substituted isoxazolyl, $R^{20}$-substituted thiazolyl, $R^{20}$-substituted furylthienyl, $R^{20}$-substituted pyridyl, $R^{20}$-substituted pyrimidyl, $R^{20}$-substituted benzothiazolyl, $R^{20}$-substituted purinyl, $R^{20}$-substituted benzimidazolyl, $R^{20}$-substituted isoquinolyl, $R^{20}$-substituted thiadiazolyl, $R^{20}$-substituted oxadiazolyl, $R^{20}$-substituted pyrrolyl, $R^{20}$-substituted diazolyl, $R^{20}$-substituted triazolyl, $R^{20}$-substituted tetrazolyl, $R^{20}$-substituted benzothiadiazolyl, $R^{20}$-substituted isothiazolyl, $R^{20}$-substituted pyrazolopyrimidinyl, $R^{20}$-substituted pyrrolopyrimidinyl, $R^{20}$-substituted benzotriazolyl, or $R^{20}$-substituted quinolyl. In embodiments, $R^3$ is independently $R^{20}$-substituted benzoxazolyl.

In embodiments, $R^3$ is independently $R^{20}$-substituted benzoxazolyl. In embodiments, $R^3$ is $R^{20}$-substituted pyrimidinyl. In embodiments, $R^3$ is $R^{20}$-substituted thiophenyl. In embodiments, $R^3$ is $R^{20}$-substituted furanyl. In embodiments, $R^3$ is $R^{20}$-substituted indolyl. In embodiments, $R^3$ is $R^{20}$-substituted benzoxadiazolyl. In embodiments, $R^3$ is $R^{20}$-substituted benzodioxolyl. In embodiments, $R^3$ is $R^{20}$-substituted benzodioxanyl. In embodiments, $R^3$ is $R^{20}$-substituted thianaphthanyl. In embodiments, $R^3$ is $R^{20}$-substituted pyrrolopyridinyl. In embodiments, $R^3$ is $R^{20}$-substituted indazolyl. In embodiments, $R^3$ is $R^{20}$-substituted quinolinyl. In embodiments, $R^3$ is $R^{20}$-substituted quinoxalinyl. In embodiments, $R^3$ is $R^{20}$-substituted pyridopyrazinyl. In embodiments, $R^3$ is $R^{20}$-substituted quinazolinonyl. In embodiments, $R^3$ is $R^{20}$-substituted benzoisoxazolyl. In embodiments, $R^3$ is $R^{20}$-substituted imidazopyridinyl. In embodiments, $R^3$ is $R^{20}$-substituted benzofuranyl. In embodiments, $R^3$ is $R^{20}$-substituted benzothiophenyl. In embodiments, $R^3$ is $R^{20}$-substituted phenyl. In embodiments, $R^3$ is $R^{20}$-substituted naphthyl. In embodiments, $R^3$ is $R^{20}$-substituted biphenyl. In embodiments, $R^3$ is $R^{20}$-substituted pyrrolyl. In embodiments, $R^3$ is $R^{20}$-substituted pyrazolyl. In embodiments, $R^3$ is $R^{20}$-substituted imidazolyl. In embodiments, $R^3$ is $R^{20}$-substituted pyrazinyl. In embodiments, $R^3$ is $R^{20}$-substituted oxazolyl. In embodiments, $R^3$ is $R^{20}$-substituted isoxazolyl. In embodiments, $R^3$ is $R^{20}$-substituted thiazolyl. In embodiments, $R^3$ is $R^{20}$-substituted furylthienyl. In embodiments, $R^3$ is $R^{20}$-substituted pyridyl. In embodiments, $R^3$ is $R^{20}$-substituted pyrimidyl. In embodiments, $R^3$ is $R^{20}$-substituted benzothiazolyl. In embodiments, $R^3$ is $R^{20}$-substituted purinyl. In embodiments, $R^3$ is $R^{20}$-substituted benzimidazolyl. In embodiments, $R^3$ is $R^{20}$-substituted isoquinolyl. In embodiments, $R^3$ is $R^{20}$-substituted thiadiazolyl. In embodiments, $R^3$ is $R^{20}$-substituted oxadiazolyl. In embodiments, $R^3$ is $R^{20}$-substituted pyrrolyl. In embodiments, $R^3$ is $R^{20}$-substituted diazolyl. In embodiments, $R^3$ is $R^{20}$-substituted triazolyl. In embodiments, $R^3$ is $R^{20}$-substituted tetrazolyl. In embodiments, $R^3$ is $R^{20}$-substituted benzothiadiazolyl. In embodiments, $R^3$ is $R^{20}$-substituted isothiazolyl. In embodiments, $R^3$ is $R^{20}$-substituted pyrazolopyrimidinyl. In embodiments, $R^3$ is $R^{20}$-substituted pyrrolopyrimidinyl. In embodiments, $R^3$ is $R^{20}$-substituted benzotriazolyl. In embodiments, $R^3$ is $R^{20}$-substituted quinolyl. In embodiments, $R^3$ is independently $R^{20}$-substituted benzoxazolyl.

$R^{20}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

In embodiments, $R^{20}$ is independently —$NH_2$. In embodiments, $R^{20}$ is independently —OH. In embodiments, $R^{20}$ is independently halogen. In embodiments, $R^{20}$ is independently —CN. In embodiments, $R^{20}$ is independently oxo. In embodiments, $R^{20}$ is independently —$CF_3$. In embodiments, $R^{20}$ is independently —COOH. In embodiments, $R^{20}$ is independently —$CONH_2$. In embodiments, $R^{20}$ is independently —$NO_2$. In embodiments, $R^{20}$ is independently —SH. In embodiments, $R^{20}$ is independently —$SO_3H$. In embodiments, $R^{20}$ is independently —$SO_4H$. In embodiments, $R^{20}$ is independently —$SO_2NH_2$. In embodiments, $R^{20}$ is independently —$NHNH_2$. In embodiments, $R^{20}$ is independently —$ONH_2$. In embodiments, $R^{20}$ is independently —NHC=(O)$NHNH_2$. In embodiments, $R^{20}$ is independently —NHC=(O)$NH_2$. In embodiments, $R^{20}$ is independently —$NHSO_2H$. In embodiments, $R^{20}$ is independently —NHC=(O)H. In embodiments, $R^{20}$ is independently —NHC(O)OH. In embodiments, $R^{20}$ is independently —NHOH. In embodiments, $R^{20}$ is independently —$OCF_3$. In embodiments, $R^{20}$ is independently —$OCHF_2$. In embodiments, $R^{20}$ is independently a halogen, —$CF_3$, —$CHF_2$, —$CH_2F$, —CN, —$NHNH_2$, —$NO_2$, —$NH_2$, —C(O)H, —C(O)OH, —C(O)$NH_2$, —OH, —NHC(O)OH, —$OCF_3$, —$OCHF_2$, $R^{21}$-substituted or unsubstituted $C_1$-$C_8$ alkyl, $R^{21}$-substituted or unsubstituted 2 to 8 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted $C_6$-$C_{10}$ aryl, or $R^{21}$-substituted or unsubstituted 5 to 10 membered heteroaryl. In embodiments, $R^{20}$ is independently a halogen, —$CF_3$, —CN, —$NH_2$, —OH, $R^{21}$-substituted or unsubstituted $C_1$-$C_4$ alkyl, $R^{21}$-substituted or unsubstituted 2 to 4 membered heteroalkyl, $R^{21}$-substituted or unsubstituted $C_3$-$C_6$ cycloalkyl, $R^{21}$-substituted or unsubstituted 3 to 6 membered heterocycloalkyl, $R^{21}$-substituted or unsubstituted phenyl, or $R^{21}$-substituted or unsubstituted 5 to 6 membered heteroaryl. In embodiments, $R^{20}$ is independently a halogen, —$CF_3$, —CN, —$NH_2$, —OH, unsubstituted $C_1$-$C_4$ alkyl, or unsubstituted 2 to 4 membered heteroalkyl. In embodiments, $R^{20}$ is independently a halogen, —$CF_3$, unsubstituted methyl, unsubstituted ethyl, unsubstituted isopropyl, unsubstituted methoxy, or unsubstituted ethoxy. In embodiments, $R^{20}$ is independently unsubstituted methyl. In embodiments, $R^{20}$ is independently unsubstituted ethyl. In embodiments, $R^{20}$ is independently unsubstituted methoxy. In embodiments, $R^{20}$ is independently unsubstituted ethoxy. In embodiments, $R^{20}$ is independently —$CCl_3$. In embodiments, $R^{20}$ is independently —$CBr_3$. In embodiments, $R^{20}$ is independently —$CI_3$. In embodiments, $R^{20}$ is independently —F. In embodiments, $R^{20}$ is independently —Cl. In embodiments, $R^{20}$ is independently —Br. In embodiments, $R^{20}$ is independently —I.

$R^{21}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In embodiments, $R^{21}$ is independently —$NH_2$. In embodiments, $R^{21}$ is independently —OH. In embodiments, $R^{21}$ is independently halogen. In embodiments, $R^{21}$ is independently —CN. In embodiments, $R^{21}$ is independently oxo. In embodiments, $R^{21}$ is independently —$CF_3$. In embodiments, $R^{21}$ is independently —COOH. In embodiments, $R^{21}$ is independently —$CONH_2$. In embodiments, $R^{21}$ is independently —$NO_2$. In embodiments, $R^{21}$ is independently —SH. In embodiments, $R^{21}$ is independently —$SO_3H$. In embodiments, $R^{21}$ is independently —$SO_4H$. In embodiments, $R^{21}$ is independently —$SO_2NH_2$. In embodiments, $R^{21}$ is independently —$NHNH_2$. In embodiments, $R^{21}$ is independently —$ONH_2$. In embodiments, $R^{21}$ is independently —NHC=(O)$NHNH_2$. In embodiments, $R^{21}$ is independently —NHC=(O)$NH_2$. In embodiments, $R^{21}$ is independently —$NHSO_2H$. In embodiments, $R^{21}$ is independently —NHC=(O)H. In embodiments, $R^{21}$ is independently —NHC(O)OH. In embodiments, $R^{21}$ is independently —NHOH. In embodiments, $R^{21}$ is independently —$OCF_3$. In embodiments, $R^{21}$ is independently —$OCHF_2$. In embodiments, $R^{21}$ is independently a halogen, —$CF_3$, —$CHF_2$, —$CH_2F$, —CN, —$NHNH_2$, —$NO_2$, —$NH_2$, —C(O)H, —C(O)OH, —C(O)$NH_2$, —OH, —NHC(O)OH, —$OCF_3$, —$OCHF_2$, $R^{22}$-substituted or unsubstituted $C_1$-$C_8$ alkyl, $R^{22}$-substituted or unsubstituted 2 to 8 membered heteroalkyl, $R^{22}$-substituted or unsubstituted $C_3$-$C_8$ cycloalkyl, $R^{22}$-substituted or unsubstituted 3 to 8 membered heterocycloalkyl, $R^{22}$-substituted or unsubstituted $C_6$-$C_{10}$ aryl, or $R^{22}$-substituted or unsubstituted 5 to 10 membered heteroaryl. In embodiments, $R^{21}$ is independently a halogen, —$CF_3$, —CN, —$NH_2$, —OH, $R^{22}$-substituted or unsubstituted $C_1$-$C_4$ alkyl, $R^{22}$-substituted or unsubstituted 2 to 4 membered heteroalkyl, $R^{22}$-substituted or unsubstituted $C_3$-$C_6$ cycloalkyl, $R^{22}$-substituted or unsubstituted 3 to 6 membered heterocycloalkyl, $R^{22}$-substituted or unsubstituted phenyl, or $R^{22}$-substituted or unsubstituted 5 to 6 membered heteroaryl. In embodiments, $R^{21}$ is independently a halogen, —$CF_3$, —CN, —$NH_2$, —OH, unsubstituted $C_1$-$C_4$ alkyl, or unsubstituted 2 to 4 membered heteroalkyl. In embodiments, $R^{21}$ is independently a halogen, —$CF_3$, unsubstituted methyl, unsubstituted ethyl, unsubstituted isopropyl, unsubstituted methoxy, or unsubstituted ethoxy. In embodiments, $R^{21}$ is independently unsubstituted methyl. In embodiments, $R^{21}$ is independently unsubstituted ethyl. In embodiments, $R^{21}$ is independently unsubstituted methoxy. In embodiments, $R^{21}$ is independently unsubstituted ethoxy. In embodiments, $R^{21}$ is independently —$CCl_3$. In embodiments, $R^{21}$ is independently —$CBr_3$. In embodiments, $R^{21}$ is independently —$CI_3$. In embodiments, $R^{21}$ is independently —F. In embodiments, $R^{21}$ is independently —Cl. In embodiments, $R^{21}$ is independently —Br. In embodiments, $R^{21}$ is independently —I.

In embodiments, $R^7$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

In embodiments, $R^7$ is independently hydrogen, —$CF_3$, —CN, —COOH, —$CONH_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl. In embodiments, $R^7$ is independently an $R^{38}$-substituted or unsubstituted $C_1$-$C_4$ alkyl, $R^{38}$-substituted or unsubstituted 2 to 4 membered heteroalkyl, $R^{38}$-substituted or unsubstituted $C_3$-$C_6$ cycloalkyl, $R^{38}$-substituted or unsubstituted 3 to 6 membered heterocycloalkyl, $R^{38}$-substituted or unsubstituted phenyl, or $R^{38}$-substituted or unsubstituted 5 to 6 membered heteroaryl. In embodiments, $R^7$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^7$ is independently an unsubstituted $C_1$-$C_4$ alkyl. In embodiments, $R^7$ is independently an unsubstituted methyl. In embodiments, $R^7$ is independently an unsubstituted ethyl. In embodiments, $R^7$ is independently an unsubstituted isopropyl. In embodiments, $R^7$ is independently an unsubstituted tert-butyl. In embodiments, $R^7$ is independently hydrogen.

$R^{38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{39}$-substituted or unsubstituted alkyl, $R^{39}$-substituted or unsubstituted heteroalkyl, $R^{39}$-substituted or unsubstituted cycloalkyl, $R^{39}$ substituted or unsubstituted heterocycloalkyl, $R^{39}$-substituted or unsubstituted aryl, or $R^{39}$-substituted or unsubstituted heteroaryl.

In embodiments, $R^{38}$ is independently —$NH_2$. In embodiments, $R^{38}$ is independently —OH. In embodiments, $R^{38}$ is independently halogen. In embodiments, $R^{38}$ is independently —CN. In embodiments, $R^{38}$ is independently oxo. In embodiments, $R^{38}$ is independently —$CF_3$. In embodiments, $R^{38}$ is independently —COOH. In embodiments, $R^{38}$ is independently —$CONH_2$. In embodiments, $R^{38}$ is independently —NO$_2$. In embodiments, R$^{38}$ is independently —SH. In embodiments, R$^{38}$ is independently —SO$_3$H. In embodiments, R$^{38}$ is independently —SO$_4$H. In embodiments, R$^{38}$ is independently —SO$_2$NH$_2$. In embodiments, R$^{38}$ is independently —NHNH$_2$. In embodiments, R$^{38}$ is independently —ONH$_2$. In embodiments, R$^{38}$ is independently —NHC=(O)NHNH$_2$. In embodiments, R$^{38}$ is independently —NHC=(O) NH$_2$. In embodiments, R$^{38}$ is independently —NHSO$_2$H. In embodiments, R$^{38}$ is independently —NHC=(O)H. In embodiments, R$^{38}$ is independently —NHC(O)—OH. In embodiments, R$^{38}$ is independently —NHOH. In embodiments, R$^{38}$ is independently —OCF$_3$. In embodiments, R$^{38}$ is independently —OCHF$_2$. In embodiments, R$^{38}$ is independently —CCl$_3$. In embodiments, R$^{38}$ is independently —CBr$_3$. In embodiments, R$^{38}$ is independently —CI$_3$. In embodiments, R$^{38}$ is independently —F. In embodiments, R$^{38}$ is independently —Cl. In embodiments, R$^{38}$ is independently —Br. In embodiments, R$^{38}$ is independently —I. In embodiments, R$^{38}$ is independently R$^{39}$-substituted C$_1$-C$_4$ alkyl. In embodiments, R$^{38}$ is independently R$^{39}$-substituted 2 to 4 membered heteroalkyl. In embodiments, R$^{38}$ is independently R$^{39}$-substituted C$_3$-C$_6$ cycloalkyl. In embodiments, R$^{38}$ is independently R$^{39}$-substituted 3 to 6 membered heterocycloalkyl. In embodiments, R$^{38}$ is independently R$^{39}$-substituted phenyl. In embodiments, R$^{38}$ is independently R$^{39}$-substituted 5 to 6 membered heteroaryl. In embodiments, R$^{38}$ is independently unsubstituted C$_1$-C$_4$ alkyl. In embodiments, R$^{38}$ is independently unsubstituted 2 to 4 membered heteroalkyl. In embodiments, R$^{38}$ is independently unsubstituted C$_3$-C$_6$ cycloalkyl. In embodiments, R$^{38}$ is independently unsubstituted 3 to 6 membered heterocycloalkyl. In embodiments, R$^{38}$ is independently unsubstituted phenyl. In embodiments, R$^{38}$ is independently unsubstituted 5 to 6 membered heteroaryl.

R$^{39}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —S(O)$_2$CHCH$_2$, —NHS(O)$_2$CHCH$_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl.

In embodiments, R$^{39}$ is independently —NH$_2$. In embodiments, R$^{39}$ is independently —OH. In embodiments, R$^{39}$ is independently halogen. In embodiments, R$^{39}$ is independently —CN. In embodiments, R$^{39}$ is independently oxo. In embodiments, R$^{39}$ is independently —CF$_3$. In embodiments, R$^{39}$ is independently —COOH. In embodiments, R$^{39}$ is independently —CONH$_2$. In embodiments, R$^{39}$ is independently —NO$_2$. In embodiments, R$^{39}$ is independently —SH. In embodiments, R$^{39}$ is independently —SO$_3$H. In embodiments, R$^{39}$ is independently —SO$_4$H. In embodiments, R$^{39}$ is independently —SO$_2$NH$_2$. In embodiments, R$^{39}$ is independently —NHNH$_2$. In embodiments, R$^{39}$ is independently —ONH$_2$. In embodiments, R$^{39}$ is independently —NHC=(O)NHNH$_2$. In embodiments, R$^{39}$ is independently —NHC=(O) NH$_2$. In embodiments, R$^{39}$ is independently —NHSO$_2$H. In embodiments, R$^{39}$ is independently —NHC=(O)H. In embodiments, R$^{39}$ is independently —NHC(O)—OH. In embodiments, R$^{39}$ is independently —NHOH. In embodiments, R$^{39}$ is independently —OCF$_3$. In embodiments, R$^{39}$ is independently —OCHF$_2$. In embodiments, R$^{39}$ is independently —CCl$_3$. In embodiments, R$^{39}$ is independently —CBr$_3$. In embodiments, R$^{39}$ is independently —CI$_3$. In embodiments, R$^{39}$ is independently —F. In embodiments, R$^{39}$ is independently —Cl. In embodiments, R$^{39}$ is independently —Br. In embodiments, R$^{39}$ is independently —I. In embodiments, R$^{39}$ is independently R$^{40}$-substituted C$_1$-C$_4$ alkyl. In embodiments, R$^{39}$ is independently R$^{40}$-substituted 2 to 4 membered heteroalkyl. In embodiments, R$^{39}$ is independently R$^{40}$-substituted C$_3$-C$_6$ cycloalkyl. In embodiments, R$^{39}$ is independently R$^{40}$-substituted 3 to 6 membered heterocycloalkyl. In embodiments, R$^{39}$ is independently R$^{40}$-substituted phenyl. In embodiments, R$^{39}$ is independently R$^{40}$-substituted 5 to 6 membered heteroaryl. In embodiments, R$^{39}$ is independently unsubstituted C$_1$-C$_4$ alkyl. In embodiments, R$^{39}$ is independently unsubstituted 2 to 4 membered heteroalkyl. In embodiments, R$^{39}$ is independently unsubstituted C$_3$-C$_6$ cycloalkyl. In embodiments, R$^{39}$ is independently unsubstituted 3 to 6 membered heterocycloalkyl. In embodiments, R$^{39}$ is independently unsubstituted phenyl. In embodiments, R$^{39}$ is independently unsubstituted 5 to 6 membered heteroaryl.

In embodiments, R$^8$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

In embodiments, R$^8$ is independently hydrogen, —CF$_3$, —CN, —COOH, —CONH$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl. In embodiments, R$^8$ is independently an R$^{41}$-substituted or unsubstituted C$_1$-C$_4$ alkyl, R$^{41}$-substituted or unsubstituted 2 to 4 membered heteroalkyl, R$^{41}$-substituted or unsubstituted C$_3$-C$_6$ cycloalkyl, R$^{41}$-substituted or unsubstituted 3 to 6 membered heterocycloalkyl, R$^{41}$-substituted or unsubstituted phenyl, or R$^{41}$ substituted or unsubstituted 5 to 6 membered heteroaryl. In embodiments, R$^8$ is independently an unsubstituted C$_1$-C$_4$ alkyl, unsubstituted 2 to 4 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. In embodiments, R$^8$ is independently an unsubstituted C$_1$-C$_4$ alkyl. In embodiments, R$^8$ is independently an unsubstituted methyl. In embodiments, R$^8$ is independently an unsubstituted ethyl. In embodiments, R$^8$ is independently an unsubstituted isopropyl. In embodiments, R$^8$ is independently an unsubstituted tert-butyl. In embodiments, R$^8$ is independently hydrogen.

R$^{41}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, —S(O)$_2$CHCH$_2$, —NHS(O)$_2$CHCH$_2$, R$^{42}$-substituted or unsubstituted alkyl, R$^{42}$-substituted or unsubstituted heteroalkyl, R$^{42}$-substituted or unsubstituted cycloalkyl, R$^{42}$ substituted or unsubstituted heterocycloalkyl, R$^{42}$-substituted or unsubstituted aryl, or R$^{42}$-substituted or unsubstituted heteroaryl.

In embodiments, R$^{41}$ is independently —NH$_2$. In embodiments, R$^{41}$ is independently —OH. In embodiments, R$^{41}$ is independently halogen. In embodiments, R$^{41}$ is independently —CN. In embodiments, $R^{41}$ is independently oxo. In embodiments, $R^{41}$ is independently —CF$_3$. In embodiments, $R^{41}$ is independently —COOH. In embodiments, $R^{41}$ is independently —CONH$_2$. In embodiments, $R^{41}$ is independently —NO$_2$. In embodiments, $R^{41}$ is independently —SH. In embodiments, $R^{41}$ is independently —SO$_3$H. In embodiments, $R^{41}$ is independently —SO$_4$H. In embodiments, $R^{41}$ is independently —SO$_2$NH$_2$. In embodiments, $R^{41}$ is independently —NHNH$_2$. In embodiments, $R^{41}$ is independently —ONH$_2$. In embodiments, $R^{41}$ is independently —NHC=(O)NHNH$_2$. In embodiments, $R^{41}$ is independently —NHC=(O) NH$_2$. In embodiments, $R^{41}$ is independently —NHSO$_2$H. In embodiments, $R^{41}$ is independently —NHC=(O)H. In embodiments, $R^{41}$ is independently —NHC(O)—OH. In embodiments, $R^{41}$ is independently —NHOH. In embodiments, $R^{41}$ is independently —OCF$_3$. In embodiments, $R^{41}$ is independently —OCHF$_2$. In embodiments, $R^{41}$ is independently —CCl$_3$. In embodiments, $R^{41}$ is independently —CBr$_3$. In embodiments, $R^{41}$ is independently —CI$_3$. In embodiments, $R^{41}$ is independently —F. In embodiments, $R^{41}$ is independently —Cl. In embodiments, $R^{41}$ is independently —Br. In embodiments, $R^{41}$ is independently —I. In embodiments, $R^{41}$ is independently $R^{42}$-substituted C$_1$-C$_4$ alkyl. In embodiments, $R^{41}$ is independently $R^{42}$-substituted 2 to 4 membered heteroalkyl. In embodiments, $R^{41}$ is independently $R^{42}$-substituted C$_3$-C$_6$ cycloalkyl. In embodiments, $R^{41}$ is independently $R^{42}$-substituted 3 to 6 membered heterocycloalkyl. In embodiments, $R^{41}$ is independently $R^{42}$-substituted phenyl. In embodiments, $R^{41}$ is independently $R^{42}$-substituted 5 to 6 membered heteroaryl. In embodiments, $R^{41}$ is independently unsubstituted C$_1$-C$_4$ alkyl. In embodiments, $R^{41}$ is independently unsubstituted 2 to 4 membered heteroalkyl. In embodiments, $R^{41}$ is independently unsubstituted C$_3$-C$_6$ cycloalkyl. In embodiments, $R^{41}$ is independently unsubstituted 3 to 6 membered heterocycloalkyl. In embodiments, $R^{41}$ is independently unsubstituted phenyl. In embodiments, $R^{41}$ is independently unsubstituted 5 to 6 membered heteroaryl.

$R^{42}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —S(O)$_2$CHCH$_2$, —NHS(O)$_2$CHCH$_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In embodiments, $R^{42}$ is independently —NH$_2$. In embodiments, $R^{42}$ is independently —OH. In embodiments, $R^{42}$ is independently halogen. In embodiments, $R^{42}$ is independently —CN. In embodiments, $R^{42}$ is independently oxo. In embodiments, $R^{42}$ is independently —CF$_3$. In embodiments, $R^{42}$ is independently —COOH. In embodiments, $R^{42}$ is independently —CONH$_2$. In embodiments, $R^{42}$ is independently —NO$_2$. In embodiments, $R^{42}$ is independently —SH. In embodiments, $R^{42}$ is independently —SO$_3$H. In embodiments, $R^{42}$ is independently —SO$_4$H. In embodiments, $R^{42}$ is independently —SO$_2$NH$_2$. In embodiments, $R^{42}$ is independently —NHNH$_2$. In embodiments, $R^{42}$ is independently —ONH$_2$. In embodiments, $R^{42}$ is independently —NHC=(O)NHNH$_2$. In embodiments, $R^{42}$ is independently —NHC=(O) NH$_2$. In embodiments, $R^{42}$ is independently —NHSO$_2$H. In embodiments, $R^{42}$ is independently —NHC=(O)H. In embodiments, $R^{42}$ is independently —NHC(O)—OH. In embodiments, $R^{42}$ is independently —NHOH. In embodiments, $R^{42}$ is independently —OCF$_3$. In embodiments, $R^{42}$ is independently —OCHF$_2$. In embodiments, $R^{42}$ is independently —CCl$_3$. In embodiments, $R^{42}$ is independently —CBr$_3$. In embodiments, $R^{42}$ is independently —CI$_3$. In embodiments, $R^{42}$ is independently —F. In embodiments, $R^{42}$ is independently —Cl. In embodiments, $R^{42}$ is independently —Br. In embodiments, $R^{42}$ is independently —I. In embodiments, $R^{42}$ is independently $R^{43}$-substituted C$_1$-C$_4$ alkyl. In embodiments, $R^{42}$ is independently $R^{43}$-substituted 2 to 4 membered heteroalkyl. In embodiments, $R^{42}$ is independently $R^{43}$-substituted C$_3$-C$_6$ cycloalkyl. In embodiments, $R^{42}$ is independently $R^{43}$-substituted 3 to 6 membered heterocycloalkyl. In embodiments, $R^{42}$ is independently $R^{43}$-substituted phenyl. In embodiments, $R^{42}$ is independently $R^{43}$-substituted 5 to 6 membered heteroaryl. In embodiments, $R^{42}$ is independently unsubstituted C$_1$-C$_4$ alkyl. In embodiments, $R^{42}$ is independently unsubstituted 2 to 4 membered heteroalkyl. In embodiments, $R^{42}$ is independently unsubstituted C$_3$-C$_6$ cycloalkyl. In embodiments, $R^{42}$ is independently unsubstituted 3 to 6 membered heterocycloalkyl. In embodiments, $R^{42}$ is independently unsubstituted phenyl. In embodiments, $R^{42}$ is independently unsubstituted 5 to 6 membered heteroaryl.

In embodiments, $R^9$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

In embodiments, $R^9$ is independently hydrogen, —CF$_3$, —CN, —COOH, —CONH$_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl. In embodiments, $R^9$ is independently an $R^{44}$-substituted or unsubstituted C$_1$-C$_4$ alkyl, $R^{44}$-substituted or unsubstituted 2 to 4 membered heteroalkyl, $R^{44}$-substituted or unsubstituted C$_3$-C$_6$ cycloalkyl, $R^{44}$-substituted 3 to 6 membered heterocycloalkyl, $R^{44}$-substituted or unsubstituted phenyl, or $R^{44}$-substituted or unsubstituted 5 to 6 membered heteroaryl. In embodiments, $R^9$ is independently an unsubstituted C$_1$-C$_4$ alkyl, unsubstituted 2 to 4 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. In embodiments, $R^9$ is independently an unsubstituted C$_1$-C$_4$ alkyl. In embodiments, $R^9$ is independently an unsubstituted methyl. In embodiments, $R^9$ is independently an unsubstituted ethyl. In embodiments, $R^9$ is independently an unsubstituted isopropyl. In embodiments, $R^9$ is independently an unsubstituted tert-butyl. In embodiments, $R^9$ is independently hydrogen.

$R^{44}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{45}$-substituted or unsubstituted alkyl, $R^{45}$-substituted or unsubstituted heteroalkyl, $R^{45}$-substituted or unsubstituted cycloalkyl, $R^{45}$ substituted or unsubstituted heterocycloalkyl, $R^{45}$-substituted or unsubstituted aryl, or $R^{45}$-substituted or unsubstituted heteroaryl.

In embodiments, $R^{44}$ is independently —$NH_2$. In embodiments, $R^{44}$ is independently —OH. In embodiments, $R^{44}$ is independently halogen. In embodiments, $R^{44}$ is independently —CN. In embodiments, $R^{44}$ is independently oxo. In embodiments, $R^{44}$ is independently —$CF_3$. In embodiments, $R^{44}$ is independently —COOH. In embodiments, $R^{44}$ is independently —$CONH_2$. In embodiments, $R^{44}$ is independently —$NO_2$. In embodiments, $R^{44}$ is independently —SH. In embodiments, $R^{44}$ is independently —$SO_3H$. In embodiments, $R^{44}$ is independently —$SO_4H$. In embodiments, $R^{44}$ is independently —$SO_2NH_2$. In embodiments, $R^{44}$ is independently —$NHNH_2$. In embodiments, $R^{44}$ is independently —$ONH_2$. In embodiments, $R^{44}$ is independently —NHC=(O)$NHNH_2$. In embodiments, $R^{44}$ is independently —NHC=(O) $NH_2$. In embodiments, $R^{44}$ is independently —$NHSO_2H$. In embodiments, $R^{44}$ is independently —NHC=(O)H. In embodiments, $R^{44}$ is independently —NHC(O)—OH. In embodiments, $R^{44}$ is independently —NHOH. In embodiments, $R^{44}$ is independently —$OCF_3$. In embodiments, $R^{44}$ is independently —$OCHF_2$. In embodiments, $R^{44}$ is independently —$CCl_3$. In embodiments, $R^{44}$ is independently —$CBr_3$. In embodiments, $R^{44}$ is independently —$CI_3$. In embodiments, $R^{44}$ is independently —F. In embodiments, $R^{44}$ is independently —Cl. In embodiments, $R^{44}$ is independently —Br. In embodiments, $R^{44}$ is independently —I. In embodiments, $R^{44}$ is independently $R^{45}$-substituted $C_1$-$C_4$ alkyl. In embodiments, $R^{44}$ is independently $R^{45}$-substituted 2 to 4 membered heteroalkyl. In embodiments, $R^{44}$ is independently $R^{45}$-substituted $C_3$-$C_6$ cycloalkyl. In embodiments, $R^{44}$ is independently $R^{45}$-substituted 3 to 6 membered heterocycloalkyl. In embodiments, $R^{44}$ is independently $R^{45}$-substituted phenyl. In embodiments, $R^{44}$ is independently $R^{45}$-substituted 5 to 6 membered heteroaryl. In embodiments, $R^{44}$ is independently unsubstituted $C_1$-$C_4$ alkyl. In embodiments, $R^{44}$ is independently unsubstituted 2 to 4 membered heteroalkyl. In embodiments, $R^{44}$ is independently unsubstituted $C_3$-$C_6$ cycloalkyl. In embodiments, $R^{44}$ is independently unsubstituted 3 to 6 membered heterocycloalkyl. In embodiments, $R^{44}$ is independently unsubstituted phenyl. In embodiments, $R^{44}$ is independently unsubstituted 5 to 6 membered heteroaryl.

$R^{45}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

In embodiments, $R^{45}$ is independently —$NH_2$. In embodiments, $R^{45}$ is independently —OH. In embodiments, $R^{45}$ is independently halogen. In embodiments, $R^{45}$ is independently —CN. In embodiments, $R^{45}$ is independently oxo. In embodiments, $R^{45}$ is independently —$CF_3$. In embodiments, $R^{45}$ is independently —COOH. In embodiments, $R^{45}$ is independently —$CONH_2$. In embodiments, $R^{45}$ is independently —$NO_2$. In embodiments, $R^{45}$ is independently —SH. In embodiments, $R^{45}$ is independently —$SO_3H$. In embodiments, $R^{45}$ is independently —$SO_4H$. In embodiments, $R^{45}$ is independently —$SO_2NH_2$. In embodiments, $R^{45}$ is independently —$NHNH_2$. In embodiments, $R^{45}$ is independently —$ONH_2$. In embodiments, $R^{45}$ is independently —NHC=(O)$NHNH_2$. In embodiments, $R^{45}$ is independently —NHC=(O) $NH_2$. In embodiments, $R^{45}$ is independently —$NHSO_2H$. In embodiments, $R^{45}$ is independently —NHC=(O)H. In embodiments, $R^{45}$ is independently —NHC(O)—OH. In embodiments, $R^{45}$ is independently —NHOH. In embodiments, $R^{45}$ is independently —$OCF_3$. In embodiments, $R^{45}$ is independently —$OCHF_2$. In embodiments, $R^{45}$ is independently —$CCl_3$. In embodiments, $R^{45}$ is independently —$CBr_3$. In embodiments, $R^{45}$ is independently —$CI_3$. In embodiments, $R^{45}$ is independently —F. In embodiments, $R^{45}$ is independently —Cl. In embodiments, $R^{45}$ is independently —Br. In embodiments, $R^{45}$ is independently —I. In embodiments, $R^{45}$ is independently $R^{46}$-substituted $C_1$-$C_4$ alkyl. In embodiments, $R^{45}$ is independently $R^{46}$-substituted 2 to 4 membered heteroalkyl. In embodiments, $R^{45}$ is independently $R^{46}$-substituted $C_3$-$C_6$ cycloalkyl. In embodiments, $R^{45}$ is independently $R^{46}$-substituted 3 to 6 membered heterocycloalkyl. In embodiments, $R^{45}$ is independently $R^{46}$-substituted phenyl. In embodiments, $R^{45}$ is independently $R^{46}$-substituted 5 to 6 membered heteroaryl. In embodiments, $R^{45}$ is independently unsubstituted $C_1$-$C_4$ alkyl. In embodiments, $R^{45}$ is independently unsubstituted 2 to 4 membered heteroalkyl. In embodiments, $R^{45}$ is independently unsubstituted $C_3$-$C_6$ cycloalkyl. In embodiments, $R^{45}$ is independently unsubstituted 3 to 6 membered heterocycloalkyl. In embodiments, $R^{45}$ is independently unsubstituted phenyl. In embodiments, $R^{45}$ is independently unsubstituted 5 to 6 membered heteroaryl.

In embodiments, $R^{10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl.

In embodiments, $R^{10}$ is independently hydrogen, —$CF_3$, —CN, —COOH, —$CONH_2$, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl. In embodiments, $R^{10}$ is independently an $R^{47}$-substituted or unsubstituted $C_1$-$C_4$ alkyl, $R^{47}$-substituted or unsubstituted 2 to 4 membered heteroalkyl, $R^{47}$-substituted or unsubstituted $C_3$-$C_6$ cycloalkyl, $R^{47}$-substituted or unsubstituted 3 to 6 membered heterocycloalkyl, $R^{47}$-substituted or unsubstituted phenyl, or $R^{47}$ substituted or unsubstituted 5 to 6 membered heteroaryl. In embodiments, $R^{10}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{10}$ is independently an unsubstituted $C_1$-$C_4$ alkyl. In embodiments, $R^{10}$ is independently an unsubstituted methyl. In embodiments, $R^0$ is independently an unsubstituted ethyl. In embodiments, $R^{10}$ is independently an unsubstituted isopropyl. In embodiments, $R^{10}$ is independently an unsubstituted tert-butyl. In embodiments, $R^0$ is independently hydrogen.

$R^{47}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —OCF$_3$, —OCHF$_2$, R$^{48}$-substituted or unsubstituted alkyl, R$^{48}$-substituted or unsubstituted heteroalkyl, R$^{48}$-substituted or unsubstituted cycloalkyl, R$^{48}$ substituted or unsubstituted heterocycloalkyl, R$^{48}$-substituted or unsubstituted aryl, or R$^{48}$-substituted or unsubstituted heteroaryl.

In embodiments, R$^{47}$ is independently —NH$_2$. In embodiments, R$^{47}$ is independently —OH. In embodiments, R$^{47}$ is independently halogen. In embodiments, R$^{47}$ is independently —CN. In embodiments, R$^{47}$ is independently oxo. In embodiments, R$^{47}$ is independently —CF$_3$. In embodiments, R$^{47}$ is independently —COOH. In embodiments, R$^{47}$ is independently —CONH$_2$. In embodiments, R$^{47}$ is independently —NO$_2$. In embodiments, R$^{47}$ is independently —SH. In embodiments, R$^{47}$ is independently —SO$_3$H. In embodiments, R$^{47}$ is independently —SO$_4$H. In embodiments, R$^{47}$ is independently —SO$_2$NH$_2$. In embodiments, R$^{47}$ is independently —NHNH$_2$. In embodiments, R$^{47}$ is independently —ONH$_2$. In embodiments, R$^{47}$ is independently —NHC=(O)NHNH$_2$. In embodiments, R$^{47}$ is independently —NHC=(O) NH$_2$. In embodiments, R$^{47}$ is independently —NHSO$_2$H. In embodiments, R$^{47}$ is independently —NHC=(O)H. In embodiments, R$^{47}$ is independently —NHC(O)—OH. In embodiments, R$^{47}$ is independently —NHOH. In embodiments, R$^{47}$ is independently —OCF$_3$. In embodiments, R$^{47}$ is independently —OCHF$_2$. In embodiments, R$^{47}$ is independently —CCl$_3$. In embodiments, R$^{47}$ is independently —CBr$_3$. In embodiments, R$^{47}$ is independently —CI$_3$. In embodiments, R$^{47}$ is independently —F. In embodiments, R$^{47}$ is independently —Cl. In embodiments, R$^{47}$ is independently —Br. In embodiments, R$^{47}$ is independently —I. In embodiments, R$^{47}$ is independently R$^{48}$-substituted C$_1$-C$_4$ alkyl. In embodiments, R$^{47}$ is independently R$^{48}$-substituted 2 to 4 membered heteroalkyl. In embodiments, R$^{47}$ is independently R$^{48}$-substituted C$_3$-C$_6$ cycloalkyl. In embodiments, R$^{47}$ is independently R$^{48}$-substituted 3 to 6 membered heterocycloalkyl. In embodiments, R$^{47}$ is independently R$^{48}$-substituted phenyl. In embodiments, R$^{47}$ is independently R$^{48}$-substituted 5 to 6 membered heteroaryl. In embodiments, R$^{47}$ is independently unsubstituted C$_1$-C$_4$ alkyl. In embodiments, R$^{47}$ is independently unsubstituted 2 to 4 membered heteroalkyl. In embodiments, R$^{47}$ is independently unsubstituted C$_3$-C$_6$ cycloalkyl. In embodiments, R$^{47}$ is independently unsubstituted 3 to 6 membered heterocycloalkyl. In embodiments, R$^{47}$ is independently unsubstituted phenyl. In embodiments, R$^{47}$ is independently unsubstituted 5 to 6 membered heteroaryl.

R$^{48}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{49}$-substituted or unsubstituted alkyl, R$^{49}$-substituted or unsubstituted heteroalkyl, R$^{49}$-substituted or unsubstituted cycloalkyl, R$^{49}$-substituted or unsubstituted heterocycloalkyl, R$^{49}$-substituted or unsubstituted aryl, or R$^{49}$-substituted or unsubstituted heteroaryl.

In embodiments, R$^{48}$ is independently —NH$_2$. In embodiments, R$^{48}$ is independently —OH. In embodiments, R$^{48}$ is independently halogen. In embodiments, R$^{48}$ is independently —CN. In embodiments, R$^{48}$ is independently oxo. In embodiments, R$^{48}$ is independently —CF$_3$. In embodiments, R$^{48}$ is independently —COOH. In embodiments, R$^{48}$ is independently —CONH$_2$. In embodiments, R$^{48}$ is independently —NO$_2$. In embodiments, R$^{48}$ is independently —SH. In embodiments, R$^{48}$ is independently —SO$_3$H. In embodiments, R$^{48}$ is independently —SO$_4$H. In embodiments, R$^{48}$ is independently —SO$_2$NH$_2$. In embodiments, R$^{48}$ is independently —NHNH$_2$. In embodiments, R$^{48}$ is independently —ONH$_2$. In embodiments, R$^{48}$ is independently —NHC=(O)NHNH$_2$. In embodiments, R$^{48}$ is independently —NHC=(O) NH$_2$. In embodiments, R$^{48}$ is independently —NHSO$_2$H. In embodiments, R$^{48}$ is independently —NHC=(O)H. In embodiments, R$^{48}$ is independently —NHC(O)—OH. In embodiments, R$^{48}$ is independently —NHOH. In embodiments, R$^{48}$ is independently —OCF$_3$. In embodiments, R$^{48}$ is independently —OCHF$_2$. In embodiments, R$^{48}$ is independently —CCl$_3$. In embodiments, R$^{48}$ is independently —CBr$_3$. In embodiments, R$^{48}$ is independently —CI$_3$. In embodiments, R$^{48}$ is independently —F. In embodiments, R$^{48}$ is independently —Cl. In embodiments, R$^{48}$ is independently —Br. In embodiments, R$^{48}$ is independently —I. In embodiments, R$^{48}$ is independently R$^{49}$-substituted C$_1$-C$_4$ alkyl. In embodiments, R$^{48}$ is independently R$^{49}$-substituted 2 to 4 membered heteroalkyl. In embodiments, R$^{48}$ is independently R$^{49}$-substituted C$_3$-C$_6$ cycloalkyl. In embodiments, R$^{48}$ is independently R$^{49}$-substituted 3 to 6 membered heterocycloalkyl. In embodiments, R$^{48}$ is independently R$^{49}$-substituted phenyl. In embodiments, R$^{48}$ is independently R$^{49}$-substituted 5 to 6 membered heteroaryl. In embodiments, R$^{48}$ is independently unsubstituted C$_1$-C$_4$ alkyl. In embodiments, R$^{48}$ is independently unsubstituted 2 to 4 membered heteroalkyl. In embodiments, R$^{48}$ is independently unsubstituted C$_3$-C$_6$ cycloalkyl. In embodiments, R$^{48}$ is independently unsubstituted 3 to 6 membered heterocycloalkyl. In embodiments, R$^{48}$ is independently unsubstituted phenyl. In embodiments, R$^{48}$ is independently unsubstituted 5 to 6 membered heteroaryl.

In embodiments, R$^{11}$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{50}$-substituted or unsubstituted alkyl, R$^{50}$-substituted or unsubstituted heteroalkyl, R$^{50}$-substituted or unsubstituted cycloalkyl, R$^{50}$-substituted or unsubstituted heterocycloalkyl, R$^{50}$-substituted or unsubstituted aryl, or R$^{50}$-substituted or unsubstituted heteroaryl.

In embodiments, R$^{11}$ is independently hydrogen, —CF$_3$, —CN, —COOH, —CONH$_2$, R$^{50}$-substituted or unsubstituted alkyl, R$^{50}$-substituted or unsubstituted heteroalkyl, R$^{50}$-substituted or unsubstituted cycloalkyl, R$^{50}$-substituted or unsubstituted heterocycloalkyl, R$^{50}$-substituted or unsubstituted aryl, or R$^{50}$-substituted or unsubstituted heteroaryl. In embodiments, R$^{11}$ is independently an R$^{50}$-substituted or unsubstituted C$_1$-C$_4$ alkyl, R$^{50}$-substituted or unsubstituted 2 to 4 membered heteroalkyl, R$^{50}$-substituted or unsubstituted C$_3$-C$_6$ cycloalkyl, R$^{50}$-substituted or unsubstituted 3 to 6 membered heterocycloalkyl, R$^{50}$-substituted or unsubstituted phenyl, or R$^{50}$-substituted or unsubstituted 5 to 6 membered heteroaryl. In embodiments, R$^{11}$ is independently an unsubstituted C$_1$-C$_4$ alkyl, unsubstituted 2 to 4 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. In embodiments, R$^{11}$ is independently an unsubstituted C$_1$-C$_4$ alkyl. In embodiments, R$^{11}$ is independently an unsubstituted methyl. In embodiments, R$^{11}$ is independently an unsubstituted ethyl. In embodiments, R$^{11}$ is independently an unsubstituted isopropyl. In embodiments, R$^{11}$ is independently an unsubstituted tert-butyl. In embodiments, R$^{11}$ is independently hydrogen. In embodiments, R$^{11}$ is independently an $R^{50}$-substituted or unsubstituted $C_1$-$C_4$ alkyl. In embodiments, $R^{11}$ is independently an $R^{50}$-substituted or unsubstituted 2 to 4 membered heteroalkyl. In embodiments, $R^{11}$ is independently an $R^{50}$-substituted or unsubstituted $C_3$-$C_6$ cycloalkyl. In embodiments, $R^{11}$ is independently an $R^{50}$-substituted or unsubstituted 3 to 6 membered heterocycloalkyl. In embodiments, $R^{11}$ is independently an $R^{50}$-substituted or unsubstituted phenyl. In embodiments, $R^{11}$ is independently an $R^{50}$-substituted or unsubstituted 5 to 6 membered heteroaryl. In embodiments, $R^{11}$ is independently an unsubstituted $C_1$-$C_4$ alkyl. In embodiments, $R^{11}$ is independently an unsubstituted 2 to 4 membered heteroalkyl. In embodiments, $R^{11}$ is independently an unsubstituted $C_3$-$C_6$ cycloalkyl. In embodiments, $R^{11}$ is independently an unsubstituted 3 to 6 membered heterocycloalkyl. In embodiments, $R^{11}$ is independently an unsubstituted phenyl. In embodiments, $R^{11}$ is independently an unsubstituted 5 to 6 membered heteroaryl.

$R^{50}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{51}$-substituted or unsubstituted alkyl, $R^{51}$-substituted or unsubstituted heteroalkyl, $R^{51}$-substituted or unsubstituted cycloalkyl, $R^{51}$-substituted or unsubstituted heterocycloalkyl, $R^{51}$-substituted or unsubstituted aryl, or $R^{s1}$-substituted or unsubstituted heteroaryl.

$R^{51}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl.

In embodiments, $R^{12}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl.

In embodiments, $R^{12}$ is independently hydrogen, —$CF_3$, —CN, —COOH, —$CONH_2$, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl. In embodiments, $R^{12}$ is independently an $R^{53}$-substituted or unsubstituted $C_1$-$C_4$ alkyl, $R^{53}$-substituted or unsubstituted 2 to 4 membered heteroalkyl, $R^{53}$-substituted or unsubstituted $C_3$-$C_6$ cycloalkyl, $R^{53}$-substituted or unsubstituted 3 to 6 membered heterocycloalkyl, $R^{53}$-substituted or unsubstituted phenyl, or $R^{53}$-substituted or unsubstituted 5 to 6 membered heteroaryl. In embodiments, $R^{12}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{12}$ is independently an unsubstituted $C_1$-$C_4$ alkyl. In embodiments, $R^{12}$ is independently an unsubstituted methyl. In embodiments, $R^{12}$ is independently an unsubstituted ethyl. In embodiments, $R^{12}$ is independently an unsubstituted isopropyl. In embodiments, $R^{12}$ is independently an unsubstituted tert-butyl. In embodiments, $R^{12}$ is independently hydrogen. In embodiments, $R^{12}$ is independently an $R^{53}$-substituted or unsubstituted $C_1$-$C_4$ alkyl. In embodiments, $R^{12}$ is independently an $R^{53}$-substituted or unsubstituted 2 to 4 membered heteroalkyl. In embodiments, $R^{12}$ is independently an $R^{53}$-substituted or unsubstituted $C_3$-$C_6$ cycloalkyl. In embodiments, $R^{12}$ is independently an $R^{53}$-substituted or unsubstituted 3 to 6 membered heterocycloalkyl. In embodiments, $R^{12}$ is independently an $R^{53}$-substituted or unsubstituted phenyl. In embodiments, $R^{12}$ is independently an $R^{53}$-substituted or unsubstituted 5 to 6 membered heteroaryl. In embodiments, $R^{12}$ is independently an unsubstituted $C_1$-$C_4$ alkyl. In embodiments, $R^{12}$ is independently an unsubstituted 2 to 4 membered heteroalkyl. In embodiments, $R^{12}$ is independently an unsubstituted $C_3$-$C_6$ cycloalkyl. In embodiments, $R^{12}$ is independently an unsubstituted 3 to 6 membered heterocycloalkyl. In embodiments, $R^{12}$ is independently an unsubstituted phenyl. In embodiments, $R^{12}$ is independently an unsubstituted 5 to 6 membered heteroaryl.

$R^{53}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{54}$-substituted or unsubstituted alkyl, $R^{54}$-substituted or unsubstituted heteroalkyl, $R^{54}$-substituted or unsubstituted cycloalkyl, $R^{54}$-substituted or unsubstituted heterocycloalkyl, $R^{54}$-substituted or unsubstituted aryl, or $R^{54}$-substituted or unsubstituted heteroaryl.

$R^{54}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl.

In embodiments, $R^{13}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl.

In embodiments, $R^{13}$ is independently hydrogen, —$CF_3$, —CN, —COOH, —$CONH_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl. In embodiments, $R^{13}$ is independently an $R^{56}$-substituted or unsubstituted $C_1$-$C_4$ alkyl, $R^{56}$-substituted or unsubstituted 2 to 4 membered heteroalkyl, $R^{56}$-substituted or unsubstituted $C_3$-$C_6$ cycloalkyl, $R^{56}$-substituted or unsubstituted 3 to 6 membered heterocycloalkyl, $R^{56}$-substituted or unsubstituted phenyl, or $R^{56}$-substituted or unsubstituted 5 to 6 membered heteroaryl. In embodiments, $R^{13}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{13}$ is independently an unsubstituted $C_1$-$C_4$ alkyl. In embodiments, $R^{13}$ is independently an unsubstituted methyl. In embodiments, $R^{13}$ is independently an unsubstituted ethyl. In embodiments, $R^{13}$ is independently an unsubstituted isopropyl. In embodiments, $R^{13}$ is independently an unsubstituted tert-butyl. In embodiments, $R^{13}$ is independently hydrogen. In embodiments, $R^{13}$ is independently an $R^{56}$-substituted or unsubstituted $C_1$-$C_4$ alkyl. In embodiments, $R^{13}$ is independently an $R^{56}$-substituted or unsubstituted 2 to 4 membered heteroalkyl. In embodiments, $R^{13}$ is independently an $R^{56}$-substituted or unsubstituted $C_3$-$C_6$ cycloalkyl. In embodiments, $R^{13}$ is independently an $R^{56}$-substituted or unsubstituted 3 to 6 membered heterocycloalkyl. In embodiments, $R^{13}$ is independently an $R^{56}$-substituted or unsubstituted phenyl. In embodiments, $R^{13}$ is independently an $R^{56}$-substituted or unsubstituted 5 to 6 membered heteroaryl. In embodiments, $R^{13}$ is independently an unsubstituted $C_1$-$C_4$ alkyl. In embodiments, $R^{13}$ is independently an unsubstituted 2 to 4 membered heteroalkyl. In embodiments, $R^{13}$ is independently an unsubstituted $C_3$-$C_6$ cycloalkyl. In embodiments, $R^{13}$ is independently an unsubstituted 3 to 6 membered heterocycloalkyl. In embodiments, $R^{13}$ is independently an unsubstituted phenyl. In embodiments, $R^{13}$ is independently an unsubstituted 5 to 6 membered heteroaryl.

$R^{56}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl.

$R^{57}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl.

In embodiments, $R^7$, $R^8$, $R^9$, $R^{10}$, $R^{11}$, $R^{12}$, and $R^{13}$ are independently hydrogen. In embodiments, $R^7$, $R^8$, $R^9$, $R^{10}$, $R^{11}$, $R^{12}$, and $R^{13}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$. In embodiments, $R^7$, $R^8$, $R^9$, $R^{10}$, $R^{11}$, $R^{12}$, and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$, $R^8$, $R^9$, $R^{10}$, $R^{11}$, $R^{12}$, and $R^{13}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^7$, $R^8$, $R^9$, $R^{10}$, $R^{11}$, $R^{12}$, and $R^{13}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_7$ cycloalkyl, substituted or unsubstituted 3 to 7 membered heterocycloalkyl, substituted or unsubstituted $C_6$-$C_{10}$ aryl, or substituted or unsubstituted 5 to 9 membered heteroaryl. In embodiments, $R^{11}$, $R^{12}$, and $R^{13}$ are independently hydrogen. In embodiments, $R^{11}$, $R^{12}$, and $R^{13}$ are independently hydrogen, substituted or unsubstituted $C_1$-$C_8$ alkyl, substituted or unsubstituted 2 to 8 membered heteroalkyl, substituted or unsubstituted $C_3$-$C_7$ cycloalkyl, substituted or unsubstituted 3 to 7 membered heterocycloalkyl, substituted or unsubstituted $C_6$-$C_{10}$ aryl, or substituted or unsubstituted 5 to 9 membered heteroaryl. In embodiments, $R^{11}$, $R^{12}$, and $R^{13}$ are independently hydrogen, unsubstituted $C_1$-$C_8$ alkyl, unsubstituted 2 to 8 membered heteroalkyl, unsubstituted $C_3$-$C_7$ cycloalkyl, unsubstituted 3 to 7 membered heterocycloalkyl, unsubstituted $C_6$-$C_{10}$ aryl, or unsubstituted 5 to 9 membered heteroaryl.

In embodiments, $L^1$ is a bond, —NH—, —$NR^{23}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is $L^2$-$L^3$-$L^4$-$L^5$. $L^2$ is connected directly to a monovalent rapamycin or a monovalent rapamycin analog. $L^2$ is a bond, —NH—, —$NR^{26}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^3$ is a bond, —NH—, —$NR^{29}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^4$ is a bond, —NH—, —$NR^{32}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^5$ is a bond, —NH—, —$NR^{35}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is a divalent linker including one or more amino acids. In embodiments, $L^1$ is a divalent linker consisting of amino acids. In embodiments, $L^1$ is a divalent linker including an amino acid analog. In embodiments, $L^1$ is a divalent linker including an amino acid mimetic. In embodiments, $L^1$ is a divalent linker consisting of amino acid analogs. In embodiments, $L^1$ is a divalent linker consisting of amino acid mimetics.

In embodiments, $L^2$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^2$ is substituted or unsubstituted 3 to 8 membered heteroalkylene. In embodiments, $L^2$ is —$CH_2CH_2OCH_2$—. In embodiments, $L^2$ is unsubstituted 3 to 8 membered heteroalkylene. In embodiments, $L^2$ is unsubstituted 3 to 6 membered heteroalkylene. In embodiments, $L^2$ is unsubstituted 3 to 5 membered heteroalkylene. In embodiments, $L^2$ is a divalent linker including one or more amino acids. In embodiments, $L^2$ is a divalent linker consisting of amino acids. In embodiments, $L^2$ is a divalent linker including an amino acid analog. In embodiments, $L^2$ is a divalent linker including an amino acid mimetic. In embodiments, $L^2$ is a divalent linker consisting of amino acid analogs. In embodiments, $L^2$ is a divalent linker consisting of amino acid mimetics.

In embodiments, $L^3$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^3$ is a substituted or unsubstituted 5 to 10 membered heteroarylene. In embodiments, $L^3$ is a bond. In embodiments, $L^3$ is a substituted or unsubstituted 5 to 6 membered heteroarylene. In embodiments, $L^3$ is a unsubstituted 5 to 6 membered heteroarylene. In embodiments, $L^3$ is unsubstituted divalent triazole. In embodiments, $L^3$ is unsubstituted divalent 1H-1,2,3-triazole. In embodiments, $L^3$ is unsubstituted divalent 2H-1,2,3-triazole. In embodiments, $L^3$ is a divalent linker including one or more amino acids. In embodiments, $L^3$ is a divalent linker consisting of amino acids. In embodiments, $L^3$ is a divalent linker including an amino acid analog. In embodiments, $L^3$ is a divalent linker including an amino acid mimetic. In embodiments, $L^3$ is a divalent linker consisting of amino acid analogs. In embodiments, $L^3$ is a divalent linker consisting of amino acid mimetics.

In embodiments, $L^4$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^4$ is a substituted or unsubstituted 2 to 12 membered heteroalkylene. In embodiments, $L^4$ is a substituted or unsubstituted 2 to 32 membered heteroalkylene. In embodiments, $L^4$ is a bond. In embodiments, $L^4$ is a divalent linker including one or more amino acids. In embodiments, $L^4$ is a divalent linker consisting of amino acids. In embodiments, $L^4$ is a divalent linker including an amino acid analog. In embodiments, $L^4$ is a divalent linker including an amino acid mimetic. In embodiments, $L^4$ is a divalent linker consisting of amino acid analogs. In embodiments, $L^4$ is a divalent linker consisting of amino acid mimetics.

In embodiments, $L^5$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^5$ is a substituted or unsubstituted 2 to 12 membered heteroalkylene. In embodiments, $L^5$ is a substituted or unsubstituted 2 to 32 membered heteroalkylene. In embodiments, $L^5$ is a bond. In embodiments, $L^5$ is a divalent linker including one or more amino acids. In embodiments, $L^5$ is a divalent linker consisting of amino acids. In embodiments, $L^5$ is a divalent linker including an amino acid analog. In embodiments, $L^5$ is a divalent linker including an amino acid mimetic. In embodiments, $L^5$ is a divalent linker consisting of amino acid analogs. In embodiments, $L^5$ is a divalent linker consisting of amino acid mimetics.

In embodiments, $L^5$ is a divalent oligomer of ethylene oxide. In embodiments, $L^5$ is a divalent polyethylene glycol. In embodiments, $L^5$ is a divalent oligomer of ethylene oxide having 2 to 30 linear atoms (carbon and oxygen) between the two termini connecting to the remainder of the compound. In embodiments, $L^5$ is a —$(CH_2)_4C(O)NH$—. In embodiments, $L^5$ is a 2 to 8 membered substituted heteroalkylene. In embodiments, $L^5$ is a 3 to 6 membered substituted heteroalkylene. In embodiments, $L^5$ is a 5 to 6 membered substituted heteroalkylene. In embodiments, $L^5$ is a 5 to 7 membered oxo substituted heteroalkylene. In embodiments, $L^5$ is an unsubstituted $C_1$-$C_6$ alkylene.

In embodiments, $L^4$ is a divalent oligomer of ethylene oxide. In embodiments, $L^4$ is a divalent polyethylene glycol. In embodiments, $L^4$ is a divalent oligomer of ethylene oxide having 2 to 30 linear atoms (carbon and oxygen) between the two termini connecting to the remainder of the compound. In embodiments, $L^4$ is —$(CH_2CH_2O)_bCH_2CH_2$— and b is an integer from 1 to 16. In embodiments, $L^4$ is —$(CH_2CH_2O)_bCH_2$— and b is an integer from 1 to 16. In embodiments, $L^4$ is —$(CH_2CH_2O)_b$— and b is an integer from 1 to 16. In embodiments, b is an integer from 2 to 15. In embodiments, b is an integer from 3 to 14. In embodiments, b is an integer from 4 to 12. In embodiments, b is an integer from 5 to 10. In embodiments, b is an integer from 5 to 8. In embodiments, b is an integer from 6 to 7.

In embodiments, $L^4$-$L^5$ is a 2 to 36 membered substituted heteroalkylene. In embodiments, $L^4$-$L^5$ is a 2 to 34 membered substituted heteroalkylene. In embodiments, $L^4$-$L^5$ is a 2 to 32 membered substituted heteroalkylene. In embodiments, $L^4$-$L^5$ is a 2 to 30 membered substituted heteroalkylene. In embodiments, $L^4$-$L^5$ is a 2 to 28 membered substituted heteroalkylene. In embodiments, $L^4$-$L^5$ is a 2 to 24 membered substituted heteroalkylene. In embodiments, $L^4$-$L^5$ is a 2 to 30 membered substituted heteroalkylene. In embodiments, $L^4$-$L^5$ is a 2 to 22 membered substituted heteroalkylene. In embodiments, $L^4$-$L^5$ is a 2 to 20 membered substituted heteroalkylene. In embodiments, $L^4$-$L^5$ is a 2 to 18 membered substituted heteroalkylene. In embodiments, $L^4$-$L^5$ is a 2 to 16 membered substituted heteroalkylene. In embodiments, $L^4$-$L^5$ is a 2 to 14 membered substituted heteroalkylene. In embodiments, $L^4$-$L^5$ is a 2 to 12 membered substituted heteroalkylene. In embodiments, $L^4$-$L^5$ is a 4 to 36 membered substituted heteroalkylene. In embodiments, $L^4$-$L^5$ is a 6 to 36 membered substituted heteroalkylene. In embodiments, $L^4$-$L^5$ is a 8 to 36 membered substituted heteroalkylene. In embodiments, $L^4$-$L^5$ is a 10 to 36 membered substituted heteroalkylene. In embodiments, $L^4$-$L^5$ is a 12 to 36 membered substituted heteroalkylene. In embodiments, $L^4$-$L^5$ is a 14 to 36 membered substituted heteroalkylene. In embodiments, $L^4$-$L^5$ is a 16 to 36 membered substituted heteroalkylene. In embodiments, $L^4$-$L^5$ is a 18 to 36 membered substituted heteroalkylene. In embodiments, $L^4$-$L^5$ is a 20 to 36 membered substituted heteroalkylene. In embodiments, $L^4$-$L^5$ is a 22 to 36 membered substituted heteroalkylene. In embodiments, $L^4$-$L^5$ is a 24 to 36 membered substituted heteroalkylene. In embodiments, $L^4$-$L^5$ is a 4 to 32 membered substituted heteroalkylene. In embodiments, $L^4$-$L^5$ is a 4 to 28 membered substituted heteroalkylene. In embodiments, $L^4$-$L^5$ is a 8 to 26 membered substituted heteroalkylene. In embodiments, $L^4$-$L^5$ is a 12 to 26 membered substituted heteroalkylene. In embodiments, $L^4$-$L^5$ is a 16 to 26 membered substituted heteroalkylene. In embodiments, $L^4$-$L^5$ is a 20 to 26 membered substituted heteroalkylene. In embodiments, $L^4$-$L^5$ is a 22 to 26 membered substituted heteroalkylene.

In embodiments, the linker is formed by a conjugation or bioconjugation reaction combining a first reactant moiety covalently bonded to the rapamycin or rapamycin analog and a second reactant moiety covalently bonded to the active site mTOR inhibitor. In such embodiments, the compound formed by such conjugation or bioconjugation reaction (including compounds as described herein) may be referred to as a conjugate.

In some embodiments, $L^1$ is $L^2$-$L^3$-$L^4$-$L^5$; $L^2$ is —$CH_2CH_2OCH_2$—; $L^3$ is 5 to 10 membered heteroarylene; $L^4$ is —$(CH_2CH_2O)_b$—; b is an integer from 2 to 8; $L^5$ is —$CH_2CH_2C$=$(O)NH(CH_2)_{b10}$—; and b10 is an integer from 1 to 6. In some embodiments, $L^1$ is $L^2$-$L^3$-$L^4$-$L^5$; $L^2$ is 2 to 8 membered heteroalkylene comprising at least one NH or O; $L^3$ is 5 to 10 membered heteroarylene; $L^4$ is —$[(CH_2)_{b11}O]_{b12}$—; b11 is an integer from 1 to 3; b12 is an integer from 1 to 8; $L^5$ is —$CH_2CH_2C$=$(O)NH(CH_2)_{b10}$—; and b10 is an integer from 1 to 6. In some embodiments, $L^1$ is $L^2$-$L^3$-$L^4$-$L^5$; $L^2$ is —$CH_2CH_2OCH_2$—; $L^3$ is 5 membered heteroarylene; $L^4$ is —$(CH_2CH_2O)_b$—; b is an integer from 4 to 8; and $L^5$ is —$CH_2CH_2C$=$(O)NH(CH_2)_4$. In some embodiments, $L^1$ is $L^2$-$L^3$-$L^4$-$L^5$; $L^2$ is —$CH_2CH_2OCH_2$—; $L^3$ is triazolylene; $L^4$ is —$(CH_2CH_2O)_b$—; b is an integer from 4 to 8; and $L^5$ is —$CH_2CH_2C$=$(O)NH(CH_2)_4$. In some embodiments, $L^1$ is $L^2$-$L^3$-$L^4$-$L^5$; $L^2$ is —$CH_2CH_2OCH_2$—; $L^3$ is 5 to 10 membered heteroarylene; $L^4$ is —$(CH_2)_b$—; b is an integer from 2 to 8; and $L^5$ is a bond.

Conjugates described herein may be synthesized using bioconjugate or conjugate chemistry. Conjugate chemistry includes coupling two molecules together to form an adduct. Conjugation may be a covalent modification. Currently favored classes of conjugate chemistry reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the bioconjugation reaction is a click chemistry reaction (Angewandte Chemie International Edition 40 (11): 2004-2021). In embodiments, the bioconjugation reaction is a Huisgen cyclization of azides. In embodiments, the bioconjugation reaction is a copper catalyzed Huisgen cyclization of azides.

Useful reactive functional groups used for conjugate chemistries herein include, for example:
 (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
 (b) hydroxyl groups which can be converted to esters, ethers, aldehydes, etc.
 (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
 (d) dienophile groups which are capable of participating in Diels-Alder reactions such as, for example, maleimido groups;
 (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
 (f) sulfonyl halide groups for subsequent reaction with amines, for example, to form sulfonamides;
 (g) thiol groups, which can be converted to disulfides, reacted with acyl halides, or bonded to metals such as gold;
 (h) amine or sulfhydryl groups, which can be, for example, acylated, alkylated or oxidized;
 (i) alkenes, which can undergo, for example, cycloadditions, acylation, Michael addition, etc;
 (j) epoxides, which can react with, for example, amines and hydroxyl compounds;
 (k) phosphoramidites and other standard functional groups useful in nucleic acid synthesis;
 (l) metal silicon oxide bonding; and
 (m) metal bonding to reactive phosphorus groups (e.g. phosphines) to form, for example, phosphate diester bonds.
 (n) azides coupled to alkynes using copper catalyzed cycloaddition click chemistry.

The reactive functional groups can be chosen such that they do not participate in, or interfere with, the chemical stability of the conjugate described herein. Alternatively, a reactive functional group can be protected from participating in the crosslinking reaction by the presence of a protecting group.

In some embodiments of the compounds provided herein, $L^1$ is independently $R^{23}$-substituted or unsubstituted alkylene, $R^{23}$-substituted or unsubstituted heteroalkylene, $R^{23}$-substituted or unsubstituted cycloalkylene, $R^{23}$-substituted or unsubstituted heterocycloalkylene, $R^{23}$-substituted or unsubstituted arylene, or $R^{23}$-substituted or unsubstituted heteroarylene.

In embodiments, $L^1$ is a bond, —NH—, —$NR^{23}$—, —S—, —O—, —C(O)—, —NHC(O)—, —C(O)NH—, —NHC(O)NH—, —NHC(NH)NH—, —C(S)—, $R^{23}$-substituted or unsubstituted $C_1$-$C_{20}$ alkylene, $R^{23}$-substituted or unsubstituted 2 to 20 membered heteroalkylene, $R^{23}$-substituted or unsubstituted $C_3$-$C_8$ cycloalkylene, $R^{23}$-substituted or unsubstituted 3 to 8 membered heterocycloalkylene, $R^{23}$-substituted or unsubstituted $C_6$-$C_{10}$ arylene, or $R^{23}$-substituted or unsubstituted 5 to 10 membered heteroarylene. In embodiments, $L^1$ is a bond. In embodiments, $L^1$ is —NH—. In embodiments, $L^1$ is —$NR^{23}$—. In embodiments, $L^1$ is —S—. In embodiments, $L^1$ is —O—. In embodiments, $L^1$ is —C(O)—. In embodiments, $L^1$ is —NHC(O)—. In embodiments, $L^1$ is —C(O)NH—. In embodiments, $L^1$ is —NHC(O)NH—. In embodiments, $L^1$ is —NHC(NH)NH—. In embodiments, $L^1$ is —C(S)—. In embodiments, $L^1$ is $R^{23}$-substituted or unsubstituted $C_1$-$C_{20}$ alkylene. In embodiments, $L^1$ is $R^{23}$-substituted or unsubstituted 2 to 20 membered heteroalkylene. In embodiments, $L^1$ is $R^{23}$-substituted or unsubstituted $C_3$-$C_8$ cycloalkylene. In embodiments, $L^1$ is $R^{23}$-substituted or unsubstituted 3 to 8 membered heterocycloalkylene. In embodiments, $L^1$ is $R^{23}$-substituted or unsubstituted $C_6$-$C_{10}$ arylene. In embodiments, $L^1$ is $R^{23}$-substituted or unsubstituted 5 to 10 membered heteroarylene. In embodiments, $L^1$ is $R^{23}$-substituted $C_1$-$C_{20}$ alkylene. In embodiments, $L^1$ is $R^{23}$-substituted 2 to 20 membered heteroalkylene. In embodiments, $L^1$ is $R^{23}$-substituted $C_3$-$C_8$ cycloalkylene. In embodiments, $L^1$ is $R^{23}$-substituted 3 to 8 membered heterocycloalkylene. In embodiments, $L^1$ is $R^{23}$-substituted $C_6$-$C_{10}$ arylene. In embodiments, $L^1$ is $R^{23}$-substituted 5 to 10 membered heteroarylene. In embodiments, $L^1$ is unsubstituted $C_1$-$C_{20}$ alkylene. In embodiments, $L^1$ is unsubstituted 2 to 20 membered heteroalkylene. In embodiments, $L^1$ is unsubstituted $C_3$-$C_8$ cycloalkylene. In embodiments, $L^1$ is unsubstituted 3 to 8 membered heterocycloalkylene. In embodiments, $L^1$ is unsubstituted $C_6$-$C_{10}$ arylene. In embodiments, $L^1$ is unsubstituted 5 to 10 membered heteroarylene. In embodiments, $L^1$ is $R^{23}$-substituted $C_1$-$C_{15}$ alkylene. In embodiments, $L^1$ is $R^{23}$-substituted 2 to 15 membered heteroalkylene. In embodiments, $L^1$ is $R^{23}$-substituted $C_3$-$C_6$ cycloalkylene. In embodiments, $L^1$ is $R^{23}$-substituted 3 to 6 membered heterocycloalkylene. In embodiments, $L^1$ is $R^{23}$-substituted phenylene. In embodiments, $L^1$ is $R^{23}$-substituted 5 to 6 membered heteroarylene. In embodiments, $L^1$ is unsubstituted $C_1$-$C_{15}$ alkylene. In embodiments, $L^1$ is unsubstituted 2 to 15 membered heteroalkylene. In embodiments, $L^1$ is unsubstituted $C_3$-$C_6$ cycloalkylene. In embodiments, $L^1$ is unsubstituted 3 to 6 membered heterocycloalkylene. In embodiments, $L^1$ is unsubstituted phenylene. In embodiments, $L^1$ is unsubstituted 5 to 6 membered heteroarylene. In embodiments, $L^1$ is $R^{23}$-substituted $C_1$-$C_{10}$ alkylene. In embodiments, $L^1$ is $R^{23}$-substituted 2 to 10 membered heteroalkylene. In embodiments, $L^1$ is $R^{23}$-substituted $C_4$-$C_6$ cycloalkylene. In embodiments, $L^1$ is $R^{23}$-substituted 4 to 6 membered heterocycloalkylene. In embodiments, $L^1$ is $R^{23}$-substituted phenylene. In embodiments, $L^1$ is $R^{23}$-substituted 5 membered heteroarylene. In embodiments, $L^1$ is $R^{23}$-substituted $C_1$-$C_8$ alkylene. In embodiments, $L^1$ is $R^{23}$-substituted 2 to 8 membered heteroalkylene. In embodiments, $L^1$ is $R^{23}$-substituted $C_5$-$C_6$ cycloalkylene. In embodiments, $L^1$ is $R^{23}$-substituted 5 to 6 membered heterocycloalkylene. In embodiments, $L^1$ is $R^{23}$-substituted 6 membered heteroarylene. In embodiments, $L^1$ is $R^{23}$-substituted $C_1$-$C_6$ alkylene. In embodiments, $L^1$ is $R^{23}$-substituted 2 to 6 membered heteroalkylene. In embodiments, $L^1$ is $R^{23}$-substituted $C_6$-$C_{20}$ alkylene. In embodiments, $L^1$ is $R^{23}$-substituted 6 to 20 membered heteroalkylene. In embodiments, $L^1$ is unsubstituted $C_1$-$C_{10}$ alkylene. In embodiments, $L^1$ is unsubstituted 2 to 10 membered heteroalkylene. In embodiments, $L^1$ is unsubstituted $C_4$-$C_6$ cycloalkylene. In embodiments, $L^1$ is unsubstituted 4 to 6 membered heterocycloalkylene. In embodiments, $L^1$ is unsubstituted phenylene. In embodiments, $L^1$ is unsubstituted 5 membered heteroarylene. In embodiments, $L^1$ is unsubstituted $C_1$-$C_8$ alkylene. In embodiments, $L^1$ is unsubstituted 2 to 8 membered heteroalkylene. In embodiments, $L^1$ is unsubstituted $C_5$-$C_6$ cycloalkylene. In embodiments, $L^1$ is unsubstituted 5 to 6 membered heterocycloalkylene. In embodiments, $L^1$ is unsubstituted 6 membered heteroarylene. In embodiments, $L^1$ is unsubstituted $C_1$-$C_6$ alkylene. In embodiments, $L^1$ is unsubstituted 2 to 6 membered heteroalkylene. In embodiments, $L^1$ is unsubstituted $C_6$-$C_{20}$ alkylene. In embodiments, $L^1$ is unsubstituted 6 to 20 membered heteroalkylene.

$R^{23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In embodiments, $R^{23}$ is independently —$NH_2$. In embodiments, $R^{23}$ is independently —OH. In embodiments, $R^{23}$ is independently halogen. In embodiments, $R^{23}$ is independently —CN. In embodiments, $R^{23}$ is independently oxo. In embodiments, $R^{23}$ is independently —$CF_3$. In embodiments, $R^{23}$ is independently —COOH. In embodiments, $R^{23}$ is independently —$CONH_2$. In embodiments, $R^{23}$ is independently —$NO_2$. In embodiments, $R^{23}$ is independently —SH. In embodiments, $R^{23}$ is independently —$SO_3H$. In embodiments, $R^{23}$ is independently —$SO_4H$. In embodiments, $R^{23}$ is independently —$SO_2NH_2$. In embodiments, $R^{23}$ is independently —$NHNH_2$. In embodiments, $R^{23}$ is independently —$ONH_2$. In embodiments, $R^{23}$ is independently —NHC=(O)$NHNH_2$. In embodiments, $R^{23}$ is independently —NHC=(O) $NH_2$. In embodiments, $R^{23}$ is independently —$NHSO_2H$. In embodiments, $R^{23}$ is independently —NHC=(O)H. In embodiments, $R^{23}$ is independently —NHC(O)—OH. In embodiments, $R^{23}$ is independently —NHOH. In embodiments, $R^{23}$ is independently —$OCF_3$. In embodiments, $R^{23}$ is independently —$OCHF_2$. In embodiments, $R^{23}$ is independently —$CCl_3$. In embodiments, $R^{23}$ is independently —$CBr_3$. In embodiments, $R^{23}$ is independently —$CI_3$. In embodiments, $R^{23}$ is independently —F. In embodiments, $R^{23}$ is independently —Cl. In embodiments, $R^{23}$ is independently —Br. In embodiments, $R^{23}$ is independently —I. In embodiments, $R^{23}$ is independently $R^{24}$-substituted $C_1$-$C_4$ alkyl. In embodiments, $R^{23}$ is independently $R^{24}$-substituted 2 to 4 membered heteroalkyl. In embodiments, $R^{23}$ is independently $R^{24}$-substituted $C_3$-$C_6$ cycloalkyl. In embodiments, $R^{23}$ is independently $R^{24}$-substituted 3 to 6 membered heterocycloalkyl. In embodiments, $R^{23}$ is independently $R^{24}$-substituted phenyl. In embodiments, $R^{23}$ is independently $R^{24}$-substituted 5 to 6 membered heteroaryl. In embodiments, $R^{23}$ is independently unsubstituted $C_1$-$C_4$ alkyl. In embodiments, $R^{23}$ is independently unsubstituted 2 to 4 membered heteroalkyl. In embodiments, $R^{23}$ is independently unsubstituted $C_3$-$C_6$ cycloalkyl. In embodiments, $R^{23}$ is independently unsubstituted 3 to 6 membered heterocycloalkyl. In embodiments, $R^{23}$ is independently unsubstituted phenyl. In embodiments, $R^{23}$ is independently unsubstituted 5 to 6 membered heteroaryl.

$R^{24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In embodiments, $R^{24}$ is independently —$NH_2$. In embodiments, $R^{24}$ is independently —OH. In embodiments, $R^{24}$ is independently halogen. In embodiments, $R^{24}$ is independently —CN. In embodiments, $R^{24}$ is independently oxo. In embodiments, $R^{24}$ is independently —$CF_3$. In embodiments, $R^{24}$ is independently —COOH. In embodiments, $R^{24}$ is independently —$CONH_2$. In embodiments, $R^{24}$ is independently —$NO_2$. In embodiments, $R^{24}$ is independently —SH. In embodiments, $R^{24}$ is independently —$SO_3H$. In embodiments, $R^{24}$ is independently —$SO_4H$. In embodiments, $R^{24}$ is independently —$SO_2NH_2$. In embodiments, $R^{24}$ is independently —$NHNH_2$. In embodiments, $R^{24}$ is independently —$ONH_2$. In embodiments, $R^{24}$ is independently —NHC=(O)$NHNH_2$. In embodiments, $R^{24}$ is independently —NHC=(O) $NH_2$. In embodiments, $R^{24}$ is independently —$NHSO_2H$. In embodiments, $R^{24}$ is independently —NHC=(O)H. In embodiments, $R^{24}$ is independently —NHC(O)—OH. In embodiments, $R^{24}$ is independently —NHOH. In embodiments, $R^{24}$ is independently —$OCF_3$. In embodiments, $R^{24}$ is independently —$OCHF_2$. In embodiments, $R^{24}$ is independently —$CCl_3$. In embodiments, $R^{24}$ is independently —$CBr_3$. In embodiments, $R^{24}$ is independently —$CI_3$. In embodiments, $R^{24}$ is independently —F. In embodiments, $R^{24}$ is independently —Cl. In embodiments, $R^{24}$ is independently —Br. In embodiments, $R^{24}$ is independently —I. In embodiments, $R^{24}$ is independently $R^{25}$-substituted $C_1$-$C_4$ alkyl. In embodiments, $R^{24}$ is independently $R^{25}$-substituted 2 to 4 membered heteroalkyl. In embodiments, $R^{24}$ is independently $R^{25}$-substituted $C_3$-$C_6$ cycloalkyl. In embodiments, $R^{24}$ is independently $R^{25}$-substituted 3 to 6 membered heterocycloalkyl. In embodiments, $R^{24}$ is independently $R^{25}$-substituted phenyl. In embodiments, $R^{24}$ is independently $R^{25}$-substituted 5 to 6 membered heteroaryl. In embodiments, $R^{24}$ is independently unsubstituted $C_1$-$C_4$ alkyl. In embodiments, $R^{24}$ is independently unsubstituted 2 to 4 membered heteroalkyl. In embodiments, $R^{24}$ is independently unsubstituted $C_3$-$C_6$ cycloalkyl. In embodiments, $R^{24}$ is independently unsubstituted 3 to 6 membered heterocycloalkyl. In embodiments, $R^{24}$ is independently unsubstituted phenyl. In embodiments, $R^{24}$ is independently unsubstituted 5 to 6 membered heteroaryl.

In some embodiments of the compounds provided herein, $L^2$ is independently a bond, $R^{26}$-substituted or unsubstituted alkylene, $R^{26}$-substituted or unsubstituted heteroalkylene, $R^{26}$-substituted or unsubstituted cycloalkylene, $R^{26}$-substituted or unsubstituted heterocycloalkylene, $R^{26}$-substituted or unsubstituted arylene, or $R^{26}$-substituted or unsubstituted heteroarylene.

In embodiments, $L^2$ is a bond, —NH—, —$NR^{26}$—, —S—, —O—, —C(O)—, —NHC(O)—, —C(O)NH—, —NHC(O)NH—, —NHC(NH)NH—, —C(S)—, $R^{26}$-substituted or unsubstituted $C_1$-$C_{20}$ alkylene, $R^{26}$-substituted or unsubstituted 2 to 20 membered heteroalkylene, $R^{26}$-substituted or unsubstituted $C_3$-$C_8$ cycloalkylene, $R^{26}$-substituted or unsubstituted 3 to 8 membered heterocycloalkylene, $R^{26}$-substituted or unsubstituted $C_6$-$C_{10}$ arylene, or $R^{26}$-substituted or unsubstituted 5 to 10 membered heteroarylene. In embodiments, $L^2$ is a bond. In embodiments, $L^2$ is —NH—. In embodiments, $L^2$ is —$NR^{26}$—. In embodiments, $L^2$ is —S—. In embodiments, $L^2$ is —O—. In embodiments, $L^2$ is —C(O)—. In embodiments, $L^2$ is —NHC(O)—. In embodiments, $L^2$ is —C(O)NH—. In embodiments, $L^2$ is —NHC(O)NH—. In embodiments, $L^2$ is —NHC(NH)NH—. In embodiments, $L^2$ is —C(S)—. In embodiments, $L^2$ is $R^{26}$-substituted or unsubstituted $C_1$-$C_{20}$ alkylene. In embodiments, $L^2$ is $R^{26}$-substituted or unsubstituted 2 to 20 membered heteroalkylene. In embodiments, $L^2$ is $R^{26}$-substituted or unsubstituted $C_3$-$C_8$ cycloalkylene. In embodiments, $L^2$ is $R^{26}$-substituted or unsubstituted 3 to 8 membered heterocycloalkylene. In embodiments, $L^2$ is $R^{26}$-substituted or unsubstituted $C_6$-$C_{10}$ arylene. In embodiments, $L^2$ is $R^{26}$-substituted or unsubstituted 5 to 10 membered heteroarylene. In embodiments, $L^2$ is $R^{26}$-substituted $C_1$-$C_{20}$ alkylene. In embodiments, $L^2$ is $R^{26}$-substituted 2 to 20 membered heteroalkylene. In embodiments, $L^2$ is $R^{26}$-substituted $C_3$-$C_8$ cycloalkylene. In embodiments, $L^2$ is $R^{26}$-substituted 3 to 8 membered heterocycloalkylene. In embodiments, $L^2$ is $R^{26}$-substituted $C_6$-$C_{10}$ arylene. In embodiments, $L^2$ is $R^{26}$-substituted 5 to 10 membered heteroarylene. In embodiments, $L^2$ is unsubstituted $C_1$-$C_{20}$ alkylene. In embodiments, $L^2$ is unsubstituted 2 to 20 membered heteroalkylene. In embodiments, $L^2$ is unsubstituted $C_3$-$C_8$ cycloalkylene. In embodiments, $L^2$ is unsubstituted 3 to 8 membered heterocycloalkylene. In embodiments, $L^2$ is unsubstituted $C_6$-$C_{10}$ arylene. In embodiments, $L^2$ is unsubstituted 5 to 10 membered heteroarylene. In embodiments, $L^2$ is $R^{26}$-substituted $C_1$-$C_{15}$ alkylene. In embodiments, $L^2$ is $R^{26}$-substituted 2 to 15 membered heteroalkylene. In embodiments, $L^2$ is $R^{26}$-substituted $C_3$-$C_6$ cycloalkylene. In embodiments, $L^2$ is $R^{26}$-substituted 3 to 6 membered heterocycloalkylene. In embodiments, $L^2$ is $R^{26}$-substituted phenylene. In embodiments, $L^2$ is $R^{26}$-substituted 5 to 6 membered heteroarylene. In embodiments, $L^2$ is unsubstituted $C_1$-$C_{15}$ alkylene. In embodiments, $L^2$ is unsubstituted 2 to 15 membered heteroalkylene. In embodiments, $L^2$ is unsubstituted $C_3$-$C_6$ cycloalkylene. In embodiments, $L^2$ is unsubstituted 3 to 6 membered heterocycloalkylene. In embodiments, $L^2$ is unsubstituted phenylene. In embodiments, $L^2$ is unsubstituted 5 to 6 membered heteroarylene. In embodiments, $L^2$ is $R^{26}$-substituted $C_1$-$C_{10}$ alkylene. In embodiments, $L^2$ is $R^{26}$-substituted 2 to 10 membered heteroalkylene. In embodiments, $L^2$ is $R^{26}$-substituted $C_4$-$C_6$ cycloalkylene. In embodiments, $L^2$ is $R^{26}$-substituted 4 to 6 membered heterocycloalkylene. In embodiments, $L^2$ is $R^{26}$-substituted phenylene. In embodiments, $L^2$ is $R^{26}$-substituted 5 membered heteroarylene. In embodiments, $L^2$ is $R^{26}$-substituted $C_1$-$C_8$ alkylene. In embodiments, $L^2$ is $R^{26}$-substituted 2 to 8 membered heteroalkylene. In embodiments, $L^2$ is $R^{26}$-substituted $C_5$-$C_6$ cycloalkylene. In embodiments, $L^2$ is $R^{26}$-substituted 5 to 6 membered heterocycloalkylene. In embodiments, $L^2$ is $R^{26}$-substituted 6 membered heteroarylene. In embodiments, $L^2$ is $R^{26}$-substituted $C_1$-$C_6$ alkylene. In embodiments, $L^2$ is $R^{26}$-substituted 2 to 6 membered heteroalkylene. In embodiments, $L^2$ is $R^{26}$-substituted $C_6$-$C_{20}$ alkylene. In embodiments, $L^2$ is $R^{26}$-substituted 6 to 20 membered heteroalkylene. In embodiments, $L^2$ is unsubstituted $C_1$-$C_{10}$ alkylene. In embodiments, $L^2$ is unsubstituted 2 to 10 membered heteroalkylene. In embodiments, $L^2$ is unsubstituted $C_4$-$C_6$ cycloalkylene. In embodiments, $L^2$ is unsubstituted 4 to 6 membered heterocycloalkylene. In embodiments, $L^2$ is unsubstituted phenylene. In embodiments, $L^2$ is unsubstituted 5 membered heteroarylene. In embodiments, $L^2$ is unsubstituted $C_1$-$C_8$ alkylene. In embodiments, $L^2$ is unsubstituted 2 to 8 membered heteroalkylene. In embodiments, $L^2$ is unsubstituted $C_5$-$C_6$ cycloalkylene. In embodiments, $L^2$ is unsubstituted 5 to 6 membered heterocycloalkylene. In embodiments, $L^2$ is unsubstituted 6 membered heteroarylene. In embodiments, $L^2$ is unsubstituted $C_1$-$C_6$ alkylene. In embodiments, $L^2$ is unsubstituted 2 to 6 membered heteroalkylene. In embodiments, $L^2$ is unsubstituted $C_6$-$C_{20}$ alkylene. In embodiments, $L^2$ is unsubstituted 6 to 20 membered heteroalkylene.

$R^{26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$ substituted or unsubstituted heterocycloalkyl, $R^{27}$-substituted or unsubstituted aryl, or $R^{27}$-substituted or unsubstituted heteroaryl.

In embodiments, $R^{26}$ is independently —$NH_2$. In embodiments, $R^{26}$ is independently —OH. In embodiments, $R^{26}$ is independently halogen. In embodiments, $R^{26}$ is independently —CN. In embodiments, $R^{26}$ is independently oxo. In embodiments, $R^{26}$ is independently —$CF_3$. In embodiments, $R^{26}$ is independently —COOH. In embodiments, $R^{26}$ is independently —$CONH_2$. In embodiments, $R^{26}$ is independently —$NO_2$. In embodiments, $R^{26}$ is independently —SH. In embodiments, $R^{26}$ is independently —$SO_3H$. In embodiments, $R^{26}$ is independently —$SO_4H$. In embodiments, $R^{26}$ is independently —$SO_2NH_2$. In embodiments, $R^{26}$ is independently —$NHNH_2$. In embodiments, $R^{26}$ is independently —$ONH_2$. In embodiments, $R^{26}$ is independently —NHC=(O)$NHNH_2$. In embodiments, $R^{26}$ is independently —NHC=(O) $NH_2$. In embodiments, $R^{26}$ is independently —$NHSO_2H$. In embodiments, $R^{26}$ is independently —NHC=(O)H. In embodiments, $R^{26}$ is independently —NHC(O)—OH. In embodiments, $R^{26}$ is independently —NHOH. In embodiments, $R^{26}$ is independently —$OCF_3$. In embodiments, $R^{26}$ is independently —$OCHF_2$. In embodiments, $R^{26}$ is independently —$CCl_3$. In embodiments, $R^{26}$ is independently —$CBr_3$. In embodiments, $R^{26}$ is independently —$CI_3$. In embodiments, $R^{26}$ is independently —F. In embodiments, $R^{26}$ is independently —Cl. In embodiments, $R^{26}$ is independently —Br. In embodiments, $R^{26}$ is independently —I. In embodiments, $R^{26}$ is independently $R^{27}$-substituted $C_1$-$C_4$ alkyl. In embodiments, $R^{26}$ is independently $R^{27}$-substituted 2 to 4 membered heteroalkyl. In embodiments, $R^{26}$ is independently $R^{27}$-substituted $C_3$-$C_6$ cycloalkyl. In embodiments, $R^{26}$ is independently $R^{27}$-substituted 3 to 6 membered heterocycloalkyl. In embodiments, $R^{26}$ is independently $R^{27}$-substituted phenyl. In embodiments, $R^{26}$ is independently $R^{27}$-substituted 5 to 6 membered heteroaryl. In embodiments, $R^{26}$ is independently unsubstituted $C_1$-$C_4$ alkyl. In embodiments, $R^{26}$ is independently unsubstituted 2 to 4 membered heteroalkyl. In embodiments, $R^{26}$ is independently unsubstituted $C_3$-$C_6$ cycloalkyl. In embodiments, $R^{26}$ is independently unsubstituted 3 to 6 membered heterocycloalkyl. In embodiments, $R^{26}$ is independently unsubstituted phenyl. In embodiments, $R^{26}$ is independently unsubstituted 5 to 6 membered heteroaryl.

$R^{27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In embodiments, $R^{27}$ is independently —$NH_2$. In embodiments, $R^{27}$ is independently —OH. In embodiments, $R^{27}$ is independently halogen. In embodiments, $R^{27}$ is independently —CN. In embodiments, $R^{27}$ is independently oxo. In embodiments, $R^{27}$ is independently —$CF_3$. In embodiments, $R^{27}$ is independently —COOH. In embodiments, $R^{27}$ is independently —$CONH_2$. In embodiments, $R^{27}$ is independently —$NO_2$. In embodiments, $R^{27}$ is independently —SH. In embodiments, $R^{27}$ is independently —$SO_3H$. In embodiments, $R^{27}$ is independently —$SO_4H$. In embodiments, $R^{27}$ is independently —$SO_2NH_2$. In embodiments, $R^{27}$ is independently —$NHNH_2$. In embodiments, $R^{27}$ is independently —$ONH_2$. In embodiments, $R^{27}$ is independently —NHC=(O)$NHNH_2$. In embodiments, $R^{27}$ is independently —NHC=(O) $NH_2$. In embodiments, $R^{27}$ is independently —$NHSO_2H$. In embodiments, $R^{27}$ is independently —NHC=(O)H. In embodiments, $R^{27}$ is independently —NHC(O)—OH. In embodiments, $R^{27}$ is independently —NHOH. In embodiments, $R^{27}$ is independently —$OCF_3$. In embodiments, $R^{27}$ is independently —$OCHF_2$. In embodiments, $R^{27}$ is independently —$CCl_3$. In embodiments, $R^{27}$ is independently —$CBr_3$. In embodiments, $R^{27}$ is independently —$CI_3$. In embodiments, $R^{27}$ is independently —F. In embodiments, $R^{27}$ is independently —Cl. In embodiments, $R^{27}$ is independently —Br. In embodiments, $R^{27}$ is independently —I. In embodiments, $R^{27}$ is independently $R^{28}$-substituted $C_1$-$C_4$ alkyl. In embodiments, $R^{27}$ is independently $R^{28}$-substituted 2 to 4 membered heteroalkyl. In embodiments, $R^{27}$ is independently $R^{28}$-substituted $C_3$-$C_6$ cycloalkyl. In embodiments, $R^{27}$ is independently $R^{28}$-substituted 3 to 6 membered heterocycloalkyl. In embodiments, $R^{27}$ is independently $R^{28}$-substituted phenyl. In embodiments, $R^{27}$ is independently $R^{28}$-substituted 5 to 6 membered heteroaryl. In embodiments, $R^{27}$ is independently unsubstituted $C_1$-$C_4$ alkyl. In embodiments, $R^{27}$ is independently unsubstituted 2 to 4 membered heteroalkyl. In embodiments, $R^{27}$ is independently unsubstituted $C_3$-$C_6$ cycloalkyl. In embodiments, $R^{27}$ is independently unsubstituted 3 to 6 membered heterocycloalkyl. In embodiments, $R^{27}$ is independently unsubstituted phenyl. In embodiments, $R^{27}$ is independently unsubstituted 5 to 6 membered heteroaryl.

In some embodiments of the compounds provided herein, $L^3$ is independently a bond, $R^{29}$-substituted or unsubstituted alkylene, $R^{29}$-substituted or unsubstituted heteroalkylene, $R^{29}$-substituted or unsubstituted cycloalkylene, $R^{29}$-substituted or unsubstituted heterocycloalkylene, $R^{29}$-substituted or unsubstituted arylene, or $R^{29}$-substituted or unsubstituted heteroarylene.

In embodiments, $L^3$ is a bond, —NH—, —$NR^{29}$—, —S—, —O—, —C(O)—, —NHC(O)—, —C(O)NH—, —NHC(O)NH—, —NHC(NH)NH—, —C(S)—, $R^{29}$-substituted or unsubstituted $C_1$-$C_{20}$ alkylene, $R^{29}$-substituted or unsubstituted 2 to 20 membered heteroalkylene, $R^{29}$-substituted or unsubstituted $C_3$-$C_8$ cycloalkylene, $R^{29}$-substituted or unsubstituted 3 to 8 membered heterocycloalkylene, $R^{29}$-substituted or unsubstituted $C_6$-$C_{10}$ arylene, or $R^{29}$-substituted or unsubstituted 5 to 10 membered heteroarylene. In embodiments, $L^3$ is a bond. In embodiments, $L^3$ is —NH—. In embodiments, $L^3$ is —$NR^{29}$—. In embodiments, $L^3$ is —S—. In embodiments, $L^3$ is —O—. In embodiments, $L^3$ is —C(O)—. In embodiments, $L^3$ is —NHC(O)—. In embodiments, $L^3$ is —C(O)NH—. In embodiments, $L^3$ is —NHC(O)NH—. In embodiments, $L^3$ is —NHC(NH)NH—. In embodiments, $L^3$ is —C(S)—. In embodiments, $L^3$ is $R^{29}$-substituted or unsubstituted $C_1$-$C_{20}$ alkylene. In embodiments, $L^3$ is $R^{29}$-substituted or unsubstituted 2 to 20 membered heteroalkylene. In embodiments, $L^3$ is $R^{29}$-substituted or unsubstituted $C_3$-$C_8$ cycloalkylene. In embodiments, $L^3$ is $R^{29}$-substituted or unsubstituted 3 to 8 membered heterocycloalkylene. In embodiments, $L^3$ is $R^{29}$-substituted or unsubstituted $C_6$-$C_{10}$ arylene. In embodiments, $L^3$ is $R^{29}$-substituted or unsubstituted 5 to 10 membered heteroarylene. In embodiments, $L^3$ is $R^{29}$-substituted $C_1$-$C_{20}$ alkylene. In embodiments, $L^3$ is $R^{29}$-substituted 2 to 20 membered heteroalkylene. In embodiments, $L^3$ is $R^{29}$-substituted $C_3$-$C_8$ cycloalkylene. In embodiments, $L^3$ is $R^{29}$-substituted 3 to 8 membered heterocycloalkylene. In embodiments, $L^3$ is $R^{29}$-substituted $C_6$-$C_{10}$ arylene. In embodiments, $L^3$ is $R^{29}$-substituted 5 to 10 membered heteroarylene. In embodiments, $L^3$ is unsubstituted $C_1$-$C_{20}$ alkylene. In embodiments, $L^3$ is unsubstituted 2 to 20 membered heteroalkylene. In embodiments, $L^3$ is unsubstituted $C_3$-$C_8$ cycloalkylene. In embodiments, $L^3$ is unsubstituted 3 to 8 membered heterocycloalkylene. In embodiments, $L^3$ is unsubstituted $C_6$-$C_{10}$ arylene. In embodiments, $L^3$ is unsubstituted 5 to 10 membered heteroarylene. In embodiments, $L^3$ is $R^{29}$-substituted $C_1$-$C_{15}$ alkylene. In embodiments, $L^3$ is $R^{29}$-substituted 2 to 15 membered heteroalkylene. In embodiments, $L^3$ is $R^{29}$-substituted $C_3$-$C_6$ cycloalkylene. In embodiments, $L^3$ is $R^{29}$-substituted 3 to 6 membered heterocycloalkylene. In embodiments, $L^3$ is $R^{29}$-substituted phenylene. In embodiments, $L^3$ is $R^{29}$-substituted 5 to 6 membered heteroarylene. In embodiments, $L^3$ is unsubstituted $C_1$-$C_{15}$ alkylene. In embodiments, $L^3$ is unsubstituted 2 to 15 membered heteroalkylene. In embodiments, $L^3$ is unsubstituted $C_3$-$C_6$ cycloalkylene. In embodiments, $L^3$ is unsubstituted 3 to 6 membered heterocycloalkylene. In embodiments, $L^3$ is unsubstituted phenylene. In embodiments, $L^3$ is unsubstituted 5 to 6 membered heteroarylene. In embodiments, $L^3$ is $R^{29}$-substituted $C_1$-$C_{10}$ alkylene. In embodiments, $L^3$ is $R^{29}$-substituted 2 to 10 membered heteroalkylene. In embodiments, $L^3$ is $R^{29}$-substituted $C_4$-$C_6$ cycloalkylene. In embodiments, $L^3$ is $R^{29}$-substituted 4 to 6 membered heterocycloalkylene. In embodiments, $L^3$ is $R^{29}$-substituted phenylene. In embodiments, $L^3$ is $R^{29}$-substituted 5 membered heteroarylene. In embodiments, $L^3$ is $R^{29}$-substituted $C_1$-$C_8$ alkylene. In embodiments, $L^3$ is $R^{29}$-substituted 2 to 8 membered heteroalkylene. In embodiments, $L^3$ is $R^{29}$-substituted $C_5$-$C_6$ cycloalkylene. In embodiments, $L^3$ is $R^{29}$-substituted 5 to 6 membered heterocycloalkylene. In embodiments, $L^3$ is $R^{29}$-substituted 6 membered heteroarylene. In embodiments, $L^3$ is $R^{29}$-substituted $C_1$-$C_6$ alkylene. In embodiments, $L^3$ is $R^{29}$-substituted 2 to 6 membered heteroalkylene. In embodiments, $L^3$ is $R^{29}$-substituted $C_6$-$C_{20}$ alkylene. In embodiments, $L^3$ is $R^{29}$-substituted 6 to 20 membered heteroarylene. In embodiments, $L^3$ is unsubstituted $C_1$-$C_{10}$ alkylene. In embodiments, $L^3$ is unsubstituted 2 to 10 membered heteroalkylene. In embodiments, $L^3$ is unsubstituted $C_4$-$C_6$ cycloalkylene. In embodiments, $L^3$ is unsubstituted 4 to 6 membered heterocycloalkylene. In embodiments, $L^3$ is unsubstituted phenylene. In embodiments, $L^3$ is unsubstituted 5 membered heteroarylene. In embodiments, $L^3$ is unsubstituted $C_1$-$C_8$ alkylene. In embodiments, $L^3$ is unsubstituted 2 to 8 membered heteroalkylene. In embodiments, $L^3$ is unsubstituted $C_5$-$C_6$ cycloalkylene. In embodiments, $L^3$ is unsubstituted 5 to 6 membered heterocycloalkylene. In embodiments, $L^3$ is unsubstituted 6 membered heteroarylene. In embodiments, $L^3$ is unsubstituted $C_1$-$C_6$ alkylene. In embodiments, $L^3$ is unsubstituted 2 to 6 membered heteroalkylene. In embodiments, $L^3$ is unsubstituted $C_6$-$C_{20}$ alkylene. In embodiments, $L^3$ is unsubstituted 6 to 20 membered heteroalkylene.

$R^{29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

In embodiments, $R^{29}$ is independently —$NH_2$. In embodiments, $R^{29}$ is independently —OH. In embodiments, $R^{29}$ is independently halogen. In embodiments, $R^{29}$ is independently —CN. In embodiments, $R^{29}$ is independently oxo. In embodiments, $R^{29}$ is independently —$CF_3$. In embodiments, $R^{29}$ is independently —COOH. In embodiments, $R^{29}$ is independently —$CONH_2$. In embodiments, $R^{29}$ is independently —$NO_2$. In embodiments, $R^{29}$ is independently —SH. In embodiments, $R^{29}$ is independently —$SO_3H$. In embodiments, $R^{29}$ is independently —$SO_4H$. In embodiments, $R^{29}$ is independently —$SO_2NH_2$. In embodiments, $R^{29}$ is independently —$NHNH_2$. In embodiments, $R^{29}$ is independently —$ONH_2$. In embodiments, $R^{29}$ is independently —NHC=(O)$NHNH_2$. In embodiments, $R^{29}$ is independently —NHC=(O) $NH_2$. In embodiments, $R^{29}$ is independently —$NHSO_2H$. In embodiments, $R^{29}$ is independently —NHC=(O)H. In embodiments, $R^{29}$ is independently —NHC(O)—OH. In embodiments, $R^{29}$ is independently —NHOH. In embodiments, $R^{29}$ is independently —$OCF_3$. In embodiments, $R^{29}$ is independently —$OCHF_2$. In embodiments, $R^{29}$ is independently —$CCl_3$. In embodiments, $R^{29}$ is independently —$CBr_3$. In embodiments, $R^{29}$ is independently —$CI_3$. In embodiments, $R^{29}$ is independently —F. In embodiments, $R^{29}$ is independently —Cl. In embodiments, $R^{29}$ is independently —Br. In embodiments, $R^{29}$ is independently —I. In embodiments, $R^{29}$ is independently $R^{30}$-substituted $C_1$-$C_4$ alkyl. In embodiments, $R^{29}$ is independently $R^{30}$-substituted 2 to 4 membered heteroalkyl. In embodiments, $R^{29}$ is independently $R^{30}$-substituted $C_3$-$C_6$ cycloalkyl. In embodiments, $R^{29}$ is independently $R^{30}$-substituted 3 to 6 membered heterocycloalkyl. In embodiments, $R^{29}$ is independently $R^{30}$-substituted phenyl. In embodiments, $R^{29}$ is independently $R^{30}$-substituted 5 to 6 membered heteroaryl. In embodiments, $R^{29}$ is independently unsubstituted $C_1$-$C_4$ alkyl. In embodiments, $R^{29}$ is independently unsubstituted 2 to 4 membered heteroalkyl. In embodiments, $R^{29}$ is independently unsubstituted $C_3$-$C_6$ cycloalkyl. In embodiments, $R^{29}$ is independently unsubstituted 3 to 6 membered heterocycloalkyl. In embodiments, $R^{29}$ is independently unsubstituted phenyl. In embodiments, $R^{29}$ is independently unsubstituted 5 to 6 membered heteroaryl.

$R^{30}$ is independently oxo, halogen, —$CF_3$, —CN, —OH, —$NH_2$, —COOH, —$CONH_2$, —$NO_2$, —SH, —$SO_3H$, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{31}$-substituted or unsubstituted alkyl, R$^{31}$-substituted or unsubstituted heteroalkyl, R$^3$-substituted or unsubstituted cycloalkyl, R$^3$-substituted or unsubstituted heterocycloalkyl, R$^{31}$-substituted or unsubstituted aryl, or R$^{31}$-substituted or unsubstituted heteroaryl.

In embodiments, R$^{30}$ is independently —NH$_2$. In embodiments, R$^{30}$ is independently —OH. In embodiments, R$^{30}$ is independently halogen. In embodiments, R$^{30}$ is independently —CN. In embodiments, R$^{30}$ is independently oxo. In embodiments, R$^{30}$ is independently —CF$_3$. In embodiments, R$^{30}$ is independently —COOH. In embodiments, R$^{30}$ is independently —CONH$_2$. In embodiments, R$^{30}$ is independently —NO$_2$. In embodiments, R$^{30}$ is independently —SH. In embodiments, R$^{30}$ is independently —SO$_3$H. In embodiments, R$^{30}$ is independently —SO$_4$H. In embodiments, R$^{30}$ is independently —SO$_2$NH$_2$. In embodiments, R$^{30}$ is independently —NHNH$_2$. In embodiments, R$^{30}$ is independently —ONH$_2$. In embodiments, R$^{30}$ is independently —NHC=(O)NHNH$_2$. In embodiments, R$^{30}$ is independently —NHC=(O) NH$_2$. In embodiments, R$^{30}$ is independently —NHSO$_2$H. In embodiments, R$^{30}$ is independently —NHC=(O)H. In embodiments, R$^{30}$ is independently —NHC(O)—OH. In embodiments, R$^{30}$ is independently —NHOH. In embodiments, R$^{30}$ is independently —OCF$_3$. In embodiments, R$^{30}$ is independently —OCHF$_2$. In embodiments, R$^{30}$ is independently —CCl$_3$. In embodiments, R$^{30}$ is independently —CBr$_3$. In embodiments, R$^{30}$ is independently —CI$_3$. In embodiments, R$^{30}$ is independently —F. In embodiments, R$^{30}$ is independently —Cl. In embodiments, R$^{30}$ is independently —Br. In embodiments, R$^{30}$ is independently —I. In embodiments, R$^{30}$ is independently R$^{31}$-substituted C$_1$-C$_4$ alkyl. In embodiments, R$^{30}$ is independently R$^{31}$-substituted 2 to 4 membered heteroalkyl. In embodiments, R$^{30}$ is independently R$^{31}$-substituted C$_3$-C$_6$ cycloalkyl. In embodiments, R$^{30}$ is independently R$^{31}$-substituted 3 to 6 membered heterocycloalkyl. In embodiments, R$^{30}$ is independently R$^{31}$-substituted phenyl. In embodiments, R$^{30}$ is independently R$^{31}$-substituted 5 to 6 membered heteroaryl. In embodiments, R$^{30}$ is independently unsubstituted C$_1$-C$_4$ alkyl. In embodiments, R$^{30}$ is independently unsubstituted 2 to 4 membered heteroalkyl. In embodiments, R$^{30}$ is independently unsubstituted C$_3$-C$_6$ cycloalkyl. In embodiments, R$^{30}$ is independently unsubstituted 3 to 6 membered heterocycloalkyl. In embodiments, R$^{30}$ is independently unsubstituted phenyl. In embodiments, R$^{30}$ is independently unsubstituted 5 to 6 membered heteroaryl.

In some embodiments of the compounds provided herein, L$^4$ is independently a bond, R$^{32}$-substituted or unsubstituted alkylene, R$^{32}$-substituted or unsubstituted heteroalkylene, R$^{32}$-substituted or unsubstituted cycloalkylene, R$^{32}$-substituted or unsubstituted heterocycloalkylene, R$^{32}$-substituted or unsubstituted arylene, or R$^{32}$-substituted or unsubstituted heteroarylene.

In embodiments, L$^4$ is a bond, —NH—, —NR$^{32}$—, —S—, —O—, —C(O)—, —NHC(O)—, —C(O)NH—, —NHC(O)NH—, —NHC(NH)NH—, —C(S)—, R$^{32}$-substituted or unsubstituted C$_1$-C$_{20}$ alkylene, R$^{32}$-substituted or unsubstituted 2 to 20 membered heteroalkylene, R$^{32}$-substituted or unsubstituted C$_3$-C$_8$ cycloalkylene, R$^{32}$-substituted or unsubstituted 3 to 8 membered heterocycloalkylene, R$^{32}$-substituted or unsubstituted C$_6$-C$_{10}$ arylene, or R$^{32}$-substituted or unsubstituted 5 to 10 membered heteroarylene. In embodiments, L$^4$ is a bond. In embodiments, L$^4$ is —NH—. In embodiments, L$^4$ is —NR$^{32}$—. In embodiments, L$^4$ is —S—. In embodiments, L$^4$ is —O—. In embodiments, L$^4$ is —C(O)—. In embodiments, L$^4$ is —NHC(O)—. In embodiments, L$^4$ is —C(O)NH—. In embodiments, L$^4$ is —NHC(O)NH—. In embodiments, L$^4$ is —NHC(NH)NH—. In embodiments, L$^4$ is —C(S)—. In embodiments, L$^4$ is R$^{32}$-substituted or unsubstituted C$_1$-C$_{20}$ alkylene. In embodiments, L$^4$ is R$^{32}$-substituted or unsubstituted 2 to 20 membered heteroalkylene. In embodiments, L$^4$ is R$^{32}$-substituted or unsubstituted C$_3$-C$_8$ cycloalkylene. In embodiments, L$^4$ is R$^{32}$-substituted or unsubstituted 3 to 8 membered heterocycloalkylene. In embodiments, L$^4$ is R$^{32}$-substituted or unsubstituted C$_6$-C$_{10}$ arylene. In embodiments, L$^4$ is R$^{32}$-substituted or unsubstituted 5 to 10 membered heteroarylene. In embodiments, L$^4$ is R$^{32}$-substituted C$_1$-C$_{20}$ alkylene. In embodiments, L$^4$ is R$^{32}$-substituted 2 to 20 membered heteroalkylene. In embodiments, L$^4$ is R$^{32}$-substituted C$_3$-C$_8$ cycloalkylene. In embodiments, L$^4$ is R$^{32}$-substituted 3 to 8 membered heterocycloalkylene. In embodiments, L$^4$ is R$^{32}$-substituted C$_6$-C$_{10}$ arylene. In embodiments, L$^4$ is R$^{32}$-substituted 5 to 10 membered heteroarylene. In embodiments, L$^4$ is unsubstituted C$_1$-C$_{20}$ alkylene. In embodiments, L$^4$ is unsubstituted 2 to 20 membered heteroalkylene. In embodiments, L$^4$ is unsubstituted C$_3$-C$_8$ cycloalkylene. In embodiments, L$^4$ is unsubstituted 3 to 8 membered heterocycloalkylene. In embodiments, L$^4$ is unsubstituted C$_6$-C$_{10}$ arylene. In embodiments, L$^4$ is unsubstituted 5 to 10 membered heteroarylene. In embodiments, L$^4$ is R$^{32}$-substituted C$_1$-C$_{15}$ alkylene. In embodiments, L$^4$ is R$^{32}$-substituted 2 to 15 membered heteroalkylene. In embodiments, L$^4$ is R$^{32}$-substituted C$_3$-C$_6$ cycloalkylene. In embodiments, L$^4$ is R$^{32}$-substituted 3 to 6 membered heterocycloalkylene. In embodiments, L$^4$ is R$^{32}$-substituted phenylene. In embodiments, L$^4$ is R$^{32}$-substituted 5 to 6 membered heteroarylene. In embodiments, L$^4$ is unsubstituted C$_1$-C$_{15}$ alkylene. In embodiments, L$^4$ is unsubstituted 2 to 15 membered heteroalkylene. In embodiments, L$^4$ is unsubstituted C$_3$-C$_6$ cycloalkylene. In embodiments, L$^4$ is unsubstituted 3 to 6 membered heterocycloalkylene. In embodiments, L$^4$ is unsubstituted phenylene. In embodiments, L$^4$ is unsubstituted 5 to 6 membered heteroarylene. In embodiments, L$^4$ is R$^{32}$-substituted C$_1$-C$_{10}$ alkylene. In embodiments, L$^4$ is R$^{32}$-substituted 2 to 10 membered heteroalkylene. In embodiments, L$^4$ is R$^{32}$-substituted C$_4$-C$_6$ cycloalkylene. In embodiments, L$^4$ is R$^{32}$-substituted 4 to 6 membered heterocycloalkylene. In embodiments, L$^4$ is R$^{32}$-substituted phenylene. In embodiments, L$^4$ is R$^{32}$-substituted 5 membered heteroarylene. In embodiments, L$^4$ is R$^{32}$-substituted C$_1$-C$_8$ alkylene. In embodiments, L$^4$ is R$^{32}$-substituted 2 to 8 membered heteroalkylene. In embodiments, L$^4$ is R$^{32}$-substituted C$_5$-C$_6$ cycloalkylene. In embodiments, L$^4$ is R$^{32}$-substituted 5 to 6 membered heterocycloalkylene. In embodiments, L$^4$ is R$^{32}$-substituted 6 membered heteroarylene. In embodiments, L$^4$ is R$^{32}$-substituted C$_1$-C$_6$ alkylene. In embodiments, L$^4$ is R$^{32}$-substituted 2 to 6 membered heteroalkylene. In embodiments, L$^4$ is R$^{32}$-substituted C$_6$-C$_{20}$ alkylene. In embodiments, L$^4$ is R$^{32}$-substituted 6 to 20 membered heteroalkylene. In embodiments, L$^4$ is unsubstituted C$_1$-C$_{10}$ alkylene. In embodiments, L$^4$ is unsubstituted 2 to 10 membered heteroalkylene. In embodiments, L$^4$ is unsubstituted C$_4$-C$_6$ cycloalkylene. In embodiments, L$^4$ is unsubstituted 4 to 6 membered heterocycloalkylene. In embodiments, L$^4$ is unsubstituted phenylene. In embodiments, L$^4$ is unsubstituted 5 membered heteroarylene. In embodiments, L$^4$ is unsubstituted C$_1$-C$_8$ alkylene. In embodiments, L$^4$ is unsubstituted 2 to 8 membered heteroalkylene. In embodiments, $L^4$ is unsubstituted $C_5$-$C_6$ cycloalkylene. In embodiments, $L^4$ is unsubstituted 5 to 6 membered heterocycloalkylene. In embodiments, $L^4$ is unsubstituted 6 membered heteroarylene. In embodiments, $L^4$ is unsubstituted $C_1$-$C_6$ alkylene. In embodiments, $L^4$ is unsubstituted 2 to 6 membered heteroalkylene. In embodiments, $L^4$ is unsubstituted $C_6$-$C_{20}$ alkylene. In embodiments, $L^4$ is unsubstituted 6 to 20 membered heteroalkylene.

$R^{32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O) $NH_2$, —$NHSO_2H$, —NHC=(O)H, —NHC(O)—OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$ substituted or unsubstituted heterocycloalkyl, $R^{33}$-substituted or unsubstituted aryl, or $R^{33}$-substituted or unsubstituted heteroaryl.

In embodiments, $R^{32}$ is independently —$NH_2$. In embodiments, $R^{32}$ is independently —OH. In embodiments, $R^{32}$ is independently halogen. In embodiments, $R^{32}$ is independently —CN. In embodiments, $R^{32}$ is independently oxo. In embodiments, $R^{32}$ is independently —$CF_3$. In embodiments, $R^{32}$ is independently —COOH. In embodiments, $R^{32}$ is independently —$CONH_2$. In embodiments, $R^{32}$ is independently —$NO_2$. In embodiments, $R^{32}$ is independently —SH. In embodiments, $R^{32}$ is independently —$SO_3H$. In embodiments, $R^{32}$ is independently —$SO_4H$. In embodiments, $R^{32}$ is independently —$SO_2NH_2$. In embodiments, $R^{32}$ is independently —$NHNH_2$. In embodiments, $R^{32}$ is independently —$ONH_2$. In embodiments, $R^{32}$ is independently —NHC=(O)$NHNH_2$. In embodiments, $R^{32}$ is independently —NHC=(O) $NH_2$. In embodiments, $R^{32}$ is independently —$NHSO_2H$. In embodiments, $R^{32}$ is independently —NHC=(O)H. In embodiments, $R^{32}$ is independently —NHC(O)—OH. In embodiments, $R^{32}$ is independently —NHOH. In embodiments, $R^{32}$ is independently —$OCF_3$. In embodiments, $R^{32}$ is independently —$OCHF_2$. In embodiments, $R^{32}$ is independently —$CCl_3$. In embodiments, $R^{32}$ is independently —$CBr_3$. In embodiments, $R^{32}$ is independently —$CI_3$. In embodiments, $R^{32}$ is independently —F. In embodiments, $R^{32}$ is independently —Cl. In embodiments, $R^{32}$ is independently —Br. In embodiments, $R^{32}$ is independently —I. In embodiments, $R^{32}$ is independently $R^{33}$-substituted $C_1$-$C_4$ alkyl. In embodiments, $R^{32}$ is independently $R^{33}$-substituted 2 to 4 membered heteroalkyl. In embodiments, $R^{32}$ is independently $R^{33}$-substituted $C_3$-$C_6$ cycloalkyl. In embodiments, $R^{32}$ is independently $R^{33}$-substituted 3 to 6 membered heterocycloalkyl. In embodiments, $R^{32}$ is independently $R^{33}$-substituted phenyl. In embodiments, $R^{32}$ is independently $R^{33}$-substituted 5 to 6 membered heteroaryl. In embodiments, $R^{32}$ is independently unsubstituted $C_1$-$C_4$ alkyl. In embodiments, $R^{32}$ is independently unsubstituted 2 to 4 membered heteroalkyl. In embodiments, $R^{32}$ is independently unsubstituted $C_3$-$C_6$ cycloalkyl. In embodiments, $R^{32}$ is independently unsubstituted 3 to 6 membered heterocycloalkyl. In embodiments, $R^{32}$ is independently unsubstituted phenyl. In embodiments, $R^{32}$ is independently unsubstituted 5 to 6 membered heteroaryl.

$R^{33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O) $NH_2$, —$NHSO_2H$, —NHC=(O)H, —NHC(O)—OH, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocloalkyl, $R^{34}$-substituted or unsubstituted aryl, or $R^{34}$-substituted or unsubstituted heteroaryl.

In embodiments, $R^{33}$ is independently —$NH_2$. In embodiments, $R^{33}$ is independently —OH. In embodiments, $R^{33}$ is independently halogen. In embodiments, $R^{33}$ is independently —CN. In embodiments, $R^{33}$ is independently oxo. In embodiments, $R^{33}$ is independently —$CF_3$. In embodiments, $R^{33}$ is independently —COOH. In embodiments, $R^{33}$ is independently —$CONH_2$. In embodiments, $R^{33}$ is independently —$NO_2$. In embodiments, $R^{33}$ is independently —SH. In embodiments, $R^{33}$ is independently —$SO_3H$. In embodiments, $R^{33}$ is independently —$SO_4H$. In embodiments, $R^{33}$ is independently —$SO_2NH_2$. In embodiments, $R^{33}$ is independently —$NHNH_2$. In embodiments, $R^{33}$ is independently —$ONH_2$. In embodiments, $R^{33}$ is independently —NHC=(O)$NHNH_2$. In embodiments, $R^{33}$ is independently —NHC=(O) $NH_2$. In embodiments, $R^{33}$ is independently —$NHSO_2H$. In embodiments, $R^{33}$ is independently —NHC=(O)H. In embodiments, $R^{33}$ is independently —NHC(O)—OH. In embodiments, $R^{33}$ is independently —NHOH. In embodiments, $R^{33}$ is independently —$OCF_3$. In embodiments, $R^{33}$ is independently —$OCHF_2$. In embodiments, $R^{33}$ is independently —$CCl_3$. In embodiments, $R^{33}$ is independently —$CBr_3$. In embodiments, $R^{33}$ is independently —$CI_3$. In embodiments, $R^{33}$ is independently —F. In embodiments, $R^{33}$ is independently —Cl. In embodiments, $R^{33}$ is independently —Br. In embodiments, $R^{33}$ is independently —I. In embodiments, $R^{33}$ is independently $R^{34}$-substituted $C_1$-$C_4$ alkyl. In embodiments, $R^{33}$ is independently $R^{34}$-substituted 2 to 4 membered heteroalkyl. In embodiments, $R^{33}$ is independently $R^{34}$-substituted $C_3$-$C_6$ cycloalkyl. In embodiments, $R^{33}$ is independently $R^{34}$-substituted 3 to 6 membered heterocycloalkyl. In embodiments, $R^{33}$ is independently $R^{34}$-substituted phenyl. In embodiments, $R^{33}$ is independently $R^{34}$-substituted 5 to 6 membered heteroaryl. In embodiments, $R^{33}$ is independently unsubstituted $C_1$-$C_4$ alkyl. In embodiments, $R^{33}$ is independently unsubstituted 2 to 4 membered heteroalkyl. In embodiments, $R^{33}$ is independently unsubstituted $C_3$-$C_6$ cycloalkyl. In embodiments, $R^{33}$ is independently unsubstituted 3 to 6 membered heterocycloalkyl. In embodiments, $R^{33}$ is independently unsubstituted phenyl. In embodiments, $R^{33}$ is independently unsubstituted 5 to 6 membered heteroaryl.

In some embodiments of the compounds provided herein, $L^5$ is independently a bond, $R^{35}$-substituted or unsubstituted alkylene, $R^{35}$-substituted or unsubstituted heteroalkylene, $R^{35}$-substituted or unsubstituted cycloalkylene, $R^{35}$-substituted or unsubstituted heterocycloalkylene, $R^{35}$-substituted or unsubstituted arylene, or $R^{35}$-substituted or unsubstituted heteroarylene.

In embodiments, $L^5$ is a bond, —NH—, —$NR^{35}$—, —S—, —O—, —C(O)—, —NHC(O)—, —C(O)NH—, —NHC(O)NH—, —NHC(NH)NH—, —C(S)—, $R^{35}$-substituted or unsubstituted $C_1$-$C_{20}$ alkylene, $R^{35}$-substituted or unsubstituted 2 to 20 membered heteroalkylene, $R^{35}$-substituted or unsubstituted $C_3$-$C_8$ cycloalkylene, $R^{35}$-substituted or unsubstituted 3 to 8 membered heterocycloalkylene, $R^{35}$-substituted or unsubstituted $C_6$-$C_{10}$ arylene, or $R^{35}$-substituted or unsubstituted 5 to 10 membered heteroarylene. In embodiments, $L^5$ is a bond. In embodiments, $L^5$ is —NH—. In embodiments, $L^5$ is —$NR^{35}$—. In embodiments, $L^5$ is —S—. In embodiments, $L^5$ is —O—. In embodiments, $L^5$ is —C(O)—. In embodiments, $L^5$ is —NHC(O)—. In embodiments, $L^5$ is —C(O)NH—. In embodiments, $L^5$ is —NHC(O)NH—. In embodiments, $L^5$ is —NHC(NH)NH—. In embodiments, $L^5$ is —C(S)—. In embodiments, $L^5$ is $R^{35}$-substituted or unsubstituted $C_1$-$C_{20}$ alkylene. In embodiments, $L^5$ is $R^{35}$-substituted or unsubstituted 2 to 20 membered heteroalkylene. In embodiments, $L^5$ is $R^{35}$-substituted or unsubstituted $C_3$-$C_8$ cycloalkylene. In embodiments, $L^5$ is $R^{35}$-substituted or unsubstituted 3 to 8 membered heterocycloalkylene. In embodiments, $L^5$ is $R^{35}$-substituted or unsubstituted $C_6$-$C_{10}$ arylene. In embodiments, $L^5$ is $R^{35}$-substituted or unsubstituted 5 to 10 membered heteroarylene. In embodiments, $L^5$ is $R^{35}$-substituted $C_1$-$C_{20}$ alkylene. In embodiments, $L^5$ is $R^{35}$-substituted 2 to 20 membered heteroalkylene. In embodiments, $L^5$ is $R^{35}$-substituted $C_3$-$C_8$ cycloalkylene. In embodiments, $L^5$ is $R^{35}$-substituted 3 to 8 membered heterocycloalkylene. In embodiments, $L^5$ is $R^{35}$-substituted $C_6$-$C_{10}$ arylene. In embodiments, $L^5$ is $R^{35}$-substituted 5 to 10 membered heteroarylene. In embodiments, $L^5$ is unsubstituted $C_1$-$C_{20}$ alkylene. In embodiments, $L^5$ is unsubstituted 2 to 20 membered heteroalkylene. In embodiments, $L^5$ is unsubstituted $C_3$-$C_8$ cycloalkylene. In embodiments, $L^5$ is unsubstituted 3 to 8 membered heterocycloalkylene. In embodiments, $L^5$ is unsubstituted $C_6$-$C_{10}$ arylene. In embodiments, $L^5$ is unsubstituted 5 to 10 membered heteroarylene. In embodiments, $L^5$ is $R^{35}$-substituted $C_1$-$C_{15}$ alkylene. In embodiments, $L^5$ is $R^{35}$-substituted 2 to 15 membered heteroalkylene. In embodiments, $L^5$ is $R^{35}$-substituted $C_3$-$C_6$ cycloalkylene. In embodiments, $L^5$ is $R^{35}$-substituted 3 to 6 membered heterocycloalkylene. In embodiments, $L^5$ is $R^{35}$-substituted phenylene. In embodiments, $L^5$ is $R^{35}$-substituted 5 to 6 membered heteroarylene. In embodiments, $L^5$ is unsubstituted $C_1$-$C_{15}$ alkylene. In embodiments, $L^5$ is unsubstituted 2 to 15 membered heteroalkylene. In embodiments, $L^5$ is unsubstituted $C_3$-$C_6$ cycloalkylene. In embodiments, $L^5$ is unsubstituted 3 to 6 membered heterocycloalkylene. In embodiments, $L^5$ is unsubstituted phenylene. In embodiments, $L^5$ is unsubstituted 5 to 6 membered heteroarylene. In embodiments, $L^5$ is $R^{35}$-substituted $C_1$-$C_{10}$ alkylene. In embodiments, $L^5$ is $R^{35}$-substituted 2 to 10 membered heteroalkylene. In embodiments, $L^5$ is $R^{35}$-substituted $C_4$-$C_6$ cycloalkylene. In embodiments, $L^5$ is $R^{35}$-substituted 4 to 6 membered heterocycloalkylene. In embodiments, $L^5$ is $R^{35}$-substituted phenylene. In embodiments, $L^5$ is $R^{35}$-substituted 5 membered heteroarylene. In embodiments, $L^5$ is $R^{35}$-substituted $C_1$-$C_8$ alkylene. In embodiments, $L^5$ is $R^{35}$-substituted 2 to 8 membered heteroalkylene. In embodiments, $L^5$ is $R^{35}$-substituted $C_5$-$C_6$ cycloalkylene. In embodiments, $L^5$ is $R^{35}$-substituted 5 to 6 membered heterocycloalkylene. In embodiments, $L^5$ is $R^{35}$-substituted 6 membered heteroarylene. In embodiments, $L^5$ is $R^{35}$-substituted $C_1$-$C_6$ alkylene. In embodiments, $L^5$ is $R^{35}$-substituted 2 to 6 membered heteroalkylene. In embodiments, $L^5$ is $R^{35}$-substituted $C_6$-$C_{20}$ alkylene. In embodiments, $L^5$ is $R^{35}$-substituted 6 to 20 membered heteroalkylene. In embodiments, $L^5$ is unsubstituted $C_1$-$C_{10}$ alkylene. In embodiments, $L^5$ is unsubstituted 2 to 10 membered heteroalkylene. In embodiments, $L^5$ is unsubstituted $C_4$-$C_6$ cycloalkylene. In embodiments, $L^5$ is unsubstituted 4 to 6 membered heterocycloalkylene. In embodiments, $L^5$ is unsubstituted phenylene. In embodiments, $L^5$ is unsubstituted 5 membered heteroarylene. In embodiments, $L^5$ is unsubstituted $C_1$-$C_8$ alkylene. In embodiments, $L^5$ is unsubstituted 2 to 8 membered heteroalkylene. In embodiments, $L^5$ is unsubstituted $C_5$-$C_6$ cycloalkylene. In embodiments, $L^5$ is unsubstituted 5 to 6 membered heterocycloalkylene. In embodiments, $L^5$ is unsubstituted 6 membered heteroarylene. In embodiments, $L^5$ is unsubstituted $C_1$-$C_6$ alkylene. In embodiments, $L^5$ is unsubstituted 2 to 6 membered heteroalkylene. In embodiments, $L^5$ is unsubstituted $C_6$-$C_{20}$ alkylene. In embodiments, $L^5$ is unsubstituted 6 to 20 membered heteroalkylene.

$R^{35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$ substituted or unsubstituted heterocycloalkyl, $R^{36}$-substituted or unsubstituted aryl, or $R^{36}$-substituted or unsubstituted heteroaryl.

In embodiments, $R^{35}$ is independently —$NH_2$. In embodiments, $R^{35}$ is independently —OH. In embodiments, $R^{35}$ is independently halogen. In embodiments, $R^{35}$ is independently —CN. In embodiments, $R^{35}$ is independently oxo. In embodiments, $R^{35}$ is independently —$CF_3$. In embodiments, $R^{35}$ is independently —COOH. In embodiments, $R^{35}$ is independently —$CONH_2$. In embodiments, $R^{35}$ is independently —$NO_2$. In embodiments, $R^{35}$ is independently —SH. In embodiments, $R^{35}$ is independently —$SO_3H$. In embodiments, $R^{35}$ is independently —$SO_4H$. In embodiments, $R^{35}$ is independently —$SO_2NH_2$. In embodiments, $R^{35}$ is independently —$NHNH_2$. In embodiments, $R^{35}$ is independently —$ONH_2$. In embodiments, $R^{35}$ is independently —NHC=(O)$NHNH_2$. In embodiments, $R^{35}$ is independently —NHC=(O) $NH_2$. In embodiments, $R^{35}$ is independently —$NHSO_2H$. In embodiments, $R^{35}$ is independently —NHC=(O)H. In embodiments, $R^{35}$ is independently —NHC(O)—OH. In embodiments, $R^{35}$ is independently —NHOH. In embodiments, $R^{35}$ is independently —$OCF_3$. In embodiments, $R^{35}$ is independently —$OCHF_2$. In embodiments, $R^{35}$ is independently —$CCl_3$. In embodiments, $R^{35}$ is independently —$CBr_3$. In embodiments, $R^{35}$ is independently —$CI_3$. In embodiments, $R^{35}$ is independently —F. In embodiments, $R^{35}$ is independently —Cl. In embodiments, $R^{35}$ is independently —Br. In embodiments, $R^{35}$ is independently —I. In embodiments, $R^{35}$ is independently $R^{36}$-substituted $C_1$-$C_4$ alkyl. In embodiments, $R^{35}$ is independently $R^{36}$-substituted 2 to 4 membered heteroalkyl. In embodiments, $R^{35}$ is independently $R^{36}$-substituted $C_3$-$C_6$ cycloalkyl. In embodiments, $R^{35}$ is independently $R^{36}$-substituted 3 to 6 membered heterocycloalkyl. In embodiments, $R^{35}$ is independently $R^{36}$-substituted phenyl. In embodiments, $R^{35}$ is independently $R^{36}$-substituted 5 to 6 membered heteroaryl. In embodiments, $R^{35}$ is independently unsubstituted $C_1$-$C_4$ alkyl. In embodiments, $R^{35}$ is independently unsubstituted 2 to 4 membered heteroalkyl. In embodiments, $R^{35}$ is independently unsubstituted $C_3$-$C_6$ cycloalkyl. In embodiments, $R^{35}$ is independently unsubstituted 3 to 6 membered heterocycloalkyl. In embodiments, $R^{35}$ is independently unsubstituted phenyl. In embodiments, $R^{35}$ is independently unsubstituted 5 to 6 membered heteroaryl.

$R^{36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In embodiments, $R^{36}$ is independently —$NH_2$. In embodiments, $R^{36}$ is independently —OH. In embodiments, $R^{36}$ is independently halogen. In embodiments, $R^{36}$ is independently —CN. In embodiments, $R^{36}$ is independently oxo. In embodiments, $R^{36}$ is independently —CF$_3$. In embodiments, $R^{36}$ is independently —COOH. In embodiments, $R^{36}$ is independently —CONH$_2$. In embodiments, $R^{36}$ is independently —NO$_2$. In embodiments, $R^{36}$ is independently —SH. In embodiments, $R^{36}$ is independently —SO$_3$H. In embodiments, $R^{36}$ is independently —SO$_4$H. In embodiments, $R^{36}$ is independently —SO$_2$NH$_2$. In embodiments, $R^{36}$ is independently —NHNH$_2$. In embodiments, $R^{36}$ is independently —ONH$_2$. In embodiments, $R^{36}$ is independently —NHC=(O)NHNH$_2$. In embodiments, $R^{36}$ is independently —NHC=(O) NH$_2$. In embodiments, $R^{36}$ is independently —NHSO$_2$H. In embodiments, $R^{36}$ is independently —NHC=(O)H. In embodiments, $R^{36}$ is independently —NHC(O)—OH. In embodiments, $R^{36}$ is independently —NHOH. In embodiments, $R^{36}$ is independently —OCF$_3$. In embodiments, $R^{36}$ is independently —OCHF$_2$. In embodiments, $R^{36}$ is independently —CCl$_3$. In embodiments, $R^{36}$ is independently —CBr$_3$. In embodiments, $R^{36}$ is independently —CI$_3$. In embodiments, $R^{36}$ is independently —F. In embodiments, $R^{36}$ is independently —Cl. In embodiments, $R^{36}$ is independently —Br. In embodiments, $R^{36}$ is independently —I. In embodiments, $R^{36}$ is independently $R^{37}$-substituted C$_1$-C$_4$ alkyl. In embodiments, $R^{36}$ is independently $R^{37}$-substituted 2 to 4 membered heteroalkyl. In embodiments, $R^{36}$ is independently $R^{37}$-substituted C$_3$-C$_6$ cycloalkyl. In embodiments, $R^{36}$ is independently $R^{37}$-substituted 3 to 6 membered heterocycloalkyl. In embodiments, $R^{36}$ is independently $R^{37}$-substituted phenyl. In embodiments, $R^{36}$ is independently $R^{37}$-substituted 5 to 6 membered heteroaryl. In embodiments, $R^{36}$ is independently unsubstituted C$_1$-C$_4$ alkyl. In embodiments, $R^{36}$ is independently unsubstituted 2 to 4 membered heteroalkyl. In embodiments, $R^{36}$ is independently unsubstituted C$_3$-C$_6$ cycloalkyl. In embodiments, $R^{36}$ is independently unsubstituted 3 to 6 membered heterocycloalkyl. In embodiments, $R^{36}$ is independently unsubstituted phenyl. In embodiments, $R^{36}$ is independently unsubstituted 5 to 6 membered heteroaryl.

In some embodiments, $R^3$ is substituted heteroaryl; $L^1$ is $L^2$-$L^3$-$L^4$-$L^5$; $L^2$ is —CH$_2$CH$_2$OCH$_2$—; $L^3$ is 5 to 10 membered heteroarylene; $L^4$ is —(CH$_2$CH$_2$O)$_b$—; b is an integer from 2 to 8; $L^5$ is —CH$_2$CH$_2$C=(O)NH(CH$_2$)$_{b10}$—; and b10 is an integer from 1 to 6. In some embodiments, $R^3$ is substituted bicyclic heteroaryl; $L^1$ is $L^2$-$L^3$-$L^4$-$L^5$; $L^2$ is —CH$_2$CH$_2$OCH$_2$—; $L^3$ is 5 to 10 membered heteroarylene; $L^4$ is —(CH$_2$CH$_2$O)$_b$—; b is an integer from 2 to 8; $L^5$ is —CH$_2$CH$_2$C=(O)NH(CH$_2$)$_{b10}$—; and b10 is an integer from 1 to 6. In some embodiments, $R^3$ is heteroaryl substituted with —NH$_2$ or —OH; $L^1$ is $L^2$-$L^3$-$L^4$-$L^5$; $L^2$ is —CH$_2$CH$_2$OCH$_2$—; $L^3$ is 5 to 10 membered heteroarylene; $L^4$ is —(CH$_2$CH$_2$O)$_b$—; b is an integer from 2 to 8; $L^5$ is —CH$_2$CH$_2$C=(O)NH(CH$_2$)$_{b10}$—; and b10 is an integer from 1 to 6. In some embodiments, $R^3$ is benzoxazolyl substituted with —NH$_2$ or —OH; $L^1$ is $L^2$-$L^3$-$L^4$-$L^5$; $L^2$ is —CH$_2$CH$_2$OCH$_2$—; $L^3$ is 5 to 10 membered heteroarylene; $L^4$ is —(CH$_2$CH$_2$O)$_b$—; b is an integer from 2 to 8; $L^5$ is —CH$_2$CH$_2$C=(O)NH(CH$_2$)$_{b10}$—; and b10 is an integer from 1 to 6. In some embodiments, $R^3$ is benzoxazolyl substituted with —NH$_2$ or —OH; $L^1$ is $L^2$-$L^3$-$L^4$-$L^5$; $L^2$ is —CH$_2$CH$_2$OCH$_2$—; $L^3$ is triazolylene; $L^4$ is —(CH$_2$CH$_2$O)$_b$—; b is an integer from 4 to 8; and $L^5$ is —CH$_2$CH$_2$C=(O)NH(CH$_2$)$_4$.

$R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and $R^{58}$, are independently hydrogen, oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —OH. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently halogen. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —CN. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently oxo. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —CF$_3$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —COOH. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —CONH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NO$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —SH. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —SO$_3$H. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —SO$_4$H. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —SO$_2$NH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHNH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —ONH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHC=(O)NHNH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHC=(O) NH$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHSO$_2$H. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHC=(O)H. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHC(O)—OH. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —NHOH. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —OCF$_3$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —OCHF$_2$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —CCl$_3$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —CBr$_3$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —CI$_3$. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —F. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —Cl. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —Br. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently —I. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently unsubstituted $C_1$-$C_4$ alkyl. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently unsubstituted 2 to 4 membered heteroalkyl. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently unsubstituted $C_3$-$C_6$ cycloalkyl. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently unsubstituted 3 to 6 membered heterocycloalkyl. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently unsubstituted phenyl. In embodiments, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, and/or $R^{58}$, are independently unsubstituted 5 to 6 membered heteroaryl.

In some embodiments, a compound as described herein may include multiple instances of $R^3$, $R^7$, $R^8$, $R^9$, $R^{10}$, X, m, n, v, and/or other variables. In such embodiments, each variable may optional be different and be appropriately labeled to distinguish each group for greater clarity. For example, where each $R^3$, $R^7$, $R^8$, $R^9$, $R^{10}$, X, m, n, and/or v, is different, they may be referred to, for example, as $R^{3.1}$, $R^{3.2}$, $R^{3.3}$, $R^{3.4}$, $R^{3.5}$, $R^{3.6}$, $R^{3.7}$, $R^{7.1}$, $R^{7.2}$, $R^{7.3}$, $R^{7.4}$, $R^{7.5}$, $R^{7.6}$, $R^{7.7}$, $R^{8.1}$, $R^{8.2}$, $R^{8.3}$, $R^{8.4}$, $R^{8.5}$, $R^{8.6}$, $R^{8.7}$, $R^{9.1}$, $R^{9.2}$, $R^{9.3}$, $R^{9.4}$, $R^{9.5}$, $R^{9.6}$, $R^{9.7}$, $R^{10.1}$, $R^{10.2}$, $R^{10.3}$, $R^{10.4}$, $R^{10.5}$, $R^{10.6}$, $R^{10.7}$, $X^{.1}$, $X^{.2}$, $X^{.3}$, $X^{.4}$, $X^{.5}$, $X^{.6}$, $X^{.7}$, $m^{.1}$, $m^{.2}$, $m^{.3}$, $m^{.4}$, $m^{.5}$, $m^{.6}$, $m^{.7}$, $n^{.1}$, $n^{.2}$, $n^{.3}$, $n^{.4}$, $n^{.5}$, $n^{.6}$, $n^{.7}$, $v^{.1}$, $v^{.2}$, $v^{.3}$, $v^{.4}$, $v^{.5}$, $v^{.6}$, $v^{.7}$, respectively, wherein the definition of $R^3$ is assumed by $R^{3.1}$, $R^{3.2}$, $R^{3.3}$, $R^{3.4}$, $R^{3.5}$, $R^{3.6}$, $R^{3.7}$, the definition of $R^7$ is assumed by $R^{7.1}$, $R^{7.2}$, $R^{7.3}$, $R^{7.4}$, $R^{7.5}$, $R^{7.6}$, $R^{7.7}$, the definition of $R^8$ is assumed by $R^{8.1}$, $R^{8.2}$, $R^{8.3}$, $R^{8.4}$, $R^{8.5}$, $R^{8.6}$, $R^{8.7}$, the definition of $R^9$ is assumed by $R^{9.1}$, $R^{9.2}$, $R^{9.3}$, $R^{9.4}$, $R^{9.5}$, $R^{9.6}$, $R^{9.7}$, the definition of $R^{10}$ is assumed by $R^{10.1}$, $R^{10.2}$, $R^{10.3}$, $R^{10.4}$, $R^{10.5}$, $R^{10.6}$, $R^{10.7}$, the definition of X is assumed by $X^{.1}$, $X^{.2}$, $X^{.3}$, $X^{.4}$, $X^{.5}$, $X^{.6}$, $X^{.7}$, the definition of m is assumed by $m^{.1}$, $m^{.2}$, $m^{.3}$, $m^{.4}$, $m^{.5}$, $m^{.6}$, $m^{.7}$, the definition of n is assumed by $n^{.1}$, $n^{.2}$, $n^{.3}$, $n^{.4}$, $n^{.5}$, $n^{.6}$, $n^{.7}$, the definition of v is assumed by $v^{.1}$, $v^{.2}$, $v^{.3}$, $v^{.4}$, $v^{.5}$, $v^{.6}$, $v^{.7}$.

The variables used within a definition of $R^3$, $R^7$, $R^8$, $R^9$, $R^{10}$, X, m, n, v, and/or other variables that appear at multiple instances and are different may similarly be appropriately labeled to distinguish each group for greater clarity.

In embodiments, the compound competes with rapamycin for binding to mTORC1. In embodiments, the compound binds an overlapping region of mTORC1 with the binding region of rapamycin. In embodiments, the compound competes with ATP for binding to mTOR. In embodiments, the compound competes with ATP for binding to mTORC1. In embodiments, the compound competes with rapamycin and ATP for binding to mTORC1.

In embodiments, the compound is an mTORC1 specific inhibitor. In embodiments, the compound has a slow off-rate from mTORC1. In embodiments, the compound has an off-rate of slower than 0.1 per minute. In embodiments, the compound has an off-rate of slower than 0.01 per minute. In embodiments, the compound has an off-rate of slower than 0.001 per minute. In embodiments, the compound has an off-rate of slower than 0.0001 per minute. In embodiments, the compound-mTORC1 complex has a half-life of at least 10 minutes. In embodiments, the compound-mTORC1 complex has a half-life of at least 100 minutes. In embodiments, the compound-mTORC1 complex has a half-life of at least 300 minutes. In embodiments, the compound-mTORC1 complex has a half-life of at least 1000 minutes. In embodiments, the compound-mTORC1 complex has a half-life of at least 3000 minutes. In embodiments, the compound-mTORC1 complex has a half-life of at least 10000 minutes.

In embodiments, the compound is

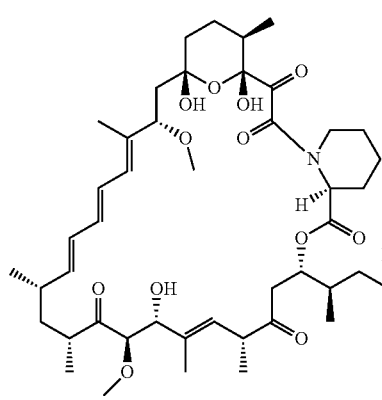
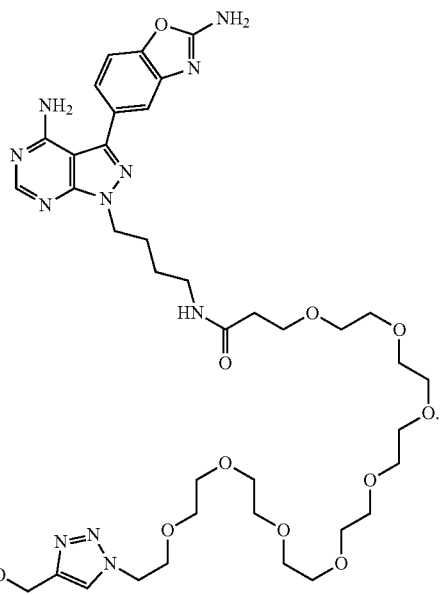

In embodiments, the compound is
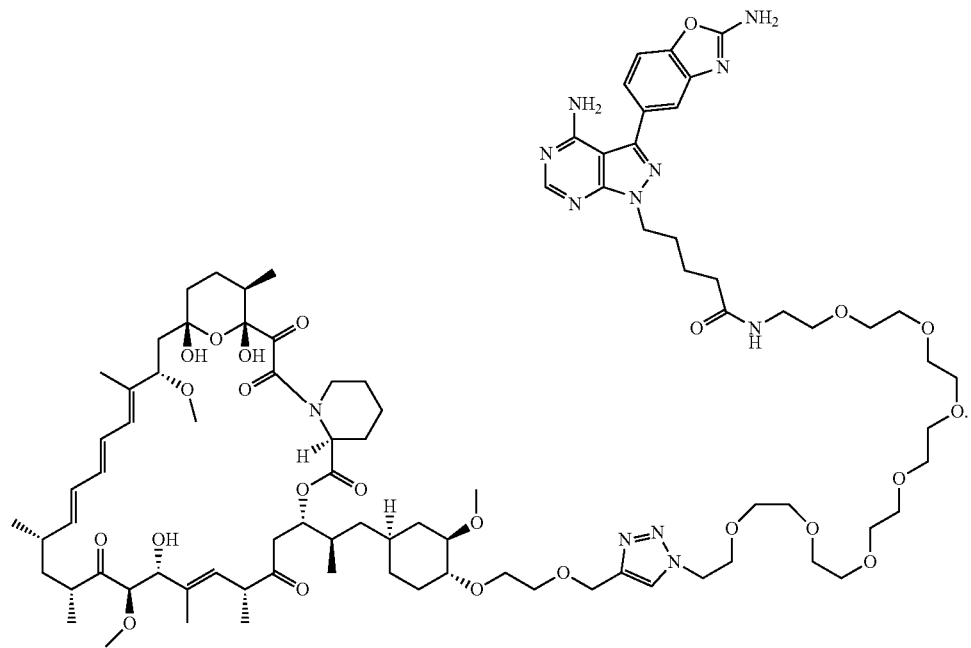 [SMILES: CO[C@H]1C[C@]2(O)CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCNC(=O)CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]
In embodiments, the compound is
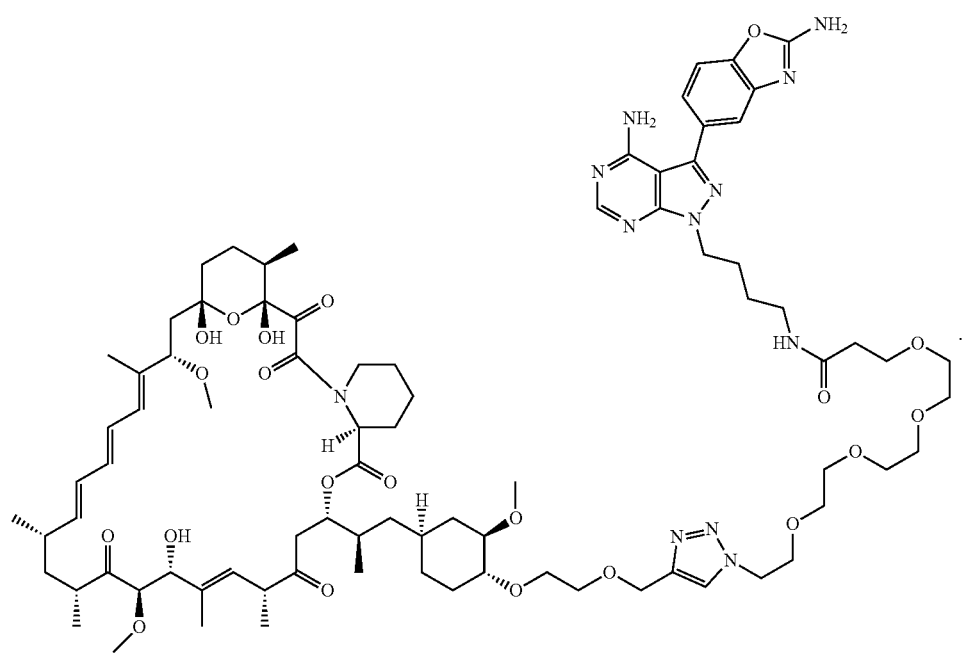 [SMILES: CO[C@H]1C[C@]2(O)CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the compound is

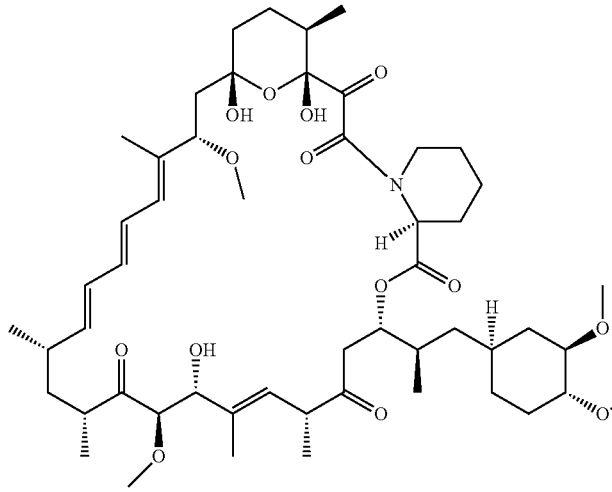

In embodiments, the compound is M-1071. In embodiments, the compound is M-1111. In embodiments, the compound is M-3059. In embodiments, the compound is M-1115. In embodiments, the compound is not M-1115. In embodiments, the compound is E1010. In embodiments, the compound is E1035.

In embodiments, the active site mTOR inhibitor is a monovalent MLN0128.

In embodiments, the active site mTOR inhibitor is

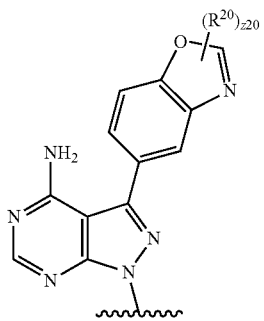

wherein $R^{20}$ is as described herein, including in embodiments. In embodiments, z20 is an integer from 0 to 4. In embodiments, z20 is 0. In embodiments, z20 is 1. In embodiments, z20 is 2. In embodiments, z20 is 3. In embodiments, z20 is 4. In embodiments, $R^{20}$ is independently —NH$_2$. In embodiments, $R^{20}$ is independently —OH. In embodiments, $R^{20}$ is independently halogen. In embodiments, $R^{20}$ is independently —CN. In embodiments, $R^{20}$ is independently oxo. In embodiments, $R^{20}$ is independently —CF$_3$. In embodiments, $R^{20}$ is independently —COOH. In embodiments, $R^{20}$ is independently —CONH$_2$. In embodiments, $R^{20}$ is independently —NO$_2$. In embodiments, $R^{20}$ is independently —SH. In embodiments, $R^{20}$ is independently —SO$_3$H. In embodiments, $R^{20}$ is independently —SO$_4$H. In embodiments, $R^{20}$ is independently —SO$_2$NH$_2$. In embodiments, $R^{20}$ is independently —NHNH$_2$. In embodiments, $R^{20}$ is independently —ONH$_2$. In embodiments, $R^{20}$ is independently —NHC=(O)NHNH$_2$. In embodiments, $R^{20}$ is independently —NHC=(O) NH$_2$. In embodiments, $R^{20}$ is independently —NHSO$_2$H. In embodiments, $R^{20}$ is independently —NHC=(O)H. In embodiments, $R^{20}$ is independently —NHC(O)—OH. In embodiments, $R^{20}$ is independently —NHOH. In embodiments, $R^{20}$ is independently —OCF$_3$. In embodiments, $R^{20}$ is independently —OCHF$_2$. In embodiments, $R^{20}$ is independently a halogen, —CF$_3$, —CHF$_2$, —CH$_2$F, —CN, —NHNH$_2$, —NO$_2$, —NH$_2$, —C(O)H, —C(O)OH, —C(O)NH$_2$, —OH, —NHC(O)OH, —OCF$_3$, —OCHF$_2$, $R^{21}$-substituted or unsubstituted C$_1$-C$_8$ alkyl, $R^{21}$-substituted or unsubstituted 2 to 8 membered heteroalkyl, $R^{21}$-substituted or unsubstituted C$_3$-C$_8$ cycloalkyl, $R^{21}$-substituted or unsubstituted 3 to 8 membered heterocycloalkyl, $R^{21}$-substituted or unsubstituted C$_6$-C$_{10}$ aryl, or $R^{21}$-substituted or unsubstituted 5 to 10 membered heteroaryl. In embodiments, $R^{20}$ is independently a halogen, —CF$_3$, —CN, —NH$_2$, —OH, $R^{21}$-substituted or unsubstituted C$_1$-C$_4$ alkyl, $R^{21}$-substituted or unsubstituted 2 to 4 membered heteroalkyl, $R^{21}$-substituted or unsubstituted C$_3$-C$_6$ cycloalkyl, $R^{21}$-substituted or unsubstituted 3 to 6 membered heterocycloalkyl, $R^{21}$-substituted or unsubstituted phenyl, or $R^{21}$-substituted or unsubstituted 5 to 6 membered heteroaryl. In embodiments, $R^{20}$ is independently a halogen, —CF$_3$, —CN, —NH$_2$, —OH, unsubstituted C$_1$-C$_4$ alkyl, or unsubstituted 2 to 4 membered heteroalkyl. In embodiments, $R^{20}$ is independently a halogen, —CF$_3$, unsubstituted methyl, unsubstituted ethyl, unsubstituted isopropyl, unsubstituted methoxy, or unsubstituted ethoxy. In embodiments, $R^{20}$ is independently unsubstituted methyl. In embodiments, $R^{20}$ is independently unsubstituted ethyl. In embodiments, $R^{20}$ is independently unsubstituted methoxy. In embodiments, $R^{20}$ is independently unsubstituted ethoxy. In embodiments, $R^{20}$ is independently —CCl$_3$. In embodiments, $R^{20}$ is independently —CBr$_3$. In embodiments, $R^{20}$ is independently —CI$_3$. In embodiments, $R^{20}$ is independently —F. In embodiments, $R^{20}$ is independently —Cl. In embodiments, $R^{20}$ is independently —Br. In embodiments, $R^{20}$ is independently —I. In embodiments, the active site mTOR inhibitor is

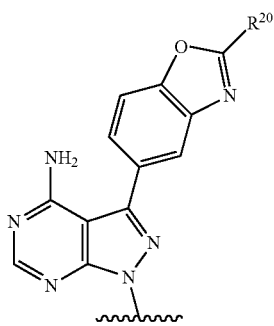

wherein R[20] is as described herein, including in embodiments. In embodiments, the active site mTOR inhibitor is

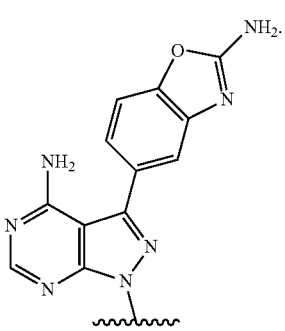 [SMILES: *n1nc(-c2ccc3oc(N)nc3c2)c2c(N)ncnc21]

In embodiments, the active site mTOR inhibitor is

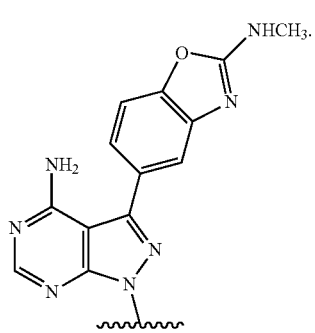 [SMILES: *n1nc(-c2ccc3oc(NC)nc3c2)c2c(N)ncnc21]

In embodiments, the active site mTOR inhibitor is

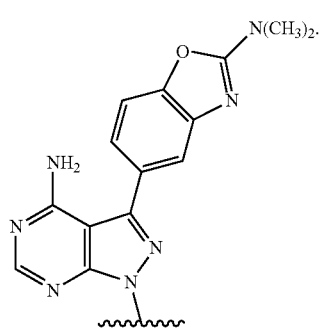 [SMILES: *n1nc(-c2ccc3oc(N(C)C)nc3c2)c2c(N)ncnc21]

In embodiments, the active site mTOR inhibitor is

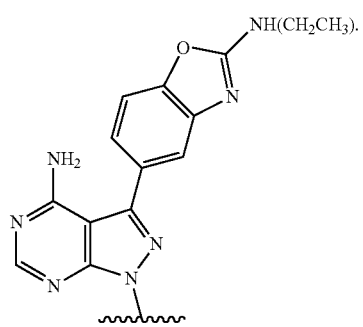

In embodiments, the active site mTOR inhibitor is

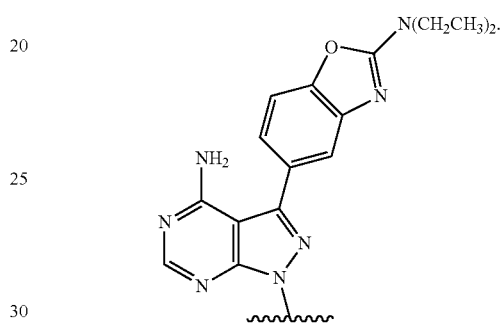

In embodiments, the active site mTOR inhibitor is

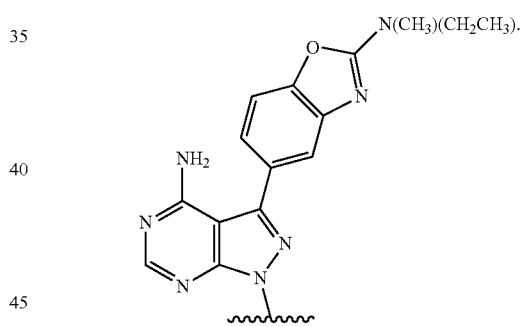

In embodiments, the active site mTOR inhibitor is

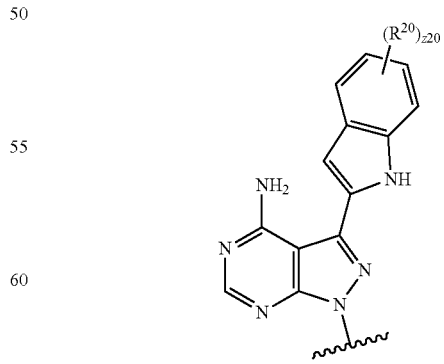

wherein R[20] is as described herein, including in embodiments. z20 is an integer from 0 to 5. In embodiments, z20 is 0. In embodiments, z20 is 1. In embodiments, z20 is 2. In embodiments, z20 is 3. In embodiments, z20 is 4. In embodiments, z20 is 5. In embodiments, $R^{20}$ is independently —$NH_2$. In embodiments, $R^{20}$ is independently —OH. In embodiments, $R^{20}$ is independently halogen. In embodiments, $R^{20}$ is independently —CN. In embodiments, $R^{20}$ is independently oxo. In embodiments, $R^{20}$ is independently —$CF_3$. In embodiments, $R^{20}$ is independently —COOH. In embodiments, $R^{20}$ is independently —$CONH_2$. In embodiments, $R^{20}$ is independently —$NO_2$. In embodiments, $R^{20}$ is independently —SH. In embodiments, $R^{20}$ is independently —$SO_3H$. In embodiments, $R^{20}$ is independently —$SO_4H$. In embodiments, $R^{20}$ is independently —$SO_2NH_2$. In embodiments, $R^{20}$ is independently —$NHNH_2$. In embodiments, $R^{20}$ is independently —$ONH_2$. In embodiments, $R^{20}$ is independently —NHC=(O)$NHNH_2$. In embodiments, $R^{20}$ is independently —NHC=(O) $NH_2$. In embodiments, $R^{20}$ is independently —$NHSO_2H$. In embodiments, $R^{20}$ is independently —NHC=(O)H. In embodiments, $R^{20}$ is independently —NHC(O)—OH. In embodiments, $R^{20}$ is independently —NHOH. In embodiments, $R^{20}$ is independently —$OCF_3$. In embodiments, $R^{20}$ is independently —$OCHF_2$. In embodiments, $R^{20}$ is independently a halogen, —$CF_3$, —$CHF_2$, —$CH_2F$, —CN, —$NHNH_2$, —$NO_2$, —$NH_2$, —C(O)H, —C(O)OH, —C(O)$NH_2$, —OH, —NHC(O)OH, —$OCF_3$, —$OCHF_2$, $R^{21}$-substituted or unsubstituted $C_1$-$C_8$ alkyl, $R^{21}$-substituted or unsubstituted 2 to 8 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted $C_6$-$C_{10}$ aryl, or $R^{21}$-substituted or unsubstituted 5 to 10 membered heteroaryl. In embodiments, $R^{20}$ is independently a halogen, —$CF_3$, —CN, —$NH_2$, —OH, $R^{21}$-substituted or unsubstituted $C_1$-$C_4$ alkyl, $R^{21}$-substituted or unsubstituted 2 to 4 membered heteroalkyl, $R^{21}$-substituted or unsubstituted $C_3$-$C_6$ cycloalkyl, $R^{21}$-substituted or unsubstituted 3 to 6 membered heterocycloalkyl, $R^{21}$-substituted or unsubstituted phenyl, or $R^{21}$-substituted or unsubstituted 5 to 6 membered heteroaryl. In embodiments, $R^{20}$ is independently a halogen, —$CF_3$, —CN, —$NH_2$, —OH, unsubstituted $C_1$-$C_4$ alkyl, or unsubstituted 2 to 4 membered heteroalkyl. In embodiments, $R^{20}$ is independently a halogen, —$CF_3$, unsubstituted methyl, unsubstituted ethyl, unsubstituted isopropyl, unsubstituted methoxy, or unsubstituted ethoxy. In embodiments, $R^{20}$ is independently unsubstituted methyl. In embodiments, $R^{20}$ is independently unsubstituted ethyl. In embodiments, $R^{20}$ is independently unsubstituted methoxy. In embodiments, $R^{20}$ is independently unsubstituted ethoxy. In embodiments, $R^{20}$ is independently —$CCl_3$. In embodiments, $R^{20}$ is independently —$CBr_3$. In embodiments, $R^{20}$ is independently —$CI_3$. In embodiments, $R^{20}$ is independently —F. In embodiments, $R^{20}$ is independently —Cl. In embodiments, $R^{20}$ is independently —Br. In embodiments, $R^{20}$ is independently —I. In embodiments, the active site mTOR inhibitor is

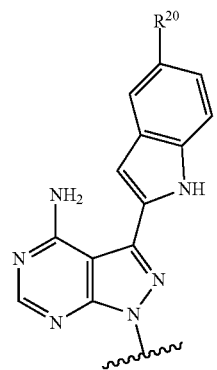

wherein $R^{20}$ is as described herein. In embodiments, the active site mTOR inhibitor is

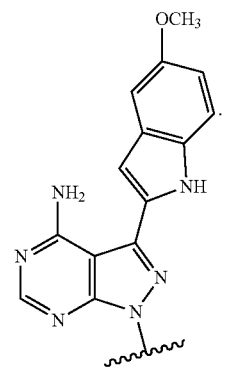 [SMILES: *n1nc(-c2cc3cc(OC)ccc3[nH]2)c2c(N)ncnc21]

In embodiments, the active site mTOR inhibitor is

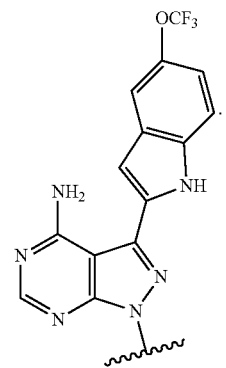 [SMILES: *n1nc(-c2cc3cc(OC(F)(F)F)ccc3[nH]2)c2c(N)ncnc21]

In embodiments, the active site mTOR inhibitor is

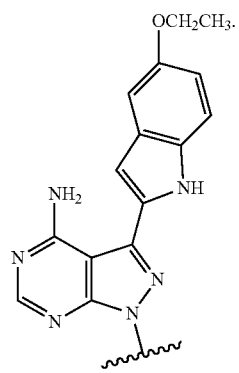 [SMILES: *n1nc(-c2cc3cc(OCC)ccc3[nH]2)c2c(N)ncnc21]

In embodiments, the active site mTOR inhibitor is

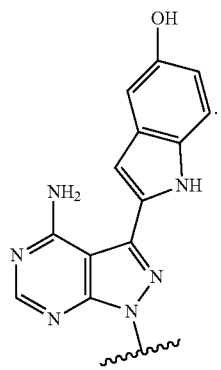 [SMILES: *n1nc(-c2cc3cc(O)ccc3[nH]2)c2c(N)ncnc21]

In embodiments, the active site mTOR inhibitor (e.g., asTORi) has a weaker binding affinity for mTOR than MLN0128. In embodiments, the active site mTOR inhibitor has a binding affinity that results in preferential binding to mTORC1 over mTORC2 that is greater than the same compound wherein the active site mTOR inhibitor is MLN0128. In embodiments, the active site mTOR inhibitor has a binding affinity that results in preferential binding to mTORC1 over mTORC2 that is greater than the same compound wherein the active site mTOR inhibitor is PP242. In embodiments, the active site mTOR inhibitor has a binding affinity that results in preferential binding to mTORC1 over mTORC2 that is greater than the same compound wherein the active site mTOR inhibitor is PP242 wherein the —OH substituent on the indoyly moiety is replaced with an unsubstituted methoxy moiety. Without being limited by mechanism, the compound may include an active site mTOR inhibitor that results in a preferential binding of the compound to mTORC1 over mTORC2 of at least 1.1-fold (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold). Without being limited by mechanism, the compound may include an active site mTOR inhibitor that results in a preferential inhibition of mTORC1 over mTORC2 by the compound of at least 1.1-fold (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In embodiments, the compound is included in a drug-eluting stent.

In embodiments, the compound is a compound described herein.

In an aspect is provided a drug-eluting stent comprising a compound as described herein.

B. Pharmaceutical Compositions

In another aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim).

In embodiments of the pharmaceutical compositions, the compound, or pharmaceutically acceptable salt thereof, is included in a therapeutically effective amount. In embodiments of the pharmaceutical compositions, the compound is included in a drug-eluting stent.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an anti-cancer agent. In embodiments, the second agent is an anti-autoimmune disease agent. In embodiments, the second agent is an anti-inflammatory disease agent. In embodiments, the second agent is an anti-neurodegenerative disease agent. In embodiments, the second agent is an anti-metabolic disease agent. In embodiments, the second agent is an anti-cardiovascular disease agent. In embodiments, the second agent is an anti-aging agent. In embodiments, the second agent is a longevity agent. In embodiments, the second agent is an agent for treating or preventing transplant rejection. In embodiments, the second agent is an agent for treating or preventing fungal infection. In embodiments, the second agent is immune system repressor. In embodiments, the second agent is an mTOR modulator. In embodiments, the second agent is an mTOR inhibitor. In embodiments, the second agent is an active site mTOR inhibitor. In embodiments, the second agent is a rapamycin. In embodiments, the second agent is a rapamycin analog. In embodiments, the second agent is an mTORC1 pathway inhibitor.

C. Methods of Treatment

In an aspect is provided a method of treating a disease associated with an aberrant level of mTORC1 activity in a subject in need of such treatment. The disease may be caused by an aberrantly high mTORC1 activity (e.g., hyperactivity of mTORC1 or increased level of activity of mTORC1 or increased amount of mTORC1 or mTOR mutations). The method includes administering to the subject a compound described herein. The method may include administering to the subject a therapeutically effective amount of a compound described herein (e.g., an mTORC1 modulator (e.g., inhibitor) as described above).

In an aspect is provided a compound as described herein for use as a medicament. In embodiments, the medicament is useful for treating a disease caused by an aberrantly high mTORC1 activity (e.g., hyperactivity of mTORC1 or increased level of activity of mTORC1 or increased amount of mTORC1). The use includes administering to the subject a compound described herein. The use may include administering to the subject a therapeutically effective amount of a compound described herein (e.g., an mTORC1 modulator (e.g., inhibitor) as described above).

In an aspect is provided a compound as described herein for use in the treatment of a disease caused by aberrant levels of mTORC1 activity in a subject in need of such treatment. The disease may be caused by an aberrantly high mTORC1 activity (e.g., hyperactivity of mTORC1 or increased level of activity of mTORC1 or increased amount of mTORC1). The use includes administering to the subject a compound described herein. The use may include administering to the subject a therapeutically effective amount of a compound described herein (e.g., an mTORC1 modulator (e.g., inhibitor) as described above).

mTORC1 hyperactivity is an increased amount of mTORC1 activity compared to normal levels of mTORC1 activity in a particular subject or a population of healthy subjects. The increased amount of mTORC1 activity may result in, for example, excessive amounts of cell proliferation thereby causing the disease state.

The subject of treatment for the disease is typically a mammal. The mammal treated with the compound (e.g., compound described herein, mTORC1 modulator (e.g., inhibitor)) may be a human, nonhuman primate, and/or non-human mammal (e.g., rodent, canine).

In another aspect is provided a method of treating an mTORC1 activity-associated disease in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for treating an mTORC1 activity-associated disease in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in the treatment of an mTORC1 activity-associated disease in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In embodiments, the mTORC1 activity-associated disease or disease associated with aberrant levels of mTORC1 activity is cancer. In embodiments, the mTORC1 activity-associated disease or disease associated with aberrant levels of mTORC1 activity is an autoimmune disease. In embodiments, the mTORC1 activity-associated disease or disease associated with aberrant levels of mTORC1 activity is an inflammatory disease. In embodiments, the mTORC1 activity-associated disease or disease associated with aberrant levels of mTORC1 activity is a neurodegenerative disease. In embodiments, the mTORC1 activity-associated disease or disease associated with aberrant levels of mTORC1 activity is a metabolic disease. In embodiments, the mTORC1 activity-associated disease or disease associated with aberrant levels of mTORC1 activity is transplant rejection. In embodiments, the mTORC1 activity-associated disease or disease associated with aberrant levels of mTORC1 activity is fungal infection. In embodiments, the mTORC1 activity-associated disease or disease associated with aberrant levels of mTORC1 activity is an inflammatory disease. In embodiments, the mTORC1 activity-associated disease or disease associated with aberrant levels of mTORC1 activity is a cardiovascular disease. In embodiments, the mTORC1 activity-associated disease or disease associated with aberrant levels of mTORC1 activity is aging. In embodiments, the mTORC1 activity-associated disease or disease associated with aberrant levels of mTORC1 activity is dying of an age-related disease. In embodiments, the mTORC1 activity-associated disease or disease associated with aberrant levels of mTORC1 activity is Cancer (e.g., carcinomas, sarcomas, adenocarcinomas, lymphomas, leukemias, solid cancers, lymphoid cancers; cancer of the kidney, breast, lung, bladder, colon, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), multiple myeloma, breast cancer (e.g., triple negative breast cancer)), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes *dorsalis*, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

In an aspect is provided a method of treating a disease including administering an effective amount of a compound as described herein. In an aspect is provided a compound as described herein for use as a medicament (e.g., for treatment of a disease). In an aspect is provided a compound as describe herein for use in the treatment of a disease (e.g., including administering an effective amount of a compound as described herein). In embodiments, the disease is cancer. In embodiments, the disease is an autoimmune disease. In embodiments, the disease is an inflammatory disease. In embodiments, the disease is a neurodegenerative disease. In embodiments, the disease is a metabolic disease. In embodiments, the disease is fungal infection. In embodiments, the disease is transplant rejection. In embodiments, the disease is an inflammatory disease. In embodiments, the disease is a cardiovascular disease. In embodiments, the disease is Cancer (e.g., carcinomas, sarcomas, adenocarcinomas, lymphomas, leukemias, solid cancers, lymphoid cancers; cancer of the kidney, breast, lung, bladder, colon, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), multiple myeloma, breast cancer (e.g., triple negative breast cancer)), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes *dorsalis*, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation). In embodiments, the disease is a polycystic disease. In embodiments, the disease is polycystic kidney disease. In embodiments, the disease is stenosis. In embodiments, the disease is restenosis. In embodiments, the disease is neointimal proliferation. In embodiments, the disease is neointimal hyperplasia.

In another aspect is provided a method of treating aging in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for treating aging in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in the treatment of aging in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a method of extending life span or inducing longevity in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for extending life span or inducing longevity in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in extending life span or inducing longevity in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In an aspect is provided a method of treating a polycystic disease in a subject in need of such treatment. The polycystic disease may be polycystic kidney disease. The method includes administering to the subject a compound described herein. The method may include administering to the subject a therapeutically effective amount of a compound described herein (e.g., an mTORC1 modulator (e.g., inhibitor) as described above).

In an aspect is provided a compound as described herein for use as a medicament. In embodiments, the medicament is useful for treating a polycystic disease. The polycystic disease may be polycystic kidney disease. The use includes administering to the subject a compound described herein. The use may include administering to the subject a therapeutically effective amount of a compound described herein (e.g., an mTORC1 modulator (e.g., inhibitor) as described above).

In an aspect is provided a compound as described herein for use in the treatment of a polycystic disease in a subject in need of such treatment. The polycystic disease may be polycystic kidney disease. The use includes administering to the subject a compound described herein. The use may include administering to the subject a therapeutically effective amount of a compound described herein (e.g., an mTORC1 modulator (e.g., inhibitor) as described above).

In an aspect is provided a method of treating stenosis in a subject in need of such treatment. The stenosis may be restenosis. The method includes administering to the subject a compound described herein. In embodiments the compound is administered in a drug eluting stent. The method may include administering to the subject a therapeutically effective amount of a compound described herein (e.g., an mTORC1 modulator (e.g., inhibitor) as described above).

In an aspect is provided a compound as described herein for use as a medicament. In embodiments, the medicament is useful for treating stenosis. The stenosis may be restenosis. The use includes administering to the subject a compound described herein. In embodiments the compound is administered in a drug eluting stent. The use may include administering to the subject a therapeutically effective amount of a compound described herein (e.g., an mTORC1 modulator (e.g., inhibitor) as described above).

In an aspect is provided a compound as described herein for use in the treatment of stenosis in a subject in need of such treatment. The stenosis may be restenosis. The use includes administering to the subject a compound described herein. In embodiments the compound is administered in a drug eluting stent. The use may include administering to the subject a therapeutically effective amount of a compound described herein (e.g., an mTORC1 modulator (e.g., inhibitor) as described above).

In embodiments, the disease is a disease described herein and the compound is a compound described herein.

D. Methods of Modulating mTORC1

In another aspect is provided a method of modulating mTORC1 activity in a subject in need thereof, including administering to the subject an effective amount of a compound as described herein, or a pharmaceutically acceptable salt thereof. In embodiments, the method includes inhibiting mTORC1 activity. In embodiments, the method includes inhibiting mTORC1 activity and not inhibiting mTORC2 activity. In embodiments, the method includes inhibiting mTORC1 activity more than inhibiting mTORC2 activity. In embodiments, the method includes inhibiting mTORC1 activity at least 1.1 fold as much as inhibiting mTORC2 activity (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In some embodiments, the mTORC1 is in a cell. In some embodiments, the cell is a mammalian cell, such as a human cell. The cell may be isolated in vitro, form part of a tissue in vitro, or may form part of an organism.

Modulating mTORC1 activity includes directly or indirectly modulating one or more functions of mTORC1 and/or one or more downstream effects of mTORC1. In other words, the function or effect of mTORC1 is altered compared to the function or effect of mTORC1 when the modulator (e.g., compound as described herein) is not present.

In embodiments, the mTORC1 modulator (e.g., compound as described herein, including in embodiments) is an mTORC1 inhibitor that decreases one or more of: activation of mTORC1, co-factor binding by mTORC1, co-factor binding by mTOR, and/or phosphorylation of 4EBP1. In embodiments, the mTORC1 modulator (e.g., compound as described herein, including in embodiments) is an mTORC1 inhibitor that decreases phosphorylation of S6 and/or S6K. In another embodiment, an effective amount of mTORC1 inhibitor is an amount sufficient to decrease mTORC1 activity in a cell (e.g., in a subject) to reduce cell proliferation relative to the amount of cell proliferation in the absence of mTORC1 inhibitor. In another embodiment, an effective amount of mTORC1 modulator (e.g., inhibitor) is an amount sufficient to increase cell death (e.g., apoptosis).

In embodiments, the compound reduces activation of eIF4E. In embodiments, the compound inhibits phosphorylation of 4E-BP1. In embodiments, the compound does not reduce phosphorylation of Akt. In embodiments, the compound does not reduce phosphorylation of Akt-473 or a residue corresponding to Akt-473. In embodiments, the compound does not cause hyperglycemia.

In an embodiment, modulating mTORC1 activity includes direct binding of the mTORC1 modulator to mTOR. In another embodiment, modulating mTORC1 activity is accomplished indirectly.

E. Additional Embodiments

1. A compound comprising a monovalent active site mTOR inhibitor covalently bound to a monovalent rapamycin or a monovalent rapamycin analog.
2. The compound of embodiment 1, wherein a divalent linker binds the monovalent active site mTOR inhibitor to the monovalent rapamycin or the monovalent rapamycin analog.
3. The compound of embodiment 2, wherein the divalent linker is at least 5 Å in length.
4. The compound of embodiment 2, wherein the divalent linker is at least 17 Å in length.
5. The compound of embodiment 2, wherein the divalent linker is at least 32 Å in length.
6. The compound of one of embodiments 2 to 5, wherein the compound comprises the divalent linker covalently bound to the monovalent active site mTOR inhibitor and the monovalent rapamycin or monovalent rapamycin analog.
7. The compound of one of embodiments 1 to 6, having the formula:

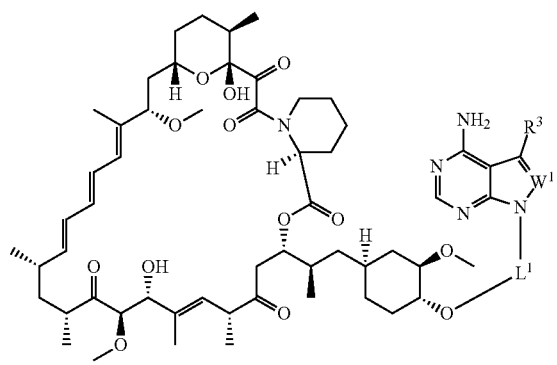

(II)

wherein,
$L^1$ is the divalent linker; $R^3$ is hydrogen, oxo, halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —NHC=(O)$NR^7R^8$, —$N(O)_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —NHC=(O)$NH_2$, —$NHSO_2H$, —NHC=(O)H, —NHC(O)OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl;

$W^1$ is N or CH; m and v are independently 1 or 2; n is independently an integer from 0 to 4; and X is independently —Cl, —Br, —I, or —F.

8. The compound of embodiment 7, having the formula:

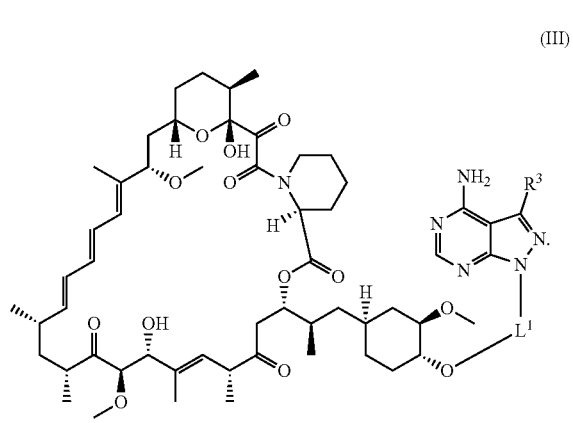

(III)

9. The compound of one of embodiments 7 to 8, wherein $R^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
10. The compound of one of embodiments 7 to 8, wherein $R^3$ is substituted or unsubstituted cycloalkyl, substituted or unsubstituted heterocycloalkyl, substituted or unsubstituted aryl, or substituted or unsubstituted heteroaryl.
11. The compound of one of embodiments 7 to 8, wherein $R^3$ is substituted or unsubstituted aryl or substituted or unsubstituted heteroaryl.
12. The compound of one of embodiments 7 to 8, wherein $R^3$ is substituted or unsubstituted fused ring aryl or substituted or unsubstituted fused ring heteroaryl.
13. The compound of one of embodiments 7 to 8, wherein $R^3$ is substituted or unsubstituted fused ring heteroaryl.
14. The compound of one of embodiments 7 to 8, wherein $R^3$ is substituted fused ring heteroaryl.
15. The compound of one of embodiments 7 to 8, wherein $R^3$ is substituted benzoxazolyl, substituted pyrimidinyl, substituted thiophenyl, substituted furanyl, substituted indolyl, substituted benzoxadiazolyl, substituted benzodioxolyl, substituted benzodioxanyl, substituted thianaphthanyl, substituted pyrrolopyridinyl, substituted indazolyl, substituted quinolinyl, substituted quinoxalinyl, substituted pyridopyrazinyl, substituted quinazolinonyl, substituted benzoisoxazolyl, substituted imidazopyridinyl, substituted benzofuranyl, substituted benzothiophenyl, substituted phenyl, substituted naphthyl, substituted biphenyl, substituted pyrrolyl, substituted pyrazolyl, substituted imidazolyl, substituted pyrazinyl, substituted oxazolyl, substituted isoxazolyl, substituted thiazolyl, substituted furylthienyl, substituted pyridyl, substituted pyrimidyl, substituted benzothiazolyl, substituted purinyl, substituted benzimidazolyl, substituted isoquinolyl, substituted thiadiazolyl, substituted oxadiazolyl, substituted pyrrolyl, substituted diazolyl, substituted triazolyl, substituted tetrazolyl, substituted benzothiadiazolyl, substituted isothiazolyl, substituted pyrazolopyrimidinyl, substituted pyrrolopyrimidinyl, substituted benzotriazolyl, or substituted quinolyl.
16. The compound of one of embodiments 7 to 15, wherein $L^1$ is $L^2$-$L^3$-$L^4$-$L^5$; $L^2$ is connected directly to the monovalent rapamycin or the monovalent rapamycin analog; $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^5$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

17. The compound of embodiment 16, wherein $L^2$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; $L^3$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; $L^4$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; and $L^5$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

18. The compound of embodiment 16, wherein $L^2$ is substituted or unsubstituted 3 to 8 membered heteroalkylene; $L^3$ is a substituted or unsubstituted 5 to 10 membered heteroarylene; $L^4$ is a substituted or unsubstituted 2 to 12 membered heteroalkylene; and $L^5$ is a substituted or unsubstituted 2 to 12 membered heteroalkylene.

19. The compound of one of embodiments 1 to 18, wherein the compound is an mTORC1 specific inhibitor.

20. A pharmaceutical composition comprising a pharmaceutically acceptable excipient and a compound of one of embodiments 1 to 19.

21. A method of inhibiting the activity of mTORC1 in a patient, the method comprising administering an effective amount of a compound of one of embodiments 1 to 19, or a pharmaceutically acceptable salt thereof, to the patient.

22. The method of embodiment 21, wherein the method comprises inhibiting the level of activity of mTORC1 at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 1000, 10000, or 100000-times the inhibition of the level of activity of TORC2.

23. A method of treating a disease associated with aberrant mTORC1 activity in a patient in need of such treatment, the method comprising administering a therapeutically effective amount of a compound of one of embodiments 1 to 19, or a pharmaceutically acceptable salt thereof, to the patient.

24. The method of embodiment 23, wherein the disease is cancer.

25. A method of treating a disease in a subject, the method comprising administering a compound of one of embodiments 1 to 19, or a pharmaceutically acceptable salt thereof, to the subject, wherein the disease is a cancer, autoimmune disease, inflammatory disease, metabolic disease, neurodegenerative disease, fungal infection, transplant rejection, aging, stenosis, neointimal proliferation, cardiovascular disease, or polycystic disease.

26. The method of embodiment 25, wherein the disease is cancer.

27. The method of embodiment 5, wherein the disease is an autoimmune disease.

28. The method of embodiment 25, wherein the disease is an inflammatory disease.

29. The method of embodiment 25, wherein the disease is a metabolic disease.

30. The method of embodiment 25, wherein the disease is a neurodegenerative disease.

31. The method of embodiment 25, wherein the disease is a fungal infection.

32. The method of embodiment 25, wherein the disease is transplant rejection.

33. The method of embodiment 25, wherein the disease is aging.

34. The method of embodiment 25, wherein the disease is stenosis.

35. The method of embodiment 34, wherein the stenosis is restenosis.

36. The method of embodiment 25, wherein the disease is neointimal proliferation.

37. The method of embodiment 25, wherein the disease is a polycystic disease.

38. The method of embodiment 37, wherein the polycystic disease is polycystic kidney disease.

39. The method of embodiment 25, wherein the compound, or a pharmaceutically acceptable salt thereof, is administered in a drug-eluting stent.

F. Examples

A. Example 1

The action of MLN0128 on TORC2 is not thought to be necessary for its anti-cancer activity. This has been analyzed in a genetically engineered mouse model of Akt-driven lymphomagenesis[10]. A non-phosphorylatable mutant of 4E-BP1 which is constitutively able to inhibit eIF4E, blocks Akt-driven lymphomagenesis, suggesting that this single substrate of mTOR is sufficient to support cancer cell growth and survival. In some animals harboring the constitutively active Akt and constitutively active 4E-BP1, some tumors which still express the 4E-BP1 mutant ($4EBP1^M$). Presumably, another pathway has been activated which bypasses the block imposed by $4EBP1^M$. These cells offer a genetic test of the mechanism of action of the asTORi class of inhibitors. If the action of asTORi on cells is mediated by 4E-BP1 phosphorylation, then there should be no effect of the drug when added to the cells which bypass $4EBP1^M$. The asTORi, PP242 has no significant effect in such cells (FIG. 1), confirming that the cell killing effects of asTORi is mediated in large part, if not completely, by phosphorylation of 4E-BP1 which leads to activation of eIF4E[10].

This assessment of the mechanism of action of various mTOR inhibitors suggests that inhibition of 4E-BP1 phosphorylation is essential for potent anti-cancer activity. Furthermore, the inhibition of TORC2, leading to dephosphorylation of Akt-473 is the key contributor to the dose limiting toxicity of hyperglycemia in clinical trials of asTORi such as MLN0128, and is dispensable for tumor cell killing.

An emerging desirable feature of kinase inhibitor drugs is the ability to inhibit kinase activity following drug washout[16]. The EGFR/HER2 inhibitor Lapatinib, exhibits slow-off kinetics from EGFR which is thought to be caused by a required conformational change in the kinase to allow drug to be released. Regardless of the mechanism, it is thought that kinase inhibitors with slow off kinetics will be better able to robustly inhibit kinase signaling in a tumor. Rather than requiring high drug levels in the blood stream 24 hr/day, such slow off drugs may demonstrate better target coverage than the more common rapidly dissociating kinase inhibitors.

B. Example 2

Design and Generation of a Third Class of mTOR Inhibitor-"Rapa-Link".

Figure 2A:
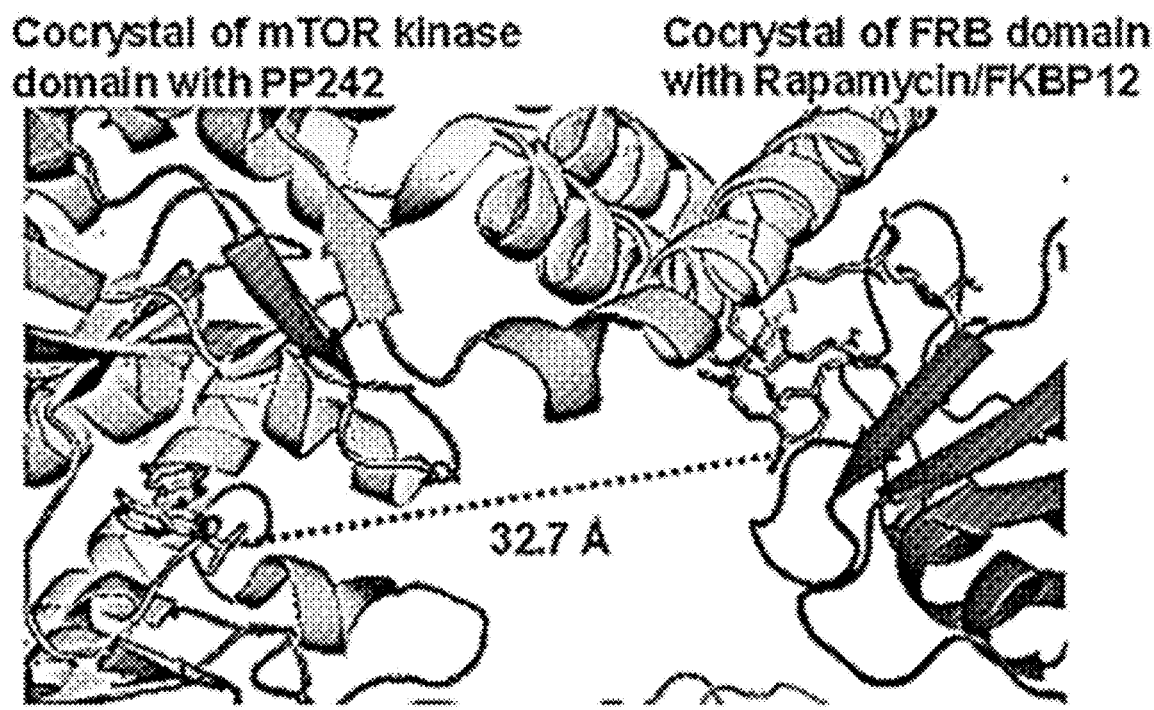
FIGS. 2A-2B. Design concept.
Figure 2B:
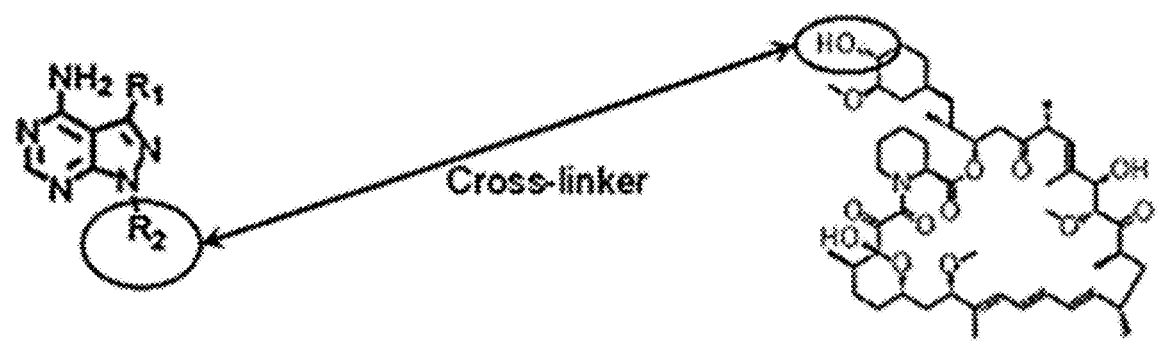

In the last year, the crystal structure of a portion of mTOR was solved by Pavletich and coworkers[17]. This structure, in conjunction with a much earlier structure of Rapamycin bound to the isolated FRB and FKBP proteins 18 provides an opportunity to develop a completely new class of mTOR inhibitors. By utilizing the TORC1 selective nature of Rapamycin, and linking Rapamycin to (in a way that does not disrupt Rapamycin's binding to FKBP12 or the FRB domain of mTOR) an asTORi (e.g., MLN0128) we predicted that a new type of pharmacological agent for targeting mTOR could be developed (FIGS. 2A and 2B). This approach to design of an mTOR inhibitor has never been proposed previously and provides a novel pharmacological means of blocking mTOR signaling. The key aspect of this design is to use Rapamycin to "deliver" an asTORi (e.g., MLN0128) to the active site of mTORC1, effectively blocking both pS6 and 4E-BP1. The second aspect of the design would be that linking Rapamycin to an asTORi (e.g., MLN0128) would result in binding to FKBP12 in cells, and in this large complex of an asTORi (e.g., MLN0128)-Rapa/FKBP12, an asTORi (e.g., MLN0128) would be diminished in its ability to bind to mTORC2 and thus would have reduced effects on Akt S473.

Figure 3A:
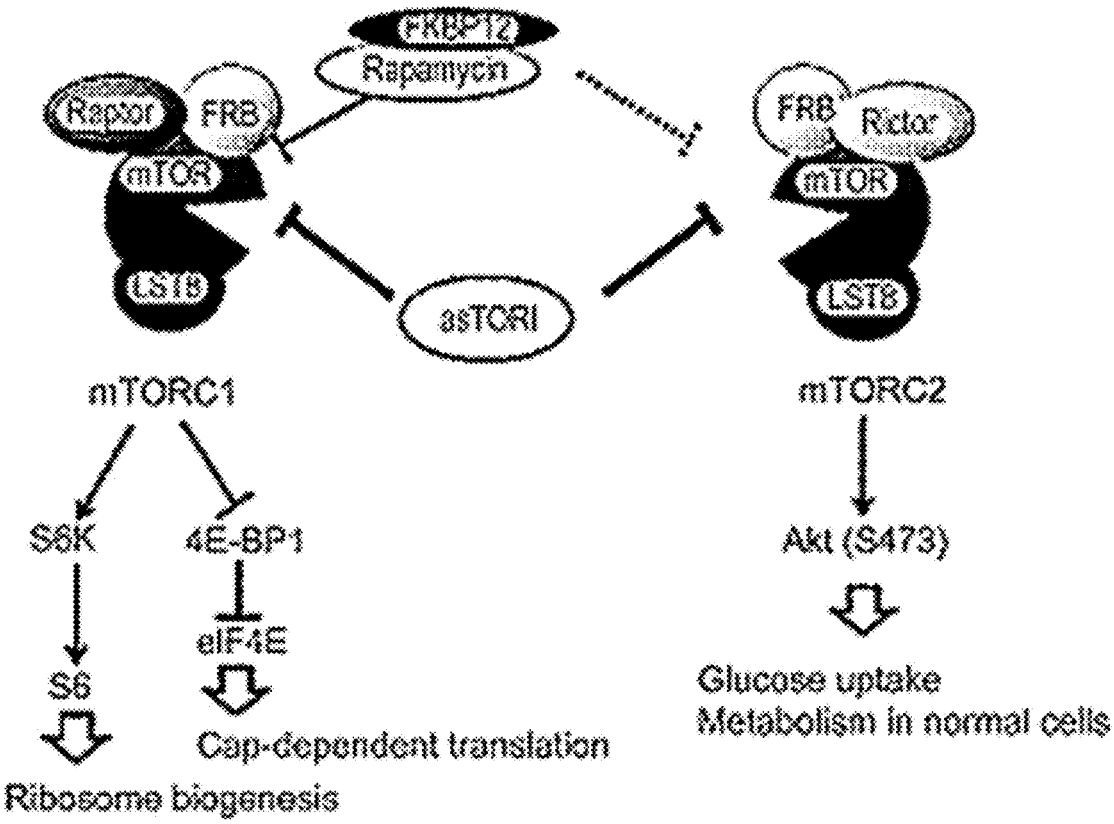
FIGS. 3A-3B. Model of mTOR signaling inhibition.
Figure 3B:
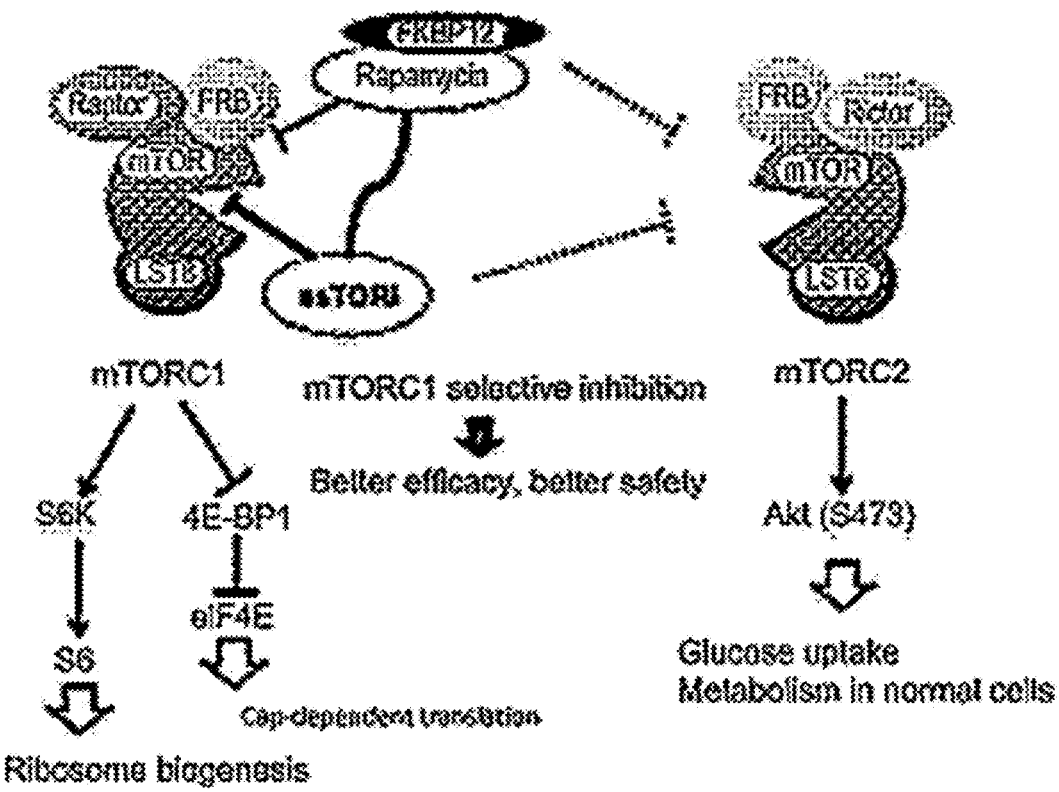

The basis for selective inhibition of mTORC1 by the new Rapamycin-asTORi (e.g., MLN0128) conjugate molecules (Rapa-Link) and their comparison to Rapamycin and asTORi (e.g., MLN0128) is shown in FIGS. 3A and 3B.

C. Example 3

Figure 4A:
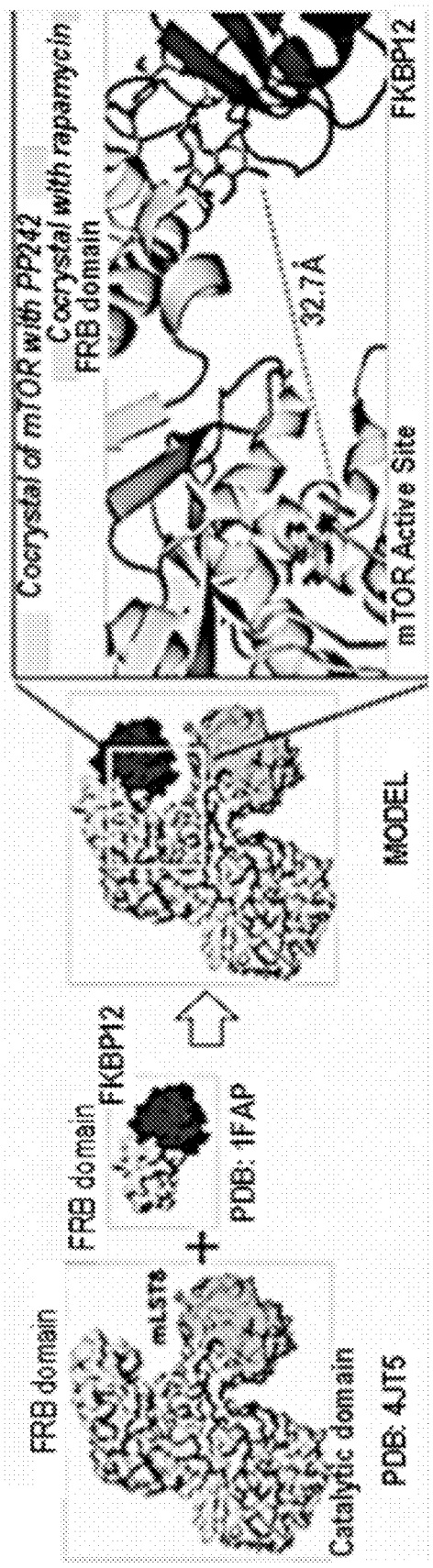
FIGS. 4A-4B. Design concept.

In order to determine the optimal regiochemistry and cross-linker length for tethering Rapamycin to an asTORi (e.g., MLN0128), two independent crystal structures of mTOR (PDB:4JT5)[17] and FRB:FKBP12:Rapamycin (1FAP)[18] were overlayed, using the common FRB domain contained in both structures (FIG. 4A).

To design the hybrid compound, the tethering positions to Rapamycin was designed in a way to minimize disruption of its binding to the FKBP12 protein and FRB domain of mTOR. Similarly, the linking group to an asTORi (e.g., MLN0128) was designed to avoid disrupting the active site inhibitor binding to catalytic domain of mTOR. Analysis of the Rapamycin cocrystal structure (1FAP)[18] revealed that the hydroxyl group at the C40 position of rapamycin is exposed to solvent region and is oriented toward the active site of mTOR (FIG. 4A). For an asTORi (e.g., MLN0128) a tethering position was selected based on co-crystal structures of mTOR using PP242 as the model ATP site ligand, which is highly related to MLN0128 (FIG. 4A). MLN0128 was selected as the asTORi for this work, because 1) MLN0128 is a clinical candidate which has good mTOR selectivity and possesses sufficient drug-like properties; 2) our structure-activity relationship (SAR) knowledge of pyrazolo[3,4-d]pyrimidine analogs is applicable to rational designs of cross-linkers.

Figure 4B:
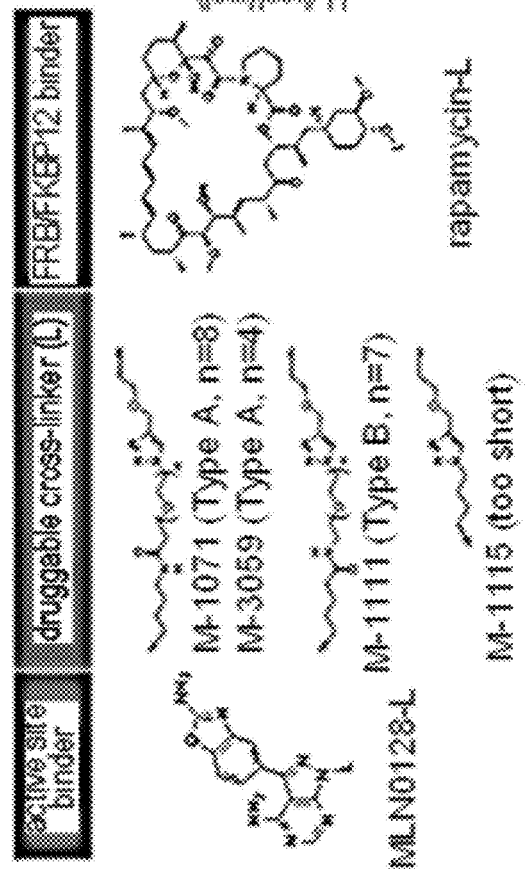

In order to design the proper cross-linker (L), we attempted to convert the distance between Rapamycin and the asTORi into a discrete number of heavy atoms using the modeling program, Molecular Operating Environment (MOE) (2013.0801). We first evaluated methylene cross-linkers, L: $(CH_2)_n$, with the length from n=10 to n=40 which tethers rapamycin with a substructure of PP242 (precursor of MLN0128) and determined that the long linker (n≥27) would be preferable (FIG. 4B). According to the results of this computational calculation, we designed the following compounds (M-1071, M-1111, M-3059 and M-1115)—see FIG. 4B for chemical structures.

D. Example 4

Chemical Synthesis. We designed Rapa-Link inhibitors (M-1071, M-1111, M-3059, M-1115, etc.) possessing a drug-like cross-linker (polyethylene glycol based) which would provide a rapid means for coupling the two halves of the molecule (azide/alkyne cyclization). We considered the structural complexity of rapamycin and its cost, and decided to apply a convergent synthetic route (Scheme 1-A). Hence, we synthesized propargyl ethyleneglycol introduced rapamycin (III-A) as a precursor (Scheme 3). For the asTORi (Scheme 2), we prepared two types of compounds (II-c) with an attachment "A"; 1) Type A has an amino group at the terminal position; 2) Type B has a carboxylate at the terminal position. Those terminal functional groups will be used to connect the active site inhibitor to the cross-linker by amide formation reaction. Among various kinds of cross-linkers, we selected the polyethylene glycol (PEG) linker since it is found in a number of pharmaceuticals[20]. We used azide PEG linkers to connect asTORi (IIc-A) followed by triazole formation reaction with propargyl derivative of Rapamycin (III-A) (Scheme 1-A). By using the key intermediates, we also synthesized a negative control compound (M-1115) which is designed to have linker predicted to be too short to allow optimal dual binding to mTOR (FIG. 4B).

Scheme 1-A
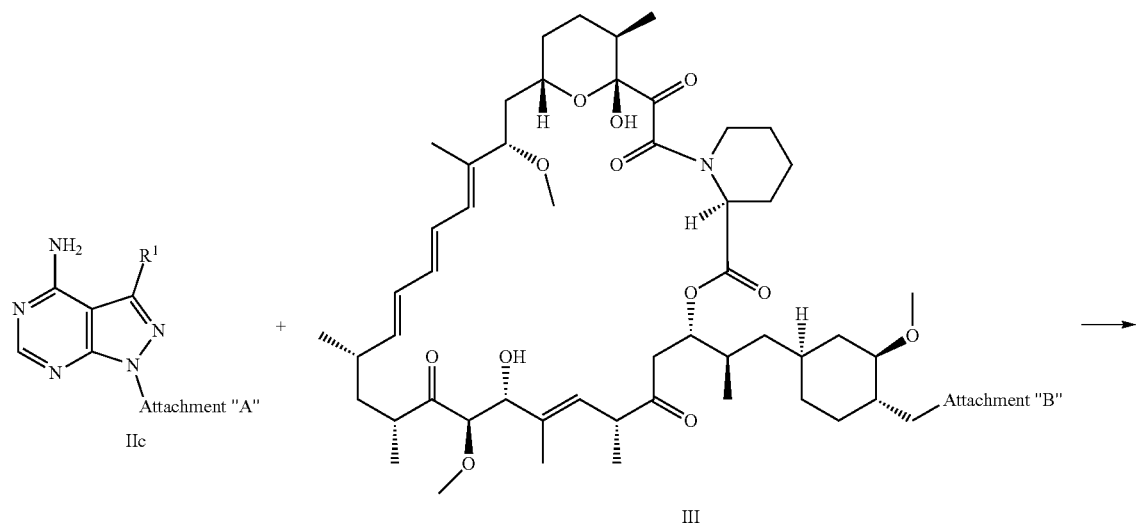
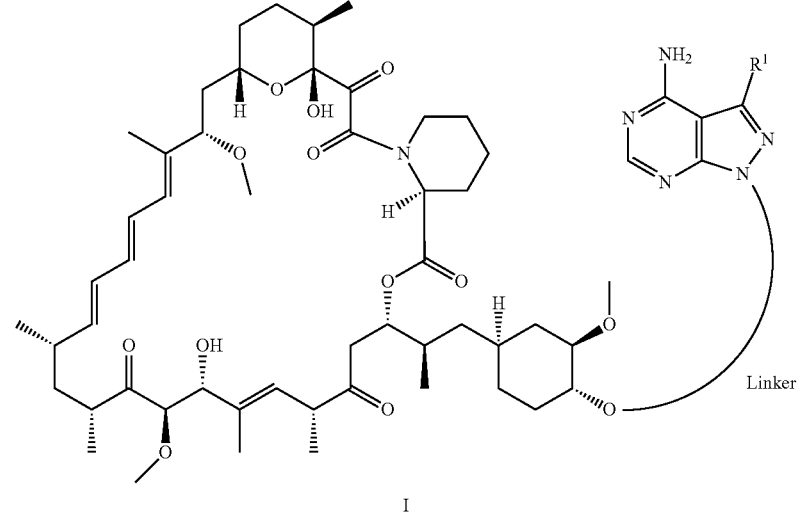

Scheme 1-B
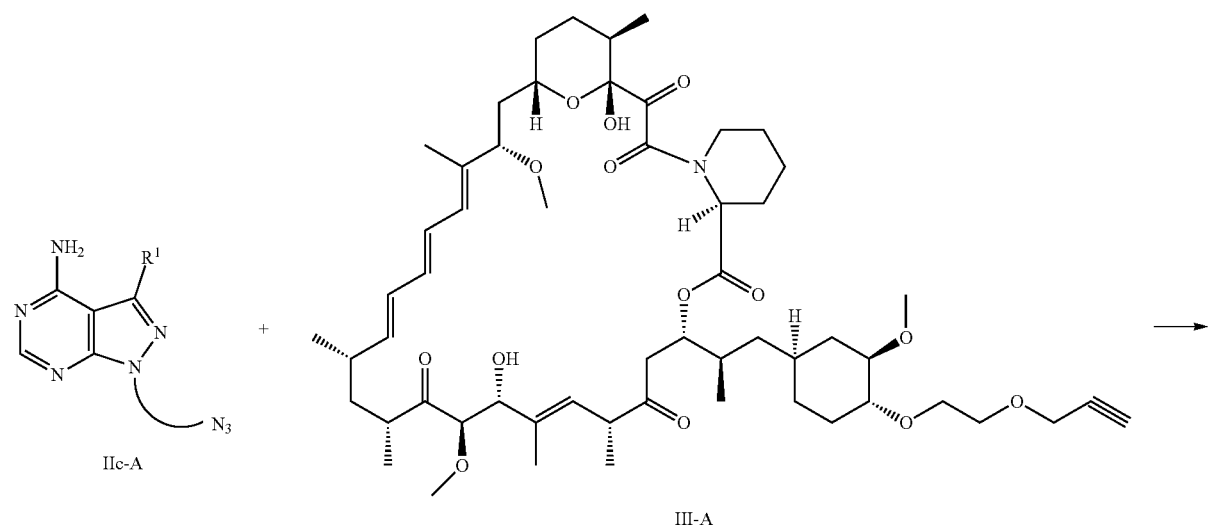
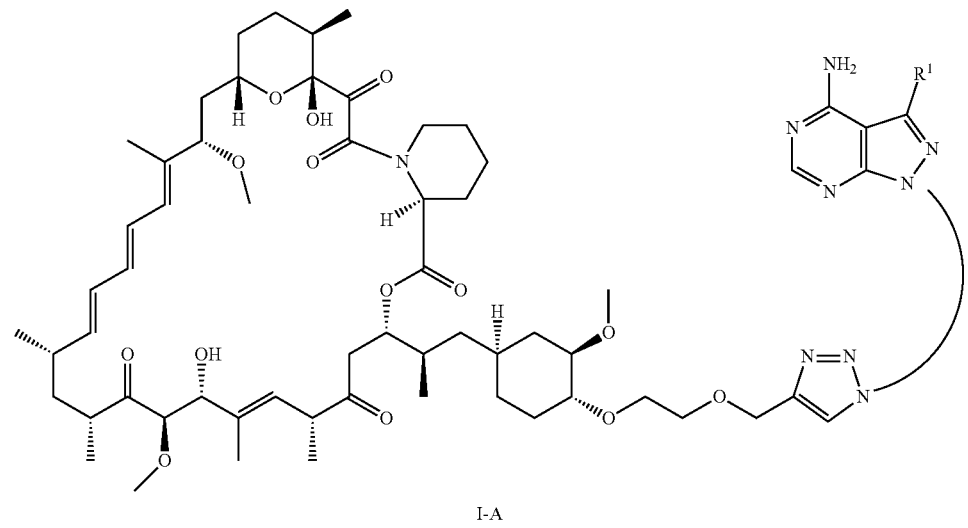

Scheme 2
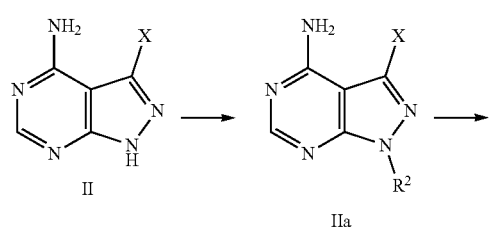
Scheme 3
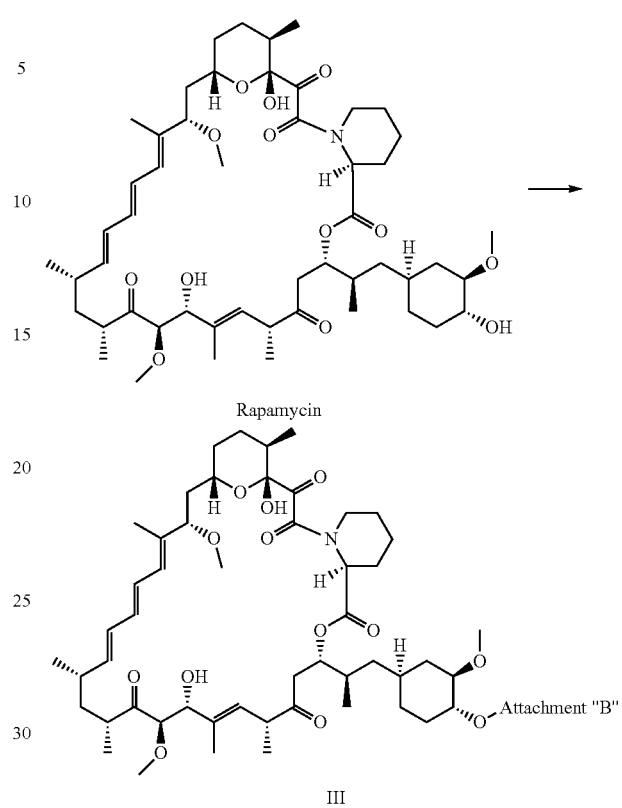
TABLE 3
| | Rapa-Link Molecules | | |
|---|---|---|---|
| Compound | Structure | Salt | Length of linker (heavy atoms) |
| M-1071 | | 2HCO₂H | 39 |

TABLE 3-continued

Rapa-Link Molecules

| Compound | Structure | Salt | Length of linker (heavy atoms) |
|---|---|---|---|
| M-1111 | 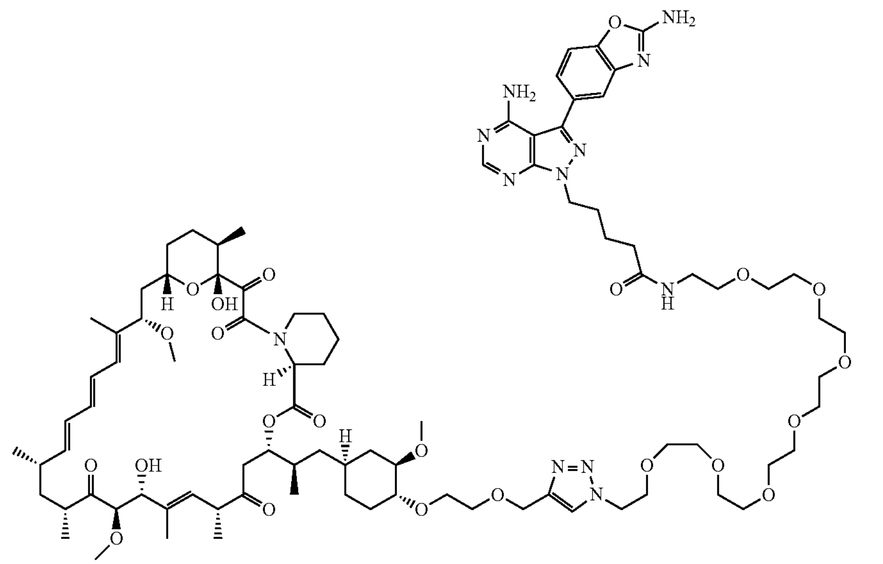 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCNC(=O)CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C] | 2HCO$_2$H | 36 |
| M-3059 | 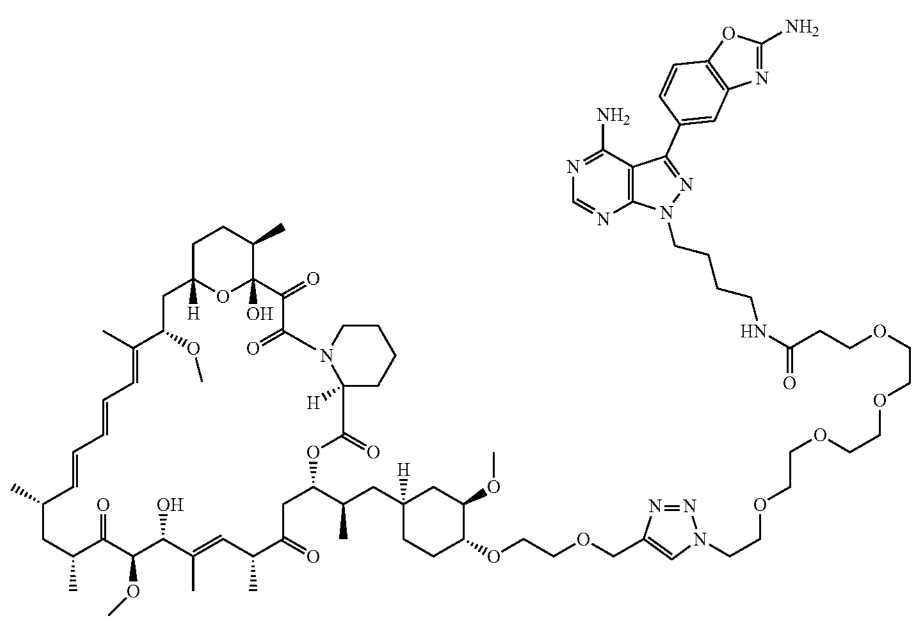 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C] | 2HCO$_2$H | 27 |

TABLE 3-continued

Rapa-Link Molecules

| Compound | Structure | Salt | Length of linker (heavy atoms) |
|---|---|---|---|
| M-1115 | 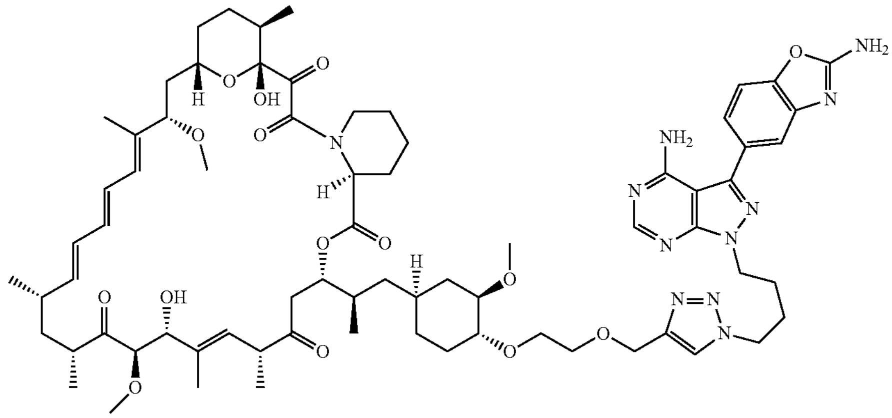 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C] | 2HCO$_2$H | 11 |
| Control: (M-1062) | 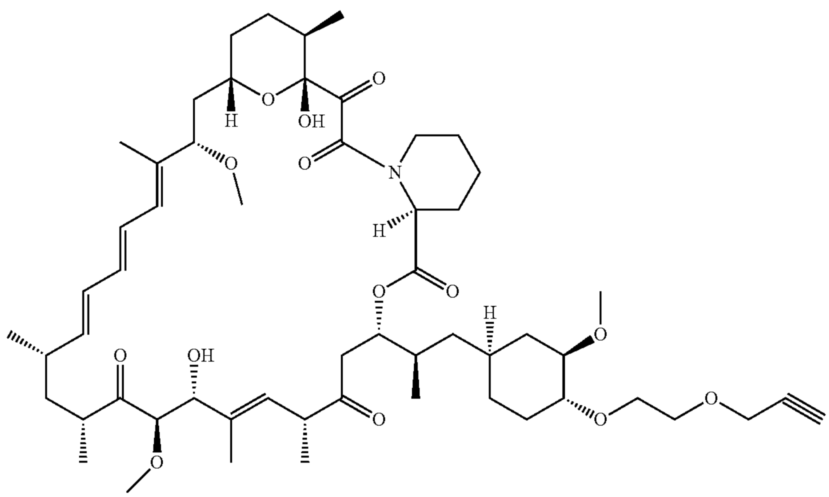 [SMILES: C#CCOCCO[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC] | Free base | N/A |

E. Example 5

Abbreviations Used in Syntheses Descriptions.

AcOH: acetic acid, DME: 1,2-dimethoxyethane, DMF: N,N-dimethylformamide, DMSO: dimethylsulfoxide, dPEG: discrete poly-(ethylene glycol), EDCI: 1-ethyl-3-(3-dimethylaminopropyl)carbodiimide, ESI: electrospray ionization, EtOAc: ethyl acetate, HOBt: 1-hydroxybenzotriazole, HPLC: high performance liquid chromatography, HR-MS: high resolution mass spectroscopy, LC-MS: liquid chromatography-mass spectrometry, LTQ-FT: linear trap quadrupole-Fourier transform, MeOH: methanol, NHS: N-hydroxysuccinimide, NMR: nuclear magnetic resonance, RP-HPLC: reverse phase-high performance liquid chromatography, THF: tetrahydrofuran, TLC: thin layer chromatography, TMS: tetramethylsilane.

Starting materials, reagents, and solvents for reactions were of reagent grade and were used as purchased. TLC was carried out using Merck Kieselgel 60, 63-200 mesh, F254 plates, or Fuji Silysia Chemical Ltd., 100-200 mesh, NH plates. Chromatographic purification was carried out using silica gel (Merck, 70-230 mesh) or basic silica gel (Fuji Silysia Chemical Ltd., DM1020, 100-200 mesh). RP-HPLC was carried out on a Waters Binary Gradient Module 2545 system equipped with an Agilent Zorbax 300-SB C18 column (5 μm, 4.6×250 mm) for analytical mode or a Waters XBridge Prep C18 column (5 am, 30×250 mm) for preparative mode. The column was eluted with CH$_3$CN/water/0.1% formic acid (gradient mode), which was monitored by Waters Photodiode Array Detector 2998 (UV at Δ=254 nm). Yields were not optimized.

$^1$H NMR spectra for intermediates were recorded on a Varian Innova (400 MHz) spectrometer. $^1$H NMR spectra, $^1$H-$^1$H COSY, HSQC, and HMBC spectra for final compounds were recorded on a Bruker Avance (800 MHz) spectrometer. $^{13}$C NMR spectra were recorded on a Bruker Avance (500 MHz) spectrometer (500 MHz for $^1$H, 126 MHz for $^{13}$C). $^1$H chemical shifts are reported in δ (ppm) as s (singlet), d (doublet), t (triplet), q (quartet), dd (double doublet), m (multiplet) or br s (broad singlet) and are referenced to TMS as an internal standard. LC-MS (ESI-MS) spectra were recorded with a Waters 2695 separations module using a Waters ACQUITY UPLC BEH C18 1.7 μm column and were used to confirm ≥95% purity of each compound. Mobile phase A was 0.1% formic acid in ultrapure water. Mobile phase B was 0.1% formic acid in acetonitrile, which was increased linearly from 5% to 95% over 1.8 min and 95% over the next 0.3 min (flow rate: 0.6 mL/min). HR-MS analysis was conducted by QB3/Chemistry Mass Spectrometry Facility at UC Berkeley. Samples were analyzed by electrospray ionization with a mass measuring accuracy of 5 ppm using the LTQ-FT instrument.

Preparation of Compound 6 (M-1062)

extracted with EtOAc (200 mL). The organic layers were combined, washed with brine (100 mL) and dried over anhydrous $MgSO_4$. The insoluble was filtered and the filtrate was evaporated in vacuo. The crude material was purified by silica gel column chromatography (silica gel: 800 g, solvent: hexanes (2 L) followed by 50% EtOAc in hexanes (4 L)). The desired fractions were combined and evaporated in vacuo to give the titled compound (9.63 g, 31%) as a yellow oil. This material was used for the next reaction without further purification.

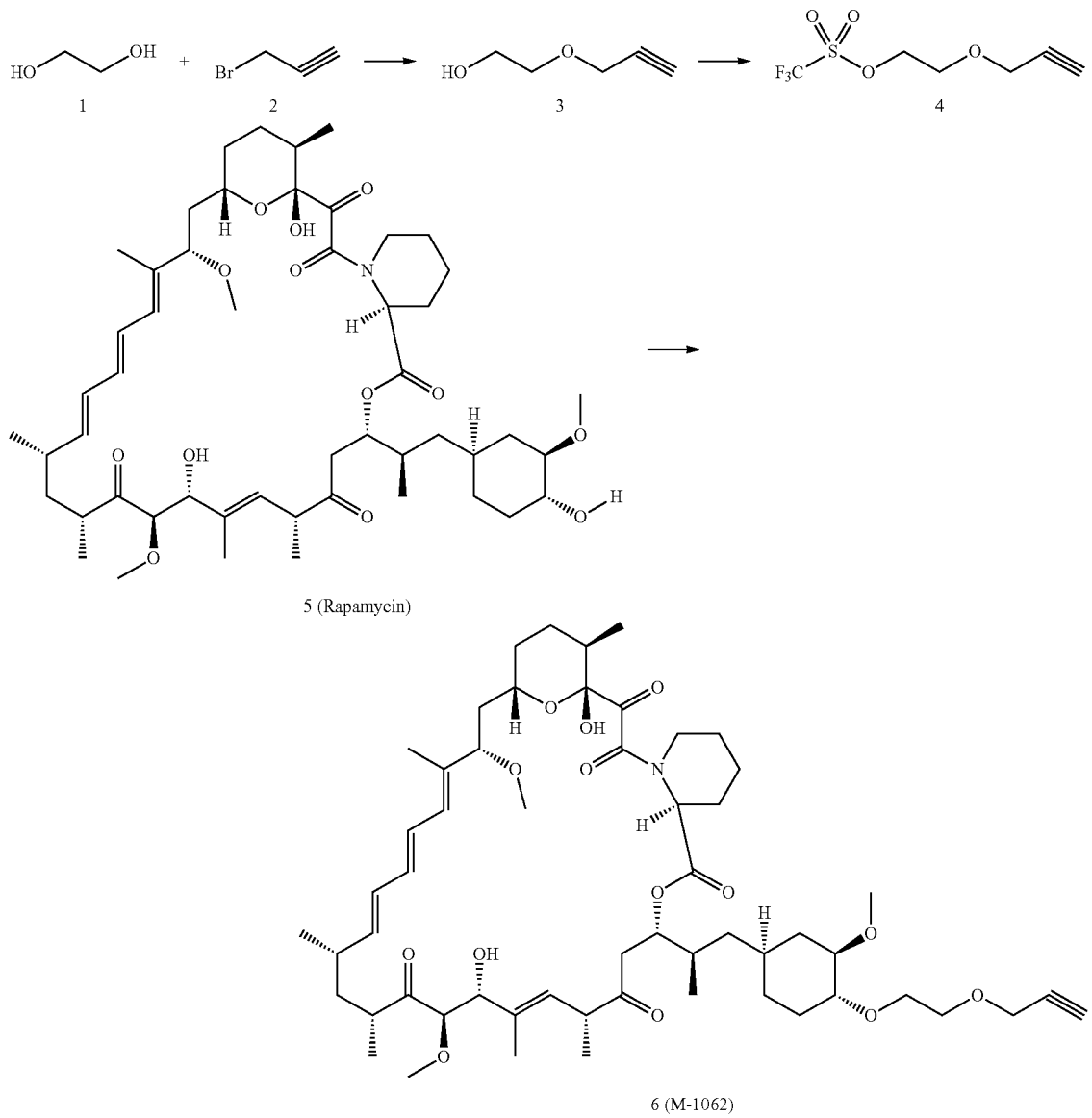

Preparation of 2-(prop-2-yn-1-yloxy)ethanol 3

To a cooled ethane-1,2-diol (1) (150 mL) was slowly added NaH oil dispersion (43.2 g) over 1 h at −30° C. The mixture was stirred at ambient temperature for additional 1 h. To the reaction mixture was slowly added 9.2 M propargyl bromide (2) solution in toluene (45.47 g) over 30 min under cooling bath (−10° C.). The mixture was stirred at 50° C. for 60 h. It was then partitioned between EtOAc (400 mL) and water (200 mL). The aqueous layer was separated and $^1$H NMR (400 MHz, $CDCl_3$) δ 4.19-4.22 (2H, m), 3.73-3.79 (2H, m), 3.63-3.67 (2H, m), 2.45 (1H, t, J=2.4 Hz), 1.96 (1H, t, J=6.0 Hz).

Preparation of 2-(prop-2-yn-1-yloxy)ethyl trifluoromethanesulfonate 4

To a solution of 2-(prop-2-yn-1-yloxy)ethanol (3) (1.50 g, 15.0 mmol) in $CH_2Cl_2$ (20 mL) was added 2,6-lutidine (2.44 mL, 21.0 mmol) followed by trifluoromethanesulfonic anhydride (3.15 mL, 18.7 mmol) at −50° C. under argon atmosphere. The mixture was stirred at −10° C. for 2 h. It was then partitioned between 50% EtOAc in hexanes (150 mL) and brine (15 mL). The organic layer was separated, washed with brine (15 mL) and dried over anhydrous MgSO$_4$. The insoluble was filtered and the filtrate was evaporated in vacuo. The crude material was purified by silica gel column chromatography (silica gel: 50 g, solvent 10% EtOAc in hexanes (500 mL)). The desired fractions were combined and evaporated in vacuo to give the titled compound (2.49 g, 72%) as a dark brown oil. This material was used for the next reaction without further purification.

$^1$H NMR (400 MHz, CDCl$_3$) δ 4.64-4.66 (2H, m), 4.22-4.25 (2H, m), 3.85-3.88 (2H, m), 2.48-2.49 (1H, m).

Preparation of 40-O-(2-(prop-2-yn-1-yloxy)ethyl)-rapamycin 6 (M-1062)

To a solution of rapamycin (5) (652 mg, 0.714 mmol) in CHCl$_3$ (1.5 mL) were added a solution of 2-(prop-2-yn-1-yloxy)ethyl trifluoromethanesulfonate (4) (1.25 g, 5.35 mmol) in CHCl$_3$ (1.5 mL) and N,N-diisopropyl-N-ethylamine (6.2 mL, 35.7 mmol) at −10° C. under argon atmosphere. The mixture was stirred at 60° C. for 30 min. An additional amount of 2-(prop-2-yn-1-yloxy)ethyl trifluoromethanesulfonate (4) (1.25 g, 5.35 mmol) in CHCl$_3$ (1.5 mL) was added. The mixture was stirred at 60° C. for additional 1 h. It was then cooled and partitioned between EtOAc (100 mL) and water (50 mL). The organic layer was washed with water (50 mL) and brine (2×25 mL), successively, and dried over anhydrous MgSO$_4$. The insoluble was filtered off and the filtrate was evaporated in vacuo. The crude material was purified by silica gel column chromatography (silica gel: 25 g, solvent: 20-80% EtOAc in hexanes). Desired fractions were combined and evaporated in vacuo. The obtained material was dissolved into 50% CH$_3$CN in water and lyophilized to give the titled compound (277 mg, 28%) as a colorless amorphous powder.

HR-MS (ESI−) Calcd for C$_{56}$H$_{84}$O$_{14}$N (M−H)$^−$ 994.5897. Found 994.5885 (Δ −1.24 ppm).

TABLE 4

NMR Analysis of M-1062

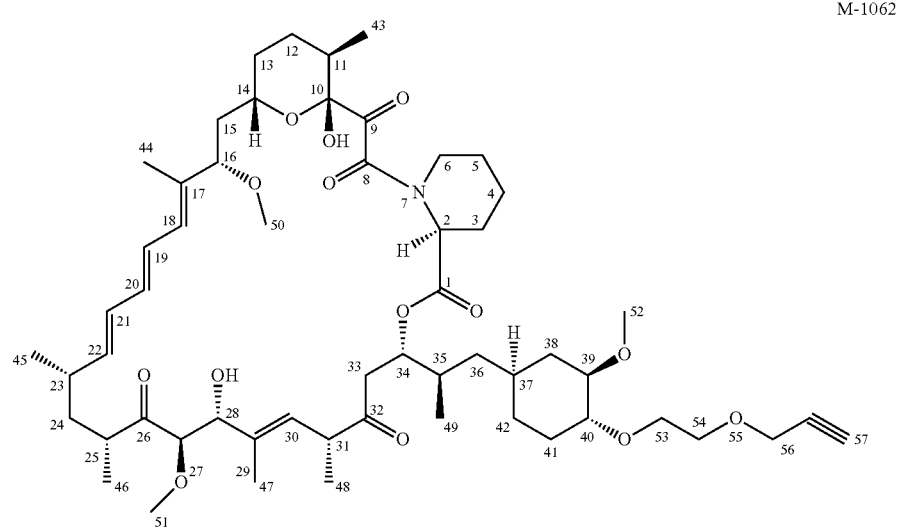

M-1062

| Atom | Atom Type | δ $^1$H Major (3:1) | δ $^{13}$C Major (3:1) | HMBC C to H | $^1$H-$^1$H COSY |
|---|---|---|---|---|---|
| 1 | C═O | | 169.2 | 2 | N/A |
| 2 | CH | 5.28 (br d, 4.8 Hz) | 51.2 | 4a, 6a | 3a,b |
| 3 | CH$_2$ | a: 2.35 (m) | 27.1 | 2 | 3b, 2, 4b |
|   |   | b: 1.74 (m) | | | 3a, 2, 4b |
| 4 | CH$_2$ | a: 1.77 (m) | 20.7 | 2 | 4b, 3a, 5b |
|   |   | b: 1.47 (m) | | | 4a, 3a |
| 5 | CH$_2$ | a: 1.74 (m) | 25.3 | 3a, 6a | 5b, 6b |
|   |   | b: 1.49 (m) | | | 5a, 4a, 6a,b |
| 6 | CH$_2$ | a: 3.57 (m) | 44.2 | 2, 4a,b | 6b, 5b |
|   |   | b: 3.44 (m) | | | 6a, 5a,b |
| 8 | C═O | N/A | 166.8 | 2, 6a | N/A |
| 9 | C═O | N/A | 192.5 | n.d. | N/A |
| 10 | O—C—OH | N/A | 98.5 | 12, 43 | N/A |
| 11 | CH | 1.97 (m) | 33.7 | 12, 43 | 12, 13a, 43 |
| 12 | CH$_2$ | 1.59 (2H, m) | 27.3 | 43 | 11, 13b |
| 13 | CH$_2$ | a: 1.61 (m) | 31.3 | 12, 15a | 11, 13b |
|    |    | b: 1.31 (m) | | | 13a, 12, 14 |
| 14 | CH—OC | 3.87 (m) | 67.2 | 12, 15a | 13b, 15a,b |
| 15 | CH$_2$ | a: 1.85 (m) | 38.8 | 16 | 15b, 14, 16 |
|    |    | b: 1.52 (m) | | | 15a, 14, 16 |
| 16 | CH—OCH$_3$ | 3.66 (m) | 84.4 | 15a, 18, 50 | 15a,b |
| 17 | ═C═ | N/A | 135.5 | 15a, 19, 44 | N/A |
| 18 | CH═C | 5.96 (d, 9.6 Hz) | 129.7 | 16, 20, 44 | 19 |

TABLE 4-continued

NMR Analysis of M-1062

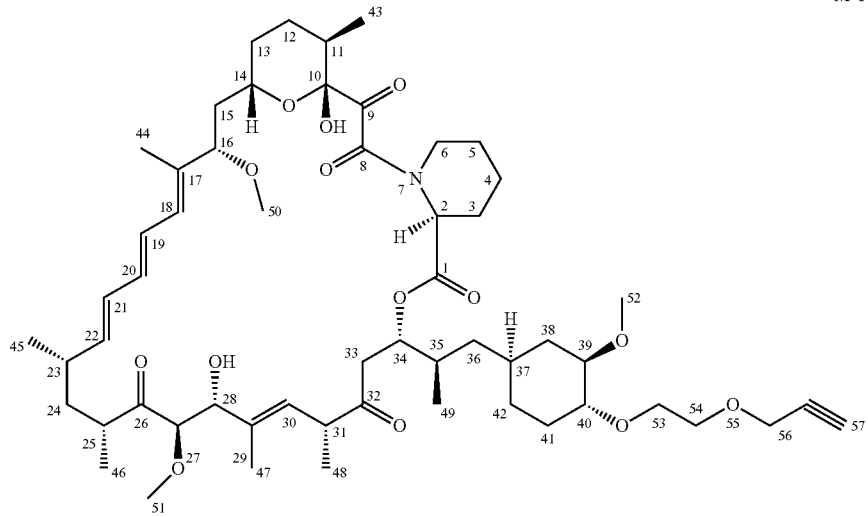

M-1062

| Atom | Atom Type | δ $^1$H Major (3:1) | δ $^{13}$C Major (3:1) | HMBC C to H | $^1$H-$^1$H COSY |
|---|---|---|---|---|---|
| 19 | CH=C | 6.38 (dd, 14.4, 10.8 Hz) | 126.4 | 20, 21, 44 | 18, 20 |
| 20 | CH=C | 6.35 (dd, 16.6, 10.2 Hz) | 133.7 | 18, 19, 21, 22 | 19, 21 |
| 21 | CH=C | 6.14 (dd, 15.2, 10.2 Hz) | 130.2 | 19 | 20, 22 |
| 22 | CH=C | 5.55 (dd, 14.8, 9.2 Hz) | 140.2 | 20, 24b, 45 | 21, 23 |
| 23 | CH | 2.33 (m) | 35.2 | 21, 22, 24a, 45 | 22, 24a, 45 |
| 24 | CH$_2$ | a: 1.49 (m) | 40.2 | 22, 25, 45, 46 | 24b, 23 |
|  |  | b: 1.21 (m) |  |  | 24a, 25 |
| 25 | CH | 2.74 (dd, 17.0, 5.8) | 41.4 | 24a,b, 46 | 24b, 46 |
| 26 | C=O | N/A | 215.7 | n.d. | N/A |
| 27 | CH—OCH$_3$ | 3.71 (m) | 84.8 | 28, 51 | 28 |
| 28 | CH—OH | 4.18 (m) | 77.3 | 27, 30, 47 | 27 |
| 29 | C=C | N/A | 136.1 | 28, 31, 47 | N/A |
| 30 | CH=C | 5.41 (d, 10.0 Hz) | 126.8 | 28, 31, 47, 48 | 31 |
| 31 | CH | 3.34 (m) | 46.6 | 30, 48 | 30, 48 |
| 32 | C=O | N/A | 208.2 | 31, 33a,b, 48 | N/A |
| 33 | CH$_2$ | a: 2.73 (m) | 40.8 | n.d. | 33b, 34 |
|  |  | b: 2.59 (m) |  |  | 33a, 34 |
| 34 | CH—OCO | 5.16 (dd, 10.0, 5.8 Hz) | 75.7 | 33a,b, 49 | 33a,b, 35 |
| 35 | CH | 1.95 (m) | 33.2 | 33a,b, 36a,b, 49 | 34, 36a,b, 49 |
| 36 | CH$_2$ | a: 1.19 (m) | 38.3 | 34, 38b, 49 | 36b, 35, 37 |
|  |  | b: 1.11 (m) |  |  | 36a, 35 |
| 37 | CH | 1.33 (m) | 33.1 | 36a,b, 38a,b, 42b | 36a, 38b, 42b |
| 38 | CH$_2$ | a: 2.03 (m) | 36.3 | 36a,b | 38b, 39 |
|  |  | b: 0.71 (m) |  |  | 38a, 37, 39 |
| 39 | CH—OCH$_3$ | 3.06 (m) | 83.2 | 38a,b, 40, 52 | 38a,b, 40 |
| 40 | CH—O— | 3.13 (m) | 83.3 | 38a,b, 39, 52, 53 | 39, 41b |
| 41 | CH$_2$ | a: 2.05 (m) | 30.1 | 42b | 41b |
|  |  | b: 1.26 (m) |  |  | 41a, 40, 42b |
| 42 | CH$_2$ | a: 1.69 (m) | 31.8 | 36a,b, 38a,b | 42b |
|  |  | b: 0.92 (m) |  |  | 42a, 37, 41b |
| 43 | 11-CH$_3$ | 0.94 (3H, d, 6.4 Hz) | 16.3 | 11, 12 | 11 |
| 44 | 17-CH$_3$ | 1.65 (3H, s) | 10.2 | 16, 18 | n.d. |
| 45 | 23-CH$_3$ | 1.05 (3H, d, 6.4 Hz) | 21.6 | 22, 24a | 23 |
| 46 | 25-CH$_3$ | 0.99 (3H, d, 6.4 Hz) | 13.8 | 24a,b, 25 | 25 |
| 47 | 29-CH$_3$ | 1.74 (3H, s) | 13.1 | 28, 30 | n.d. |
| 48 | 31-CH$_3$ | 1.10 (3H, d, 6.8 Hz) | 16.0 | 30, 31 | 31 |
| 49 | 35-CH$_3$ | 0.91 (3H, d, 6.8 Hz) | 16.9 | 36b | 35 |
| 50 | 16-OCH$_3$ | 3.14 (3H, s) | 55.9 | 16 | n.d. |
| 51 | 27-OCH$_3$ | 3.34 (3H, s) | 59.5 | 27 | n.d. |
| 52 | 39-OCH$_3$ | 3.46 (3H, s) | 58.0 | 39 | n.d. |
| 53 | 40-OCH$_2$— | 3.72-3.79 (2H, m) | 69.3 | 54, 40 | 54 |
| 54 | —CH$_2$—O— | 3.64-3.71 (2H, m) | 69.6 | 53, 55 | 53, 55 |
| 55 | —O—CH$_2$ | 4.20-4.22 (2H, m) | 58.6 | 54, 57 | 54, 57 |
| 56 | —C≡ | N/A | 79.8 | 55, 57 | N/A |
| 57 | ≡CH | 2.41 (t, 2.2 Hz) | 74.4 | 55 | 55 |

OH protons were not identified.

Preparation of Compound 11a (M-1115)
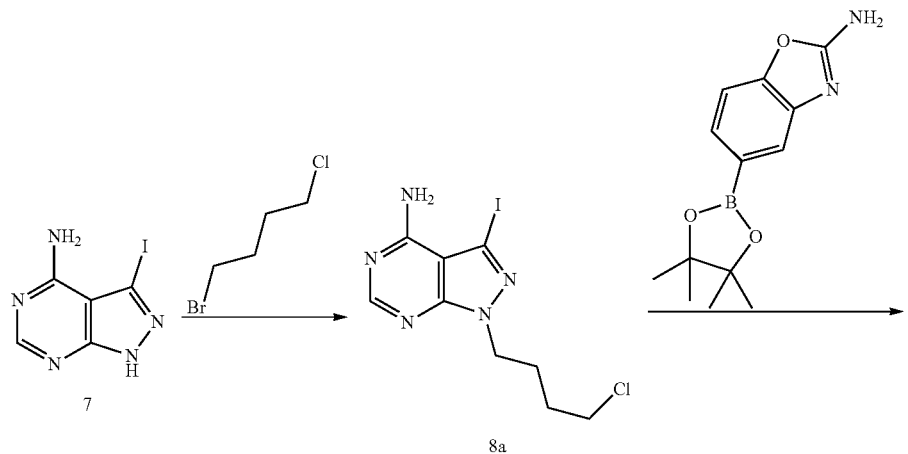
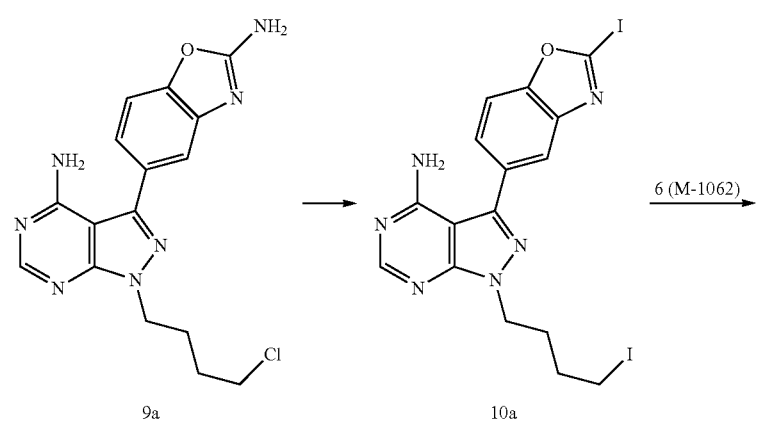
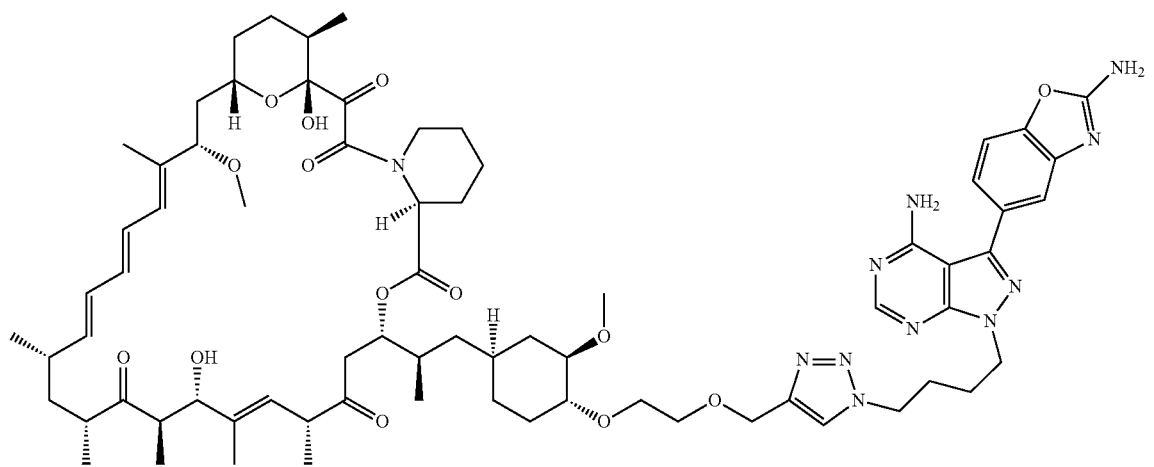

Preparation of 1-(4-chlorobutyl)-3-iodo-1H-pyrazolo[3,4-d]pyrimidin-4-amine 8a To a suspension of 3-iodo-1H-pyrazolo[3,4-d]pyrimidin-4-amine (7) (2.11 g, 8.08 mmol) (prepared by a similar method to that described in *Nature Chemical Biology*, 2008, 691-699) in DMF (25 mL) was added NaH oil dispersion (485 mg, 12.1 mmol) at 4° C. The mixture was stirred at 4° C. for 30 min. To the reaction mixture was added 1-bromo-4-chlorobutane (1.45 g, 8.46 mmol) at 4° C. The mixture was stirred at room temperature for 14 h. To the mixture was added water (25 mL) at room temperature. The mixture was cooled to 4° C. and stirred for 30 min. The resulting precipitate was collected by filtration. The obtained crude material was purified by silica gel column chromatography (silica gel: 40 g, solvent: 20-100% EtOAc in hexanes, 0-30% MeOH in EtOAc, and then DMF). Desired fractions were combined and evaporated in vacuo. The obtained DMF solution (ca. 100 mL) including desired material was diluted with water (150 mL). The resulting suspension was stirred at 4° C. for 30 min. The precipitate was collected by filtration. Drying the solid gave the titled compound (2.01 g, 71%) as a pale beige solid.

$^1$H NMR (400 MHz, DMSO-$d_6$) δ 8.20 (1H, s), 4.30 (2H, t, J=6.8 Hz), 3.65 (2H, t, J=6.8 Hz), 1.85-1.95 (2H, m), 1.61-1.70 (2H, m), NH$_2$ protons were not identified.

LC-MS (ESI) m/z=352.05 (M+H)$^+$.

Preparation of 5-(4-amino-1-(4-chlorobutyl)-1H-pyrazolo[3,4-d]pyrimidin-3-yl)benzo[d]oxazol-2-amine 9a To a bi-phasic suspension of 1-(4-chlorobutyl)-3-iodo-1H-pyrazolo[3,4-d]pyrimidin-4-amine (8a) (703 mg, 2.00 mmol), 5-(4,4,5,5-tetramethyl-1,3,2-dioxaborolan-2-yl)benzo[d]oxazol-2-amine (780 mg, 3.00 mmol) (prepared by a similar method to that described in WO2010/051042A1), and saturated aqueous Na$_2$CO$_3$ solution (10 mL) in DME (30 mL) and water (10 mL) was added tetrakis(triphenylphosphine)palladium (0) (232 mg, 200 μmol) at room temperature under argon atmosphere. The mixture was stirred at 110° C. for 3 h. It was then cooled and partitioned between EtOAc (200 mL) and water (100 mL). The aqueous layer was separated and extracted with EtOAc (100 mL). The organic layers were combined, washed with brine (50 mL) and dried over anhydrous MgSO$_4$. The insoluble was filtered off and the filtrate was concentrated in vacuo. The crude material was purified by silica gel column chromatography (basic silica gel: 25 g, solvent: 20% MeOH in EtOAc (100 mL)). The desired fractions were combined and the obtained solid was triturated with EtOAc (50 mL) for 30 min. The precipitate was collected by filtration. Drying the solid gave the titled compound (445 mg, 62%) as a pale beige solid.

$^1$H NMR (400 MHz, DMSO-$d_6$) δ 8.25 (1H, s), 7.53 (2H, s), 7.47 (1H, d, J=8.0 Hz), 7.41 (1H, br s), 7.25 (1H, dd, J=8.4, 1.2 Hz), 4.37 (2H, t, J=6.8 Hz), 3.67 (2H, t, J=6.8 Hz), 1.93-2.02 (2H, m), 1.67-1.76 (2H, m), NH$_2$ protons were not identified.

LC-MS (ESI) m/z=358.20 (M+H)$^+$.

Preparation of 5-(4-amino-1-(4-azidobutyl)-1H-pyrazolo[3,4-d]pyrimidin-3-yl)benzo[d]oxazol-2-amine 10a To a solution of 5-(4-amino-1-(4-chlorobutyl)-1H-pyrazolo[3,4-d]pyrimidin-3-yl)benzo[d]oxazol-2-amine (9a) (140 mg, 0.391 mmol) in DMF (3 mL) were added sodium azide (33.0 mg, 0.507 mmol) and potassium iodide (12.0 mg, 72.3 μmol) at room temperature. The mixture was stirred at 70° C. for 6 h. It was then cooled and partitioned between EtOAc (100 mL) and water (20 mL). The aqueous layer was separated and extracted with EtOAc (50 mL). The organic layers were combined, washed with brine (20 mL), and dried over anhydrous MgSO$_4$. The insoluble was filtered off and the filtrate was evaporated in vacuo. The obtained material was triturated with EtOAc (5 mL) for 15 min. The precipitate was collected by filtration. Drying the solid gave the titled compound (121 mg, 85%) as a pale beige powder.

$^1$H NMR (400 MHz, DMSO-$d_6$) δ 8.24 (1H, s), 7.53 (2H, s), 7.47 (1H, d, J=8.0 Hz), 7.41 (1H, d, J=1.6 Hz), 7.24 (1H, dd, J=8.0, 1.6 Hz), 4.37 (2H, t, J=6.8 Hz), 3.36 (2H, t, J=6.8 Hz), 1.86-1.95 (2H, m), 1.48-1.57 (2H, m), NH$_2$ protons were not identified.

LC-MS (ESI) m/z=365.21 (M+H)$^+$.

Preparation of 40-O-(2-((1-(4-(4-amino-3-(2-aminobenzo[d]oxazol-5-yl)-1H-pyrazolo[3,4-d]pyrimidin-1-yl)butyl)-1H-1,2,3-triazol-4-yl)methoxy)ethyl)-rapamycin 11a (M-1115)

To a solution of 5-(4-amino-1-(4-azidobutyl)-1H-pyrazolo[3,4-d]pyrimidin-3-yl)benzo[d]oxazol-2-amine (10a) (16 mg, 43.9 μmol) in a mixed solvent of MeOH (8 mL) and CH$_2$Cl$_2$ (4 mL) was added 40-O-(2-(prop-2-yn-1-yloxy)ethyl)-rapamycin (6) (32.5 mg, 32.6 μmol). To the mixture were added 1 M aqueous CuSO$_4$ solution (100 μL, 100 μmol) and 1 M aqueous sodium ascorbate solution (100 μL, 100 μmol). The mixture was stirred at room temperature for 4 h. It was then concentrated in vacuo. The crude material was partitioned between 20% THF in EtOAc (20 mL) and water (5 mL). The aqueous layer was separated and extracted with 20% THF in EtOAc (10 mL). The organic layers were combined, washed with brine (20 mL), and dried over anhydrous MgSO$_4$. The mixture was dissolved into DMSO (4 mL) and 50% CH$_3$CN in water (4 mL) and the solution was passed through a pad of Celite (#545). The filtrate was purified by preparative RP-HPLC (20-95% CH$_3$CN in water containing 0.1% formic acid). The desired fractions were combined and lyophilized to give formic acid salt of the titled compound (9.1 mg, 19%) as a colorless amorphous powder.

LC-MS (ESI−) m/z=1358.47 (M−H)$^-$.

HR-MS (ESI−) Calcd for $C_{72}H_{100}O_{15}N_{11}$ (M−H)$^-$ 1358.7406, Found 1358.7372 (Δ −2.49 ppm).

TABLE 5

NMR analysis of M-1115

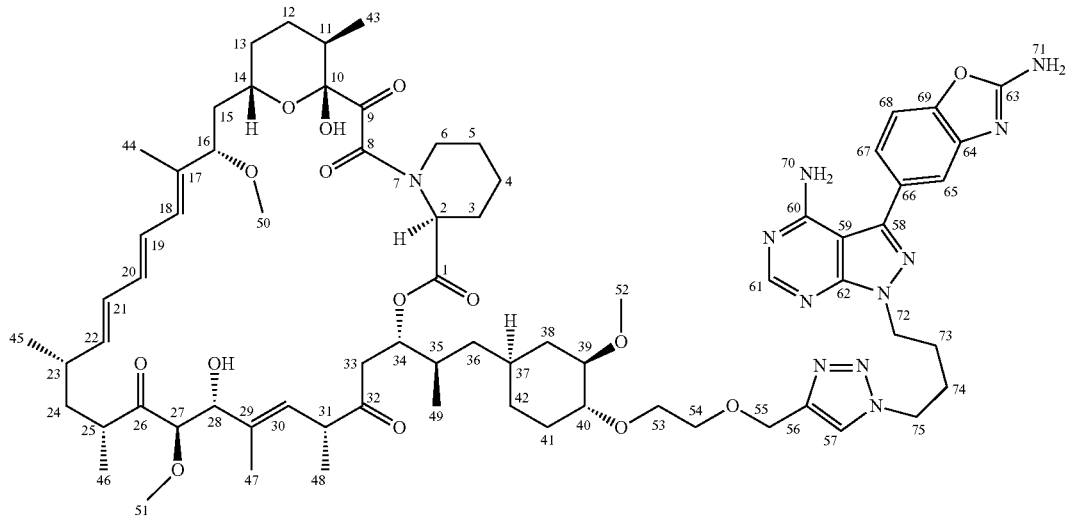 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

M-1115

| Atom | Atom Type | δ¹H Major (3:1) | δ¹³C Major (3:1) | HMBC C to H | ¹H-¹H COSY |
|---|---|---|---|---|---|
| 1 | C=O | N/A | 169.3 | 2 | N/A |
| 2 | CH | 5.28 (d, 5.6 Hz) | 51.3 | 4a, 6a | 3b |
| 3 | CH₂ | a: 2.33 (m) | 27.0 | 2, 5a | 3b, 4a,b |
|   |   | b: 1.73 (m) |   |   | 3a, 2, 4a,b |
| 4 | CH₂ | a: 1.78 (m) | 20.7 | 2, 6a,b | 4b, 3a,b, 5a,b |
|   |   | b: 1.48 (m) |   |   | 4a, 3a,b, 5a,b |
| 5 | CH₂ | a: 1.72 (m) | 25.3 | 3a, 4a, 6a,b | 5b, 4a,b |
|   |   | b: 1.46 (m) |   |   | 5a, 4a,b, 6a,b |
| 6 | CH₂ | a: 3.54 (m) | 44.2 | 2, 4a, 5b | 6b, 5b |
|   |   | b: 3.41 (m) |   |   | 6a, 5b |
| 8 | C=O | N/A | 166.7 | 2, 6a,b | N/A |
| 9 | C=O | N/A | 193.3 | n.d. | N/A |
| 10 | O—C—OH | N/A | 98.6 | 11, 12, 43 | N/A |
| 11 | CH | 2.01 (m) | 34.0 | 43 | 12, 43 |
| 12 | CH₂ | 1.60 (2H, m) | 27.2 | 11, 43 | 11, 13a,b |
| 13 | CH₂ | a: 1.66 (m) | 31.3 | 12, 15a | 13b, 12 |
|   |   | b: 1.30 (m) |   |   | 13a, 12, 14 |
| 14 | CH—OC | 3.91 (m) | 67.2 | 12, 15a, 16 | 13b, 15a,b |
| 15 | CH₂ | a: 1.87 (m) | 39.2 | 16 | 15b, 14, 16 |
|   |   | b: 1.44 (m) |   |   | 15a, 14, 16 |
| 16 | CH—OCH₃ | 3.65 (m) | 84.1 | 15a,b, 18, 50 | 15a,b |
| 17 | —C= | N/A | 136.2 | 15a, 19, 44 | N/A |
| 18 | CH=C | 5.98 (d, 10.8 Hz) | 129.1 | 16, 20, 44 | 19 |
| 19 | CH=C | 6.38 (dd, 14.2, 10.8 Hz) | 126.6 | 20, 21 | 18, 20 |
| 20 | CH=C | 6.30 (dd, 14.4, 10.2 Hz) | 133.3 | 18, 19, 21, 22 | 19, 21 |
| 21 | CH=C | 6.13 (dd, 14.8, 10.4 Hz) | 130.3 | 19, 20 | 20, 22 |
| 22 | CH=C | 5.53 (dd, 14.8, 8.8 Hz) | 139.7 | 20, 24a,b, 45 | 21, 23 |
| 23 | CH | 2.32 (m) | 35.0 | 21, 22, 24a,b, 45 | 22, 24a, 45 |
| 24 | CH₂ | a: 1.43 (m) | 40.3 | 22, 25, 45, 46 | 24b, 23 |
|   |   | b: 1.20 (m) |   |   | 24a, 25 |
| 25 | CH | 2.65 (m) | 41.6 | 24a,b, 46 | 24b, 46 |
| 26 | C=O | N/A | 214.6 | n.d. | N/A |
| 27 | CH—OCH₃ | 3.84 (d, 4.2 Hz) | 85.0 | 28, 51 | 28 |
| 28 | CH—OH | 4.24 (d, 4.0 Hz) | 76.8 | 27, 30, 47 | 27 |
| 29 | C=C | N/A | 135.9 | 28, 30, 47 | N/A |
| 30 | CH=C | 5.45 (d, 9.6 Hz) | 126.2 | 28, 31, 47, 48 | 31 |
| 31 | CH | 3.30 (m) | 46.6 | 30, 48 | 30, 48 |
| 32 | C=O | N/A | 208.3 | 31, 33a,b, 48 | N/A |
| 33 | CH₂ | a: 2.68 (m) | 40.5 | n.d. | 33b, 34 |
|   |   | b: 2.55 (m) |   |   | 33a, 34 |
| 34 | CH—OCO | 5.16 (m) | 75.6 | 33a,b, 36a,b, 49 | 33a,b, 35 |
| 35 | CH | 1.91 (m) | 33.3 | 33a,b, 36b, 49 | 34, 36b, 49 |
| 36 | CH₂ | a: 1.16 (m) | 38.5 | 38b, 49 | 36b, 37 |
|   |   | b: 1.07 (m) |   |   | 36a, 35 |
| 37 | CH | 1.32 (m) | 33.0 | 36b, 38a,b, 42b | 36a, 38b, 42a,b |
| 38 | CH₂ | a: 1.99 (m) | 36.4 | 36a,b | 38b, 39 |
|   |   | b: 0.69 (m) |   |   | 38a, 37, 39 |
| 39 | CH—OCH₃ | 3.02 (m) | 83.0 | 38a,b, 40, 52 | 38a,b, 40 |
| 40 | CH—O— | 3.09 (m) | 83.1 | 38a,b, 39, 52, 53 | 39, 41a,b |

TABLE 5-continued

NMR analysis of M-1115

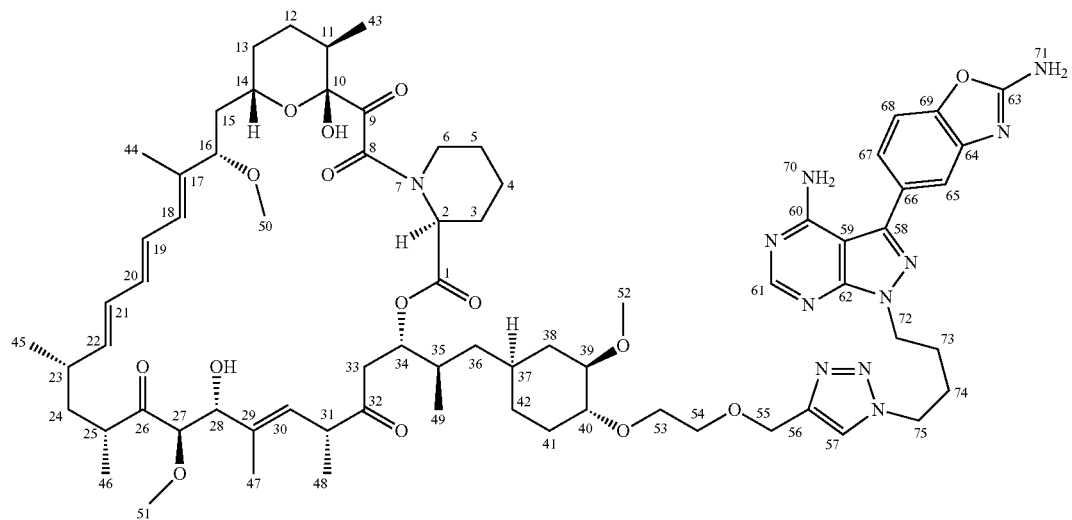

M-1115

| Atom | Atom Type | δ¹H Major (3:1) | δ¹³C Major (3:1) | HMBC C to H | ¹H-¹H COSY |
|---|---|---|---|---|---|
| 41 | CH$_2$ | a: 2.00 (m) | 30.0 | 42b | 41b, 40, 42a,b |
|  |  | b: 1.22 (m) |  |  | 41a, 40, 42b |
| 42 | CH$_2$ | a: 1.64 (m) | 31.6 | 36a,b, 38a,b | 42b, 37, 41a |
|  |  | b: 0.88 (m) |  |  | 42a, 37, 41a,b |
| 43 | 11-CH$_3$ | 0.95 (3H, d, 6.6 Hz) | 16.2 | 11, 12 | 11 |
| 44 | 17-CH$_3$ | 1.66 (3H, s) | 10.2 | 16, 18 | n.d. |
| 45 | 23-CH$_3$ | 1.05 (3H, d, 6.6 Hz) | 21.4 | 22, 24a,b | 23 |
| 46 | 25-CH$_3$ | 0.98 (3H, d, 6.4 Hz) | 13.4 | 24a,b, 25 | 25 |
| 47 | 29-CH$_3$ | 1.79 (3H, s) | 13.7 | 28, 30 | n.d. |
| 48 | 31-CH$_3$ | 1.07 (3H, d, 6.6 Hz) | 15.9 | 30, 31 | 31 |
| 49 | 35-CH$_3$ | 0.89 (3H, d, 6.6 Hz) | 15.7 | 34, 36b | 35 |
| 50 | 16-OCH$_3$ | 3.14 (3H, s) | 55.9 | 16 | n.d. |
| 51 | 27-OCH$_3$ | 3.33 (3H, s) | 58.9 | 27 | n.d. |
| 52 | 39-OCH$_3$ | 3.40 (3H, s) | 57.8 | 39 | n.d. |
| 53 | 40-OCH$_2$ | 3.72 (2H, m) | 69.2 | 40, 54 | 54 |
| 54 | —CH$_2$O— | 3.64 (2H, m) | 70.2 | 53, 55 | 53 |
| 55 | —OCH$_2$triazole | 4.67 (2H, s) | 64.7 | 54 | 57 |
| 56 | —C= | N/A | 145.4 | 55, 57 | N/A |
| 57 | =CH | 7.55 (s) | 122.4 | 55, 57 | 55 |
| 58 | PP—C | N/A | 143.7 | 68 | N/A |
| 59 | PP—C | N/A | 98.5 | 61 | N/A |
| 60 | PP—C—NH$_2$ | N/A | 158.0 | 61 | N/A |
| 61 | PP—CH | 8.35 (s) | 155.8 | n.d. | n.d. |
| 62 | PP—C | N/A | 154.4 | 61, 72 | N/A |
| 63 | BO—C—NH$_2$ | N/A | 162.8 | n.d. | N/A |
| 64 | BO—C | N/A | 144.8 | 65, 67 | N/A |
| 65 | BO—CH | 7.63 (s) | 116.2 | 67 | 67 |
| 66 | BO—C | N/A | 129.2 | 68 | N/A |
| 67 | BO—CH | 7.40 (br d, 7.8 Hz) | 121.8 | 65 | 65, 68 |
| 68 | BO—CH | 7.42 (d, 7.8 Hz) | 109.8 | 65 | 67 |
| 69 | BO—C | N/A | 149.2 | 65, 67 | N/A |
| 72 | N—CH$_2$ | 4.49 (2H, m) | 46.1 | 73, 74 | 73 |
| 73 | CH$_2$ | 2.01 (2H, m) | 26.6 | 72, 74, 75 | 72, 74 |
| 74 | CH$_2$ | 1.95 (2H, m) | 27.4 | 72, 73, 75 | 73, 75 |
| 75 | CH$_2$ | 4.41 (2H, t, 6.8 Hz) | 49.6 | 57, 73, 74 | 74 |

PP stands for pyrazolo[3,4-d]pyrimidine and BO stands for benzo[d]oxazole

OH protons and NHx protons were not identified.

Preparation of Compound 11b (M-1071; Example 1)
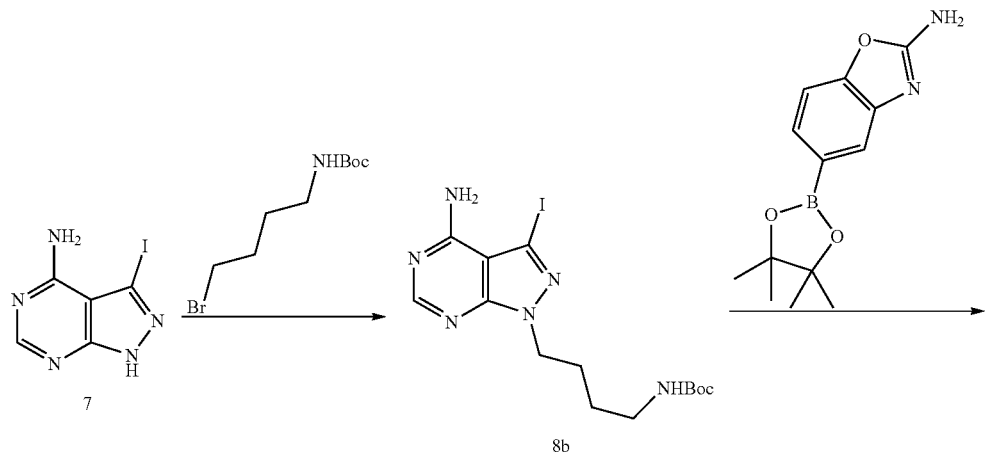
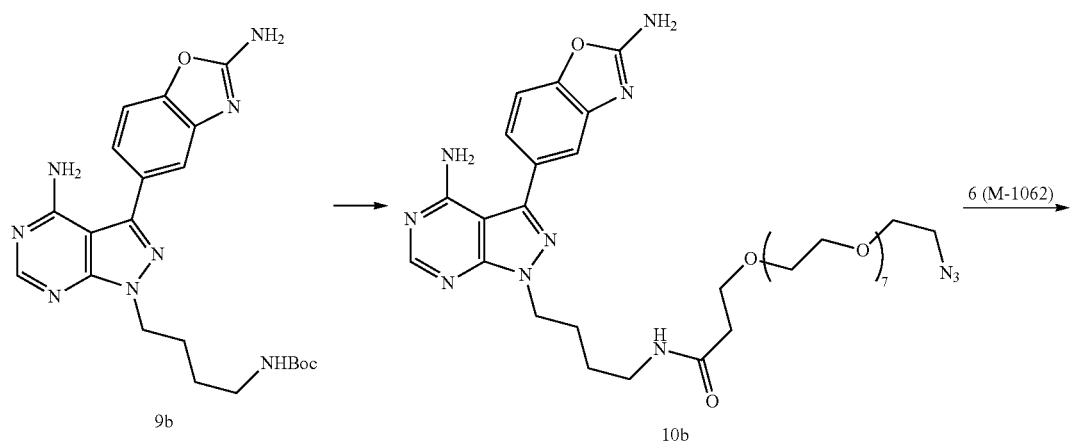

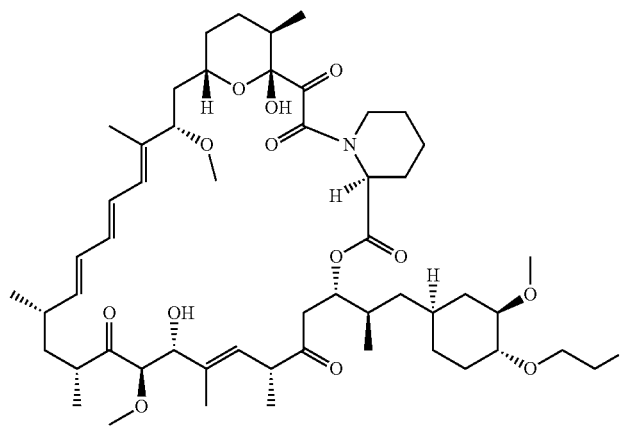
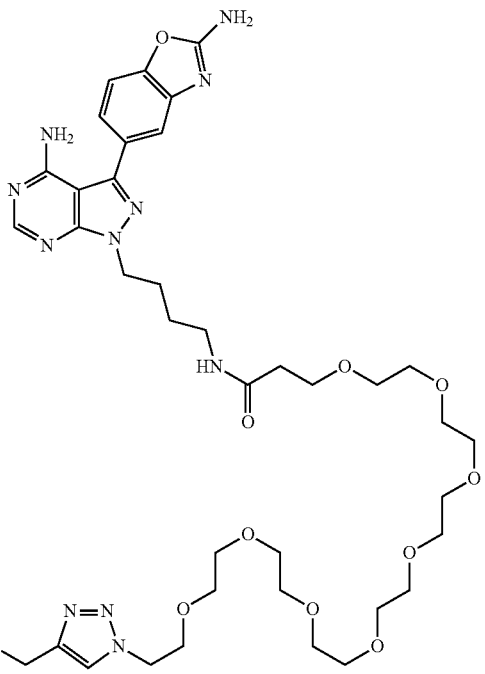

11b (M-1071)

Preparation of tert-butyl (4-(4-amino-3-iodo-1H-pyrazolo[3,4-d]pyrimidin-1-yl)butyl)carbamate 8b To a suspension of 3-iodo-1H-pyrazolo[3,4-d]pyrimidin-4-amine (7) (2.11 g, 8.08 mmol) in DMF (25 mL) was added NaH oil dispersion (485 mg, 12.1 mmol) at 4° C. The mixture was stirred at 4° C. for 30 min. To the reaction mixture was added tert-butyl (4-bromobutyl)carbamate (2.50 g, 8.92 mmol) in DMF (5 mL) at 4° C. The mixture was stirred at room temperature for 14 h. To the mixture was added water (100 mL) at room temperature. The mixture was cooled to 4° C. and stirred for 30 min. The resulting precipitate was collected by filtration. Drying the solid gave the titled compound (3.01 g, 86%) as a colorless powder.

$^1$H NMR (400 MHz, DMSO-$d_6$) δ 8.33 (1H, s), 5.86 (2H, br s), 4.61 (1H, br s), 4.39 (2H, t, J=7.2 Hz), 3.05-3.25 (2H, br s), 1.90-1.98 (2H, m), 1.44-1.55 (2H, m), 1.43 (9H, s).
LC-MS (ESI) m/z=433.09 (M+H)$^+$.

Preparation of tert-butyl (4-(4-amino-3-(2-aminobenzo[d]oxazol-5-yl)-1H-pyrazolo[3,4-d]pyrimidin-1-yl)butyl)carbamate 9b To a bi-phasic suspension of tert-butyl (4-(4-amino-3-iodo-1H-pyrazolo[3,4-d]pyrimidin-1-yl)butyl)carbamate (8b) (435 mg, 1.00 mmol), 5-(4,4,5,5-tetramethyl-1,3,2-dioxaborolan-2-yl)benzo[d]oxazol-2-amine (390 mg, 1.50 mmol), and Na$_2$CO$_3$ (530 mg, 5.00 mmol) in DME (10 mL) and water (5 mL) was added tetrakis(triphenylphosphine)palladium (0) (116 mg, 100 μmol) at room temperature under argon atmosphere. The mixture was stirred at 110° C. for 3 h. It was then cooled and partitioned between EtOAc (90 mL) and water (30 mL). The aqueous layer was separated and extracted with EtOAc (2×30 mL). The organic layers were combined, washed with brine (2×30 mL) and dried over anhydrous MgSO$_4$. The insoluble was filtered off and the filtrate was concentrated in vacuo. The crude material was purified by silica gel column chromatography (silica gel: 75 g, solvent: 50% EtOAc in hexanes (400 mL) followed by 20% MeOH in EtOAc (800 mL)). The desired fractions were combined and evaporated in vacuo. The obtained solid was recrystallized from MeOH/water to give the titled compound (332 mg, 76%) as a colorless solid.

$^1$H NMR (400 MHz, DMSO-$d_6$) δ 8.23 (1H, s), 7.52 (2H, s), 7.46 (1H, d, J=8.0 Hz), 7.41 (1H, s), 7.23 (1H, dd, J=8.0, 1.2 Hz), 6.79 (1H, t, J=5.6 Hz), 4.32 (2H, t, J=5.6 Hz), 3.26-3.33 (2H, m), 2.88-2.96 (2H, m), 1.77-1.87 (2H, m), 1.35 (9H, s), NH$_2$ protons were not identified.
LC-MS (ESI) m/z=439.28 (M+H)$^+$.

Preparation of N-(4-(4-amino-3-(2-aminobenzo[d]oxazol-5-yl)-1H-pyrazolo[3,4-d]pyrimidin-1-yl)butyl)-1-azido-3,6,9,12,15,18,21,24-octaoxaheptacosan-27-amide 10b To a cooled liquid of TFA (3 mL) was added tert-butyl (4-(4-amino-3-(2-aminobenzo[d]oxazol-5-yl)-1H-pyrazolo[3,4-d]pyrimidin-1-yl)butyl)carbamate (9b) (300 mg, 0.68 mmol) at 4° C. The mixture was stirred at ambient temperature for 1 h. It was then evaporated in vacuo. The oily residue was triturated with Et$_2$O for 10 min. The supernatant was removed and then the precipitate was triturated with 2 M hydrochloride in Et$_2$O solution (3 mL) for 30 min. The precipitate was collected by filtration under argon atmosphere. Drying the solid gave the salt of Boc-cleaved compound (362 mg). The obtained material (136 mg) was dissolved into DMF (4 mL). To the mixture was added triethylamine (146 μL, 1.05 mmol) followed by a solution of azide-dPEG8-NHS ester (Catalog number 10503, Quanta BioDesign, Ltd., Powell, Ohio USA) (200 mg, 0.35 mmol) in DMF (4 mL) under argon atmosphere. The mixture was stirred at room temperature for 13 h. It was then evaporated in vacuo. The residue was partitioned between 10% THF in EtOAc (100 mL) and brine (20 mL). The aqueous layer was separated and extracted with EtOAc (50 mL). The organic layers were combined and dried over anhydrous $MgSO_4$. The insoluble was filtered off and the filtrate was evaporated in vacuo. The resulting crude material was purified by silica gel column chromatography (silica gel: 25 g, 2-25% MeOH in $CH_2Cl_2$). Desired fractions were combined and evaporated in vacuo to give the titled compound (145 mg, 72% in 2 steps) as a colorless wax.

$^1$H NMR (400 MHz, $CDCl_3$) δ 8.36 (1H, s), 7.63 (1H, s), 7.38-7.40 (2H, m), 6.74 (1H, br s), 5.73 (1H, s), 4.46-4.48 (2H, m), 3.58-3.67 (31H, m), 3.39-3.41 (2H, m), 3.28-3.30 (2H, m), 2.45 (2H, br s), 2.01 (2H, br s), 1.59 (2H, br s), 4H protons were not identified.

LC-MS (ESI) m/z=786.34 (M−H)⁻.

Preparation of 40-O-(2-((1-(32-(4-amino-3-(2-aminobenzo[d]oxazol-5-yl)-1H-pyrazolo[3,4-d]pyrimidin-1-yl)-27-oxo-3,6,9,12,15,18,21,24-octaoxa-28-azadotriacontyl)-1H-1,2,3-triazol-4-yl)methoxy) ethyl)-rapamycin 11b (M-1071)

To a solution of N-(4-(4-amino-3-(2-aminobenzo[d]oxazol-5-yl)-1H-pyrazolo[3,4-d]pyrimidin-1-yl)butyl)-1-azido-3,6,9,12,15,18,21,24-octaoxaheptacosan-27-amide (10b) (25.6 mg, 32.5 µmol) in MeOH (9 mL) was added 40-O-(2-(prop-2-yn-1-yloxy)ethyl)-rapamycin (6) (32.5 mg, 32.6 µmol). To the mixture were added 1 M aqueous $CuSO_4$ solution (120 µL, 120 µmol) and 1 M aqueous sodium ascorbate solution (60.0 µL, 60.0 µmol). The mixture was stirred at room temperature for 1 h. An additional amount of (10b) (10.5 mg, 13.3 µmol) was added. The mixture was stirred for additional 2 h. It was then concentrated in vacuo. The crude material was partitioned between 20% THF in EtOAc (50 mL) and water (20 mL). The aqueous layer was separated and extracted with 20% THF in EtOAc (50 mL). The combined organic layer was dried over anhydrous $MgSO_4$. The mixture was passed through a pad of Celite (#545) using EtOAc. The filtrate was concentrated in vacuo and the crude material was purified by preparative RP-HPLC (20-95% $CH_3CN$ in water containing 0.1% formic acid). The desired fractions were combined and lyophilized to give formic acid salt of the titled compound (13.3 mg, 22%) as a colorless amorphous powder.

LC-MS (ESI−) m/z=1781.79 (M−H)⁻.

HR-MS (ESI−) Calcd for $C_{91}H_{137}O_{24}N_{12}$ (M−H)⁻ 1781.9874, Found 1781.9826 (Δ −2.70 ppm).

TABLE 6

NMR analysis of M-1071

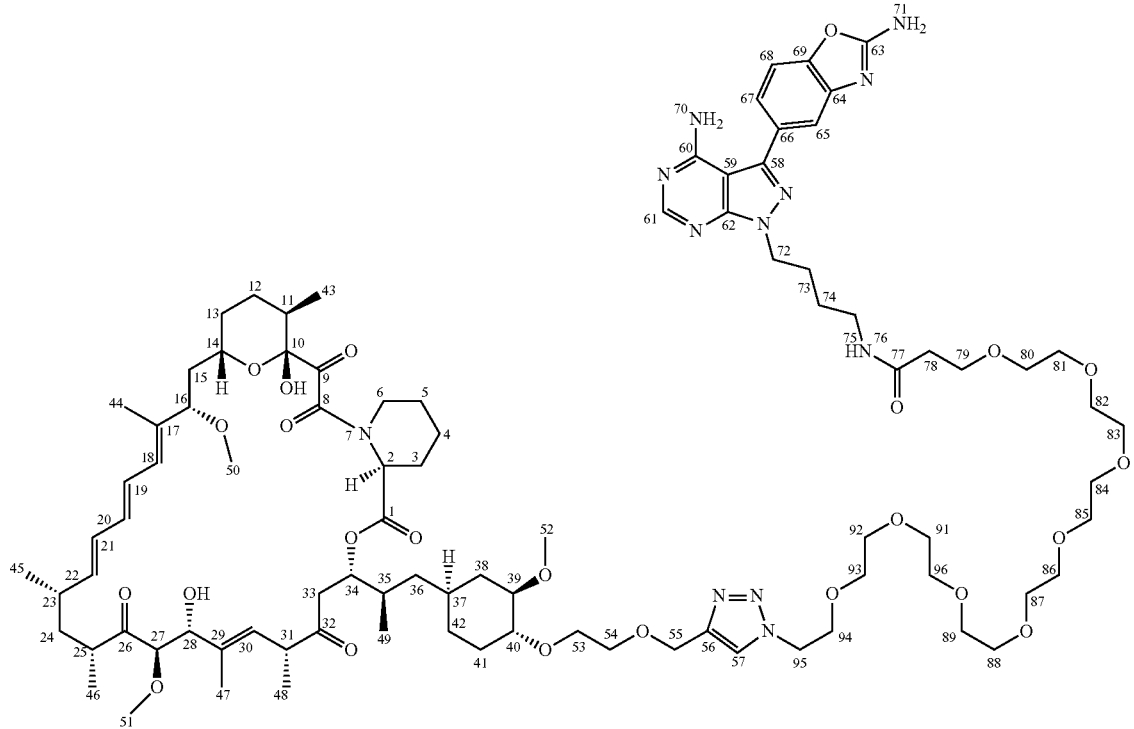

M-1071

| Atom | Atom Type | δ$^1$H Major (3:1) | δ$^{13}$C Major (3:1) | HMBC C to H | $^1$H-$^1$H COSY |
|---|---|---|---|---|---|
| 1 | C=O | N/A | 169.3 | 2 | N/A |
| 2 | CH | 5.28 (d, 5.6 Hz) | 51.3 | 3a,b, 6a | 3b |
| 3 | $CH_2$ | a: 2.34 (m) | 27.1 | 2, 5a | 3b, 4b |
|  |  | b: 1.76 (m) |  |  | 3a, 2 |
| 4 | $CH_2$ | a: 1.78 (m) | 20.7 | 2, 6a,b | 4b, 5a,b |

TABLE 6-continued

NMR analysis of M-1071

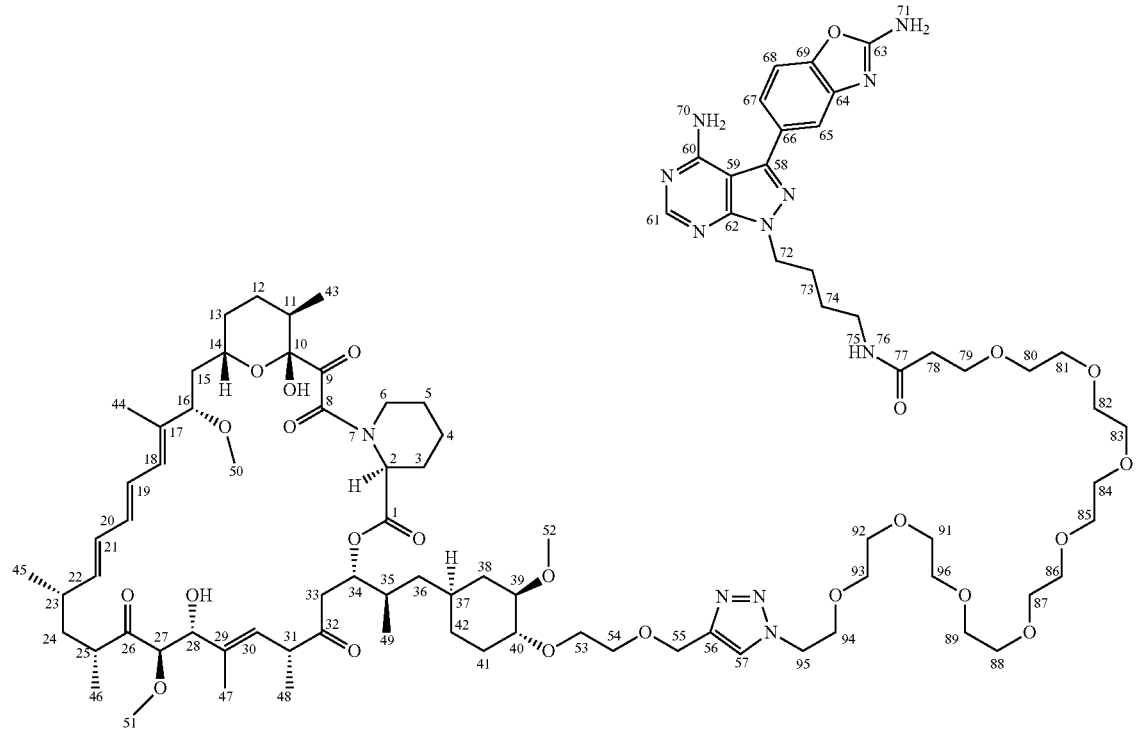 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

M-1071

| Atom | Atom Type | δ¹H Major (3:1) | δ¹³C Major (3:1) | HMBC C to H | ¹H-¹H COSY |
|---|---|---|---|---|---|
| 5 | $CH_2$ | b: 1.47 (m)<br>a: 1.74 (m) | 25.3 | 3a, 4b | 4a, 3a, 5a,b<br>5b, 4a,b |
| 6 | $CH_2$ | b: 1.47 (m)<br>a: 3.56 (m)<br>b: 3.43 (m) | 44.2 | 2, 4a,b, 5b | 5a, 4a,b, 6b<br>6b<br>6a, 5b |
| 8 | C=O | N/A | 166.7 | 2, 6a | N/A |
| 9 | C=O | N/A | 196.3 | n.d. | N/A |
| 10 | O—C—OH | N/A | 98.5 | 11, 12, 43 | N/A |
| 11 | CH | 2.00 (m) | 33.8 | 12, 43 | 12, 43 |
| 12 | $CH_2$ | 1.60 (2H, m) | 27.2 | 43 | 11, 13a,b |
| 13 | $CH_2$ | a: 1.64 (m)<br>b: 1.31 (m) | 31.2 | 12, 15a | 13b, 12<br>13a, 12, 14 |
| 14 | CH—OC | 3.88 (m) | 67.2 | 12, 15a | 13b, 15a,b |
| 15 | $CH_2$ | a: 1.85 (m)<br>b: 1.49 (m) | 38.9 | 16 | 15b, 14, 16<br>15a, 14, 16 |
| 16 | CH—$OCH_3$ | 3.65 (m) | 84.3 | 15a, 18, 44, 50 | 15a,b |
| 17 | —C= | N/A | 135.7 | 15a, 44 | N/A |
| 18 | CH=C | 5.98 (d, 11.2 Hz) | 129.4 | 44 | 19 |
| 19 | CH=C | 6.39 (dd, 14.8, 10.8 Hz) | 126.5 | 20, 21 | 18, 20 |
| 20 | CH=C | 6.31 (dd, 14.8, 10.4 Hz) | 133.5 | 18, 19, 21, 22 | 19, 21 |
| 21 | CH=C | 6.14 (dd, 14.8, 10.4 Hz) | 130.2 | 19 | 20, 22 |
| 22 | CH=C | 5.55 (dd, 15.4, 8.6 Hz) | 140.0 | 20, 24a,b, 45 | 21, 23 |
| 23 | CH | 2.32 (m) | 35.0 | 21, 22, 24a,b, 25, 45 | 22, 24a, 45 |
| 24 | $CH_2$ | a: 1.47 (m)<br>b: 1.21 (m) | 40.3 | 22, 25, 45, 46 | 24b, 23<br>24a, 25 |
| 25 | CH | 2.70 (m) | 41.5 | 24a,b, 46 | 24b, 46 |
| 26 | C=O | N/A | n.d. (>210) | n.d. | N/A |
| 27 | CH—$OCH_3$ | 3.78 (m) | 84.9 | 28, 51 | 28 |
| 28 | CH—OH | 4.20 (d, 4.8 Hz) | 77.1 | 27, 30, 47 | 27 |
| 29 | —C= | N/A | 136.0 | 28, 31, 47 | N/A |
| 30 | CH=C | 5.42 (d, 10.4 Hz) | 126.5 | 28, 31, 47, 48 | 31 |
| 31 | CH | 3.29 (d, 10.4 Hz) | 46.6 | 30, 48 | 30, 48 |
| 32 | C=O | N/A | 208.3 | 30, 31, 33a,b, 48 | N/A |
| 33 | $CH_2$ | a: 2.70 (m)<br>b: 2.58 (m) | 40.7 | n.d. | 33b, 34<br>33a, 34 |
| 34 | CH—OCO | 5.16 (dd, 10.4, 6.4 Hz) | 75.6 | 33a,b, 49 | 33a,b, 35 |
| 35 | CH | 1.93 (m) | 33.2 | 33a,b, 49 | 34, 36a,b, 49 |
| 36 | $CH_2$ | a: 1.17 (m)<br>b: 1.09 (m) | 38.4 | 34, 38b, 49 | 36b, 35, 37<br>36a, 35, 37 |

TABLE 6-continued

NMR analysis of M-1071

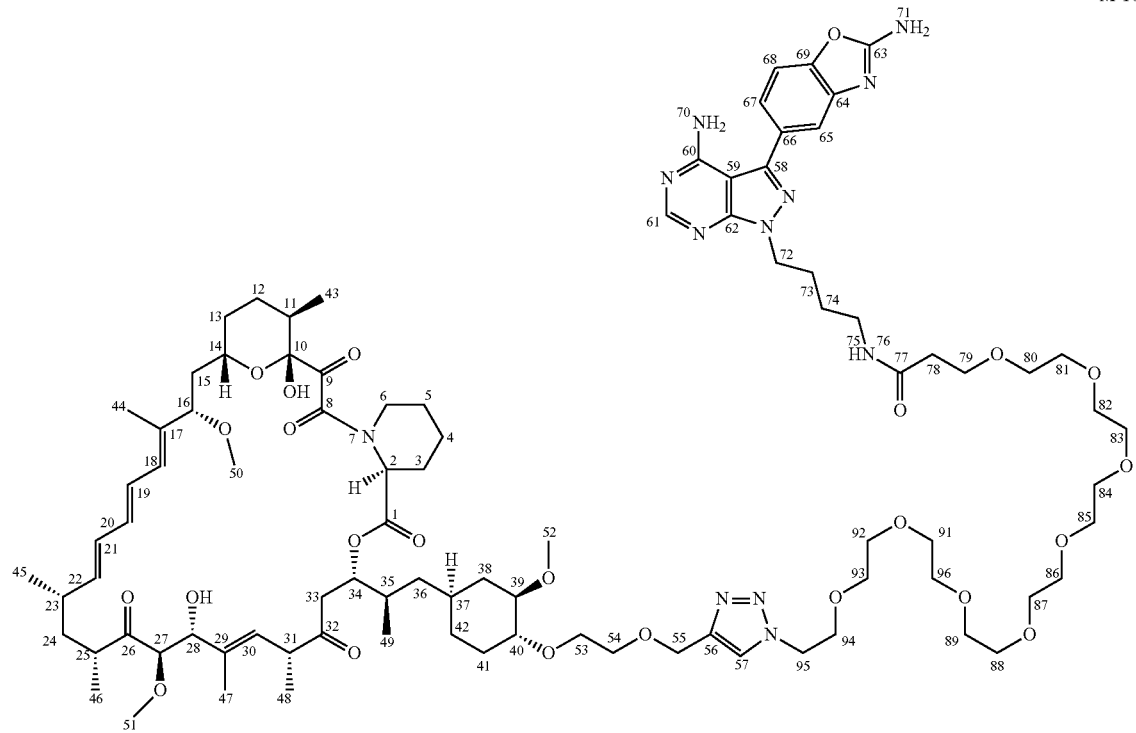

M-1071

| Atom | Atom Type | δ¹H Major (3:1) | δ¹³C Major (3:1) | HMBC C to H | ¹H-¹H COSY |
|---|---|---|---|---|---|
| 37 | CH | 1.33 (m) | 33.0 | 36a,b, 38a,b, 42a,b | 36a,b, 38b, 42a,b |
| 38 | CH$_2$ | a: 2.02 (m) | 36.3 | 36a,b, 42a | 38b, 39 |
|  |  | b: 0.69 (m) |  |  | 38a, 37, 39 |
| 39 | CH—OCH$_3$ | 3.05 (m) | 83.0 | 38a,b, 40, 52 | 38a,b, 40 |
| 40 | CH—O— | 3.11 (m) | 83.1 | 38a,b, 39, 52, 53 | 39, 41a,b |
| 41 | CH$_2$ | a: 2.01 (m) | 30.0 | 42b. | 41b, 40, 42b |
|  |  | b: 1.24 (m) |  |  | 41a, 40, 42b |
| 42 | CH$_2$ | a: 1.66 (m) | 31.7 | 36b, 38a,b | 42b, 37 |
|  |  | b: 0.89 (m) |  |  | 42a, 37, 41a,b |
| 43 | 11-CH$_3$ | 0.95 (3H, d, 6.7 Hz) | 16.2 | 11, 12 | 11 |
| 44 | 17-CH$_3$ | 1.65 (3H, s) | 10.2 | 16, 18 | n.d. |
| 45 | 23-CH$_3$ | 1.05 (3H, d, 6.4 Hz) | 21.5 | 22, 24a,b | 23 |
| 46 | 25-CH$_3$ | 0.99 (3H, d, 6.5 Hz) | 13.6 | 24a,b, 25 | 25 |
| 47 | 29-CH$_3$ | 1.76 (3H, s) | 13.4 | 28, 30 | n.d. |
| 48 | 31-CH$_3$ | 1.09 (3H, d, 6.7 Hz) | 16.0 | 30, 31 | 31 |
| 49 | 35-CH$_3$ | 0.90 (3H, d, 6.8 Hz) | 15.8 | 36a,b | 35 |
| 50 | 16-OCH$_3$ | 3.13 (3H, s) | 55.9 | 16 | n.d. |
| 51 | 27-OCH$_3$ | 3.33 (3H, s) | 59.2 | 27 | n.d. |
| 52 | 39-OCH$_3$ | 3.43 (3H, s) | 57.8 | 39 | n.d. |
| 53 | 40-OCH$_2$ | 3.72 (2H, m) | 69.2 | 40, 54 | 54 |
| 54 | —CH$_2$—O— | 3.67 (2H, m) | 70.2 | 53, 55 | 53 |
| 55 | —OCH$_2$triazole | 4.68 (2H, s) | 64.6 | 54 | n.d. |
| 56 | —C= | N/A | 145.0 | 55, 57 | N/A |
| 57 | =CH | 7.76 (s) | 123.8 | 55, 95 | n.d. |
| 58 | PP—C | N/A | 144.5 | 65, 67, 68 | N/A |
| 59 | PP—C | N/A | 98.5 | 61 | N/A |
| 60 | PP—C—NH$_2$ | N/A | 157.5 | n.d. | N/A |
| 61 | PP—CH | 8.36 (s) | 155.5 | n.d. | n.d. |
| 62 | PP—C | N/A | 154.1 | 61, 72 | N/A |
| 63 | BO—C—NH$_2$ | N/A | 162.8 | n.d. | N/A |
| 64 | BO—C | N/A | 144.2 | 65, 68 | N/A |
| 65 | BO—CH | 7.62 (s) | 116.3 | 67, 68 | 67 |
| 66 | BO—C | N/A | 129.1 | 68 | N/A |
| 67 | BO—CH | 7.38 (dd, 8.4, 1.4 Hz) | 121.6 | 65 | 65, 68 |
| 68 | BO—CH | 7.40 (d, 8.4 Hz) | 109.6 | 65, 67 | 67 |
| 69 | BO—C | N/A | 149.3 | 65, 67, 68 | N/A |
| 72 | N—CH$_2$ | 4.47 (2H, t, 6.8 Hz) | 46.6 | 73, 74 | 73 |
| 73 | CH$_2$ | 2.01 (2H, m) | 27.2 | 72, 74, 75 | 72, 74 |
| 74 | CH$_2$ | 1.58 (2H, m) | 26.5 | 72, 73, 75 | 73, 75 |

TABLE 6-continued

NMR analysis of M-1071

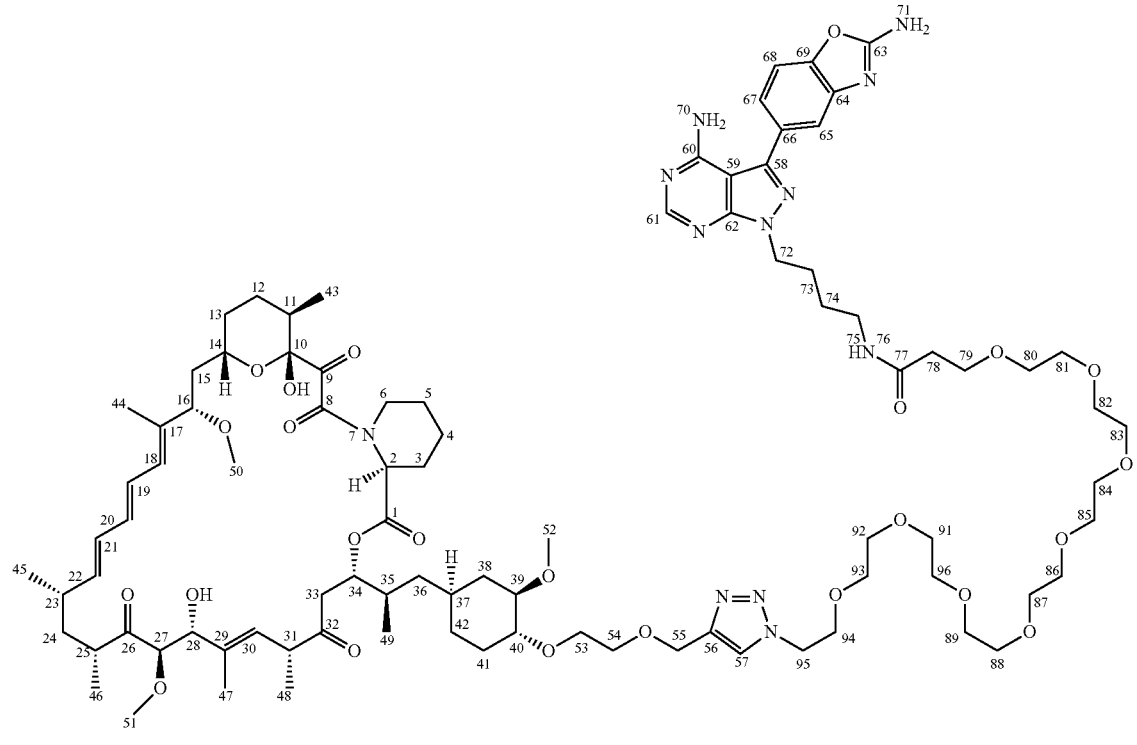

M-1071

| Atom | Atom Type | $\delta^1$H Major (3:1) | $\delta^{13}$C Major (3:1) | HMBC C to H | $^1$H-$^1$H COSY |
|---|---|---|---|---|---|
| 75 | CH$_2$—NHCO | 3.30 (2H, m) | 38.9 | 73, 74, 76 | 74 |
| 76 | NH | 6.77 (t, 4.8 Hz) | N/A | N/A | n.d. |
| 77 | CO | N/A | 171.6 | 75, 76, 78, 79 | N/A |
| 78 | CH$_2$ | 2.44 (2H, t, 5.8 Hz) | 37.0 | 79 | 79 |
| 79 | CH$_2$ | 3.69 (2H, t, 5.8 Hz) | 67.4 | 78 | 78 |
| 80-93 | O—(CH$_2$CH$_2$O)$_7$ | 3.54-3.64 (28H, m) | 70.3-70.6 | multi | multi- |
| 94 | OCH$_2$ | 3.87 (2H, t, 4.8 Hz) | 69.5 | 95 | 95 |
| 95 | CH$_2$-triazole | 4.54 (2H, t, 4.8 Hz) | 50.2 | 94 | 94 |

PP stands for pyrazolo[3,4-d]pyrimidine and BO stands for benzo[d]oxazole
OH protons and NHx protons were not identified.

Preparation of Compound 11c (M-1111; Example 2)

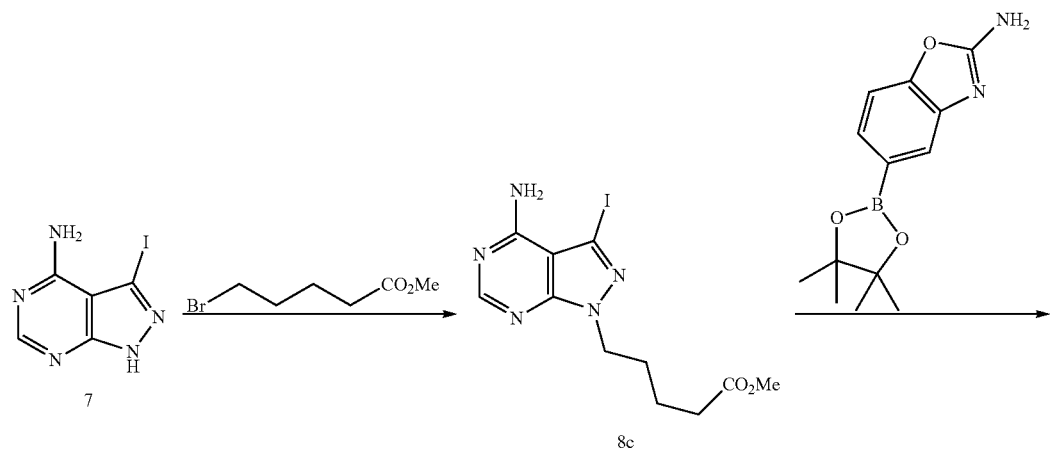

145
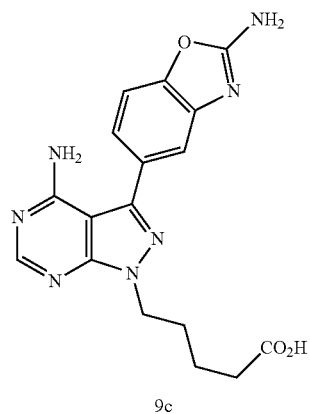
9c
146
-continued
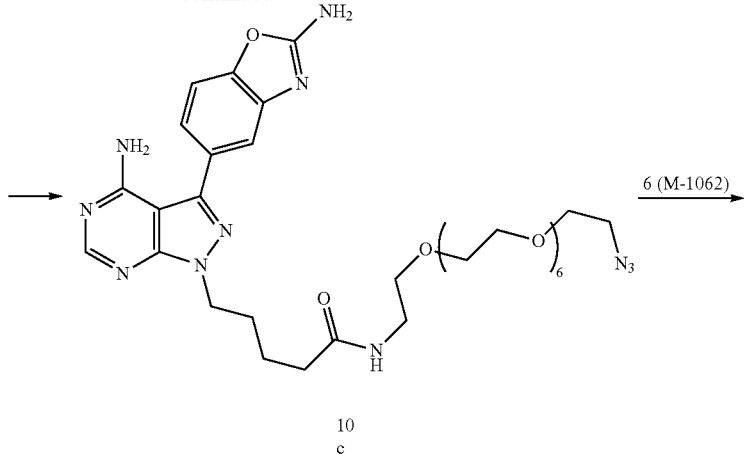
10c
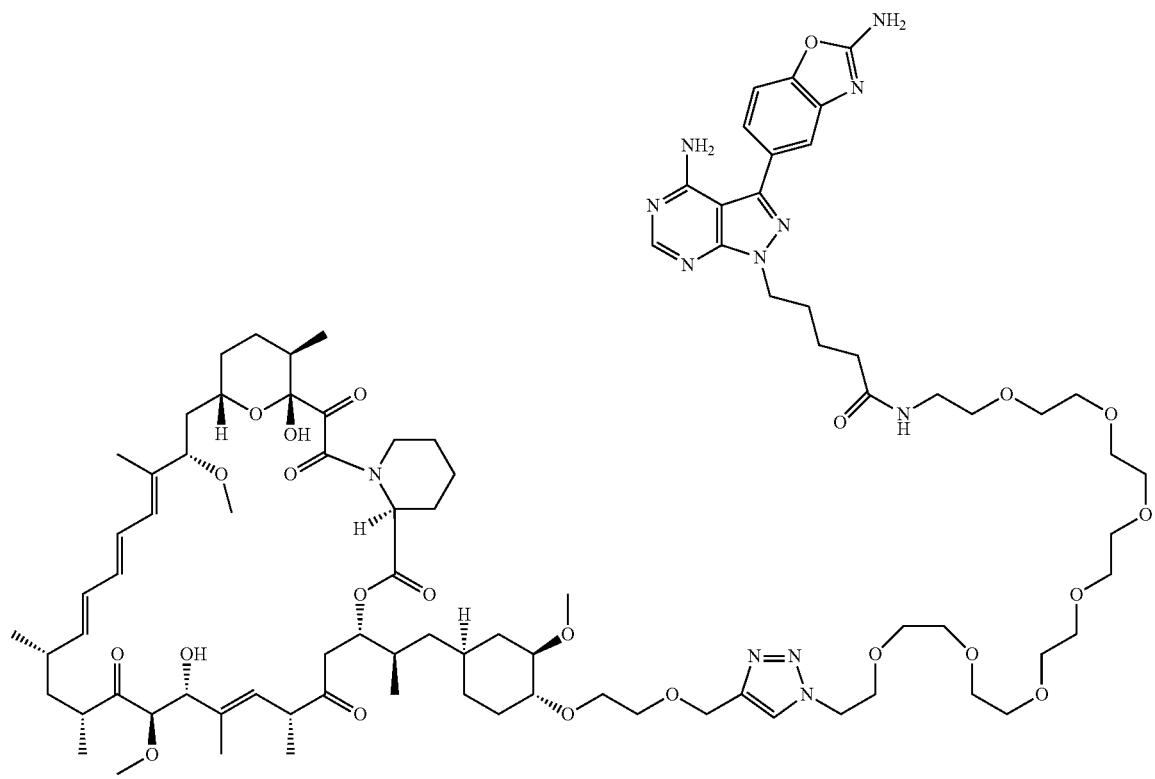
11c (M-1111)

Preparation of 5-(4-amino-3-iodo-1H-pyrazolo[3,4-d]pyrimidin-1-yl)pentanoic Acid 8c To a suspension of 3-iodo-1H-pyrazolo[3,4-d]pyrimidin-4-amine (7) (2.11 g, 8.08 mmol) in DMF (25 mL) was added NaH oil dispersion (485 mg, 12.1 mmol) at 4° C. The mixture was stirred at 4° C. for 30 min. To the reaction mixture was added methyl 5-bromopentanoate (1.79 g, 8.90 mmol) in DMF (5 mL) at 4° C. The mixture was stirred at room temperature for 108 h. It was then partitioned between EtOAc (200 mL) and water (100 mL). The aqueous layer was separated and extracted with EtOAc (100 mL). The organic layers were combined, washed with brine (50 mL), and dried over anhydrous $MgSO_4$. The insoluble was filtered off and the filtrate was evaporated in vacuo. The obtained material was triturated with 20% EtOAc in hexanes (100 mL) for 15 min. The resulting precipitate was collected by filtration. Drying the solid gave the titled compound (1.94 g, 64%) as a pale beige powder.

$^1$H NMR (400 MHz, DMSO-$d_6$) δ 8.20 (1H, s), 4.27 (2H, t, J=6.8 Hz), 3.56 (3H, s), 2.32 (2H, t, J=7.6 Hz), 1.74-1.84 (2H, m), 1.40-1.50 (2H, m), 2H protons were not identified.
LC-MS (ESI) m/z=376.14 (M+H)$^+$.

Preparation of 5-(4-amino-3-(2-aminobenzo[d]oxazol-5-yl)-1H-pyrazolo[3,4-d]pyrimidin-1-yl)pentanoic Acid 9c To a bi-phasic suspension of 5-(4-amino-3-iodo-1H-pyrazolo[3,4-d]pyrimidin-1-yl)pentanoic acid (8c) (375 mg, 1.00 mmol), 5-(4,4,5,5-tetramethyl-1,3,2-dioxaborolan-2-yl)benzo[d]oxazol-2-amine (390 mg, 1.50 mmol), and saturated aqueous $Na_2CO_3$ solution (2.5 mL) in DME (10 mL) and water (2.5 mL) was added tetrakis(triphenylphosphine)palladium (0) (116 mg, 100 μmol) at room temperature under argon atmosphere. The mixture was stirred at 110° C. for 3 h. The reaction mixture was cooled to 60° C. and diluted with MeOH (10 mL) and THF (10 mL). To the reaction mixture was added 4 M aqueous LiOH solution (5 mL). The mixture was stirred at 60° C. for additional 2 h. It was then cooled and acidified using AcOH to adjust pH to be 3-4. The mixture was partitioned between EtOAc (200 mL) and water (10 mL). The organic layer was washed with brine (20 mL) and dried over anhydrous $MgSO_4$. The insoluble was filtered off and the filtrate was concentrated in vacuo. The crude material was purified by silica gel column chromatography (silica gel: 25 g, solvent: 2-30% MeOH in $CH_2Cl_2$). The desired fractions were combined and evaporated in vacuo. The obtained solid was triturated with 20% EtOAc in hexanes. The resulting precipitate was collected by filtration. Drying the solid gave the titled compound (207 mg, 56%) as a pale pink powder.

$^1$H NMR (400 MHz, DMSO-$d_6$) δ 12.00 (1H, s), 8.24 (1H, s), 7.52 (2H, s), 7.46 (1H, d, J=8.0 Hz), 7.41 (1H, d, J=1.6 Hz), 7.24 (1H, dd, J=8.0, 1.6 Hz), 4.33 (2H, t, J=6.8 Hz), 2.25 (2H, t, J=7.2 Hz), 1.82-1.91 (2H, m), 1.44-1.53 (2H, m), 2H protons were not identified.

LC-MS (ESI) m/z=368.22 (M+H)$^+$.

Preparation of 5-(4-amino-3-(2-aminobenzo[d]oxazol-5-yl)-1H-pyrazolo[3,4-d]pyrimidin-1-yl)-N-(23-azido-3,6,9,12,15,18,21-heptaoxatricosyl)pentanamide 10c To a solution of 5-(4-amino-3-(2-aminobenzo[d]oxazol-5-yl)-1H-pyrazolo[3,4-d]pyrimidin-1-yl)pentanoic acid (9c) (170 mg, 0.46 mmol) in DMF (4 mL) was added triethylamine (193 μL, 1.39 mmol) followed by azide-dPEG7-amine (Catalog number 10523, Quanta BioDesign, Ltd., Powell, Ohio USA) (219 mg, 0.56 mmol), EDCI (133 mg, 0.69 mmol), and HOBt (93.6 mg, 0.693 mmol). The mixture was stirred at room temperature for 6 h and then stirred at 40° C. for 13 h. It was then partitioned between EtOAc (100 mL) and water (50 mL). The aqueous layer was separated and extracted with EtOAc (100 mL). The organic layers were combined, washed with brine (20 mL), and dried over anhydrous $MgSO_4$. The insoluble was filtered off and the filtrate was evaporated in vacuo. The resulting crude material was purified by silica gel column chromatography (silica gel: 25 g, 2-25% MeOH in $CH_2Cl_2$). Desired fractions were combined and evaporated in vacuo to give the titled compound (286 mg, 83%) as a pale brown wax. This material was used for the next reaction without further purification.

LC-MS (ESI) m/z=744.32 (M+H)$^+$.

Preparation of 40-O-(2-((1-(29-(4-amino-3-(2-aminobenzo[d]oxazol-5-yl)-1H-pyrazolo[3,4-d]pyrimidin-1-yl)-25-oxo-3,6,9,12,15,18,21-heptaoxa-24-azanonacosyl)-1H-1,2,3-triazol-4-yl)methoxy)ethyl)-rapamycin 11c (M-1111)

To a solution of 5-(4-amino-3-(2-aminobenzo[d]oxazol-5-yl)-1H-pyrazolo[3,4-d]pyrimidin-1-yl)-N-(23-azido-3,6,9,12,15,18,21-heptaoxatricosyl)pentanamide (10c) (32.0 mg, 43.0 μmol) in MeOH (5 mL) and THF (1 mL) was added 40-O-(2-(prop-2-yn-1-yloxy)ethyl)-rapamycin (6) (32.5 mg, 32.6 μmol). To the mixture were added 1 M aqueous $CuSO_4$ solution (100 μL, 100 μmol) and 1 M aqueous sodium ascorbate solution (50.0 μL, 50.0 μmol). The mixture was stirred at room temperature for 2 h. It was then concentrated in vacuo. After removing the insoluble material by filtration through a pad of silica gel, the crude material was partitioned between 20% THF in EtOAc (50 mL) and water (5 mL). The organic layer was evaporated in vacuo. The resulting crude material was purified by preparative RP-HPLC (20-95% $CH_3CN$ in water containing 0.1% formic acid). The desired fractions were combined and lyophilized to give formic acid salt of the titled compound (7.6 mg, 13%) as a colorless amorphous powder.

LC-MS (ESI−) m/z=1737.69 (M−H)$^-$
HR-MS (ESI−) Calcd for $C_{89}H_{133}O_{23}N_{12}$ (M−H)$^-$ 1737.9612, Found 1737.9561 (Δ −2.94 ppm).

TABLE 7

NMR analysis of M-1111

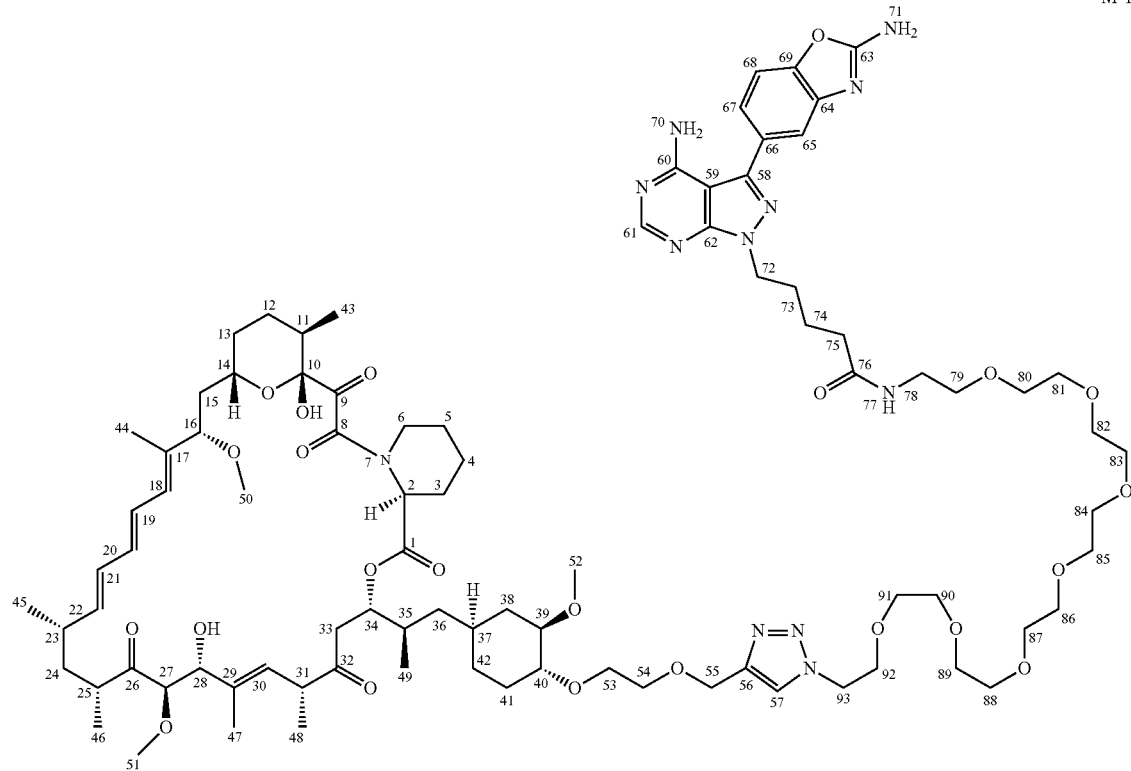

M-1111

| Atom | Atom Type | δ¹H Major (3:1) | δ¹³C Major (3:1) | HMBC C to H | ¹H-¹H COSY |
|---|---|---|---|---|---|
| 1 | C=O | N/A | 169.3 | 2 | N/A |
| 2 | CH | 5.27 (d, 4.8 Hz) | 51.3 | 4a, 6a | 3b |
| 3 | CH₂ | a: 2.33 (m)<br>b: 1.74 (m) | 27.1 | 2 | 3b, 4a,b<br>3a, 2, 4a,b |
| 4 | CH₂ | a: 1.78 (m)<br>b: 1.46 (m) | 20.7 | 2, 6a | 4b, 3a,b, 5a,b<br>4a, 3a,b, 5a,b |
| 5 | CH₂ | a: 1.73 (m)<br>b: 1.45 (m) | 25.3 | 3a, 6a | 5b, 4a,b, 6a,b<br>5a, 4a,b, 6a,b |
| 6 | CH₂ | a: 3.54 (m)<br>b: 3.41 (m) | 44.2 | 2, 4a,b | 6b, 5a,b<br>6a, 5a,b |
| 8 | C=O | N/A | 166.8 | 2, 6a | N/A |
| 9 | C=O | N/A | 197.2 | n.d. | N/A |
| 10 | O—C—OH | N/A | 98.5 | 11, 12, 43 | N/A |
| 11 | CH | 1.99 (m) | 33.9 | 12, 43 | 12, 13a, 43 |
| 12 | CH₂ | 1.60 (m) | 27.2 | 43 | 11, 13b |
| 13 | CH₂ | a: 1.63 (m)<br>b: 1.32 (m) | 31.2 | 12, 15a. | 13b, 11<br>13a, 12, 14 |
| 14 | CH—OC | 3.88 (m) | 67.2 | 12, 15a, 16 | 13b, 15a,b |
| 15 | CH₂ | a: 1.85 (m)<br>b: 1.47 (m) | 39.0 | 16 | 15b, 14, 16<br>15a, 14, 16 |
| 16 | CH—OCH₃ | 3.66 (m) | 84.3 | 15a, 18, 44, 50 | 15a,b |
| 17 | —C= | N/A | 135.9 | 15a, 19, 44 | N/A |
| 18 | CH=C | 5.97 (d, 10.4 Hz) | 129.4 | 20, 44 | 19 |
| 19 | CH=C | 6.38 (dd, 14.4, 11.2 Hz) | 126.5 | 18, 20, 21, 22, 44 | 18, 20 |
| 20 | CH=C | 6.30 (dd, 14.4, 10.4 Hz) | 133.5 | 18, 19, 21, 22 | 19, 21 |
| 21 | CH=C | 6.13 (dd, 15.2, 10.4 Hz) | 130.2 | 19, 20 | 20, 22 |
| 22 | CH=C | 5.54 (dd, 15.2, 8.8 Hz) | 140.0 | 20, 24a,b, 45 | 21, 23 |
| 23 | CH | 2.32 (m) | 35.0 | 21, 22, 24a,b, 25, 45 | 22, 24a, 45 |
| 24 | CH₂ | a: 1.46 (m)<br>b: 1.20 (m) | 40.3 | 22, 25, 45, 46 | 24b, 23<br>24a, 25 |
| 25 | CH | 2.69 (m) | 41.5 | 24a,b, 45, 46 | 24b, 46 |
| 26 | C=O | N/A | 213.4 | n.d. | N/A |
| 27 | CH—OCH₃ | 3.78 (d, 5.6 Hz) | 84.9 | 28, 51 | 28 |
| 28 | CH—OH | 4.20 (d, 4.8 Hz) | 77.0 | 27, 30, 47 | 27 |
| 29 | —C= | N/A | 136.0 | 28, 30, 31, 47 | N/A |
| 30 | CH=C | 5.43 (d, 10.4 Hz) | 126.5 | 28, 31, 47, 48 | 31 |
| 31 | CH | 3.32 (m) | 46.6 | 30, 48 | 30, 48 |
| 32 | C=O | N/A | 208.3 | 30, 31, 33a,b, 48 | N/A |

TABLE 7-continued

NMR analysis of M-1111

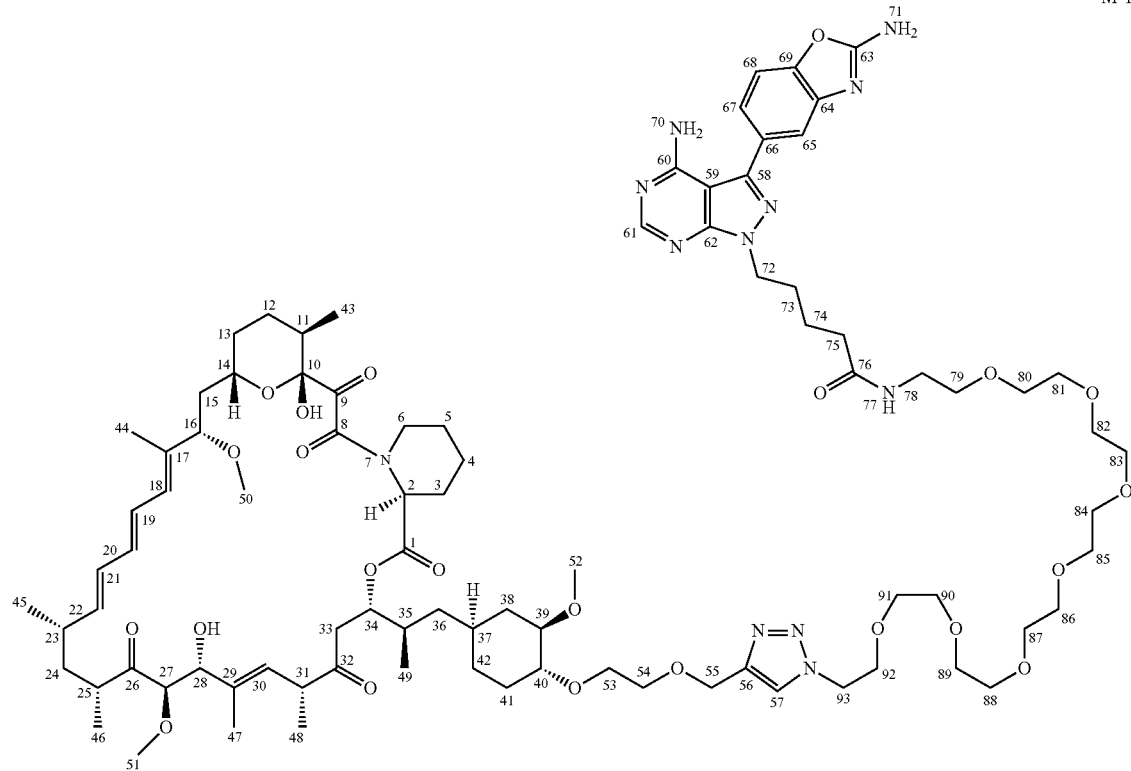

M-1111

| Atom | Atom Type | δ¹H Major (3:1) | δ¹³C Major (3:1) | HMBC C to H | ¹H-¹H COSY |
|---|---|---|---|---|---|
| 33 | $CH_2$ | a: 2.69 (m) | 40.6 | n.d. | 33b, 34 |
|  |  | b: 2.57 (m) |  |  | 33a, 34 |
| 34 | CH—OCO | 5.15 (dd, 10.4, 5.6 Hz) | 75.6 | 33a,b, 49 | 33a,b, 35 |
| 35 | CH | 1.92 (m) | 33.2 | 33a,b, 36a,b, 49 | 34, 36a,b, 49 |
| 36 | $CH_2$ | a: 1.16 (m) | 38.4 | 38b, 49 | 36b, 35, 37 |
|  |  | b: 1.08 (m) |  |  | 36a, 35, 37 |
| 37 | CH | 1.32 (m) | 33.0 | 36a,b, 38a,b, 42b | 36a,b, 38b, 42a,b |
| 38 | $CH_2$ | a: 2.01 (m) | 36.3 | 36a,b | 38b, 39 |
|  |  | b: 0.70 (m) |  |  | 38a, 37 |
| 39 | CH—$OCH_3$ | 3.05 (m) | 83.0 | 38a,b, 40, 52 | 38a, 41a |
| 40 | CH—O— | 3.11 (m) | 83.1 | 38a,b, 39, 52 | 41b |
| 41 | $CH_2$ | a: 2.01 (m) | 30.0 | 42b | 41b, 39, 42a |
|  |  | b: 1.23 (m) |  |  | 41a, 40, 42b |
| 42 | $CH_2$ | a: 1.65 (m) | 31.7 | 36a,b, 38a,b | 42b, 37, 41a |
|  |  | b: 0.90 (m) |  |  | 42a, 37, 41b |
| 43 | 11-$CH_3$ | 0.94 (3H, d, 6.4 Hz) | 16.2 | 11, 12 | 11 |
| 44 | 17-$CH_3$ | 1.65 (3H, s) | 10.2 | 16, 18 | n.d. |
| 45 | 23-$CH_3$ | 1.05 (3H, d, 7.2 Hz) | 21.5 | 22, 23, 24a,b | 23 |
| 46 | 25-$CH_3$ | 0.98 (3H, d, 6.4 Hz) | 13.6 | 24a,b, 25 | 25 |
| 47 | 29-$CH_3$ | 1.75 (3H, s) | 13.4 | 28, 30 | n.d. |
| 48 | 31-$CH_3$ | 1.09 (3H, d, 6.4 Hz) | 16.0 | 30, 31 | 31 |
| 49 | 35-$CH_3$ | 0.90 (3H, d, 6.4 Hz) | 15.8 | 34, 36a,b | 35 |
| 50 | 16-$OCH_3$ | 3.14 (s) | 55.9 | 16 | n.d. |
| 51 | 27-$OCH_3$ | 3.33 (s) | 59.2 | 27 | n.d. |
| 52 | 39-$OCH_3$ | 3.43 (s) | 57.8 | 39 | n.d. |
| 53 | 40-$OCH_2$ | 3.74 (2H, m) | 69.2 | 40, 54 | 54 |
| 54 | —$CH_2$—O— | 3.67 (2H, m) | 70.2 | 53, 55 | 53 |
| 55 | —$OCH_2$triazole | 4.68 (2H, s) | 64.6 | 54 | 57 |
| 56 | —C= | N/A | 145.0 | 55, 57 | N/A |
| 57 | =CH | 7.76 (s) | 123.8 | 55, 93 | 55 |
| 58 | PP—C | N/A | 144.4 | 65, 67, 68 | N/A |
| 59 | PP—C | N/A | 98.4 | 61 | N/A |
| 60 | PP—C—$NH_2$ | N/A | 157.9 | 61 | N/A |
| 61 | PP—CH | 8.36 (s) | 155.8 | n.d. | n.d. |
| 62 | PP—C | N/A | 154.3 | 61, 72 | N/A |
| 63 | BO—C—$NH_2$ | N/A | 162.8 | n.d. | N/A |
| 64 | BO—C | N/A | 144.0 | 65, 68 | N/A |
| 65 | BO—CH | 7.62 (s) | 116.3 | 67, 68 | 67 |

TABLE 7-continued

NMR analysis of M-1111

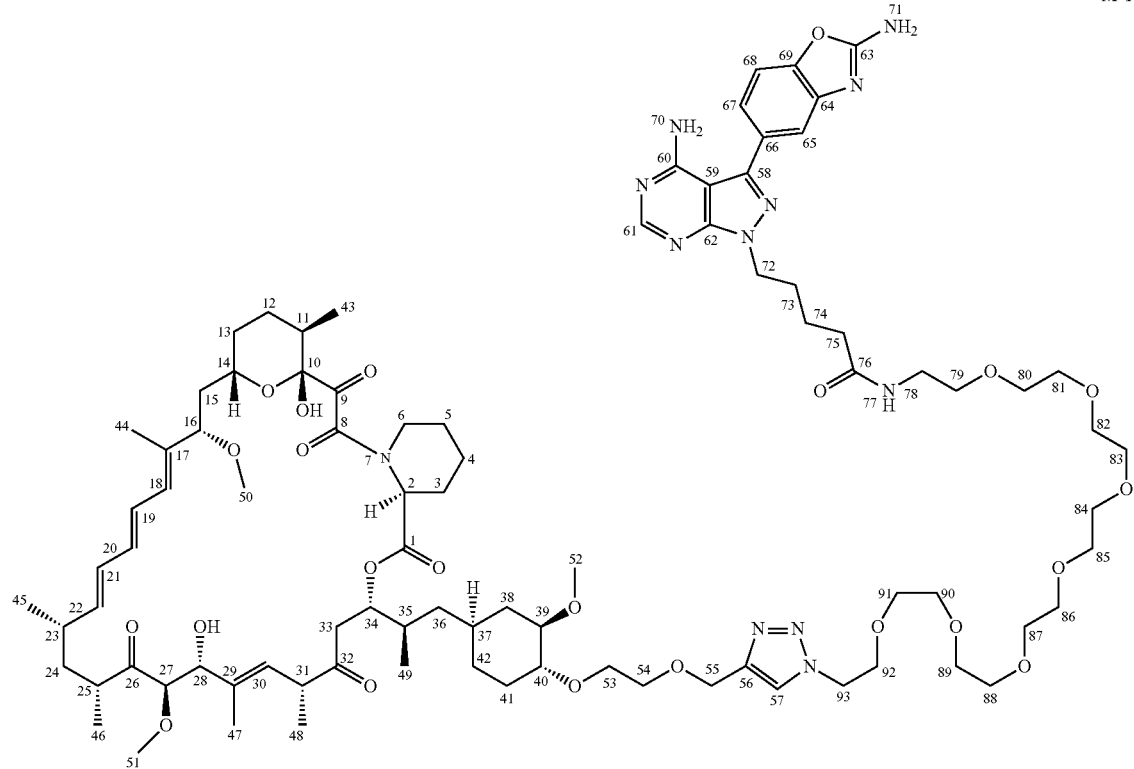 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCNC(=O)CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

M-1111

| Atom | Atom Type | δ¹H Major (3:1) | δ¹³C Major (3:1) | HMBC C to H | ¹H-¹H COSY |
|---|---|---|---|---|---|
| 66 | BO—C | N/A | 129.3 | 68 | N/A |
| 67 | BO—CH | 7.38 (d, 8.0 Hz) | 121.7 | 65 | 65, 68 |
| 68 | BO—CH | 7.40 (d, 8.0 Hz) | 109.6 | 65, 67 | 67 |
| 69 | BO—C | N/A | 149.2 | 65, 67, 68 | N/A |
| 72 | N—CH$_2$ | 4.45 (2H, t, 6.8 Hz) | 46.5 | 73, 74 | 73 |
| 73 | CH$_2$ | 2.01 (2H, m) | 29.1 | 72, 74, 75 | 72, 74 |
| 74 | CH$_2$ | 1.70 (2H, m) | 22.8 | 72, 73, 75 | 73, 75 |
| 75 | CH$_2$—CO | 2.27 (2H, t, 7.6 Hz) | 35.8 | 73, 74 | 74 |
| 76 | CO | N/A | 172.8 | 74, 75, 78 | N/A |
| 77 | NH | 6.55 (br) | N/A | N/A | N/A |
| 78 | CH$_2$ | 3.41 (2H, t, 5.0 Hz) | 39.2 | 79 | 79 |
| 79 | CH$_2$ | 3.51 (2H, t, 5.0 Hz) | 70.0 | 78 | 78 |
| 80-91 | O—(CH$_2$CH$_2$O)$_6$ | 3.54-3.64 (24H, m) | 70.2-70.6 | multi | multi |
| 92 | OCH$_2$ | 3.87 (2H, t, 5.2 Hz) | 69.5 | 93 | 93 |
| 93 | CH$_2$-triazole | 4.53 (2H, t, 5.2 Hz) | 50.2 | 92 | 92 |

PP stands for pyrazolo[3,4-d]pyrimidine and BO stands for benzo[d]oxazole
OH protons and NHx protons were not identified.

Preparation of Compound 11d (M-3059; Example 3)

40-O-(2-((1-(20-(4-amino-3-(2-aminobenzo[d]oxazol-5-yl)-1H-pyrazolo[3,4-d]pyrimidin-1-yl)-15-oxo-3,6,9,12-tetraoxa-16-azaicosyl)-1H-1,2,3-triazol-4-yl)methoxy)ethyl)-rapamycin 11d was synthesized by a similar method to that described in the preparation of compound 1b (M-1071).

Formic acid salt of the titled compound (41.6 mg; colorless amorphous powder)

LC-MS (ESI−) m/z=1606.18 (M−H)⁻

HR-MS (ESI+) Calcd for $C_{83}H_{122}O_{20}N_{12}Na$ (M+Na)⁺ 1629.8791, Found 1629.8791 (Δ 0.03 ppm).

TABLE 8

NMR analysis of M-3059

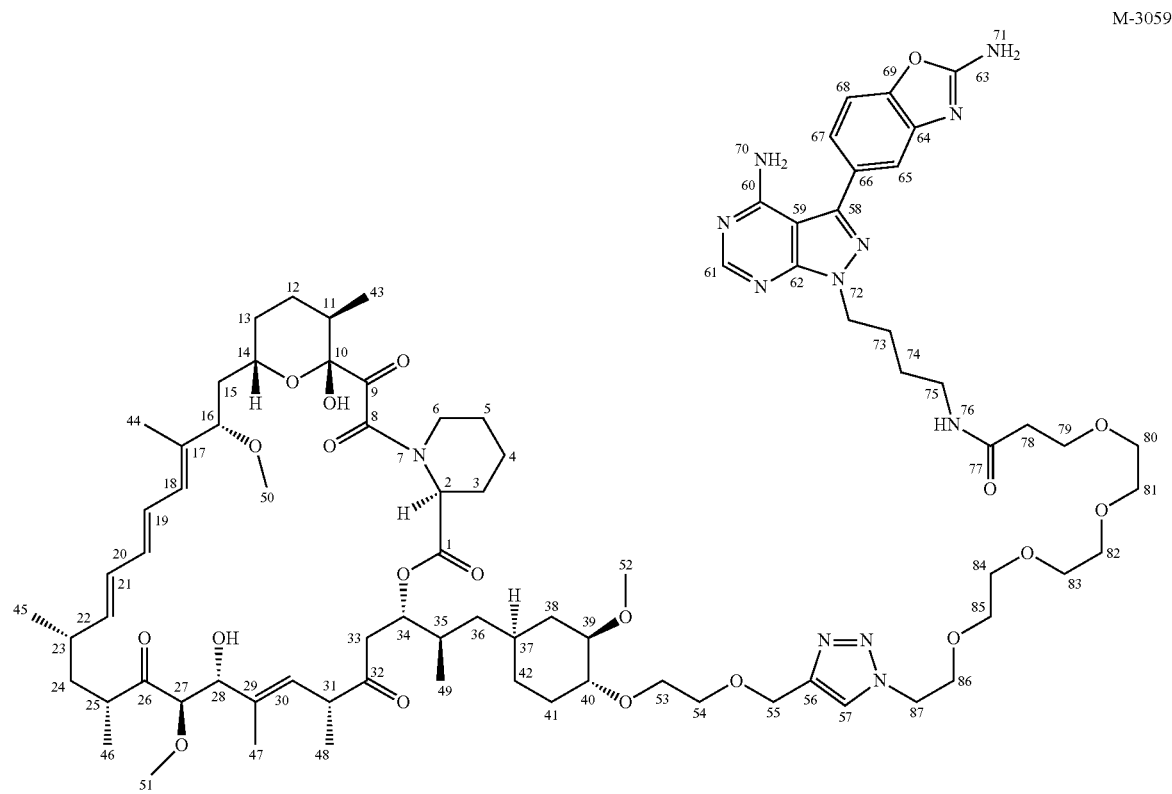

M-3059

| Atom | Atom Type | δ 1H Major (3:1) | δ 13C Major (3:1) | HMBC C to H | 1H-1H COSY |
|---|---|---|---|---|---|
| 1 | C=O | N/A | 169.3 | 2 | N/A |
| 2 | CH | 5.28 (d, 5.5 Hz) | 51.3 | 3a,b, 6a | 3b |
| 3 | CH₂ | a: 2.33 (m) | 27.1 | 2, 5a | 3b, 4b |
|   |     | b: 1.76 (m) |      |        | 3a, 2 |
| 4 | CH₂ | a: 1.77 (m) | 20.7 | 2, 6a,b | 4b, 5a,b |
|   |     | b: 1.47 (m) |      |         | 4a, 3a, 5a,b |
| 5 | CH₂ | a: 1.73 (m) | 25.3 | 3a, 4a,b, 6a | 5b, 4a,b |
|   |     | b: 1.47 (m) |      |              | 5a, 4a,b, 6b |
| 6 | CH₂ | a: 3.56 (m) | 44.2 | 2, 4a,b, 5b | 6b |
|   |     | b: 3.42 (m) |      |             | 6a, 5b |
| 8 | C=O | N/A | 166.7 | 2, 6a | N/A |
| 9 | C=O | N/A | 193.4 | 11 | N/A |
| 10 | O—C—OH | N/A | 98.6 | 11, 12, 43 | N/A |
| 11 | CH | 2.02 (m) | 33.9 | 12, 43 | 12, 43 |
| 12 | CH₂ | 1.61 (2H, m) | 27.2 | 43 | 11, 13a,b |
| 13 | CH₂ | a: 1.66 (m) | 31.2 | 12, 15a | 13b, 12 |
|    |     | b: 1.31 (m) |      |         | 13a, 12, 14 |
| 14 | CH—OC | 3.90 (m) | 67.2 | 12, 15a | 13b, 15a,b |
| 15 | CH₂ | a: 1.88 (m) | 38.9 | 16 | 15b, 14, 16 |
|    |     | b: 1.46 (m) |      |    | 15a, 14, 16 |
| 16 | CH—OCH₃ | 3.59 (m) | 84.3 | 15a, 18, 44, 50 | 15a,b |
| 17 | —C= | N/A | 136.0 | 15a, 44 | N/A |
| 18 | CH=C | 5.96 (d, 11.3 Hz) | 129.2 | 44, 20 | 19, 44 |
| 19 | CH=C | 6.39 (dd, 15.0, 11.0 Hz) | 126.6 | 20, 21 | 18, 20 |
| 20 | CH=C | 6.30 (dd, 14.8, 10.5 Hz) | 133.4 | 18, 19, 21, 22 | 19, 21 |
| 21 | CH=C | 6.14 (dd, 15.3, 10.5 Hz) | 130.3 | 19, 20 | 20, 22 |
| 22 | CH=C | 5.53 (dd, 15.1, 8.8 Hz) | 139.8 | 20, 24a,b, 45 | 21, 23 |
| 23 | CH | 2.33 (m) | 35.0 | 21, 22, 24a,b, 45 | 22, 24a, 45 |
| 24 | CH₂ | a: 1.45 (m) | 40.3 | 22, 25, 45, 46 | 24b, 23 |
|    |     | b: 1.22 (m) |      |                | 24a, 25 |
| 25 | CH | 2.68 (m) | 41.6 | 24a,b, 46 | 24b, 46 |
| 26 | C=O | N/A | n.d. (>210) | n.d. | N/A |
| 27 | CH—OCH₃ | 3.83 (m) | 85.0 | 28, 51 | 28 |
| 28 | CH—OH | 4.23 (d, 4.4 Hz) | 76.7 | 27, 30, 47 | 27 |
| 29 | —C= | N/A | 136.3 | 28, 31, 47 | N/A |
| 30 | CH=C | 5.43 (d, 9.8 Hz) | 126.3 | 28, 31, 47, 48 | 31, 47 |
| 31 | CH | 3.31 (m) | 46.6 | 30, 48 | 30, 48 |
| 32 | C=O | N/A | 208.3 | 30, 31, 33a,b, 48 | N/A |

TABLE 8-continued

NMR analysis of M-3059

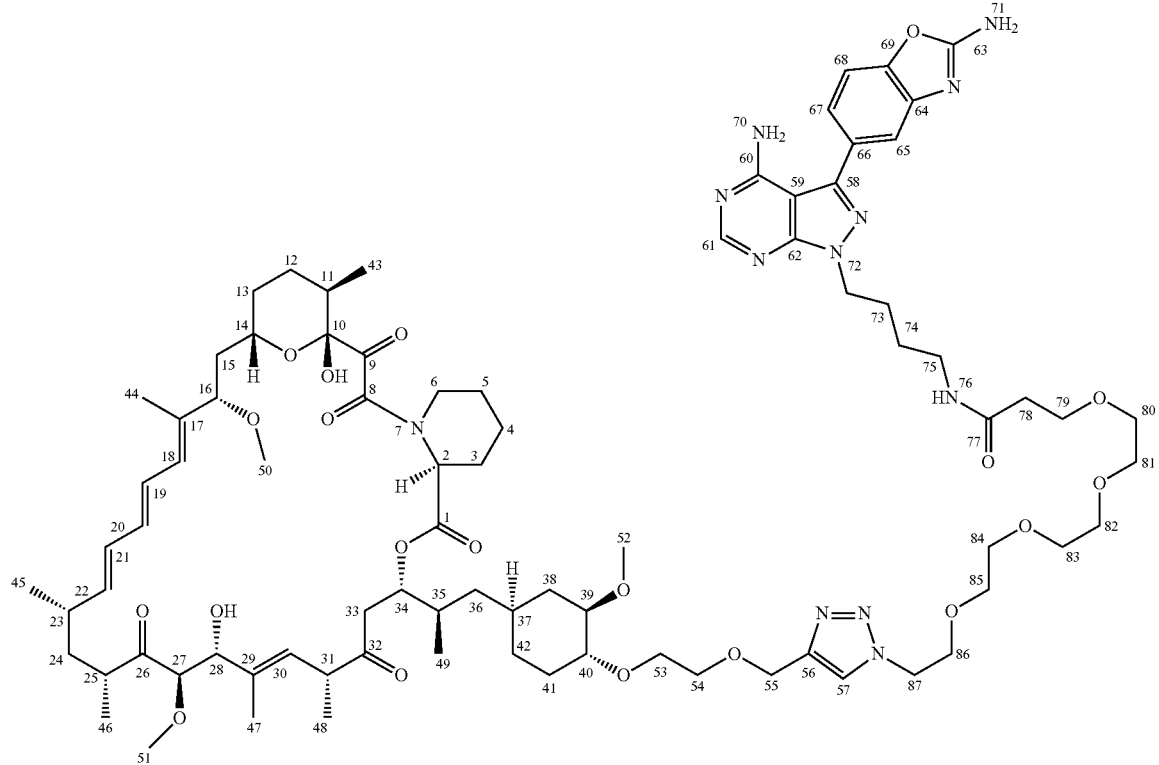 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

M-3059

| Atom | Atom Type | δ 1H Major (3:1) | δ 13C Major (3:1) | HMBC C to H | 1H-1H COSY |
|---|---|---|---|---|---|
| 33 | $CH_2$ | a: 2.69 (m) | 40.5 | n.d. | 33b, 34 |
|  |  | b: 2.57 (m) |  |  | 33a, 34 |
| 34 | CH—OCO | 5.15 (dd, 10.8, 5.5 Hz) | 75.6 | 33a,b, 49 | 33a,b, 35 |
| 35 | CH | 1.92 (m) | 33.3 | 33a,b, 49 | 34, 36a,b, 49 |
| 36 | $CH_2$ | a: 1.17 (m) | 38.4 | 34, 38b, 49 | 36b, 35 |
|  |  | b: 1.09 (m) |  |  | 36a, 35 |
| 37 | CH | 1.33 (m) | 33.0 | 36a,b, 38a,b, 42a,b | 38b, 42a,b |
| 38 | $CH_2$ | a: 2.02 (m) | 36.2 | 36a,b, 42a | 38b, 39 |
|  |  | b: 0.70 (m) |  |  | 38a, 37, 39 |
| 39 | CH—$OCH_3$ | 3.04 (m) | 83.0 | 38a,b, 40, 41b, 52 | 38a,b, 40 |
| 40 | CH—O— | 3.11 (m) | 83.0 | 38a,b, 39, 52 | 39, 41a,b |
| 41 | $CH_2$ | a: 2.01 (m) | 30.0 | 42b. | 41b, 40, 42b |
|  |  | b: 1.22 (m) |  |  |  |
|  |  |  |  |  | 41a, 40, 42b |
| 42 | $CH_2$ | a: 1.67 (m) | 31.6 | 38a,b | 42b, 37 |
|  |  | b: 0.88 (m) |  |  | 42a, 37, 41a,b |
| 43 | 11-$CH_3$ | 0.95 (3H, d, 6.6 Hz) | 16.1 | 11, 12 | 11 |
| 44 | 17-$CH_3$ | 1.66 (3H, s) | 10.2 | 16, 18 | 18 |
| 45 | 23-$CH_3$ | 1.05 (3H, d, 6.6 Hz) | 21.4 | 22, 24a,b | 23 |
| 46 | 25-$CH_3$ | 0.98 (3H, d, 6.3 Hz) | 13.5 | 24a,b, 25 | 25 |
| 47 | 29-$CH_3$ | 1.77 (3H, s) | 13.5 | 28, 30 | 30 |
| 48 | 31-$CH_3$ | 1.07 (3H, d, 6.8 Hz) | 15.9 | 30, 31 | 31 |
| 49 | 35-$CH_3$ | 0.89 (3H, d, 6.8 Hz) | 15.7 | 36a | 35 |
| 50 | 16-$OCH_3$ | 3.14 (3H, s) | 55.9 | 16 | n.d. |
| 51 | 27-$OCH_3$ | 3.34 (3H, s) | 59.0 | 27 | n.d. |
| 52 | 39-$OCH_3$ | 3.42 (3H, s) | 57.7 | 39 | n.d. |
| 53 | 40-$OCH_2$ | 3.73 (2H, m) | 69.1 | 40, 54 | 54 |
| 54 | —$CH_2$—O— | 3.66 (2H, m) | 70.1 | 53, 55 | 53 |
| 55 | —$OCH_2$triazole | 4.68 (2H, s) | 64.5 | 54 | 57 |
| 56 | —C= | N/A | 145.0 | 55, 57 | N/A |
| 57 | =CH | 7.77 (s) | 123.9 | 55, 95 | 55 |
| 58 | PP—C | N/A | 144.6 | 65, 67, 68 | N/A |
| 59 | PP—C | N/A | 98.8 | 61 | N/A |
| 60 | PP—C—$NH_2$ | N/A | 157.9 | 61 | N/A |
| 61 | PP—CH | 8.33 (s) | 155.5 | n.d. | n.d. |
| 62 | PP—C | N/A | 154.2 | 61, 72 | N/A |
| 63 | BO—C—$NH_2$ | N/A | 165.8 | n.d. | N/A |
| 64 | BO—C | N/A | 144.6 | 65, 68 | N/A |

TABLE 8-continued

NMR analysis of M-3059

M-3059

| Atom | Atom Type | δ 1H Major (3:1) | δ 13C Major (3:1) | HMBC C to H | 1H-1H COSY |
|---|---|---|---|---|---|
| 65 | BO—CH | 7.61 (s) | 116.1 | 67, 68 | 67 |
| 66 | BO—C | N/A | 129.2 | 68 | N/A |
| 67 | BO—CH | 7.37 (d, 8.4 Hz) | 121.6 | 65 | 65, 68 |
| 68 | BO—CH | 7.39 (d, 8.4 Hz) | 109.7 | 65, 67 | 67 |
| 69 | BO—C | N/A | 149.1 | 65, 67, 68 | N/A |
| 72 | N—$CH_2$ | 4.45 (2H, t, 7.0 Hz) | 46.6 | 73, 74 | 73 |
| 73 | $CH_2$ | 2.01 (2H, m) | 27.3 | 72, 74, 75 | 72, 74 |
| 74 | $CH_2$ | 1.58 (2H, m) | 26.5 | 72, 73, 75 | 73, 75 |
| 75 | $CH_2$—NHCO | 3.31 (2H, m) | 38.9 | 73, 74, 76 | 74 |
| 76 | NH | 6.86 (t, 5.5 Hz) | N/A | N/A | n.d. |
| 77 | CO | N/A | 171.6 | 75, 76, 78, 79 | N/A |
| 78 | $CH_2$ | 2.45 (2H, t, 6.0 Hz) | 37.0 | 79 | 79 |
| 79 | $CH_2$ | 3.70 (2H, t, 6.0 Hz) | 67.4 | 78 | 78 |
| 80-85 | O—$(CH_2CH_2O)_7$ | 3.54-3.64 (12H, m) | 70.2-70.6 | multi | multi |
| 86 | $OCH_2$ | 3.85 (2H, t, 5.0 Hz) | 69.5 | 95 | 95 |
| 87 | $CH_2$-triazole | 4.52 (2H, t, 5.1 Hz) | 50.2 | 94 | 94 |

PP stands for pyrazolo[3,4-d]pyrimidine and BO stands for benzo[d]oxazole
OH protons and NHx protons were not identified.

F. Example 6

Comparison Between Three Classes of mTOR Inhibitors (Rapamycin-Class I, MLN0128-Class II, and Rapa-Link-Class III).

Human colorectal carcinoma cell line HCT-15, human hepatocellular carcinoma cell line SNU-449, human renal cancer cell line 786-O, L6 myoblasts and 3T3-L1 cells were purchased from American Type Culture Collection (ATCC) (Manassas, Va. USA). The cells were grown in appropriate medium (vender recommended) supplemented with 10% heat-inactivated fetal bovine serum (FBS), in tissue culture dishes placed in a humidified incubator maintained at 37° C. in an atmosphere of 5% $CO_2$ and 95% air.

Cell Viability Assay.

Cells were seeded in a 96-multiwell plate at 3000-4000 cells per well in medium containing FBS and cells were incubated at 37° C. overnight. After 18-20 h, compounds in 10×DMSO solution (n=3) were added to the cells and were incubated for additional 3 days in a humidified incubator in an atmosphere of 5% $CO_2$ and 95% air. After treatment of Cell Titer-Glo® luminescent cell viability assay reagent (Promega Corporation, Madison, Wis. USA), the luminescence value was recorded using SpectraMax M5 Multi-Mode Microplate Readers (Molecular Devices, LLC, Sunnyvale, Calif. USA). Concentration response curves were generated on GraphPad Prism (GraphPad Software, La Jolla, Calif. USA) by calculating the decrease in luminescence values in compound-treated samples relative to the DMSO controls.

Anti-proliferative effects of compounds were evaluated in human colorectal cancer HCT-15 cells (mutation: KRAS, PIK3CA), human hepatocellular carcinoma SNU-449 (mutation: TP53, CDKN2A), SNU-398 (mutation: CTNNB1), SNU-182 (mutation: TP53) and renal adenocarcinoma 786-O (mutation: VHL, PTEN, TP53, CDKN2A) in 72 h after compound treatment. Rapa-Link inhibitors M-1071 and M-1111 showed potent growth inhibitory activity (Table 9). Stronger anti-proliferative activities [$EC_{50}$ (nM): M-1071; ++++ (SNU-398), ++++ (SNU-449), ++++ (786-O), ++++ (HCT-15), ++++ (SNU-182), and M-1111; ++++ (SNU-398), ++++ (SNU-449), +++ (786-O), +++ (HCT-15), ++++ (SNU-182)] were observed compared to MLN0128 [$EC_{50}$ (nM): +++ (SNU-398), +++ (SNU-449), ++ (786-O), ++ (HCT-15), ++ (SNU-182)]. In contrast, a shorter version of RapaLINK M-1115 shows less anti-proliferative activity [$EC_{50}$ (nM): +++ (SNU-182), +++ (SNU-398), + (HCT-15), + (SNU-449 and 786-O)].

TABLE 9

$EC_{50}$ (nM) values of Rapa-LINK inhibitors (vs. asTORi)

| | SNU-398 | SNU-449 | 786-O | HCT-15 | SNU-182 |
|---|---|---|---|---|---|
| M-1071 | ++++ | ++++ | ++++ | ++++ | ++++ |
| M-1111 | ++++ | ++++ | +++ | +++ | ++++ |
| M-1115 | +++ | + | + | + | +++ |
| MLN0128 | +++ | +++ | ++ | ++ | ++ |

(++++ = <10 nM, 10 nM < +++ < 50 nM, 50 nM < ++ < 100 nM, 100 nM < +)

Table 10 represents % inhibition at 10 µM of Rapa-LINK inhibitors (vs. Rapamycin). Rapa-LINK inhibitors showed more potent inhibition in cellular proliferation compared to Rapamycin

TABLE 10

% inhibition at 10 µM of Rapa-LINK inhibitors (vs. Rapamycin)

| | SNU-398 | SNU-449 | 786-O | HCT-15 | SNU-182 |
|---|---|---|---|---|---|
| M-1071 | +++ | ++ | ++ | +++ | ++ |
| M-1111 | +++ | ++ | +++ | +++ | ++ |
| M-3059 | +++ | + | n.d. | n.d. | + |
| Rapamycin | ++ | + | + | ++ | + |

(n.d.: not determined, + = ≤25%, 25% < ++ ≤ 50%, 50% < +++ ≤ 100%)

Figure 5A:
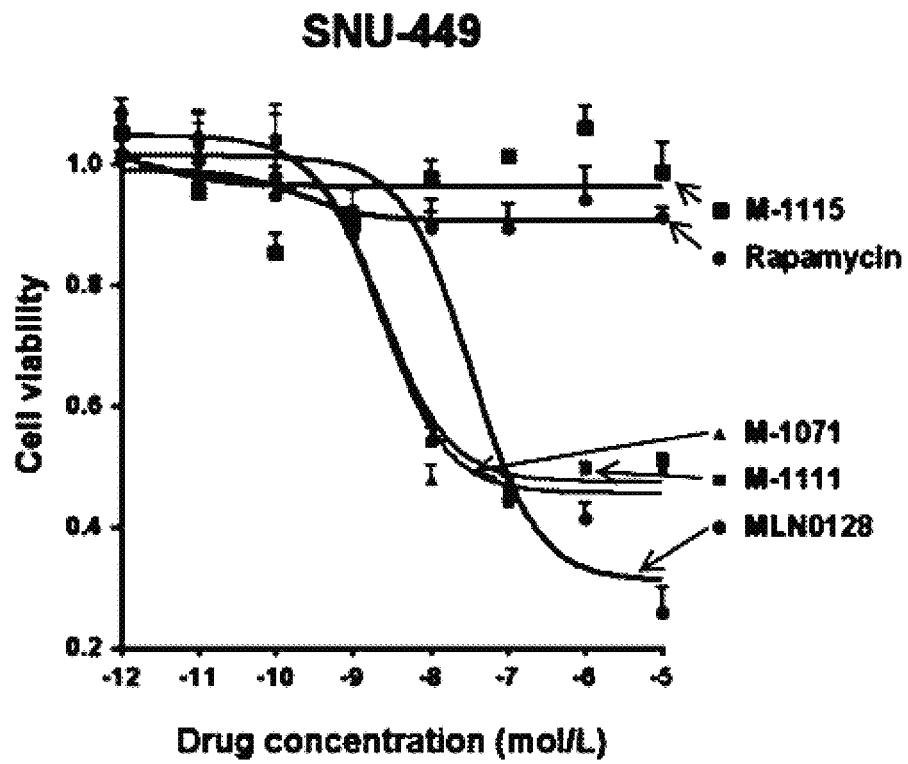
FIGS. 5A-5B. Cell viability assays of SNU-449 Cells treated with (FIG. 5A) M-1115, Rapamycin, M-1071, M-1111, and MLN0128.
Figure 5B:
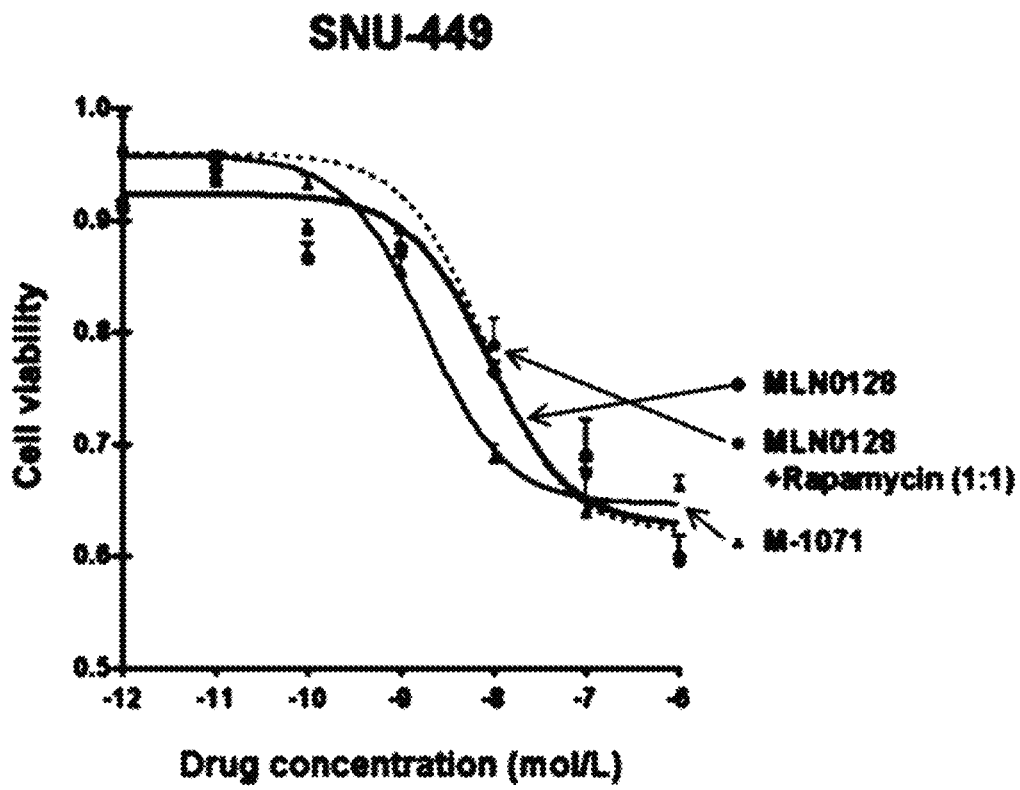
Figure 6A:
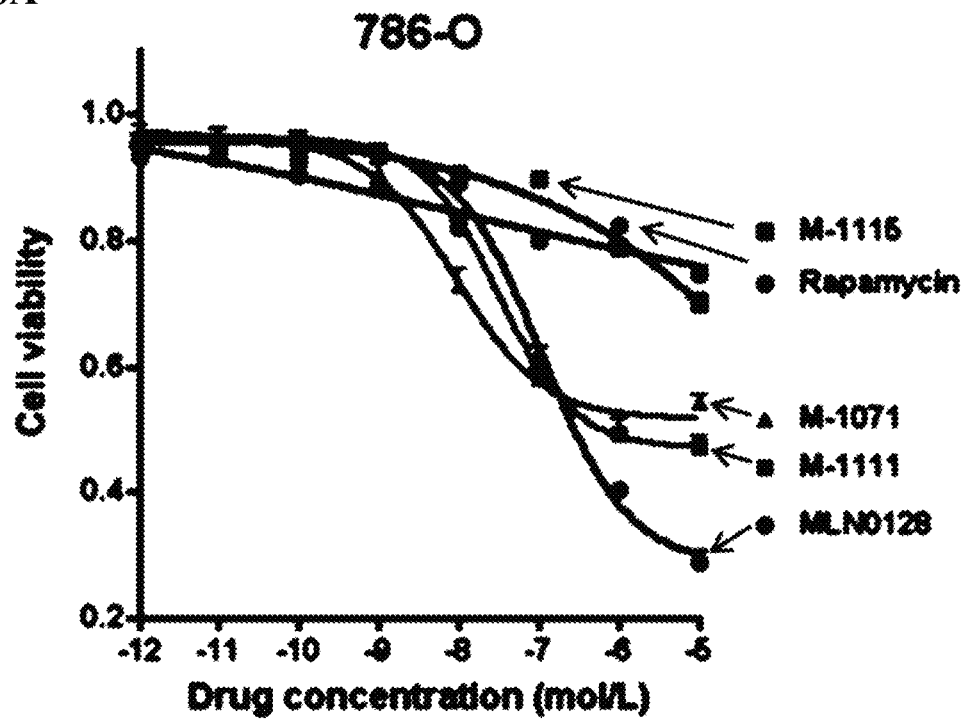
FIGS. 6A-6B. Cell viability assays of 786-O Cells treated with (FIG. 6A) M-1115, Rapamycin, M-1071, M-1111, and MLN0128.
Figure 6B:
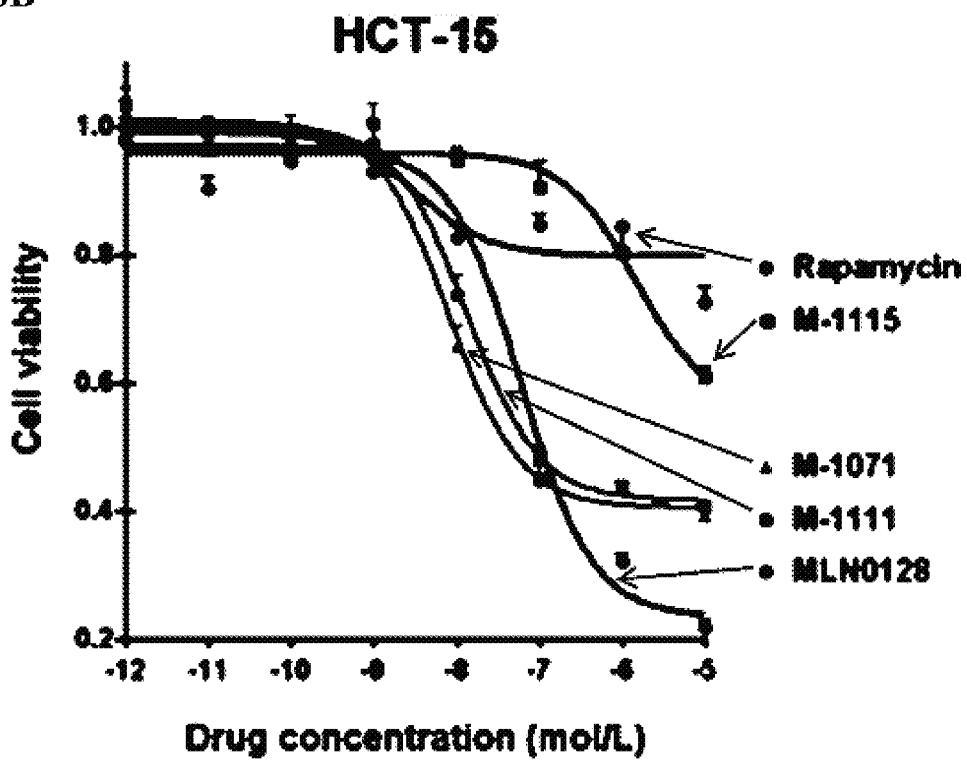

Since the Rapa-Link compound contains two classes of mTOR inhibitor, we wondered if the superior efficacy of M-1071 could be attributed to a "linker independent" synergy of these two agents, as reported by others[21]. We compared the effect of M-1071 with a combination of rapamycin and MLN0128 (FIG. 5B). Even when both Rapamycin and MLN0128 were combined, their efficacy was inferior to M-1071. These results suggest that the enhanced anti-proliferative effect of the Class III mTOR inhibitor, M-1071 is derived from its particular property of being a single "linked" molecule, and not simply a mixture of an asTORi with Rapamycin.

G. Example 7

Cellular Signaling Effects of Class I-II-III mTOR Inhibitors.

Cells were seeded in 60 mm cell culture dishes and incubated 1-2 days until 70-90% confluency. Cells were treated with compound solution in DMSO (1000×) and incubated at 37° C. in a 5% $CO_2$ humidified incubator for a given length of time. Whole cell lysates were prepared using RIPA buffer (R3792) (TEKnova, Hollister, Calif. USA) with a phosphatase inhibitor cocktail tablet PhosStop and a protease inhibitor cocktail tablet cOmplete Mini (Roche Diagnostics GmbH, Mannheim, Germany). Cell lysates (based on a certain amount of protein determined by Pierce BCA Protein Assay Kit (PI-23225) (Thermo Fisher Scientific Inc., Waltham, Mass. USA)) were electrophoresed using a Criterion Tris-HCl gel 4-20% (Bio-Rad Laboratories, Hercules, Calif. USA) and transferred to a nitrocellulose membrane (162-0115) (Bio-Rad Laboratories, Hercules, Calif. USA). After incubation for more than 1 h with a blocking buffer at room temperature, membranes were labeled with primary antibodies by overnight incubation at 4° C., followed by 1 hour incubation with horseradish peroxidase-conjugated (HRP-conjugated) secondary antibodies at room temperature. The following antibodies were used for immunoblot: phospho-Akt (S473) (#9271), phospho-Akt (T308) (#2965), total-Akt (#9272), phospho-S6 (Ser240/Ser244) (#2215L), S6 ribosomal protein (#2217), phospho-4E-BP1 (T37/T46) (#2855), total 4E-BP1 (#9644) (Cell Signaling Technology, Inc., Danvers, Mass. USA), FKBP12 (sc-28814) mouse β-actin (sc-8432) (Santa Cruz Biotechnology, Inc., Dallas, Tex. USA), anti-rabbit IgG conjugated with horseradish peroxidase (HRP) (#7074), and anti-mouse IgG conjugated with HRP (#7076) (Cell Signaling Technology, Inc., Danvers, Mass. USA). Nitrocellulose membranes were exposed with SuperSignal® West Pico Chemiluminescent Substrate or Femto Maximum Sensitivity Substrate (Thermo Fisher Scientific Inc., Waltham, Mass. USA) and signals were recorded on a CL-Xposure film (Thermo Fisher Scientific Inc., Waltham, Mass. USA).

Figure 7:
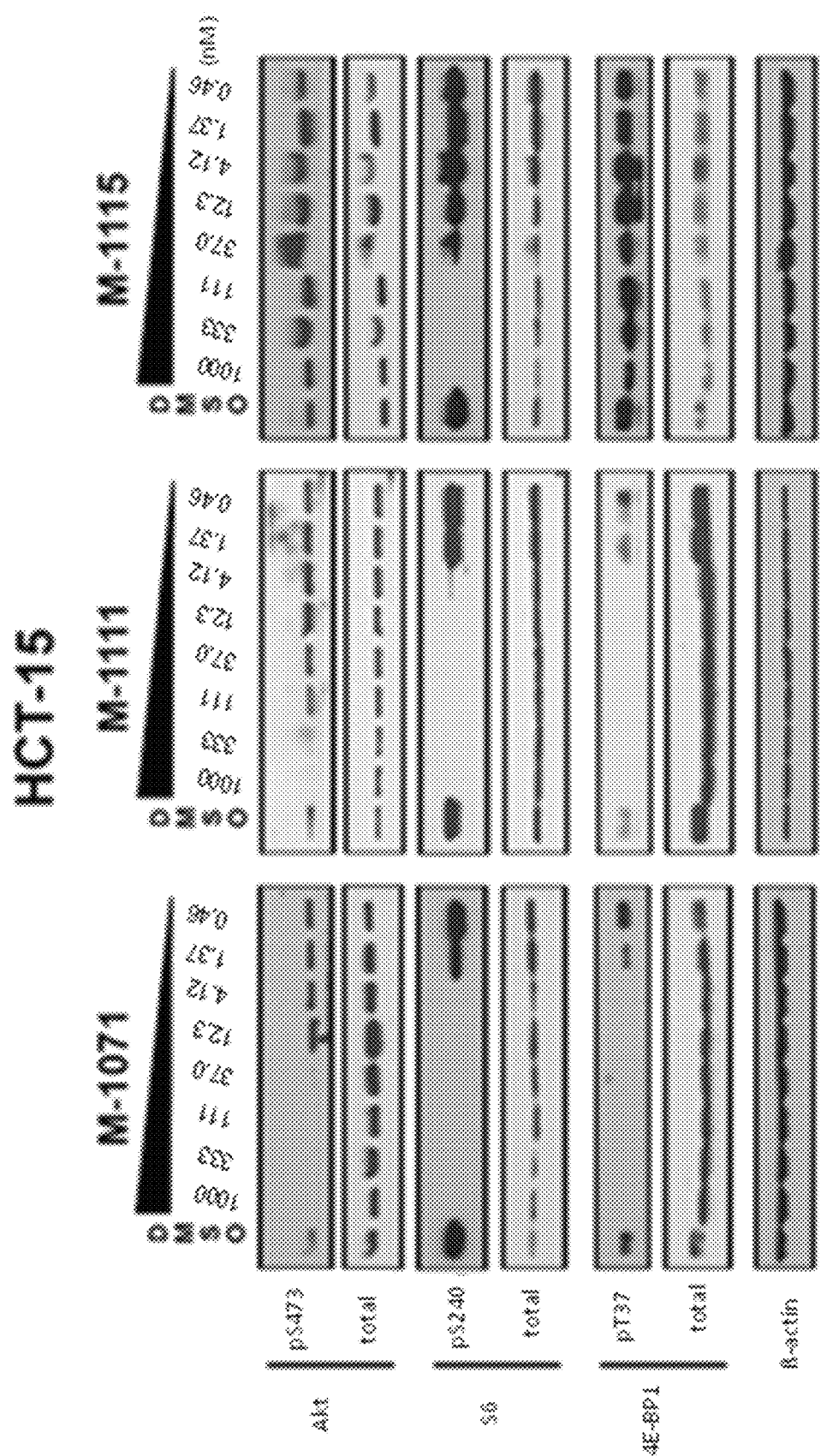
FIG. 7. Dose dependent effects on TORC1 and TORC2 outputs for (left) M-1071, (center) M-1111, and (right) M-1115 in HCT-15 Cells.

Downstream signaling of mTOR was tested using an immunoblotting method at 3 h after compound treatment. Although the active site inhibitor MLN0128 shows pan-mTORC1/2 downstream inhibition (pS6, p4E-BP1 and pAkt S473) in both HCT-15 and SNU-449 cells (FIG. 7, and FIG. 8A), hybrid inhibitors M-1071 and M-1111 showed stronger inhibition of mTORC1 signaling (pS6 and p4E-BP1) compared to mTORC2 downstream Akt S473 phosphorylation. Interestingly, M-1071 and M-1111 showed complete p4E-BP1 inhibition at drug concentrations in which pAkt S473 is not inhibited. These selective modulations of mTORC1 vs mTORC2 have not been achieved by asTORi. On the other hand, M-1115 with a short cross-linker showed weaker p4E-BP1 inhibition. These structure activity relationships explain that potent anti-proliferative activity is derived from mTORC1 complete inhibition (p4E-BP1 and pS6) and that TORC2 inhibition (pAkt) may not enhance anti-proliferative activity in these cell lines.

Figure 8A:
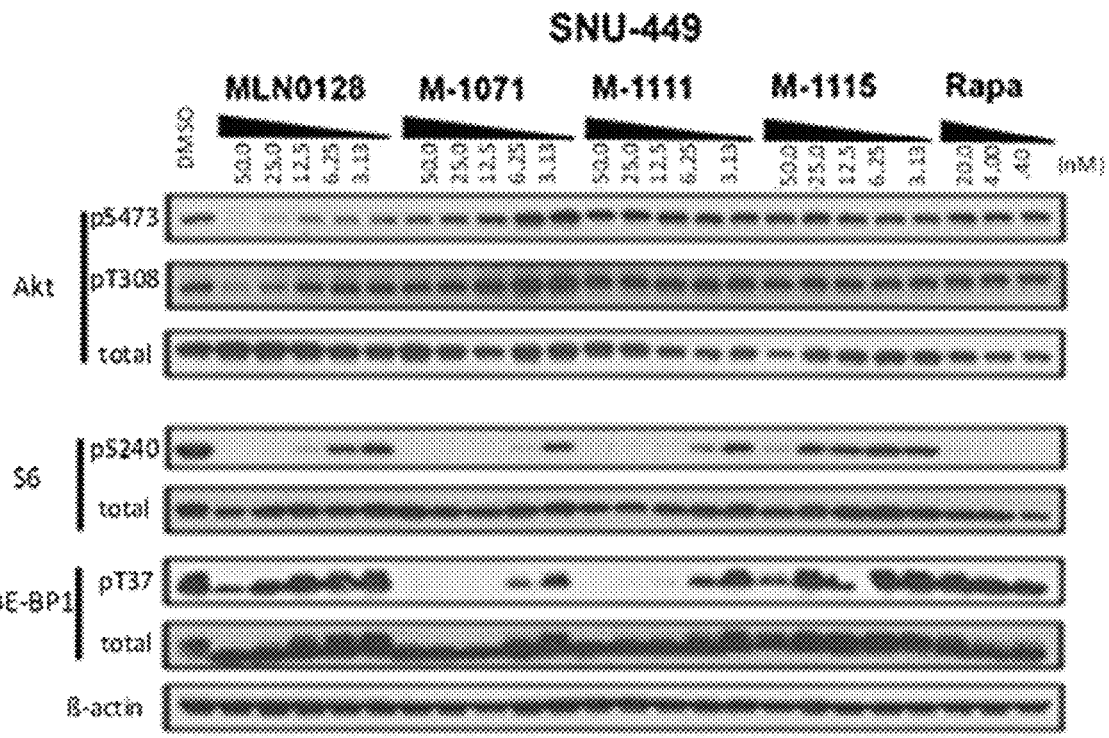
FIGS. 8A-8B. Dose dependent effects on TORC1 and TORC2 (FIG. 8A) outputs for MLN0128, Rapamycin, M-1071, M-1111, and M-1115 in SNU-449 Cells.
Figure 8B:
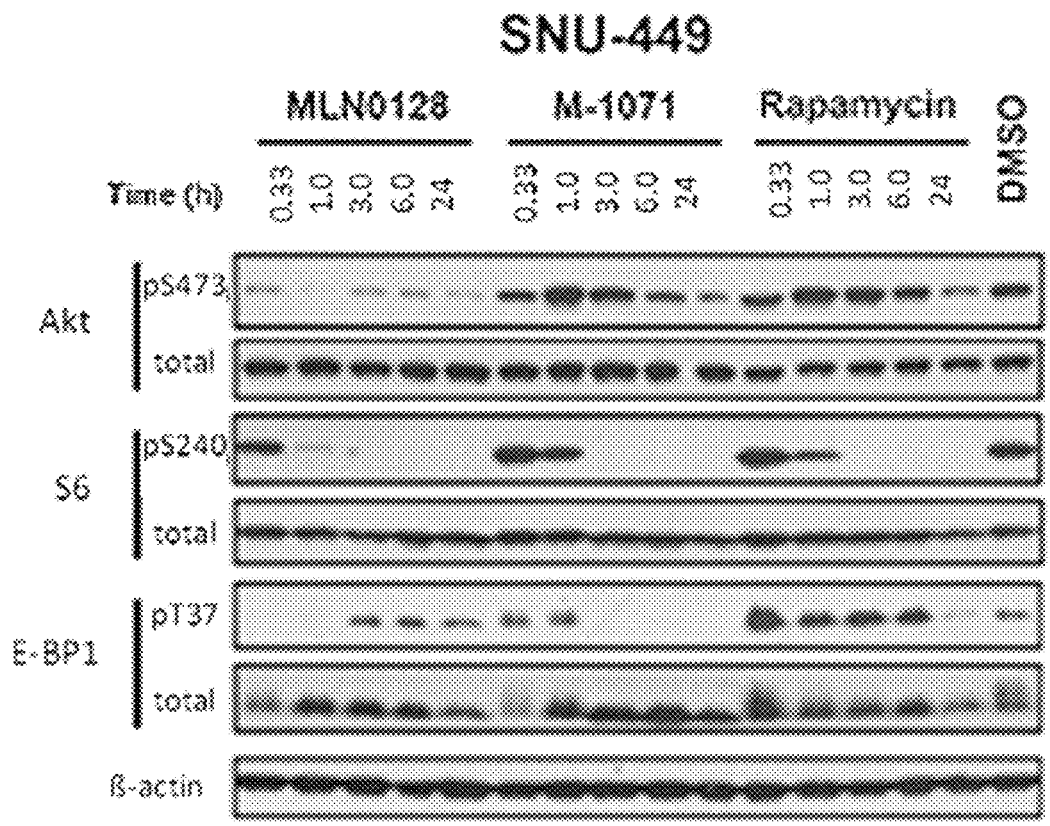

Although short-term rapamycin treatment shows selective inhibition of mTORC1, it was reported that prolonged treatment of rapamycin also inhibits mTORC2 in various cells[22]. We examined time-course effects of a Rapa-Link inhibitor on mTORC1 and mTORC2 signaling in SNU-449 (FIG. 8B). Treatment of MLN0128 blocked phosphorylation of pAkt S473 continuously during 0.33-24 h. Treatment of M-1071 or rapamycin treatment underwent transient feedback activation on Akt S473 at 1 and 3 h, and then a slight inhibition was observed at 24 h. The feedback activation following Rapamycin treatment has been reported by Rosen and colleauges[23]. pS6 was consistently inhibited by all inhibitors after 3 h to 24 h. Interestingly, response of p4E-BP1 inhibition was varied among inhibitors. Treatment of MLN0128 completely inhibited p4E-BP1 in early onset (0.33-1 h) and then partial phosphorylation of 4E-BP1 was observed after 3 h to 24 h. This is likely mediated by feedback reactivation of the Akt-mTOR pathway as reported by Rosen and colleagues[24]. In contrast, M-1071 treatment provided continuous complete inhibition of TORC1 outputs within 3-24 h. Treatment of rapamycin showed moderate inhibitory activity against p4E-BP and the potency slightly increased in time-dependent manner. We conclude that M-1071's continuous and strong cellular activities (such as inhibition of p4E-BP1) might be derived from the ability to bind to both the FRB domain and the ATP site of mTOR.

H. Example 8

Pharmacodynamic studies of M1071 in human renal cancer 786-O xenograft tumor in mice. M-1071 was intraperitoneally administered to tumor transplanted mice by using Cremophor EL-ethanol [2/1 w/w], and diluting this 1:5 with 5% w/v glucose in water as a vehicle. Tumor samples were collected at 3 h after drug administration. For the MWF group, M-1071 was administered once daily every other day. At 4 h after the last administration, tumor samples were collected. After the freezing tumor samples, they were homogenized and treated with RIPA buffer containing phosphatase inhibitor and protease inhibitor. The following western blotting analysis were conducted in a similar way to abovementioned method.

Figure 9:
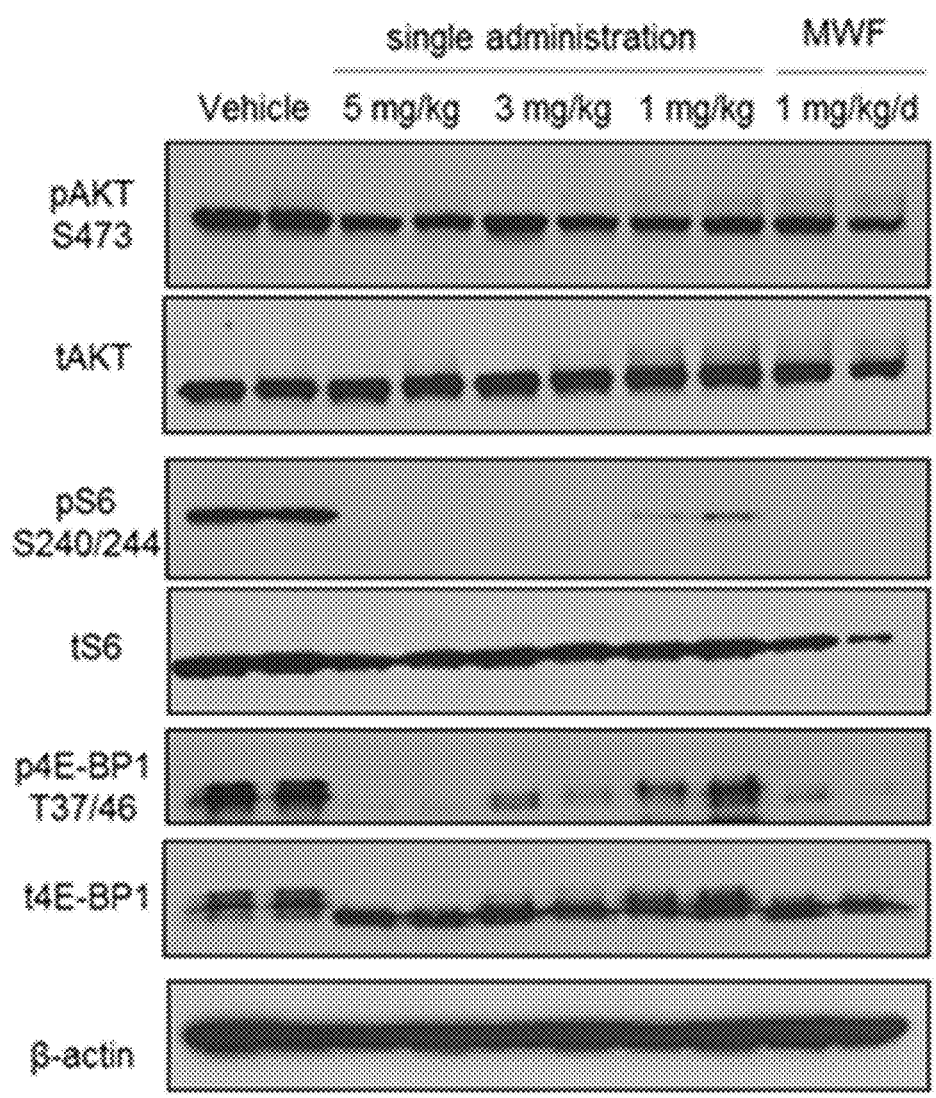
FIG. 9. In vivo effects of M-1071 on 786-O tumor bearing mice following single or multiple day dosing.

In the drug treated groups, dose dependent inhibition against phospho-4E-BP1 was observed (FIG. 9). Phosphorylation of S6 was also inhibited by the treatment of M-1071. On the other hand, inhibition of phospho-S473 of Akt was slight even at highest dosing of 5 mg/kg which demonstrated the complete inhibition of pS6 and p4EBP-1.

I. Example 9

Effect on blood glucose level. M-1071, Rapamycin and MLN0128 were intraperitoneally administered to mice (n=3) by using Cremophor EL-ethanol [2/1 w/w], and diluting this 1:5 with 5% w/v glucose in water as a vehicle. Blood glucose levels (mg/dL) were monitored.

Figure 10:
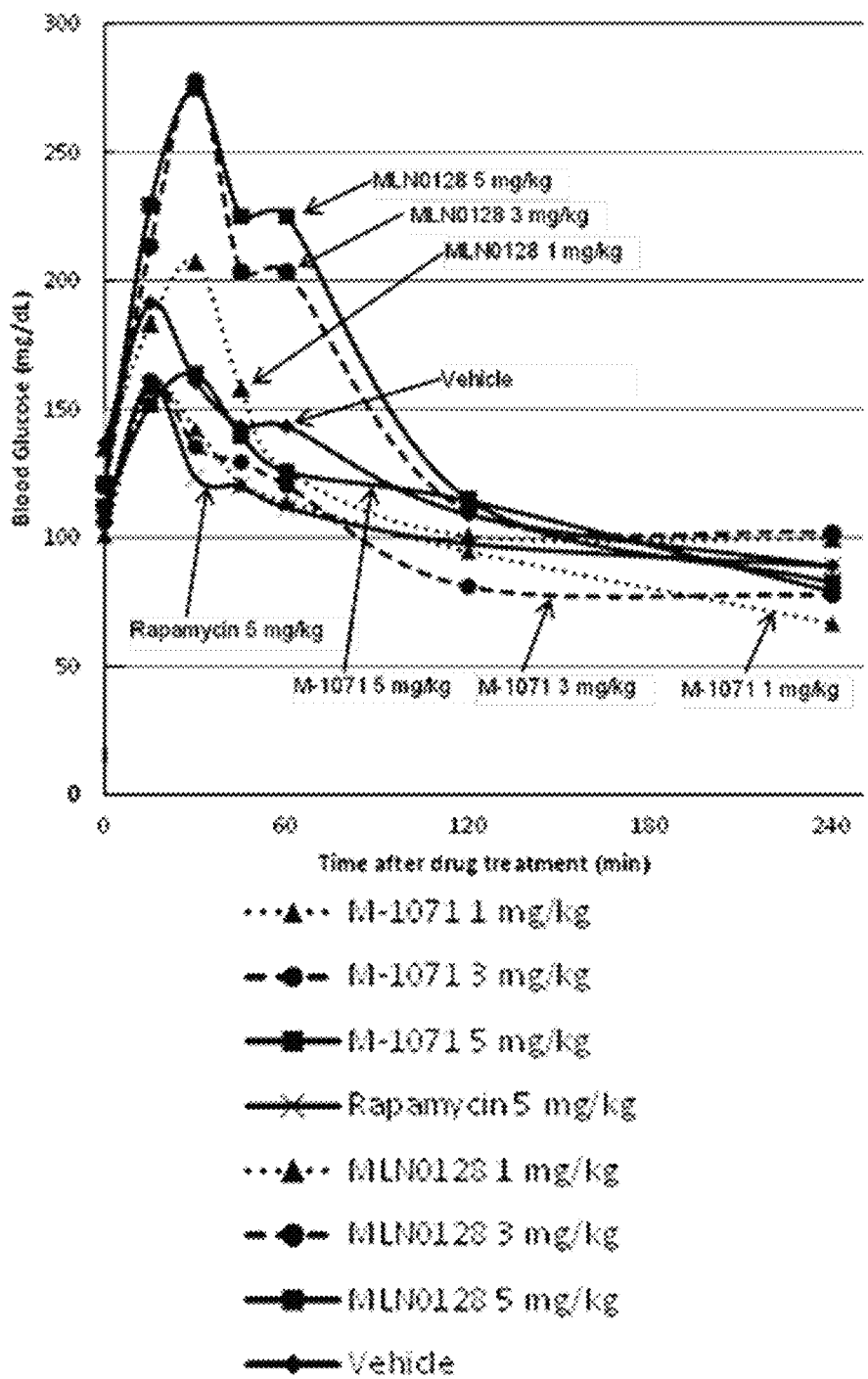
FIG. 10. Mean blood glucose levels (n=3) after drug treatment in mice. Legend: M-1077 1 mg/kg (triangle in dotted line); M-1071 3 mg/kg (circle in dashed line); M-1071 5 mg/kg (square in solid line); Rapamycin 5 mg/kg (cross in solid line); MLN0128 1 mg/kg (triangle in dotted line); MLN0128 3 mg/kg (circle in dashed line); MLN0128 5 mg/kg (square in solid line); Vehicle (diamond in solid line).
Figure 11:
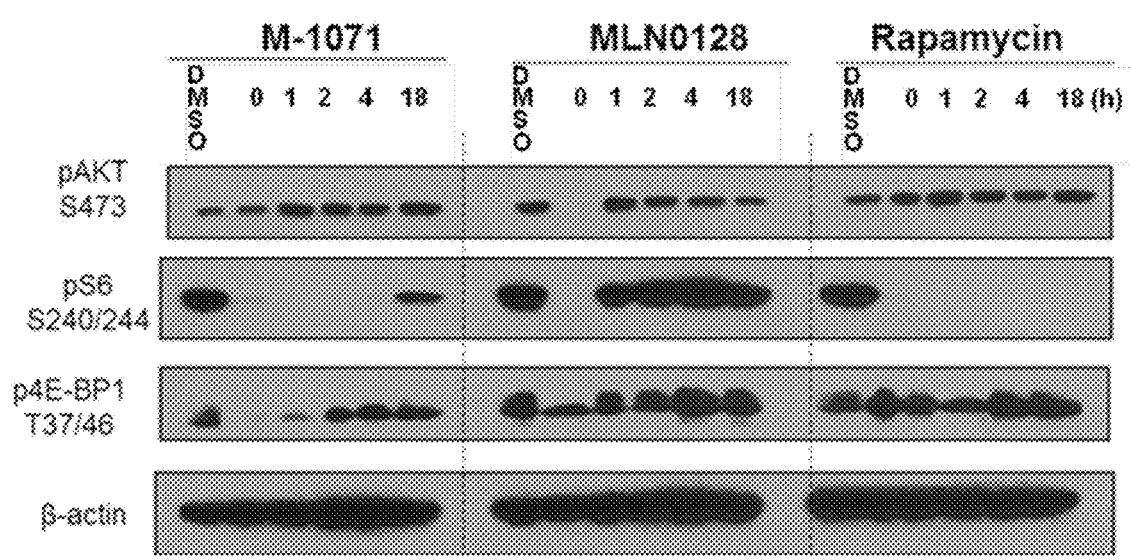
FIG. 11. TORC1 and TORC2 outputs at times after washout for (left) M-1071, (center) MLN0128, and (right) Rapamycin in SNU-449 cells.

It was reported that Akt inhibition by the treatment with Akt inhibitor results in a transient increase in blood glucose in mice[25]. Because mTORC2 plays a central role in full activation of Akt via phosphorylation of S473 on Akt, monitoring the blood glucose level is thought to be a good readout for mTORC2 inhibition by an mTOR inhibitor. Compared with the vehicle treatment group which showed a slight increase in blood glucose at 15 min, perhaps due to the injection of glucose containing vehicle, MLN0128 treatment groups (1, 3, 5 mg/kg) showed a transient increase in blood glucose level at 30 min (FIG. 10). In contrast, the M-1071 treatment group (5 mg/kg) showed a significantly smaller increase in blood glucose level at 30 min. Furthermore, M-1071 (1, 3 mg/kg) and Rapamycin treatment groups showed no increase in blood glucose levels.

In combination with the aforementioned in vivo pharmacodynamic study results, these results indicate that M-1071 demonstrates mTORC1 selectivity vs. mTORC2 in a mouse model at efficacious doses of mTORC1 inhibition.

J. Example 10

Drug Washout Experiment. SNU-449 cells were treated with 30 nM of compounds for 3 h. The medium was aspirated out and cells were washed with fresh 10% FBS in RPMI1640 medium. Then, cells were incubated with fresh 10% FBS in RPMI1640 medium at 37° C. for described time period.

In contrast to MLN0128 washout in which inhibitory effects rapidly disappeared within 1 h, M-1071 treatment showed sustained inhibitory effects in both p4E-BP1 (at least 2 h) and pS6 (at least 4 h). Based on these results, we assumed that the effects with MLN0128 are concentration-dependent because asTORi competes with high concentration of cellular ATP. In contrast, Rapamycin effects tend to be maintained longer after washout compared to asTORi because Rapamycin is not binding to the catalytic site. By utilizing the allosteric characteristics of Rapamycin, the ATP site inhibitor portion of the Rapa-link compound is most likely to be able to stay in the ATP site and overcomes the competition with high concentration of cellular ATP.

REFERENCES

1. Kim, D.-H. et al. Cell 110, 163-175 (2002) 2. Hara, K. et al. Cell 110, 177-189 (2002). 3. Sarbassov, D. D. et al. Curr Biol 14, 1296-1302 (2004). 4. Jacinto, E. et al. Nat Cell Biol 6, 1122-1128 (2004). 5. Ruggero, D. et al. Nature Medicine 10, 484-486 (2004). 6. Feldman, M. E. et al. PLoS Biol 7, e38 (2009). 7. Neasta, J., et al. Journal of Neurochemistry (2014). doi:10.1111/jnc.127258. Thoreen, C. C. et al. J Biol Chem 284, 8023-8032 (2009). 9. Liu, Y., et al. Science (2010). 10. Hsieh, A. C. et al. Cancer Cell 17, 249-261 (2010). 11. Hsieh, A. C. et al. Nature 485, 55-61 (2012). 12. Infante, J. R. et al. Abstract C252: A phase 1, dose-escalation study of MLN0128, an investigational oral mammalian target of rapamycin complex 1/2 (mTORC1/2) catalytic inhibitor, in patients (pts) with advanced non-hematologic malignancies. Mol. Cancer Ther., 12; C252, (2013). 13. Shih, K. C. et al. J Clin Oncol 30, (2012). 14. Naing, A. et al. Br J Cancer 107, 1093-1099 (2012). 15. O'Donnell, A. et al. J Clin Oncol 26, 1588-1595 (2008). 16. Wood, E. R. et al. Cancer Res 64, 6652-6659 (2004). 17. Yang, H. et al. Nature 1-8 (2013). doi:10.1038/nature1212218. Choi, J., et al. Science 273, 239-242 (1996). 19. Ayral-Kaloustian, S. et al. J Med Chem 53, 452-459 (2010). 20. Banerjee, S. S., et al. J Drug Deliv 2012, 103973 (2012). 21. Xu, C.-X. et al. PLoS ONE 6, e20899 (2011). 22. Hsu, P. P., et al. Mol Cell (2006). 23. O'Reilly, K. E. et al. Cancer Res 66, 1500-1508 (2006). 24. Rodrik-Outmezguine, V. S. et al. Cancer Discovery 1, 248-259 (2011). 25. Rhodes, N. et al. Cancer Res 68, 2366-2374 (2008).

K. Example 11

Additional Rapa-LINK Compounds.

Two additional Rapa-LINK compounds, E1010 and E1035, were synthesized to explore the effects of a weaker binder to the ATP site of mTOR.

Figure 12:
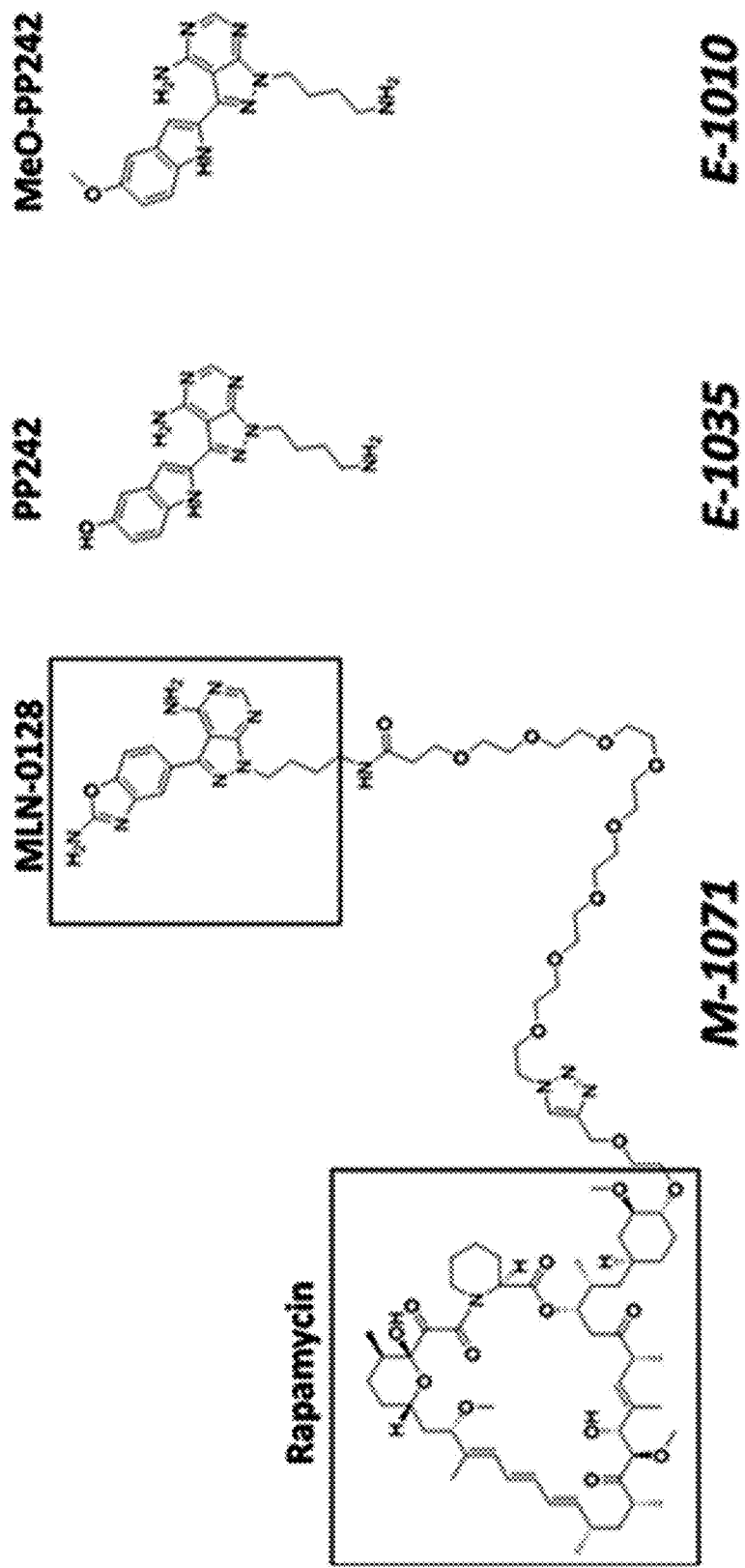
FIG. 12. Chemical drawings depicting the Rapa-LINK inhibitor M1071 combining the allosteric inhibitor, rapamycin, with the ASi, MLN-0128. Compounds E1035 and E1010 combined rapamycin with the known ASi, PP242, and a PP242 derivative, MeO-PP242, respectively, as depicted.

The first Rapa-LINK inhibitor, M1071, combined the allosteric inhibitor, rapamycin, with the ASi, MLN-0128. E1035 and E1010 combined rapamycin with the known ASi, PP242, and a PP242 derivative, MeO-PP242, respectively (FIG. 12).

Figure 13A:
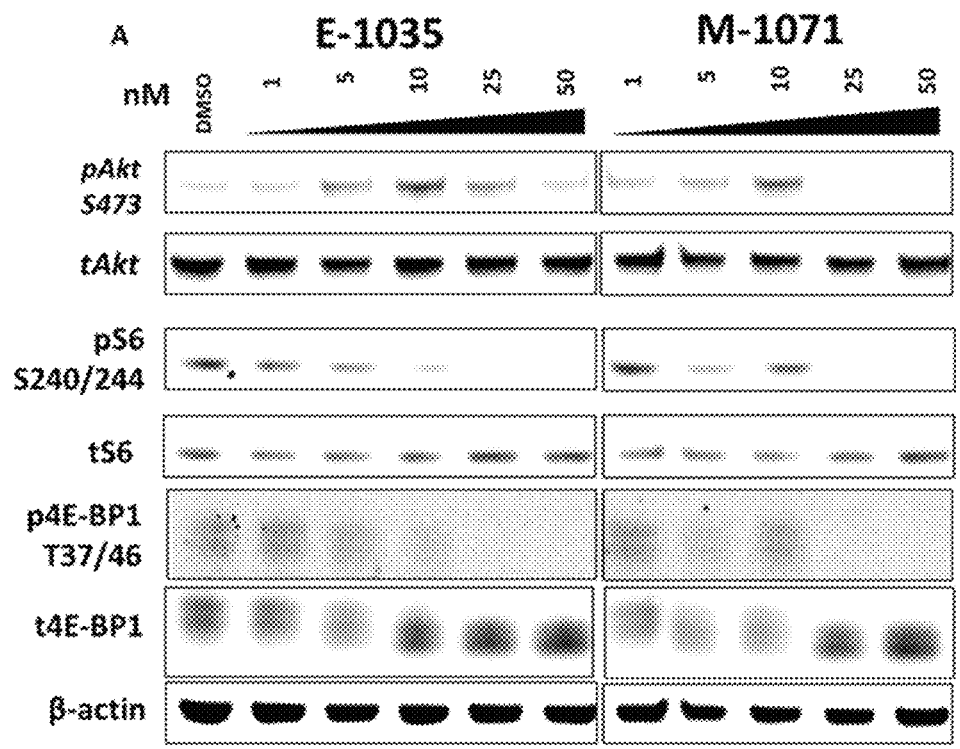
FIGS. 13A-13B.
Figure 13B:
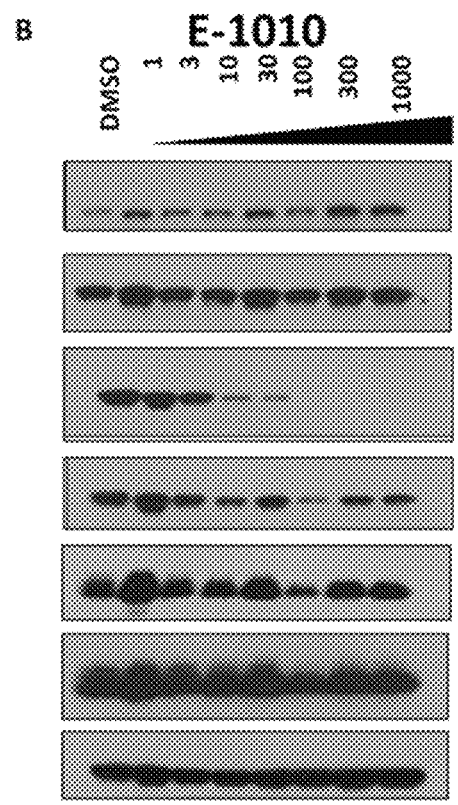

The potency of the ASi mTOR inhibition in the Rapa-LINK compounds order from strongest to weakest as follows: MLN0128 (<1 nM), PP242 (IC50=8 nM Feldman, M. E., et al. (2009). *PLoS Biology*, 7(2), e38), MeO-PP242 (>10 M). The strongest ASi, MLN0128, in M1071 leads to a potent mTORC1 inhibition (10-25 nM) (FIG. 13A). In this concentration range, M1071 also inhibits mTORC2. However, E1035, which uses PP242 as the ASi, shows a similar mTORC1 inhibition concentration range (10-25 nM) but requires a higher concentration range for mTORC2 inhibition (partial inhibition at 50 nM) (FIG. 13A). Lastly, the weakest ASi, MeO-PP242, in E1010 leads to inhibition of pS6 (S240/244) but little or no inhibition of P-4EBP1 (FIG. 13B). This pattern of inhibition is similar to rapamycin induced phosphorylation changes with only phosphorylation of S6 after E1010 treatment (FIG. 8A and FIG. 13B). Thus, the specificity of the Rapa-LINK compounds shifts more towards mTORC1 as the ASi potency decreases.

Figure 14A:
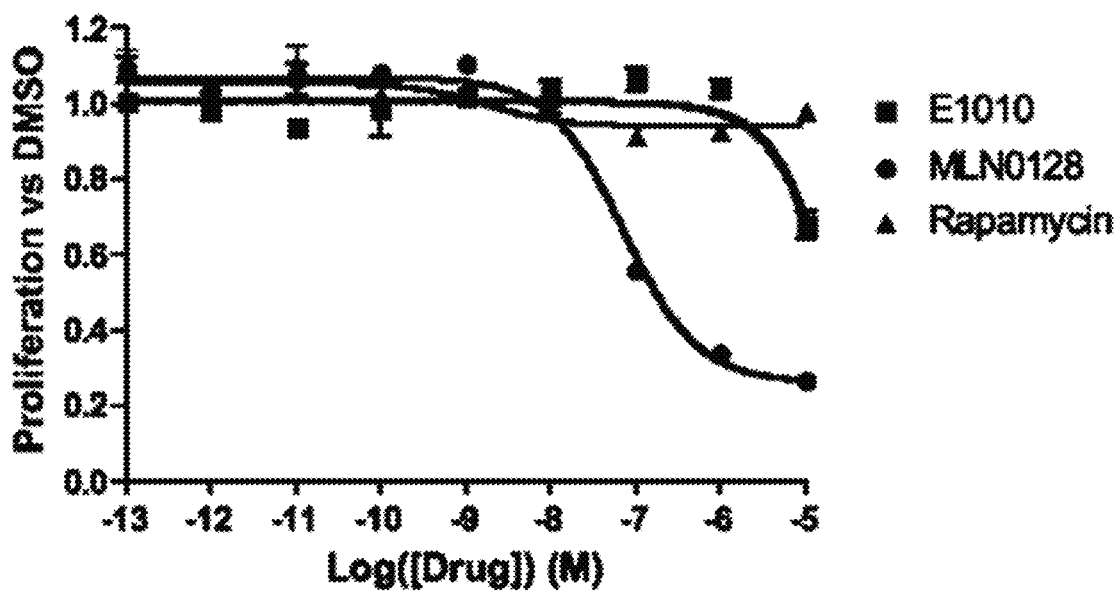
FIGS. 14A-14B.
Figure 14B:
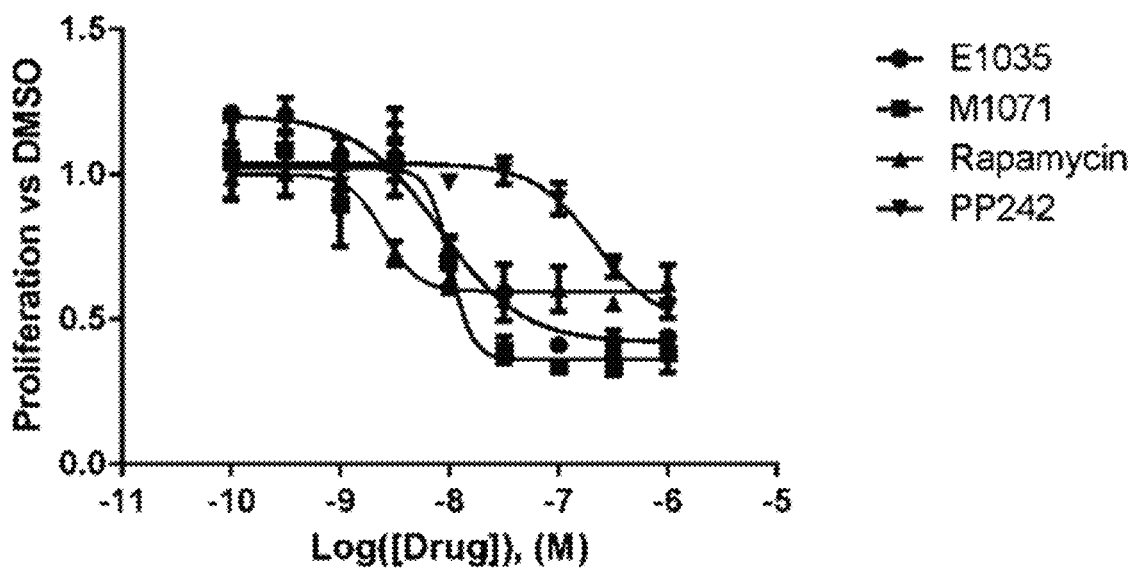

We assessed the effects of mTORC1 inhibition by Rapa-LINK compounds on cell proliferation. E1010 and rapamycin had similar effects on cell proliferation in 786-O cells (FIG. 14A). This agrees with the E1010 rapamycin-like mTOR inhibition profile seen in FIGS. 13A-13B. In measuring cell proliferation effects of the more potent Rapa-Link compounds, E1035 and M1071 both have potent effects on cell proliferation (FIG. 13B). The cell proliferation effects of E1035 and M1071 are quite similar, even though the former exhibits a larger window between TORC1 and TORC2 inhibition. This data supports the view that anti-proliferative effects rely on TORC1 rather than TORC2 inhibition, as discussed above.

Methods.

Chemical Synthesis.

All compounds were synthesized from commercially available starting materials and purified by RP-HPLC.

Cell Culture and Western Blot Analysis.

Cells were grown in 6-well plates and treated with inhibitor at the indicated concentrations or with vehicle (0.1% DMSO). Treated cells were lysed, and lysates were resolved by SDS-PAGE, transferred to nitrocellulose and blotted. All antibodies were purchased from Cell Signaling Technology.

Cell Proliferation Assays.

Cells grown in 96-well plates were treated with inhibitor in triplicate or vehicle (0.1% DMSO). After 72 h, cell viability was assessed with the CELLTITER-GLO® Luminescent Cell Viability Assay (Promega). Cell proliferation curves were generated using Prism.

Supplementary Information

Abbreviations.

AcOH: acetic acid, DCM: dichloromethane, DME: 1,2-dimethoxyethane, DMF: N,N-dimethylformamide, DMSO: dimethylsulfoxide, dPEG: discrete poly-(ethylene glycol), ESI: electrospray ionization, EtOAc: ethyl acetate, HPLC: high performance liquid chromatography, HR-MS: high resolution mass spectroscopy, LC-MS: liquid chromatography-mass spectrometry, LTQ-FT: linear trap quadrupole-Fourier transform, MeOH: methanol, NHS: N-hydroxysuccinimide, NMR: nuclear magnetic resonance, RP-HPLC: reverse phase-high performance liquid chromatography, THF: tetrahydrofuran, TLC: thin layer chromatography, TMS: tetramethylsilane.

Materials and Methods.

Starting materials, reagents, and solvents for reactions were of reagent grade and were used as purchased. Chromatographic purification was carried out using silica gel (Merck, 70-230 mesh). RP-HPLC was carried out on a Waters Binary Gradient Module 2545 system equipped with an Agilent Zorbax 300-SB C18 column (5 jam, 4.6×250 mm) for analytical mode or a Waters XBridge Prep C18 column (5 jam, 30×250 mm) for preparative mode. The column was eluted with CH3CN/water/0.1% formic acid (gradient mode), which was monitored by Waters Photodiode Array Detector 2998 (UV at $\lambda$=254 nm). Yields were not optimized.

$^1$H NMR spectra for intermediates were recorded on a Varian INOVA™ (400 MHz) spectrometer. $^1$H NMR spectra, $^1$H-$^1$H COSY, HSQC, and HMBC spectra for final compounds were recorded on a Bruker AVANCE™ (800 MHz) spectrometer. $^{13}$C NMR spectra were recorded on a Bruker AVANCE™ (500 MHz) spectrometer (500 MHz for $^1$H, 126 MHz for $^{13}$C). $^1$H chemical shifts are reported in $\delta$ (ppm) as s (singlet), d (doublet), t (triplet), q (quartet), dd (double doublet), m (multiplet) or br s (broad singlet) and are referenced to TMS (trimethylsilane) as an internal standard. LC-MS (ESI-MS) spectra were recorded with a Waters 2695 separations module using a Waters ACQUITY UPLC® BEH $C_{18}$ 1.7 µm column and were used to confirm ≥95% purity of each compound. Mobile phase A was 0.1% formic acid in ultrapure water. Mobile phase B was 0.1% formic acid in acetonitrile. (flow rate: 0.6 mL/min). HR-MS analysis was conducted by QB3/Chemistry Mass Spectrometry Facility in UC Berkeley. Samples were analyzed by electrospray ionization with a mass measuring accuracy of 5 ppm using the LTQ-FT instrument.

Experimental Procedures
Preparation of Compound (E1010)
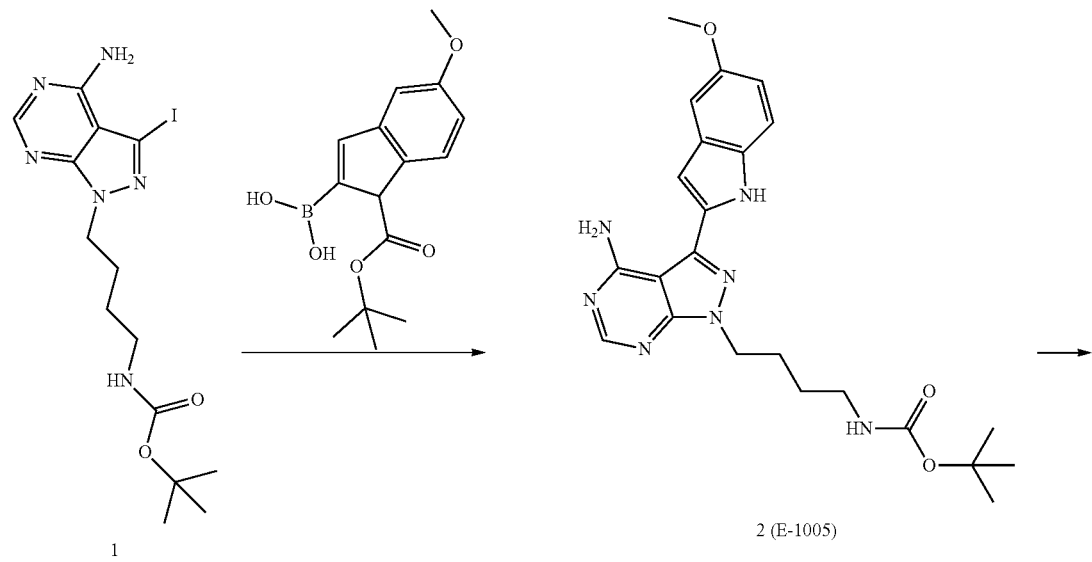
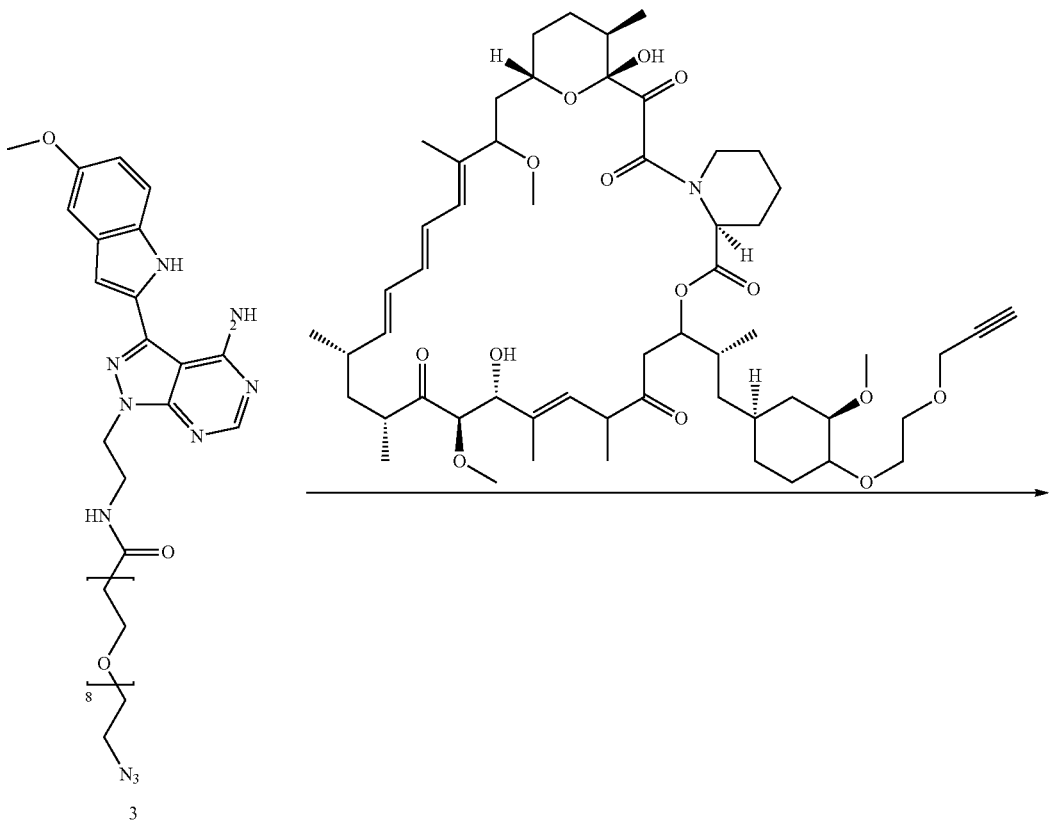

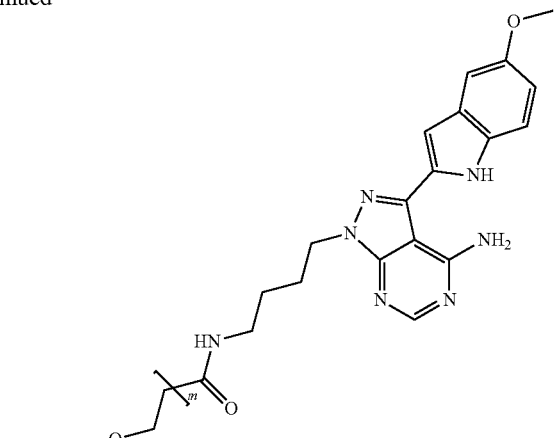
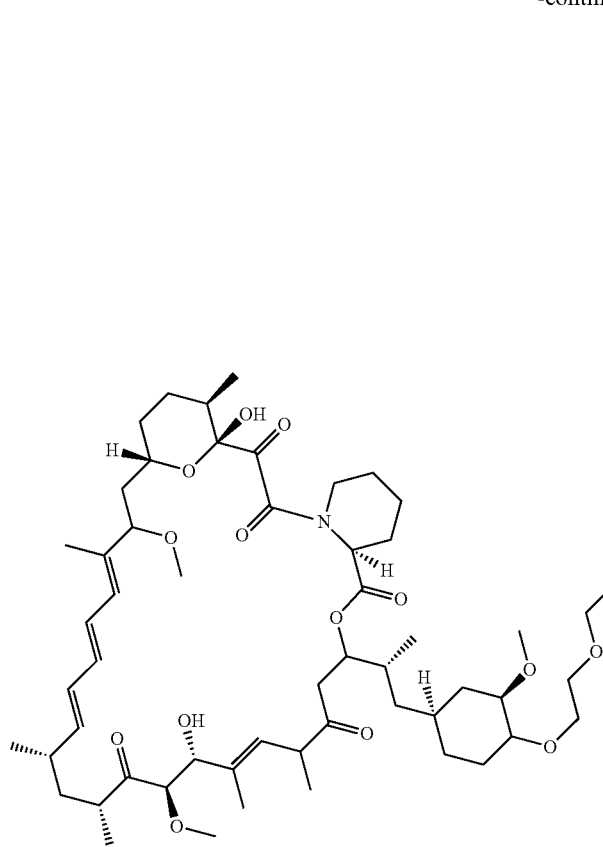

Preparation of tert-butyl (4-(4-amino-3-(5-methoxy-1H-indol-2-yl)-1H-pyrazolo[3,4-d]pyrimidin-1-yl)butyl)carbamate 2

To a bi-phasic suspension of tert-butyl (4-(4-amino-3-iodo-1H-pyrazolo[3,4-d]pyrimidin-1-yl)butyl)carbamate (1) (260 mg, 0.604 mmol), (2) and 1-BOC-5-methoxyindole-2-boronic acid (444 mg, 1.52 mmol), and saturated aqueous Na$_2$CO$_3$ solution (2 mL) in DME (10 mL) was added tetrakis(triphenylphosphine) palladium(0) (69.3 mg, 60 µmol) at room temperature under argon atmosphere. The mixture was stirred at 85° C. for 20 h. It was then cooled and partitioned between EtOAc (50 mL) and water (50 mL). The aqueous layer was separated and extracted with EtOAc (50 mL). The organic layers were combined, washed with brine (50 mL) and dried over anhydrous MgSO$_4$. The insoluble was filtered off and the filtrate was concentrated in vacuo. The crude material was purified by silica gel column chromatography (silica gel: 125 g, solvent: 100% EtOAc followed by 30% MeOH in EtOAc). $^1$H NMR (400 MHz, CDCl$_3$) δ 9.84 (1H, br s), 8.36 (1H, s), 7.36 (1H, d, J=8.8 Hz), 7.12 (1H, d, J=2.2 Hz), 6.92 (1H, dd, J=8.8, 2.5 Hz), 6.80 (1H, s), 6.43 (2H, t, br s), 4.82 (1H, br s), 4.43 (2H, t), 3.86 (3H, s), 1.44 (9H, s), 6H protons were not identified. LC-MS (ESI) m/z=452.79 (M+H)+.

Preparation of N-(4-(4-amino-3-(5-methoxy-1H-indol-2-yl)-1H-pyrazolo[3,4-d]pyrimidin-1-yl)butyl)-1-azido-3,6,9,12,15,18,21,24-octaoxaheptacosan-27-amide 3

To an aliquot of TFA (2 mL) was added tert-butyl (4-(4-amino-3-(5-methoxy-1H-indol-2-yl)-1H-pyrazolo[3,4-d]pyrimidin-1-yl)butyl)carbamate (2) (205 mg, 0.454 mmol) at 4° C. The mixture was stirred at ambient temperature for 30 min. It was then evaporated in vacuo. Drying the solid gave the salt of Boc-cleaved compound. The obtained material was dissolved into DMF (4 mL). To the mixture was added triethylamine (144 µL, 1.03 mmol) followed by a solution of azide-dPEG8-NHS ester (175 mg, 0.310 mmol) in DMF (1 mL) under argon atmosphere. The mixture was stirred at room temperature for 1 h. It was then evaporated in vacuo. The residue was partitioned between 10% THF in EtOAc (100 mL) and brine (70 mL). The aqueous layer was separated and extracted with EtOAc (70 mL). The organic layers were combined and dried over anhydrous MgSO$_4$. The insoluble was filtered off and the filtrate was evaporated in vacuo. The resulting crude material was purified by silica gel column chromatography (silica gel: 25 g, 0-15% MeOH in DCM). Desired fractions were combined and evaporated in vacuo to give the titled compound (123 mg, 59.3% in 2 steps) as a wax. $^1$H NMR (400 MHz, CDCl3) δ 9.94 (1H, br s), 8.37 (1H, s), 7.40 (1H, d, J=8.9 Hz), 7.11 (1H, d, J=2.4 Hz), 6.92 (1H, dd, J=8.8, 2.4 Hz), 6.79 (1H, s), 6.06 (2H, br s), 4.48 (2H, m), 3.88 (3H, s), 3.70 (2H, m), 3.61 (30H, m), 3.37 (2H, m), 3.32 (2H, m), 2.44 (2H, m), 2.01 (4H, m). LC-MS (ESI) m/z=802.08 (M+H)+.

Preparation of E1010 4

To a solution of 3 (32.0 mg, 43.0 µmol) in MeOH (4 mL) was added 40-O-(2-(prop-2-yn-1-yloxy)ethyl)-rapamycin (32.5 mg, 32.6 µmol). To the mixture were added 1 M aqueous CuSO4 solution (100 µL, 100 µmol) and 1 M aqueous ascorbic acid solution (50.0 µL, 50.0 µmol). The mixture was stirred at room temperature for 1.5 h. It was then concentrated in vacuo. The obtained material was triturated with 10% THF in EtOAc (10 mL) for 10 min. After removing the insoluble material by filtration through Celite filter-aid, the solution was evaporated in vacuo. The resulting crude material was purified by preparative RP-HPLC (40-85% $CH_3CN$ in water containing 0.1% formic acid). The desired fractions were combined and lyophilized to give a formic acid salt of the titled compound (2.6 mg, 4%) as a colorless amorphous powder. LC-MS (ESI–) m/z=1796.51 (M–H)–. HR-MS (ESI–) Calcd for $C_{93}H_{141}O_{24}N_{11}$ (M–Na)+1819.0043, Found 1819.0034 (Δ –0.50 ppm).

TABLE 11

NMR results for E-1010.

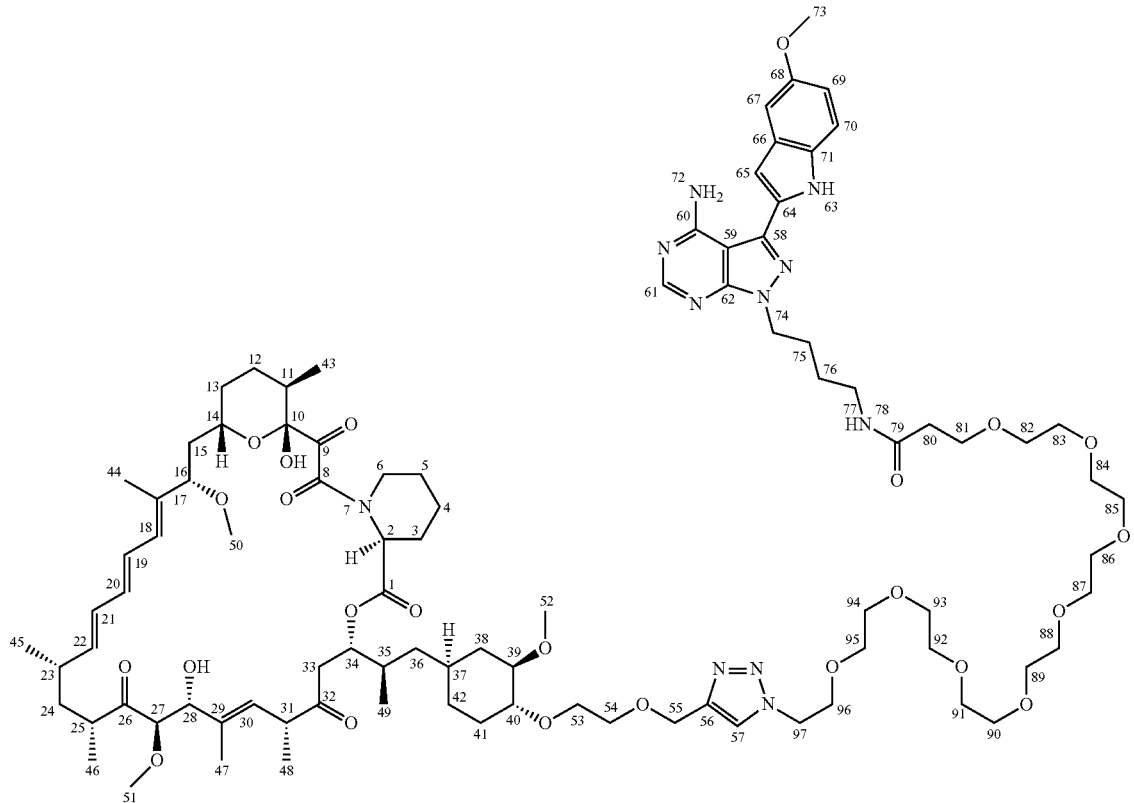 [SMILES: COc1ccc2[nH]c(-c3nn(CCCCNC(=O)CCOCCOCCOCCOCCOCCOCCOCCOCCn4cc(COCCO[C@@H]5CC[C@@H](C[C@@H](C)[C@@H]6CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)nn4)c4ncnc(N)c34)cc2c1]

E-1010

| Atom | Atom Type | δ $^1$H Major (3:1) | δ $^{13}$C Major (3:1) | HMBC C to H | $^1$H-$^1$H COSY |
|---|---|---|---|---|---|
| 1 | C=O | N/A | 169.2 | 2 | N/A |
| 2 | CH | 5.28 (d, 5.7 Hz) | 51.3 | 3a,b, 6a | 3b |
| 3 | $CH_2$ | a: 2.33 (s) | 27.1 | 2, 5a | 3b, 4b |
|   |   | b: 1.75 (m) |   |   | 3a, 2 |
| 4 | $CH_2$ | a: 1.78 (m) | 20.7 | 2, 6a,b | 4b, 5a,b |
|   |   | b: 1.47 (m) |   |   | 4a, 3a, 5a,b |
| 5 | $CH_2$ | a: 1.74 (m) | 25.3 | 3a, 4b | 5b, 4a,b |
|   |   | b: 1.47 (m) |   |   | 5a, 4a,b, 6b |
| 6 | $CH_2$ | a: 3.56 (m) | 44.2 | 2, 4b, 5b | 6b |
|   |   | b: 3.43 (m) |   |   | 6a, 5b |
| 8 | C=O | N/A | 166.7 | 2, 6a | N/A |
| 9 | C=O | N/A | 196.2 | n.d. | N/A |
| 10 | O—C—OH | N/A | 98.5 | 12, 43 | N/A |
| 11 | CH | 2.00 (m) | 33.8 | 12, 43 | 12, 43 |
| 12 | $CH_2$ | 1.60 (2H, m) | 27.2 | 43 | 11, 13a,b |
| 13 | $CH_2$ | a: 1.63 (m) | 31.2 | 12, 15a | 13b, 12 |
|   |   | b: 1.31 (m) |   |   | 13a, 12, 14 |
| 14 | CH—OC | 3.88 (m) | 67.3 | 12, 15a | 13b, 15a,b |
| 15 | $CH_2$ | a: 1.85 (m) | 38.9 | 16 | 15b, 14, 16 |
|   |   | b: 1.49 (m) |   |   | 15a, 14, 16 |
| 16 | CH—$OCH_3$ | 3.65 (m) | 84.3 | 15a, 18, 44, 50 | 15a,b |
| 17 | =C= | N/A | 135.7 | 15a, 44 | N/A |
| 18 | CH=C | 5.97 (d, 10.9 Hz) | 129.4 | 44 | 19 |
| 19 | CH=C | 6.38 (dd, 14.5, 11.6 Hz) | 126.6 | 20, 21 | 18, 20 |
| 20 | CH=C | 6.31 (dd, 14.8, 10.4 Hz) | 133.5 | 18, 19, 21, 22 | 19, 21 |
| 21 | CH=C | 6.14 (dd, 14.8, 10.4 Hz) | 130.2 | 19 | 20, 22 |
| 22 | CH=C | 5.55 (dd, 15.1, 8.9 Hz) | 140.0 | 20, 24a,b, 45 | 21, 23 |
| 23 | CH | 2.32 (m) | 35.0 | 21, 22, 24a,b, 25, 45 | 22, 24a, 45 |

TABLE 11-continued

NMR results for E-1010.

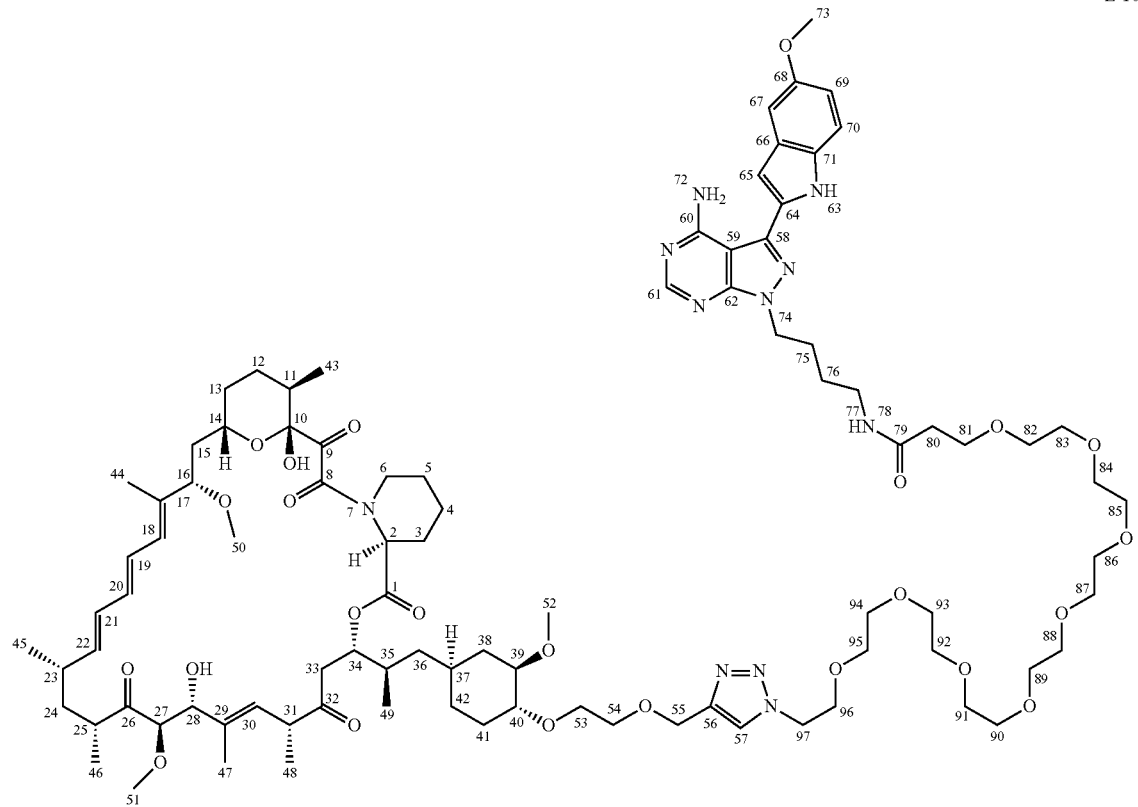

E-1010

| Atom | Atom Type | δ ¹H Major (3:1) | δ ¹³C Major (3:1) | HMBC C to H | ¹H-¹H COSY |
|---|---|---|---|---|---|
| 24 | CH₂ | a: 1.47 (m) | 40.3 | 22, 25, 45, 46 | 24b, 23 |
|  |  | b: 1.21 (m) |  |  | 24a, 25 |
| 25 | CH | 2.70 (m) | 40.8 | 24a,b, 46 | 24b, 46 |
| 26 | C=O | N/A | n.d. (>210) | n.d. | N/A |
| 27 | CH—OCH₃ | 3.78 (m) | 84.9 | 28, 51 | 28 |
| 28 | CH—OH | 4.19 (d, 5.24 Hz) | 77.1 | 27, 30, 47 | 27 |
| 29 | —C= | N/A | 136.0 | 28, 31, 47 | N/A |
| 30 | CH=C | 5.42 (d, 9.9 Hz) | 126.6 | 28, 31, 47, 48 | 31 |
| 31 | CH | 3.29 (d, 10.4 Hz) | 46.6 | 30, 48 | 30, 48 |
| 32 | C=O | N/A | 208.3 | 30, 31, 33a,b, 48 | N/A |
| 33 | CH₂ | a: 2.70 (m) | 40.7 | n.d. | 33b, 34 |
|  |  | b: 2.58 (dd, 15.7, 8.6 Hz) |  |  | 33a, 34 |
| 34 | CH—OCO | 5.16 (dd, 10.7, 5.9 Hz) | 75.8 | 33a,b, 49 | 33a,b, 35 |
| 35 | CH | 1.93 (m) | 33.2 | 33a,b, 49 | 34, 36a,b, 49 |
| 36 | CH₂ | a: 1.17 (m) | 38.3 | 38b, 49 | 36b, 35, 37 |
|  |  | b: 1.09 (m) |  |  | 36a, 35, 37 |
| 37 | CH | 1.33 (m) | 33.1 | 36a,b, 38b, 42b | 36a,b, 38b, 42a,b |
| 38 | CH₂ | a: 2.02 (m) | 36.3 | 36a,b, 42a | 38b, 39 |
|  |  | b: 0.70 (m) |  |  | 38a, 37, 39 |
| 39 | CH—OCH₃ | 3.04 (m) | 83.2 | 38a,b, 40, 52 | 38a,b, 40 |
| 40 | CH—O— | 3.10 (m) | 83.2 | 38a,b, 39, 52, 53 | 39, 41a,b |
| 41 | CH₂ | a: 2.01 (m) | 30.1 | n.d. | 41b, 40, 42b |
|  |  | b: 1.24 (m) |  |  | 41a, 40, 42b |
| 42 | CH₂ | a: 1.66 (m) | 31.8 | 36b, 38a | 42b, 37 |
|  |  | b: 0.90 (m) |  |  | 42a, 37, 41a,b |
| 43 | 11-CH₃ | 0.95 (3H, d, 6.7 Hz) | 16.2 | n.d. | 11 |
| 44 | 17-CH₃ | 1.65 (3H, s) | 10.2 | 16, 18 | n.d. |
| 45 | 23-CH₃ | 1.05 (3H, d, 6.4 Hz) | 21.5 | 22, 24a,b | 23 |
| 46 | 25-CH₃ | 0.99 (3H, d, 6.4 Hz) | 13.7 | 24a,b, 25 | 25 |
| 47 | 29-CH₃ | 1.75 (3H, s) | 13.2 | 28, 30 | n.d. |
| 48 | 31-CH₃ | 1.09 (3H, d, 6.9 Hz) | 16.0 | 30, 31 | 31 |
| 49 | 35-CH₃ | 0.90 (3H, d, 6.4 Hz) | 15.9 | 36a,b | 35 |
| 50 | 16-OCH₃ | 3.14 (3H, s) | 55.9 | 16 | n.d. |
| 51 | 27-OCH₃ | 3.33 (3H, s) | 59.3 | 27 | n.d. |
| 52 | 39-OCH₃ | 3.43 (3H, s) | 57.9 | 39 | n.d. |
| 53 | 40-OCH₂ | 3.70 (2H, m) | 69.3 | 40, 54 | 54 |

TABLE 11-continued

NMR results for E-1010.

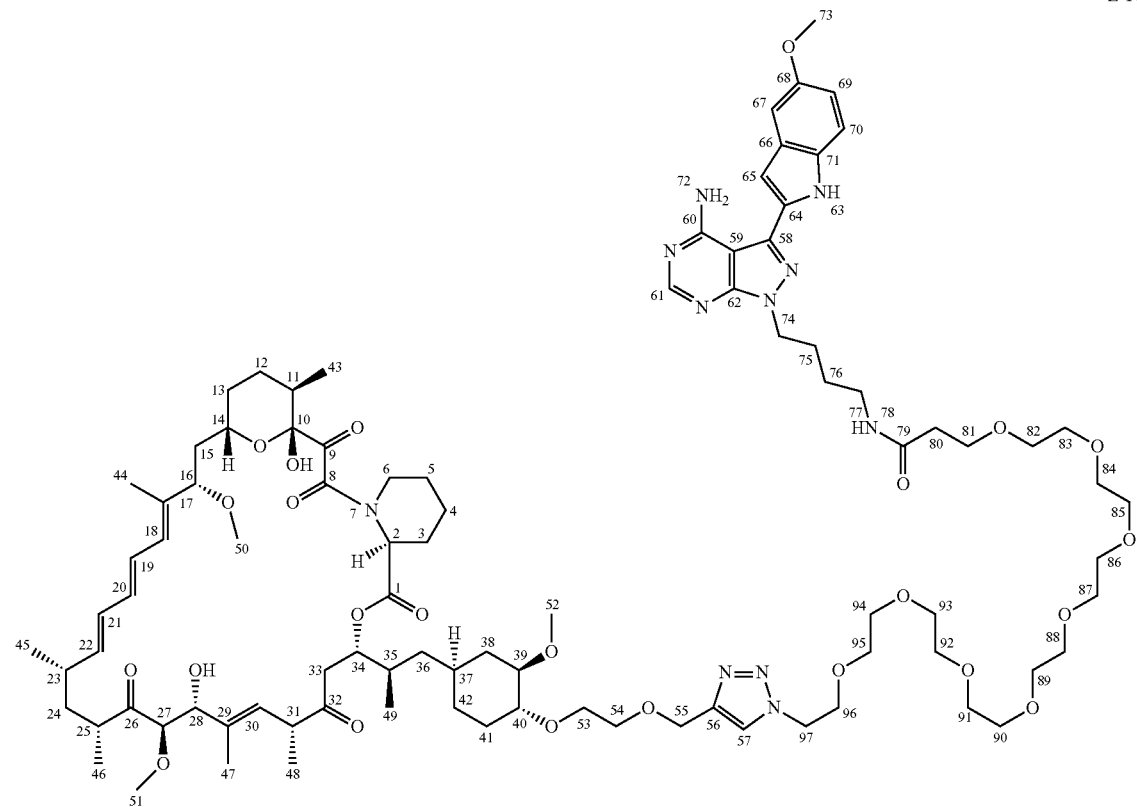

E-1010

| Atom | Atom Type | δ $^1$H Major (3:1) | δ $^{13}$C Major (3:1) | HMBC C to H | $^1$H-$^1$H COSY |
|---|---|---|---|---|---|
| 54 | —CH$_2$—O— | 3.66 (2H, m) | 70.1 | 53, 55 | 53 |
| 55 | —OCH$_2$triazole | 4.68 (2H, d, 4.9 Hz) | 64.6 | 54 | n.d. |
| 56 | —C= | N/A | 145.0 | 55, 57 | N/A |
| 57 | =CH | 7.71 (s) | 123.8 | 55, 97 | n.d. |
| 58 | PP—C | N/A | 144.5 | 65 | N/A |
| 59 | PP—C | N/A | 98.5 | 61 | N/A |
| 60 | PP—C—NH$_2$ | N/A | 157.5 | n.d. | N/A |
| 61 | PP—CH | 8.36 (s) | 156.0 | n.d. | n.d. |
| 62 | PP—C | N/A | 154.1 | 61, 74 | N/A |
| 63 | Ind—NH | 9.99 (s, br) | N/A | N/A | n.d. |
| 64 | Ind—C | N/A | 131.1 | 63, 65 | N/A |
| 65 | Ind—CH | 6.80 (s) | 101.7 | n.d. | n.d. |
| 66 | Ind—C | N/A | 101.7 | 65, 67, 70 | N/A |
| 67 | Ind—CH | 7.11 (d, 1.3 Hz) | 102.0 | n.d. | 69 |
| 68 | Ind—C | N/A | 113.7 | 67, 69 | N/A |
| 69 | Ind—CH | 6.92 (dd, 2.1, 9.1 Hz) | 113.7 | n.d. | 67, 70 |
| 70 | Ind—CH | 7.40 (d, 8.0 Hz) | 112.5 | n.d. | 69 |
| 71 | Ind—C | N/A | 130.0 | 63, 70 | N/A |
| 73 | Ind—O—CH$_3$ | 3.87 (3H, s) | 55.9 | n.d. | n.d |
| 74 | N—CH$_2$ | 4.48 (2H, t, 6.7 Hz) | 46.6 | 75, 76 | 75 |
| 75 | CH$_2$ | 2.01 (2H, m) | 26.8 | 74, 75, 76 | 74, 75 |
| 76 | CH$_2$ | 1.56 (2H, m) | 26.4 | 74, 75, 77 | 75, 77 |
| 77 | CH$_2$—NHCO | 3.32 (2H, m) | 38.8 | 75, 76 | 76 |
| 78 | NH | 6.83 (s) | N/A | N/A | n.d. |
| 79 | CO | N/A | 171.6 | 77, 80, 81 | N/A |
| 80 | CH$_2$ | 2.45 (2H, t, 5.3 Hz) | 37.1 | 81 | 81 |
| 81 | CH$_2$ | 3.74 (2H, t, 4.4 Hz) | 67.4 | 80 | 80 |
| 82-95 | O—(CH$_2$CH$_2$O)$_7$ | 3.56-3.60 (28H, m) | 70.4-70.5 | multi | multi |
| 96 | OCH$_2$ | 3.84 (2H, t, 5.3 Hz) | 69.5 | 97 | 97 |
| 97 | CH$_2$-triazole | 4.51 (2H, t, 5.1 Hz) | 50.2 | 96 | 96 |

PP stands for pyrazolo[3,4-d]pyrimidine and Ind stands for 1H-Indole
OH proton was observed at 4.81 (1H, s) for 10-OH or 28-OH. Another OH proton was not identified.
NHx protons were observed at 6.08 (br) for PP—NH$_2$.

Preparation of E1035 8
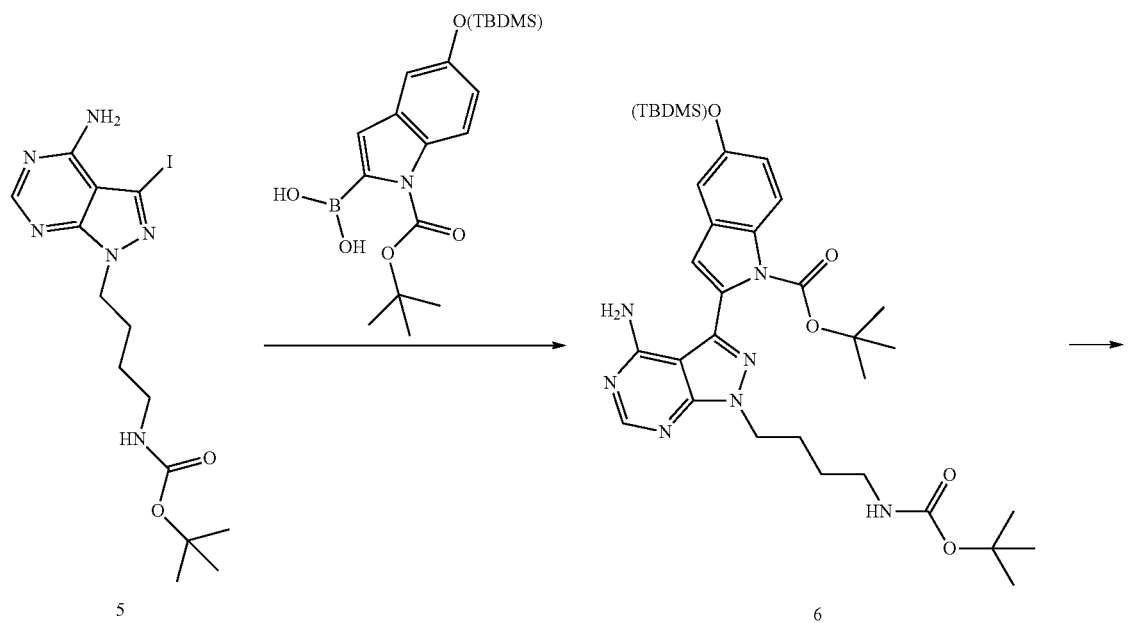
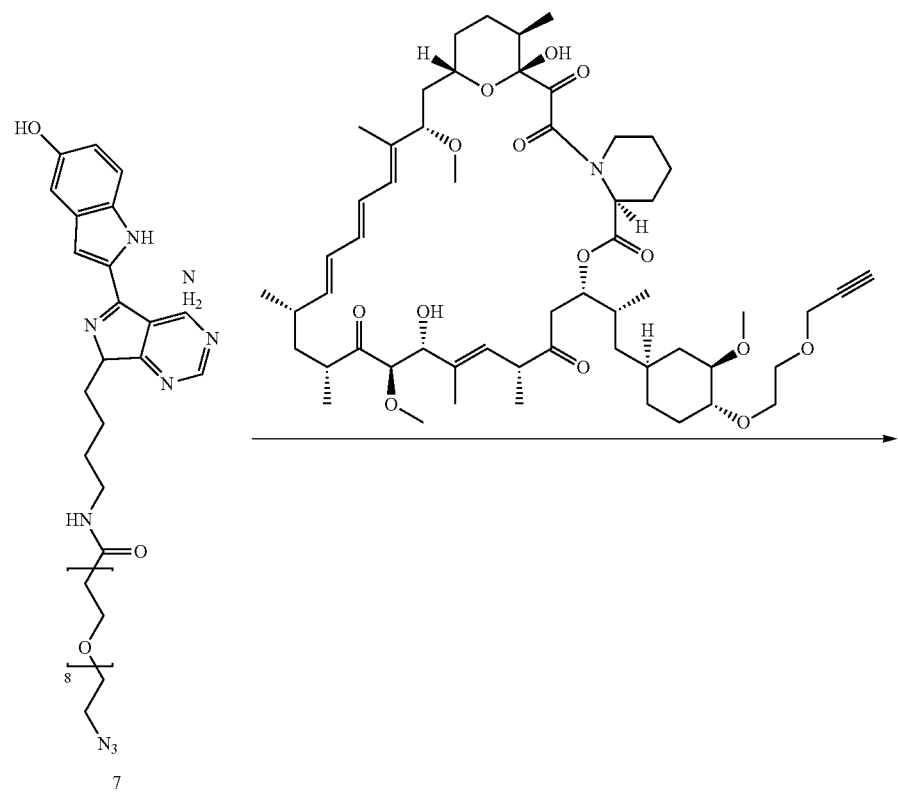

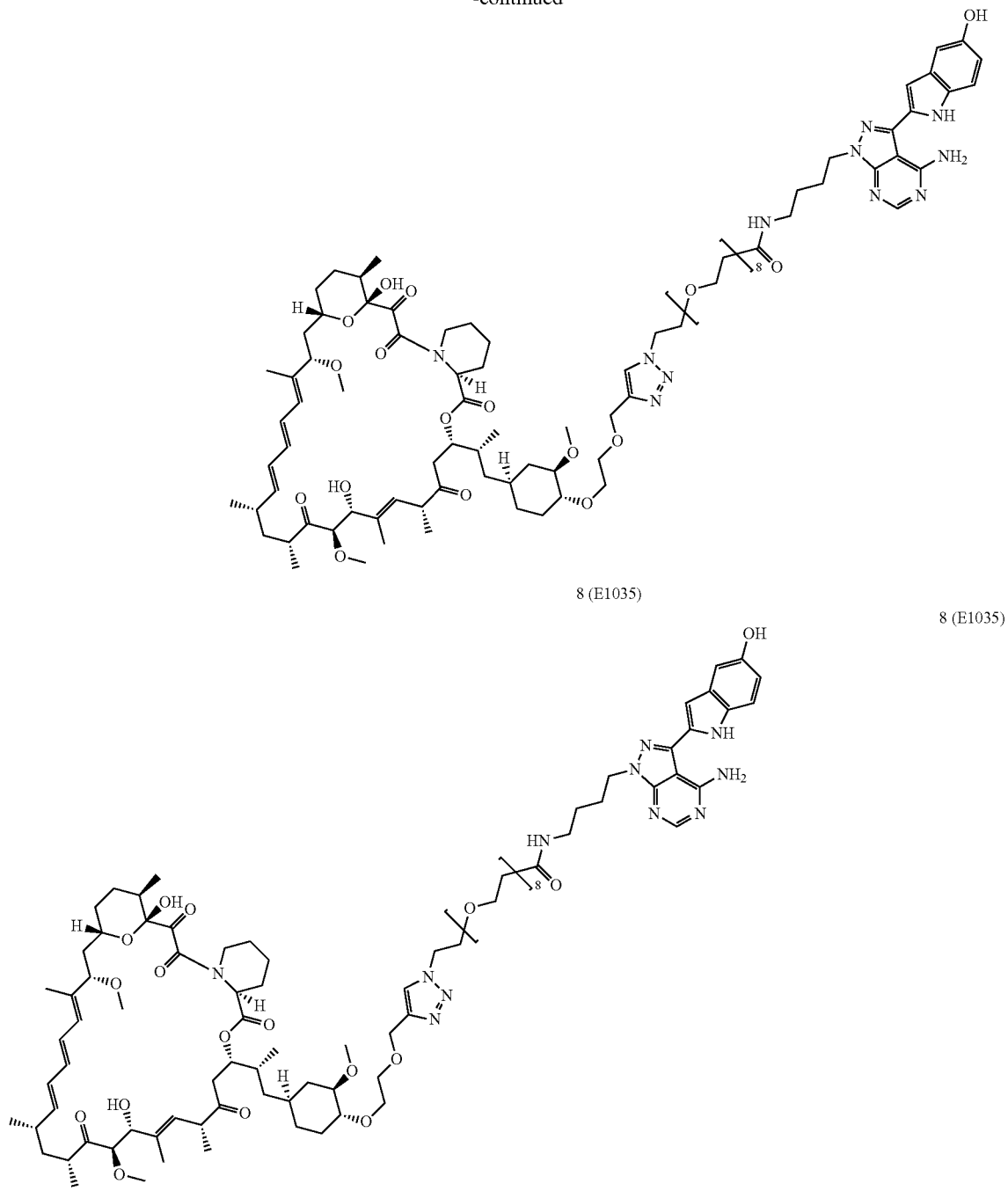

8 (E1035)

Preparation of tert-butyl 2-(4-amino-1-(4-((tert-butoxycarbonyl)amino)butyl)-1H-pyrazolo[3,4-d]pyrimidin-3-yl)-5-((tert-butyldimethylsilyl)oxy)-1H-indole-1-carboxylate 6

To an aliquot of dioxane:H$_2$O (3:1) (1 mL) was added 1-Boc-5-TBDMS-O-indole-2-boronic acid (5) (previously synthesized) (50 mg, 0.12 mmol), (1-(tert-butoxycarbonyl)-5-((tert-butyldimethylsilyl)oxy)-1H-indol-2-yl)boronic acid (135 mg, 0.35 mmol), K$_3$PO$_4$ (34 mg, 0.35 mmol), SPhos (10.2 mg, 24.8 μmol) and tris(dibenzylideneacetone)dipalladium(0) (12.2 mg, 13.3 μmol) at room temperature under argon atmosphere. The mixture was heated via microwave at 150° C. for 20 min. It was then cooled and partitioned between H$_2$O (5 mL) and DCM (5 mL). The aqueous layer was separated and extracted with DCM (5 mL×2). The organic layers were combined and dried over anhydrous MgSO$_4$. The insoluble was filtered off and the filtrate was concentrated in vacuo. The crude material was purified by silica gel column chromatography (silica gel: 125 g, solvent: 100% DCM followed by 0-10% MeOH in DCM). $^1$H NMR (400 MHz, DMSO-d6) δ 11.43 (1H, br s), 8.42 (1H, s), 8.27 (1H, s), 7.25 (1H, d, J=8.8 Hz), 7.12 (2H, br s), 6.92 (1H, d, J=2.3 Hz), 6.69 (1H, dd, J=8.3, 2.3 Hz), 6.68 (1H, br s), 4.38

(2H, t, J=6.4 Hz), 3.58 (2H, br s), 2.76 (2H, t, J=7.1 Hz), 1.92 (2H, m), 1.50 (2H, m). LC-MS (ESI) m/z=550.81 (M−H)−.

Preparation of N-(4-(4-amino-3-(5-hydroxy-1H-indol-2-yl)-1H-pyrazolo[3,4-d]pyrimidin-1-yl)butyl)-1-azido-3,6,9,12,15,18,21,24-octaoxaheptacosan-27-amide 7

To an aliquot of TFA (4 mL) was added tert-butyl-2-(4-amino-1-(4-((tert-butoxycarbonyl)amino)butyl)-1H-pyrazolo[3,4-d]pyrimidin-3-yl)-5-(tertbutyldimethylsilyl)oxy)-1H-indole-1-carboxylate (2) (60 mg, 0.092 mmol). The mixture was stirred at ambient temperature for 1 hr. It was then evaporated in vacuo. The resulting crude material was purified by preparative RP-HPLC (40-85% $CH_3CN$ in water containing 0.1% formic acid). The desired fractions were combined and lyophilized to give a formic acid salt of the material as a colorless amorphous powder. The obtained material (29 mg, 0.067 mmol) was dissolved in DMF (1 mL). To the mixture was added triethylamine (37.38 μL, 0.268 mmol) followed by a solution of azide-dPEG8-NHS ester (46 mg, 0.081 mmol) in DMF (0.5 mL) under argon atmosphere. The mixture was stirred at room temperature for 1 h. The resulting crude material was purified by preparative RP-HPLC (40-85% $CH_3CN$ in water containing 0.1% formic acid). Desired fractions were combined and evaporated in vacuo to give the titled compound (40 mg, 75.9% in 2 steps) as an orange oil. $^1$H NMR (400 MHz, CDCl3) δ 9.96 (1H, br s), 8.31 (1H, s), 7.24 (1H, d, J=8.5 Hz), 7.02 (1H, d, J=1.9 Hz), 6.85 (1H, br s), 6.81 (1H, dd, J=8.1, 2.2 Hz), 6.64 (1H, s), 6.28 (2H, br s), 4.39 (2H, t, J=6.85 Hz), 3.57 (32H, m), 3.24 (2H, m), 3.22 (2H, m), 2.39 (2H, m), 1.93 (2H, m), 1.47 (2H, m), NH not identified. LC-MS (ESI) m/z=788.03 (M+H)+.

Preparation of E1035 8

To a solution of 3 (25 mg, 32.6 μmol) in MeOH (2 mL) was added 40-O-(2-(prop-2-yn-1-yloxy)ethyl)-rapamycin (24.8 mg, 24.9 μmol). To the mixture were added 1 M aqueous $CuSO_4$ solution (37.7 μL, 37.7 μmol) and 1 M aqueous ascorbic acid solution (42.7 μL, 42.7 μmol). The mixture was stirred at room temperature for 1.5 h. It was then concentrated in vacuo. The obtained material was triturated with 10% THF in EtOAc (10 mL) for 10 min. After removing the insoluble material by filtration through Celite filter-aid, the solution was evaporated in vacuo. The resulting crude material was purified by preparative RP-HPLC (40-85% $CH_3CN$ in water containing 0.1% formic acid). The desired fractions were combined and lyophilized to give a formic acid salt of the titled compound (1.9 mg, 4%) as a colorless amorphous powder. LC-MS (ESI−) m/z=1781.45 (M−H)−

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound having the formula:

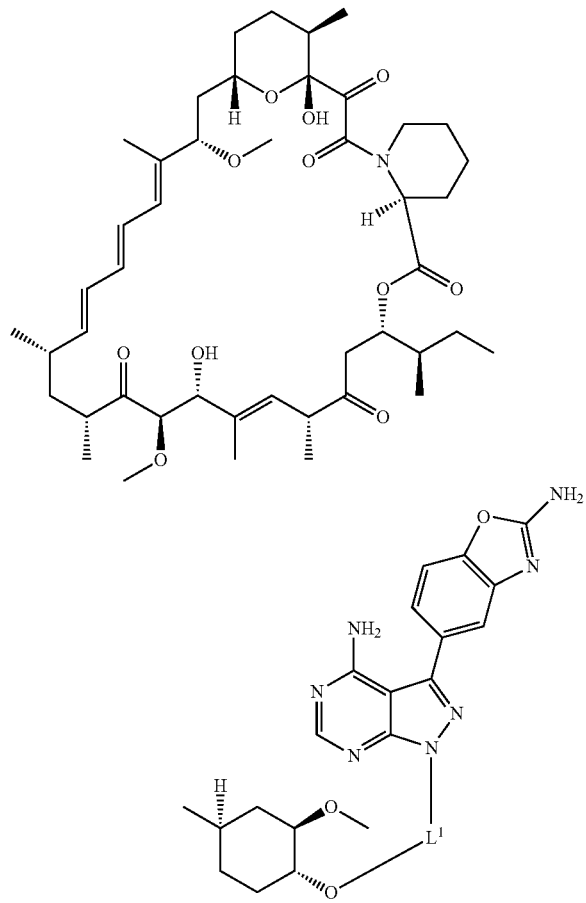

or a pharmaceutically acceptable salt thereof, wherein
$L^1$ is $L^2$-$L^3$-$L^4$-$L^5$;
$L^2$ is connected directly to a monovalent rapamycin or a monovalent rapamycin analog;
$L^2$ is a $R^{26}$-substituted or unsubstituted 2 to 8 membered heteroalkylene;
$L^3$ is a $R^{29}$-substituted or unsubstituted 5 to 10 membered heteroarylene;
$L^4$ is a $R^{32}$-substituted or unsubstituted 2 to 20 membered heteroalkylene;
$L^5$ is a $R^{35}$-substituted or unsubstituted 2 to 20 membered heteroalkylene;
$R^{26}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl;
$R^{27}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl;
$R^{29}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl;
$R^{30}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl;
$R^{32}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{33}$-substituted or unsubstituted alkyl, $R^{33}$-substituted or unsubstituted heteroalkyl, $R^{33}$-substituted or unsubstituted cycloalkyl, $R^{33}$ substituted or unsubstituted heterocycloalkyl, $R^{33}$-substituted or unsubstituted aryl, or $R^{33}$-substituted or unsubstituted heteroaryl;
$R^{33}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl;
$R^{35}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl;
$R^{36}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{37}$-substituted or unsubstituted alkyl, R$^{37}$-substituted or unsubstituted heteroalkyl, R$^{37}$-substituted or unsubstituted cycloalkyl, R$^{37}$-substituted or unsubstituted heterocycloalkyl, R$^{37}$-substituted or unsubstituted aryl, or R$^{37}$-substituted or unsubstituted heteroaryl; and R$^{28}$, R$^{31}$, R$^{34}$, and R$^{37}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

2. The compound of claim 1, or a pharmaceutically acceptable salt thereof, wherein
L$^2$ is a R$^{26}$-substituted or unsubstituted 2 to 8 membered heteroalkylene;
L$^3$ is a R$^{29}$-substituted or unsubstituted 5 to 10 membered heteroarylene;
L$^4$ is a R$^{32}$-substituted or unsubstituted 2 to 10 membered heteroalkylene; and
L$^5$ is a R$^{35}$-substituted or unsubstituted 2 to 10 membered heteroalkylene.

3. The compound of claim 1, or a pharmaceutically acceptable salt thereof, wherein
L$^2$ is 2 to 8 membered heteroalkylene comprising at least one NH or O;
L$^3$ is 5 to 10 membered heteroarylene;
L$^4$ is [(CH$_2$)$_{b11}$O]$_{b12}$—;
L$^5$ is CH$_2$CH$_2$C(O)NH(CH$_2$)$_{b10}$;
b10 is an integer from 1 to 6;
b11 is an integer from 1 to 3; and
b12 is an integer from 1 to 8.

4. The compound of claim 1, or a pharmaceutically acceptable salt thereof, wherein
L$^2$ is —CH$_2$CH$_2$OCH$_2$—;
L$^3$ is triazolylene;
L$^4$ is —(CH$_2$CH$_2$O)$_b$—;
L$^5$ is —CH$_2$CH$_2$C=(O)NH(CH$_2$)$_4$; and
b is an integer from 4 to 8.

5. The compound of claim 1, or a pharmaceutically acceptable salt thereof, wherein
L$^2$ is R$^{26}$-substituted or unsubstituted 2 to 8 membered heteroalkylene;
L$^3$ is a 10-substituted or unsubstituted 5 to 10 membered heteroarylene;
L$^4$ is a 1C-substituted or unsubstituted 2 to 15 membered heteroalkylene; and
L$^5$ is a R$^{35}$-substituted or unsubstituted 2 to 15 membered heteroalkylene.

6. A pharmaceutical composition comprising a pharmaceutically acceptable excipient and a compound of claim 1, or a pharmaceutically acceptable salt thereof.

7. A method of treating a disease in a subject in need thereof, said method comprising administering to said subject an effective amount of a compound of claim 1, or a pharmaceutically acceptable salt thereof, wherein said disease is a cancer.

8. The method of claim 7, wherein said administering is through a drug-eluting stent.

\* \* \* \* \*